US012648947B2

(12) United States Patent
Flückiger-Mangual et al.

(10) Patent No.: US 12,648,947 B2
(45) Date of Patent: Jun. 9, 2026

(54) HETEROCYCLIC DERIVATIVES, PHARMACEUTICAL COMPOSITIONS AND THEIR USE IN THE TREATMENT, AMELIORATION OR PREVENTION OF FIBROTIC DISEASE

(71) Applicant: TOLREMO THERAPEUTICS AG, Muttenz (CH)

(72) Inventors: Stefanie Flückiger-Mangual, Muttenz (CH); Thomas Bohnacker, Muttenz (CH)

(73) Assignee: Tolremo Therapeutics AG, Muttenz (CH)

( * ) Notice: Subject to any disclaimer, the term of this patent is extended or adjusted under 35 U.S.C. 154(b) by 747 days.

(21) Appl. No.: 18/011,734

(22) PCT Filed: Jun. 24, 2021

(86) PCT No.: PCT/EP2021/067347

§ 371 (c)(1),
(2) Date: Dec. 20, 2022

(87) PCT Pub. No.: WO2021/260110

PCT Pub. Date: Dec. 30, 2021

(65) Prior Publication Data

US 2023/0226057 A1 Jul. 20, 2023

(30) Foreign Application Priority Data

Jun. 25, 2020 (EP) .................................... 20182379

(51) Int. Cl.
*A61K 31/506* (2006.01)
*A61K 31/5386* (2006.01)
*A61P 11/00* (2006.01)

(52) U.S. Cl.
CPC ........ *A61K 31/506* (2013.01); *A61K 31/5386* (2013.01); *A61P 11/00* (2018.01)

(58) Field of Classification Search
CPC .... A61K 31/506; A61K 31/5386; A61P 11/00
See application file for complete search history.

(56) References Cited

U.S. PATENT DOCUMENTS

| | | | |
|---|---|---|---|
| 3,773,919 | A | 11/1973 | Boswell |
| 4,485,045 | A | 11/1984 | Regen |
| 4,544,545 | A | 10/1985 | Ryan |
| 6,570,036 | B1 | 5/2003 | Reuter |
| 10,648,983 | B2 | 5/2020 | Filvaroff et al. |
| 2016/0046608 | A1 | 2/2016 | Cohen |
| 2016/0317632 | A1 | 11/2016 | Albrecht |
| 2017/0291902 | A1 | 10/2017 | Perl |
| 2018/0334454 | A1 | 11/2018 | Lanman |
| 2019/0144444 | A1 | 5/2019 | Blake |
| 2023/0233558 | A1 | 7/2023 | Fluckiger-Mangual |
| 2023/0255966 | A1 | 8/2023 | Fluckiger-Mangual |

FOREIGN PATENT DOCUMENTS

| | | | |
|---|---|---|---|
| CN | 1473161 | A | 2/2004 |
| CN | 107406454 | A | 11/2017 |
| CN | 110621316 | A | 12/2019 |
| CN | 110996960 | A | 4/2020 |

(Continued)

OTHER PUBLICATIONS

Atzrodt et al, "Synthesis of stable isotope labelled internal standards for drug-drug interaction (DDI) studies," Bioogranic Medicinal Chemistry, vol. 20, Issue 18, Sep. 15, 2012, pp. 5658-5667.
Boumahdi et al, "The great escape: tumour cell plasticity in resistance to targeted therapy," Nat Rev Drug Discov. Jan. 19, 2019.
Cai et al, "Intratumoral De Novo Steroid Synthesis Activates Androgen Receptor in Castration-Resistant Prostate Cancer and Is Upregulated by Treatment with CYP17A1 Inhibitors," Therapeutics, Targets, and Chemical Biology, American Association for Cancer Research, 71 (20), Oct. 15, 2011.
Canon et al., "The clinical Kras (G12C) inhibitor AMG 510 drives anti-tumor immunity," Nature, vol. 575 (Oct. 2019).
Fell et al., "Identification of the Clinical Development Candidate MRTX849, a covalent KRASG12C Inhibitor for the Treatment of Cancer," Journal of Medicinal Chemistry, vol. 63 (Apr. 2020).Fell et al., "Identification of the Clinical Development Candidate MRTX849, a covalent KRASG12C Inhibitor for the Treatment of Cancer," Journal of Medicinal Chemistry, vol. 63 (Apr. 2020).

(Continued)

*Primary Examiner* — Erich A Leeser
(74) *Attorney, Agent, or Firm* — KDW Firm PLLC

(57) ABSTRACT

The present invention relates to a compound of formula (I), optionally in the form of a pharmaceutically acceptable salt, solvate, cocrystal, tautomer, racemate, enantiomer, or diastereomer or mixture thereof and to pharmaceutical compositions comprising a compound of formula (I), as well as to the use of a compound of formula (I), or a pharmaceutically acceptable salt, solvate, cocrystal, tautomer, racemate, enantiomer, or diastereomer or mixture thereof, in the treatment of fibrotic diseases, preferably idiopathic pulmonary fibrosis (IPF) or non-alcoholic steatohepatitis (NASH). Further aspects of the present invention include combination therapies in which a compound of formula (I), optionally in the form of a pharmaceutically acceptable salt, solvate, cocrystal, tautomer, racemate, enantiomer, or diastereomer or mixture thereof, is used in combination with a known anti-fibrotic or anti-inflammatory agents for fibrotic diseases.

(I)

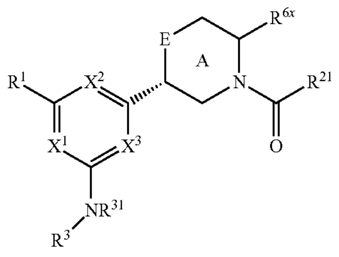

20 Claims, 2 Drawing Sheets

(56) References Cited

FOREIGN PATENT DOCUMENTS

| | | | | |
|---|---|---|---|---|
| CN | 110996962 A | 4/2020 | | |
| CN | 111328283 A | 6/2020 | | |
| DE | 3218121 A1 | 11/1983 | | |
| EP | 0036676 A1 | 9/1981 | | |
| EP | 0052322 A2 | 5/1982 | | |
| EP | 0088046 A2 | 9/1983 | | |
| EP | 0102324 A2 | 3/1984 | | |
| EP | 0133988 A2 | 3/1985 | | |
| EP | 0142641 A2 | 5/1985 | | |
| EP | 0143949 A1 | 6/1985 | | |
| JP | 2001089452 A | 4/2001 | | |
| JP | 2015524798 A | 8/2015 | | |
| WO | 9741833 A1 | 11/1997 | | |
| WO | 9916419 A1 | 4/1999 | | |
| WO | 01085136 A2 | 11/2001 | | |
| WO | 0222607 A1 | 3/2002 | | |
| WO | 0222608 A1 | 3/2002 | | |
| WO | 03053411 A1 | 7/2003 | | |
| WO | 2005100341 A1 | 10/2005 | | |
| WO | 2008006583 A1 | 1/2008 | | |
| WO | 2009050183 A2 | 4/2009 | | |
| WO | 2013148114 A1 | 10/2013 | | |
| WO | 2014177524 A1 | 11/2014 | | |
| WO | 2015103355 A1 | 7/2015 | | |
| WO | 2016123054 A2 | 8/2016 | | |
| WO | 2016197009 A1 | 12/2016 | | |
| WO | 2018203256 A1 | 11/2018 | | |
| WO | 2019045824 A1 | 3/2019 | | |
| WO | 2019097078 A1 | 5/2019 | | |
| WO | 2020023768 A1 | 1/2020 | | |
| WO | 2020035065 A1 | 2/2020 | | |
| WO | WO 2020/035065 * | 2/2020 | ........... | C07D 403/14 |
| WO | 2020045941 A1 | 3/2020 | | |
| WO | 2020055755 A1 | 3/2020 | | |
| WO | 2020055756 A1 | 3/2020 | | |
| WO | 2020055758 A1 | 3/2020 | | |
| WO | 2020055761 A1 | 3/2020 | | |
| WO | 2020118066 A1 | 6/2020 | | |
| WO | 2020127200 A1 | 6/2020 | | |
| WO | 2021064142 A1 | 4/2021 | | |
| WO | 2021194326 A1 | 9/2021 | | |

OTHER PUBLICATIONS

Gabizon et al., "Hitting KRAS When It's Down," Journal of Medicinal Chemistry, vol. 63 (Jul. 2020).
Hay et al, "Discovery and Optimization for Small-Molecule Ligands for CBP/p300 Bromodomains," Journal of the American Chemical Society, vol. 136, pp. 9308-9319, Jun. 19, 2014.
Leonnetti et al, "Resistance mechanisms to osimertinib in EGFR-mutated non-small cell lung cancer, " British Journal of Cancer, Mar. 5, 2019.
Li et al., "A potent CBP/p300-Snail interaction inhibitor suppresses tumor growth and metastasis in wild-type p53-expressing cancer," Science Advances, Research Article, vol. 6: 17 pages (2020).
Lockley et al, "Metal-catalysed hydrogen isotope exhange labeling: a brief overview," Journal of Labelled Componds and Radiopharmceuticals, vol. 53, Issue 11-12, pp. 635-644, Dec. 17, 2010.
Masters et al, "Spray Drying Handbook," K. Masters Longman Group Ltd, Harlow, Essex, 710 pp. Apr. 25, 2007.
Ogiwara et al., "Targeting p300 Addiction in CBP-Deficient Cancers Causes Synthetic Lethality by Apoptotic Cell Death due to Abrogation of MYC Expression," American Association for Cancer Research, 2015.
Picaud et al, "Generation of a Selective Small Molecule Inhibitor of the CBP/p300 Bromodomain for Leukemia Therapy," Therapeutics, Targets, And Chemical Biology, Cancer Research, 75 (23) pp. 5106-5119, 2015.
Romero et al, "Supporting Information GNE-781, A Highly Advanced Potent and Selective Bromodomain Inhibitor of Cyclic Adenosine Monophosphate Response Element Binding Protein, Binding Protein (CBP)," Genentech, Inc, 2017.
Springuel et al, "The importance of solvent selection for stoichimetrically diverse cocrystal systems: Caffeine/Maleic Acid 1:1 and 2:1 cocrystals," Universite Catholique de Louvain, IMCN, 2012.
Uprety et al., "KRAS: From undruggable to druggable Cancer Target," Cancer Treatment Reviews, vol. 89 (Jul. 2020).
Van Maldegem et al., "Mutant KRAS at the Heart of Tumor Immune Evasion," Immunity, vol. 52 (Jan. 2020).
Wang et al, "Clopidogrel with Aspirin in Acute Minor Stroke or Transient Ischemic Attack," The New England Journal of Medicine, Jul. 4, 2013.
Wang et al., "Expression of p300/CBP and Smad4 and its significance in non-small-cell lung cancer," Journal of Wannan Medical College, vol. 30, No. 6: 452-456 (2011).
Welti et al, "Targeting the p300/CBP Axis in Lethal Prostate Cancer," Cancer Discovery, vol. 11, Issue 5, May 1, 2021.
Zhang et al., "A Novel Histone Acetyltransferase Inhibitor A485 Improves Sensitivity of Non-Small-Cell Lung Carcinoma Cells to TRAIL," Biochemical Pharmacology, vol. 175: 10 pages (2020).
Zhang-Xu et al., "Current Development of CBP/300 inhibitors in the last decade," European Journal of Medicinal Chemistry, vol. 209: 2-11 (2020).
Zhong et al, "p300 Acetyltransferase Regulates Androgen Receptor Degradation and PTEN-Deficient Prostate Tumorigeneis," Tumor and Stem Cell Biology, Cancer Research, 74(6) Mar. 5, 2014.
Australian Office Action for Application No. 2020360709, dated Oct. 9, 2023.
International Search Report and Written Opinion corresponding to International Patent Application No. PCT/EP2019/085557, dated Apr. 14, 2020.
International Search Report and Written Opinion corresponding to International Patent Application No. PCT/EP2020/077595, dated Dec. 4, 2020.
International Search Report and Written Opinion of the International Searching Authority issued in International Application No. PCT/EP2021/067346, mailed Aug. 27, 2021, 12 pages.
International Search Report for Application No. PCT/EP2022/059295, dated May 30, 2022.
Japanese Office Action for Application No. 2022520681, dated Oct. 31, 2023.
Office Action corresponding to CA Application No. 3122354, dated Aug. 17, 2022.
Bai et al., "Application progress in pyrimidine compound," Shanxi Chemical Industry, Issue 1: 16-19 (Feb. 2009)—Abstract.
Elbadawy et al., "Emerging Roles of C-Myc in Cancer Stem Cell-Related Signaling and Resistance to Cancer Chemotherapy: A Potential Therapeutic Target Against Colorectal Cancer," International Journal of Molecular Sciences, vol. 20, No. 2340: 16 pages (2019).
Garcia-Carpizo et al., "CREBBP/EP300 bromodomains are critical to sustain the GATA1/MYC regulatory axis in proliferation," Epigenetics Chromatin, vol. 11, No. 30: 15 pages (2018).
Liu et al., "Idiopathic Pulmonary Fibrosis: Current Status, Recent Progress, and Emerging Targets," Journal of Medicinal Chemistry, vol. 60, Issue 2: 527-553 (2017)—Abstract.
Schleger et al., "c-MYC Activation in Primary and Metastatic Ductal Adenocarcinoma of the Pancreas: Incidence, Mechanisms, and Clinical Significance," Modern Pathology, vol. 15, No. 4: 462-469 (2002).
Zhuang et al., "Physiological Activity of Maillard Reaction Products (MRPs) and Technical Measures for Increasing their Production," Liquor-Making, vol. 36, No. 3: 80-83 (May 2009)—Abstract.
Chinese Office Action in CN Application 202180045103.8, dated Aug. 28, 2028, 7 pages.
Mullard, "Cracking KRAS," Nature Reviews Drug Discovery, vol. 18, No. 12: 887-891 (Nov. 2019).
Wu et al., "A chemical toolbox for the study of bromodomains and epigenetic signaling," Nature Communications, vol. 10, No. 1 (Apr. 2019).

(56) References Cited

OTHER PUBLICATIONS

European Office Action in EP Application 21733159.4 dated May 31, 2024, 12 pages.

* cited by examiner

HETEROCYCLIC DERIVATIVES, PHARMACEUTICAL COMPOSITIONS AND THEIR USE IN THE TREATMENT, AMELIORATION OR PREVENTION OF FIBROTIC DISEASE

CROSS-REFERENCE TO RELATED PATENT APPLICATIONS

This application is a national phase application of PCT International Patent Application No. PCT/EP2021/067347, filed Jun. 24, 2021, which claims the benefit of European Patent Application Serial No. EP20182379.6, filed Jun. 25, 2020; the disclosure of each of which is incorporated herein by reference in its entirety.

FIELD OF THE INVENTION

The present invention relates to a compound of formula (I), optionally in the form of a pharmaceutically acceptable salt, solvate, cocrystal, tautomer, racemate, enantiomer, or diastereomer or mixture thereof (I)

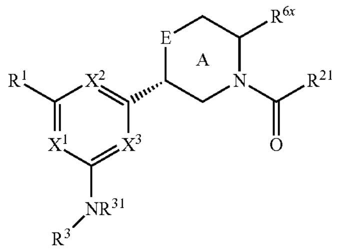

and to pharmaceutical compositions comprising a compound of formula (I), as well as to the use of a compound of formula (I), or a pharmaceutically acceptable salt, solvate, cocrystal, tautomer, racemate, enantiomer, or diastereomer or mixture thereof, in the treatment of fibrotic diseases, preferably idiopathic pulmonary fibrosis (IPF) or non-alcoholic steatohepatitis (NASH). Further aspects of the present invention include combination therapies in which a compound of formula (I), optionally in the form of a pharmaceutically acceptable salt, solvate, cocrystal, tautomer, racemate, enantiomer, or diastereomer or mixture thereof, is used in combination with known anti-fibrotic or anti-inflammatory agents for fibrotic diseases.

BACKGROUND OF THE INVENTION

Pulmonary fibrosis can be caused by a number of different conditions, including sarcoidosis, hypersensitivity pneumonitis, collagen vascular disease, and inhalant exposure. The diagnosis of these conditions can usually be made by careful history, physical examination, chest radiography, including a high resolution computer tomographic scan (HRCT), and open lung or transbronchial biopsies. However, in a significant number of patients, no underlying cause for the pulmonary fibrosis can be found. These conditions of unknown etiology have been termed idiopathic interstitial pneumonias. Histologic examination of tissue obtained at open lung biopsy allows classification of these patients into several categories, including Usual Interstitial Pneumonia (UIP), Desquamative Interstitial Pneumonia (DIP), and Non-Specific Interstitial Pneumonia (NSIP).

Idiopathic pulmonary fibrosis (IPF) is the most common form of idiopathic interstitial pneumonia and is characterized by the UIP pattern on histology. Idiopathic pulmonary fibrosis and other interstitial lung diseases (ILD) are severe conditions of progressive lung scarring with extracellular matrix deposition and lung matrix destruction leading to loss of lung function. IPF pathology is chronic and progressive. IPF is ultimately fatal with a median survival of 3.8 years. Anti-inflammatory, immunosuppressive therapies including corticosteroids have shown limited efficacy in treating IPF. Recommended pharmacologic treatment options for pulmonary fibrosis currently consist of the anti-fibrotic effects of Nintedanib and of Pirfenidone. Nintedanib acts as a multi receptor tyrosine kinase (RTK) inhibitor, blocking VEGF-, FGF- and PDGF-receptor signalling, thereby reducing fibroblast proliferation and differentiation. Pirfenidone interferes with TGF-β signalling thus reducing fibroblast proliferation and differentiation into myofibroblasts.

Both pharmacologic interventions at most achieve a prolongation of progression free survival or reduce the disease burden without a benefit on patient survival. An important unmet need is thus to identify new molecular targets and agents that interfere with key molecular pathways involved in pulmonary fibrosis pathology to prevent progression or reverse fibrosis in patients.

Hepatic steatosis, also sometimes referred to as fatty liver disease, is a condition generally characterized by an abnormal retention of lipids in cells of the liver. Fatty liver disease can have various causes. For example, non-alcoholic fatty liver disease (NAFLD) generally refers to a spectrum of hepatic lipid disorders characterized by hepatic steatosis with no known secondary cause. NAFLD can be subcategorized into (a) nonalcoholic fatty liver (NAFL), defined as the presence of steatosis in the absence of histological evidence of hepatocellular injury, and (b) non-alcoholic steatohepatitis (NASH), hepatic steatosis accompanied by hepatocyte injury and inflammation; NASH may occur with or without fibrosis, but may progress to fibrosis and cirrhosis. There are presently no approved pharmaceuticals for the treatment of NAFLD/NASH.

Thus, an objective of the present invention is to provide compounds which are able to treat fibrosis or to prevent the development of fibrosis. Furthermore, it is an objective of the present invention to provide improved treatment options for patients suffering from fibrotic disease, preferably idiopathic pulmonary fibrosis using the compounds of the invention alone or in combination therapy.

BRIEF SUMMARY OF THE INVENTION

The present invention provides methods of treating fibrotic disease preferrably idiopathic pulmonary fibrosis (IPF) or non-alcoholic steatohepatitis (NASH); methods of increasing survival time in an individual with fibrotic disease; and methods of reducing risk of death in an individual with fibrotic disease. The methods generally involve administering a therapeutically effective amount of compounds of the formula (I), optionally in the form of a pharmaceutically acceptable salt, solvate, cocrystal, tautomer, racemate, enantiomer, or diastereomer or mixture thereof, to an individual with fibrotic disease.

Thus, in a first aspect, the present invention provides a compound of formula (I), optionally in the form of a pharmaceutically acceptable salt, solvate, cocrystal, tautomer, racemate, enantiomer, or diastereomer or mixture thereof, for use in a method of treating fibrotic disease (I)

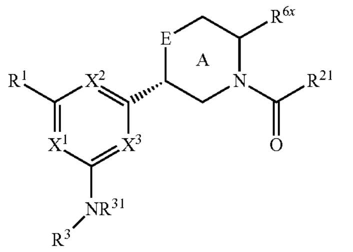

wherein $R^1$ is selected from halogen and -(optionally substituted hydrocarbon group which contains from 1 to 20 carbon atoms and optionally 1 to 15 heteroatoms selected from O, N and S);

$R^{21}$ is selected from hydrogen, -(optionally substituted $C_{1-6}$ alkyl) which may contain one to three oxygen atoms between carbon atoms, and -(optionally substituted $C_{3-6}$ cycloalkyl);

$R^3$ is selected from -(optionally substituted heterocyclyl), -(optionally substituted carbocyclyl), -(optionally substituted $C_{1-6}$ alkylene)-(optionally substituted heterocyclyl) and -(optionally substituted $C_{1-6}$ alkylene)-(optionally substituted carbocyclyl);

each of $X^1$, $X^2$ and $X^3$ is independently selected from N, CH and $CR^x$, wherein at least one of said $X^1$, $X^2$ and $X^3$ is N, wherein further preferably at least one of said $X^2$ and $X^3$ is N; and wherein again further preferably $X^2$ and $X^3$ are both N, and wherein still further preferably $X^2$ and $X^3$ are both N, and $X^1$ is CH;

$R^{31}$ is selected from -hydrogen, —$C_{1-6}$-alkyl, and —($C_{1-6}$-alkyl substituted with one or more F); wherein $R^3$ and any $R^{31}$ can be optionally linked; and E is either absent or is selected from —$CH_2$—, —$CHR^x$—, —$CR^x_2$—, —NH—, —$NR^x$—, —O—, -$L^1$-$L^2$- and -$L^2$-$L^1$-, wherein $L^1$ is selected from —$CH_2$—, —$CHR^x$—, —$CR^x_2$—, —NH—, —$NR^x$— and —O— and $L^2$ is selected from —$CH_2$—, —$CHR^x$— and —$CR^x_2$—;

$R^{6x}$ is -halogen, —OH, =O, $C_{1-6}$ alkyl, $C_{1-6}$ haloalkyl, $C_{1-6}$ alkyl substituted with one or more OH, monocyclic aryl optionally substituted with one or more $R^{xb}$, monocyclic heteroaryl optionally substituted with one or more $R^{xb}$, monocyclic cycloalkyl optionally substituted with one or more $R^{xb}$, monocyclic heterocycloalkyl optionally substituted with one or more $R^{xb}$, monocyclic cycloalkenyl optionally substituted with one or more $R^{xb}$, monocyclic heterocycloalkenyl optionally substituted with one or more $R^{xb}$, wherein said $R^{xb}$ is independently selected from -halogen, —OH, =O, $C_{1-4}$ alkyl, $C_{1-2}$ haloalkyl, $C_{1-2}$ alkyl substituted with one or two OH;

wherein Ring A may further be substituted with one or more groups $R^x$, wherein any two $R^x$ groups at ring A can be optionally linked and/or any $R^x$ group at ring A can be optionally linked with $R^{21}$; and/or wherein Ring A may be further substituted with one group $R^x$ so as to form together with $R^{6x}$ a bicyclic moiety having the following partial structure:

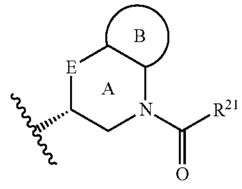

wherein Ring B is an -(optionally substituted heterocycle) or -(optionally substituted carbocycle); each $R^x$ is independently selected from -halogen, —OH, —O-(optionally substituted $C_{1-6}$ alkyl), —NH-(optionally substituted $C_{1-6}$ alkyl), —N(optionally substituted $C_{1-6}$ alkyl)$_2$, =O, -(optionally substituted $C_{1-6}$ alkyl), -(optionally substituted carbocyclyl), -(optionally substituted heterocyclyl), -(optionally substituted $C_{1-6}$ alkylene)-(optionally substituted carbocyclyl), -(optionally substituted $C_{1-6}$ alkylene)-(optionally substituted heterocyclyl), —O-(optionally substituted $C_{1-6}$ alkylene)-(optionally substituted carbocyclyl), and —O-(optionally substituted $C_{1-6}$ alkylene)-(optionally substituted heterocyclyl), and wherein the optional substituent of the optionally substituted hydrocarbon group, optionally substituted $C_{1-6}$ cycloalkyl, optionally substituted heterocyclyl, optionally substituted heterocycle, optionally substituted carbocyclyl, optionally substituted carbocycle and optionally substituted $C_{1-6}$ alkylene is independently selected from —($C_{1-6}$ alkyl which is optionally substituted with one or more halogen), -halogen, —CN, —$NO_2$, oxo, —C(O)R*, —COOR*, —C(O)NR*R*, —NR*R*, —N(R*)—C(O)R*, —N(R*)—C(O)—OR*, —N(R*)—C(O)—NR*R*, —N(R*)—$S(O)_2R$*, —OR*, —O—C(O)R*, —O—C(O)—NR*R*, —SR*, —S(O)R*, —$S(O)_2R$*, —$S(O)_2$—NR*R*, —N(R*)—$S(O)_2$—NR*R*, heterocyclyl which is optionally substituted with halogen or $C_{1-6}$ alkyl, and carbocyclyl which is optionally substituted with halogen or $C_{1-6}$ alkyl; wherein each R* is independently selected from H, $C_{1-6}$ alkyl which is optionally substituted with halogen, heterocyclyl which is optionally substituted with halogen or $C_{1-6}$ alkyl, and carbocyclyl which is optionally substituted with halogen or $C_{1-6}$ alkyl; wherein any two R* connected to the same nitrogen atom can be optionally linked, and wherein the optional substituent of the optionally substituted $C_{1-6}$ alkyl and of the optionally substituted $C_{1-6}$ alkylene is independently selected from -halogen, —CN, —$NO_2$, oxo, —C(O)R, —COOR, —C(O)NRR, —NRR, —N(R)—C(O)R, —N(R)—C(O)—OR, —N(R)—C(O)—NRR, —N(R)—$S(O)_2R$, —OR, —O—C(O)R, —O—C(O)—NRR, —SR, —S(O)R, —$S(O)_2$ R, —$S(O)_2$—NRR, and —N(R)—$S(O)_2$—NRR; wherein R is independently selected from H, $C_{1-6}$ alkyl which is optionally substituted with halogen, heterocyclyl which is optionally substituted with halogen or $C_{1-6}$ alkyl, and carbocyclyl which is optionally substituted with halogen or $C_{1-6}$ alkyl; wherein any two R** connected to the same nitrogen atom can be optionally linked.

In particular, the present invention provides a compound of formula (I), optionally in the form of a pharmaceutically acceptable salt, solvate, cocrystal, tautomer, racemate, enantiomer, or diastereomer or mixture thereof, for use in a method of treating fibrotic disease (I)

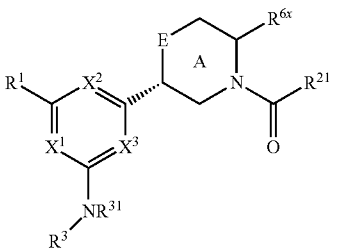

wherein $R^1$ is selected from halogen and optionally substituted hydrocarbon group which contains from 1 to 20 carbon atoms and optionally 1 to 15 heteroatoms selected from O, N and S;

$R^{21}$ is selected from hydrogen, optionally substituted $C_{1-6}$ alkyl which may contain one to three oxygen atoms between carbon atoms, and optionally substituted $C_{1-6}$ cycloalkyl;

$R^3$ is selected from optionally substituted heterocyclyl, optionally substituted carbocyclyl, optionally substituted $C_{1-6}$ alkylene-heterocyclyl, and optionally substituted $C_{1-6}$ alkylene-carbocyclyl);

each of $X^1$, $X^2$ and $X^3$ is independently selected from N, CH and $CR^X$, wherein at least one of said $X^1$, $X^2$ and $X^3$ is N;

$R^{31}$ is selected from hydrogen, $C_{1-6}$-alkyl, and $C_{1-6}$-alkyl substituted with one or more F; wherein $R^3$ and any $R^{31}$ can be optionally linked; and E is either absent or is selected from —$CH_2$—, —$CHR^x$—, —$CR^x_2$—, —NH—, —$NR^x$—, —O—, -$L^1$-$L^2$- and -$L^2$-$L^1$-, wherein $L^1$ is selected from —$CH_2$—, —$CHR^x$—, —$CR^x_2$—, —NH—, —$NR^x$— and —O— and $L^2$ is selected from —$CH_2$—, —$CHR^x$— and —$CR^x_2$—;

$R^{6x}$ is halogen, OH, =O, $C_{1-6}$ alkyl, $C_{1-6}$ haloalkyl, $C_{1-6}$ alkyl substituted with one or more OH, monocyclic aryl optionally substituted with one or more $R^{xb}$, monocyclic heteroaryl optionally substituted with one or more $R^{xb}$, monocyclic cycloalkyl optionally substituted with one or more $R^{xb}$, monocyclic heterocycloalkyl optionally substituted with one or more $R^{xb}$, monocyclic cycloalkenyl optionally substituted with one or more $R^{xb}$, monocyclic heterocycloalkenyl optionally substituted with one or more $R^{xb}$, wherein said $R^{xb}$ is independently selected from halogen, OH, =O, $C_{1-4}$ alkyl, $C_{1-2}$ haloalkyl, $C_{1-2}$ alkyl substituted with one or two OH;

wherein Ring A may further be substituted with one or more groups $R^x$, wherein any two $R^x$ groups at ring A can be optionally linked and/or any $R^x$ group at ring A can be optionally linked with $R^{21}$; and/or wherein Ring A may be further substituted with one group $R^x$ so as to form together with $R^{6x}$ a bicyclic moiety having the following partial structure:

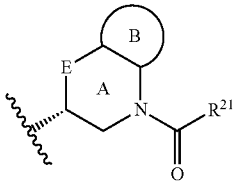

wherein Ring B is an optionally substituted heterocycle or optionally substituted carbocycle; each $R^x$ is independently selected from halogen, OH, optionally substituted O—$C_{1-6}$ alkyl, optionally substituted NH—$C_{1-6}$ alkyl), optionally substituted N($C_{1-6}$ alkyl)$_2$, =O, optionally substituted $C_{1-6}$ alkyl, optionally substituted carbocyclyl, optionally substituted heterocyclyl, optionally substituted $C_{1-6}$ alkylene-carbocyclyl), optionally substituted $C_{1-6}$ alkylene-heterocyclyl), optionally substituted O—$C_{1-6}$ alkylene-carbocyclyl, and optionally substituted O—$C_{1-6}$ alkylene-heterocyclyl, and wherein the optional substituent of the optionally substituted hydrocarbon group, optionally substituted $C_{3-6}$ cycloalkyl, optionally substituted heterocyclyl, optionally substituted heterocycle, optionally substituted carbocyclyl, optionally substituted carbocycle and optionally substituted $C_{1-6}$ alkylene is independently selected from $C_{1-6}$ alkyl which is optionally substituted with one or more halogen, halogen, CN, $NO_2$, oxo, —C(O)R*, —COOR*, —C(O)NR*R*, —NR*R*, —N(R*)—C(O)R*, —N(R*)—C(O)—OR*, —N(R*)—C(O)—NR*R*, —N(R*)—S(O)$_2$R*, —OR*, —O—C(O)R*, —O—C(O)—NR*R*, —SR*, —S(O)R*, —S(O)$_2$R*, —S(O)$_2$—NR*R*, —N(R*)—S(O)$_2$—NR*R*, heterocyclyl which is optionally substituted with halogen or $C_{1-6}$ alkyl, and carbocyclyl which is optionally substituted with halogen or $C_{1-6}$ alkyl; wherein each R* is independently selected from H, $C_{1-6}$ alkyl which is optionally substituted with halogen, heterocyclyl which is optionally substituted with halogen or $C_{1-6}$ alkyl, and carbocyclyl which is optionally substituted with halogen or $C_{1-6}$ alkyl; wherein any two R* connected to the same nitrogen atom can be optionally linked, and wherein the optional substituent of the optionally substituted $C_{1-6}$ alkyl and of the optionally substituted $C_{1-6}$ alkylene is independently selected from -halogen, —CN, —$NO_2$, oxo, —C(O)R, —COOR, —C(O)NRR, —NRR, —N(R)—C(O)R, —N(R)—C(O)—OR, —N(R)—C(O)—NRR, —N(R)—S(O)$_2$R, —OR, —O—C(O)R, —O—C(O)—NRR, —SR, —S(O)R, —S(O)$_2$R, —S(O)$_2$—NRR, and —N(R)—S(O)$_2$—NRR; wherein R is independently selected from H, $C_{1-6}$ alkyl which is optionally substituted with halogen, heterocyclyl which is optionally substituted with halogen or $C_{1-6}$ alkyl, and carbocyclyl which is optionally substituted with halogen or $C_{1-6}$ alkyl; wherein any two R** connected to the same nitrogen atom can be optionally linked.

In a preferred embodiment of the invention, the compound of formula (I) is a compound of formula (V)

(V)

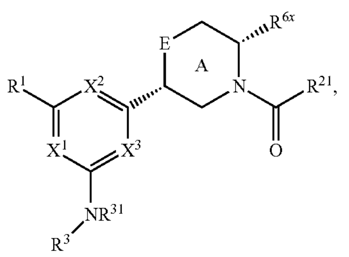

In a more preferred embodiment of the invention, the compound of formula (I) is a compound of formula (VI)

(VI)

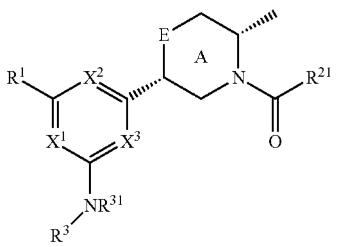

In another preferred embodiment of the invention, $X^2$ and $X^3$ are N, and wherein preferably $X^1$ is CH.

In another preferred embodiment of the invention, $R^{21}$ is $CH_3$ or $CH_2CH_3$, and wherein preferably $R^{21}$ is $CH_3$.

In another preferred embodiment of the invention, $R^{31}$ is selected from hydrogen and $C_{1-2}$-alkyl, and wherein preferably $R^{31}$ is hydrogen.

In another preferred embodiment of the invention, E is selected from —$CH_2$—, —O—, —$CH_2$—O— and —$CH_2$—$CH_2$—, and wherein preferably E is —$CH_2$—.

In another preferred embodiment of the invention, the number of groups $R^x$ in Ring A is 0, 1, or 2, and wherein preferably each $R^x$ is independently selected from halogen, OH, O—$C_{1-2}$ alkyl optionally substituted with one or more $R^{xa}$, NH—$C_{1-2}$ alkyl optionally substituted with one or more $R^{xa}$, N($C_{1-2}$ alkyl)$_2$ optionally substituted with one or more $R^{xa}$, =O, $C_{1-3}$alkyl optionally substituted with one or more $R^{xa}$, $C_{1-2}$ haloalkyl, —W-monocyclic carbocyclyl optionally substituted with one or more $R^{xa}$, —W-monocyclic heterocyclyl optionally substituted with one or more $R^{xa}$, and wherein —W— is absent, —$C_{1-2}$ alkylene- or —O—$C_{1-2}$ alkylene-, and wherein monocyclic carbocyclyl is selected from phenyl and $C_{3-6}$ cycloalkyl, and wherein monocyclic heterocyclyl is selected from thiophenyl, pyridyl, pyrazinyl and pyrimidinyl, and wherein said $R^{xa}$ is independently selected from Cl, F, and OH.

In another preferred embodiment of the invention, $R^1$ is selected from optionally substituted heterocyclyl and optionally substituted carbocyclyl, and wherein preferably $R^1$ is selected from phenyl, a 5- or 6-membered monocyclic heteroaryl and a 8-10 membered bicyclic heteroaryl, each independently comprising one or more ring heteroatoms independently selected from 0, S and N, wherein one or two carbon ring atoms of said monocyclic or said bicyclic heteroaryl are optionally oxidized, and wherein said phenyl, said 5- or 6-membered monocyclic heteroaryl and said 8-10 membered bicyclic heteroaryl is independently optionally substituted with one or more, substituents selected from halogen, $C_{1-6}$ alkyl, $C_{1-6}$ haloalkyl, —O—$C_{1-6}$ alkyl, —O—$C_{1-6}$ haloalkyl, OH, CN, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 3-6 membered monocyclic carbocyclyl and 3-6 membered monocyclic heterocyclyl comprising 1 to 4 heteroatoms selected from 0, S and N, each monocyclic carbocyclyl and heterocyclyl independently optionally substituted with one or more substituents independently selected from halogen, $C_{1-4}$ alkyl, $C_{1-4}$ haloalkyl, —O—$C_{1-4}$ alkyl, —O—$C_{1-4}$ haloalkyl, —OH, =O, —C(O)R* and —C(O)NR*R*; wherein each R* is independently selected from H, $C_{1-4}$ alkyl, $C_{1-4}$ haloalkyl and/or wherein each monocyclic heterocyclyl is independently optionally substituted with one bivalent substituent selected from $C_{1-3}$alkylene, $C_{1-3}$alkylene substituted with 1 to 4 F, —$CH_2$—O—$CH_2$— and —$CH_2$—NH—$CH_2$—.

In another preferred embodiment of the invention, $R^3$ is selected from phenyl, a 6-membered monocyclic heteroaryl and a 8-10 membered bicyclic heteroaryl, each independently comprising one or more ring heteroatoms independently selected from O, B, S and N, wherein one or two carbon ring atoms of said monocyclic or said bicyclic heteroaryl are optionally oxidized, and wherein said phenyl, said 6-membered monocyclic heteroaryl and said 8-10 membered bicyclic heteroaryl is independently optionally substituted with one or more substituents selected from halogen, $C_{1-6}$ alkyl, $C_{1-6}$ haloalkyl, —O—$C_{1-6}$ alkyl, —O—$C_{1-6}$ haloalkyl, —OH, —CN, =O, —C(O)R*, —COOR*, —C(O)NR*R*, —NR*R*, —N(R**)—C(O)R*, —N(R**)—C(O)—OR*, —N(R**)—C(O)—NR*R*, —O—C(O)R*, —O—C(O)—NR*R*, and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more substituents independently selected from halogen, cyclopropyl, —$C_{1-4}$ alkyl, $C_{1-4}$ haloalkyl, —O—$C_{1-4}$ alkyl, —O—$C_{1-4}$ haloalkyl, —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl, cyclopropyl, cyclobutyl, oxetanyl, —$C_{1-2}$alkylene-OH, —$C_{1-2}$alkylene-O—$C_{1-2}$alkyl, phenyl, and wherein each R** is independently selected from H, $C_{1-4}$ alkyl, $C_{1-4}$ haloalkyl, and/or wherein each monocyclic heterocyclyl is independently optionally substituted with one bivalent substituent selected from $C_{1-3}$alkylene such as —$CH_2$—$CH_2$— and —$CH_2$—$CH_2$—$CH_2$—, $C_{1-3}$alkylene substituted with 1 to 4 F, —$CH_2$—O—$CH_2$— and —$CH_2$—NH—$CH_2$—.

In another preferred embodiment of the invention, $X^2$ and $X^3$ are N, and $X^1$ is CH;

E is —$CH_2$—;

$R^{21}$ is $CH_3$;

$R^{6x}$ is $CH_3$; and

Ring A does not form a bicyclic moiety.

In another preferred embodiment of the invention, the fibrotic disease is selected from the group consisting of pulmonary fibrosis, idiopathic pulmonary fibrosis, radiation-induced pneumonitis, radiation fibrosis, acute respiratory distress syndrome, chronic obstructive pulmonary disease, interstitial lung disease, myocardial infarction, cardiac fibrosis and hypertrophy, ischemic stroke, ischemic kidney disease, renal fibrosis, rheumatoid arthritis, liver fibrosis, NASH (non-alcoholic steatohepatitis), chronic hepatitis, cirrhosis, inflammatory bowel disease, Crohn's disease, scleroderma, keloid, post-operative fibrosis, chemotherapy induced fibrosis (e.g., chemotherapy induced pulmonary fibrosis or ovarian cortical fibrosis), nephrogenic systemic fibrosis, retroperitoneal fibrosis, myelofibrosis, mediastinal fibrosis, cystic fibrosis, asbestosis, asthma, pulmonary hypertension, systemic fibrosis, skin fibrosis, hypertension induced renal and cardiac fibrosis.

In another preferred embodiment of the invention, the fibrotic disease is interstitial lung disease (IDL), optionally the interstitial lung disease is idiopathic interstitial pneumonia (IIP).

In a more preferred embodiment of the invention, the idiopathic interstitial pneumonia is selected from the group consisting of chronic fibrosing interstitial pneumonia, smoking-related interstitial pneumonia and acute/subacute interstitial pneumonia.

In another more preferred embodiment of the invention, the chronic fibrosing interstitial pneumonia is idiopathic pulmonary fibrosis (IPF).

In another preferred embodiment of the invention, the fibrotic disease is non-hepatic steatohepatitis (NASH).

Further aspects and embodiments of the present invention will be become apparent as this description continues.

DETAILED DESCRIPTION OF THE INVENTION

Figure 1:
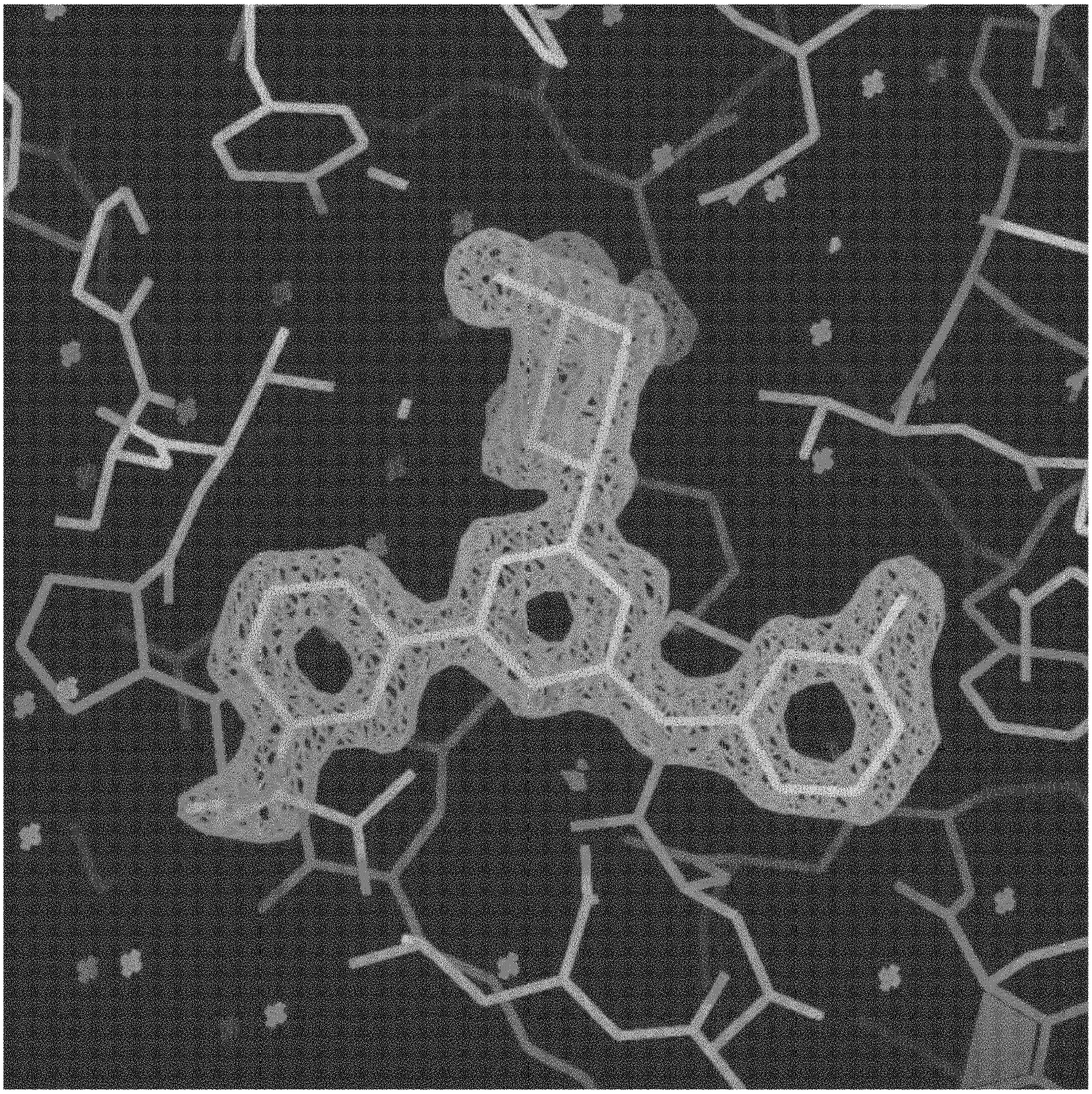
FIG. 1. The initial Fo-Fc difference electron density map of the model (contoured at 4.0 σ) resulting from refinement of the initial model prior to modelling of the compound with REFMAC5, in the determination of the crystal structure of the bromodomain of human CREBBP in complex with compound 00004.

Unless defined otherwise, all technical and scientific terms used herein have the same meanings as commonly understood by one of ordinary skill in the art to which this invention belongs. The herein described and disclosed embodiments, preferred embodiments and very preferred embodiments should apply to all aspects and other embodiments, preferred embodiments and very preferred embodiments irrespective of whether is specifically again referred to or its repetition is avoided for the sake of conciseness.

The articles "a" and "an", as used herein, refer to one or to more than one (i.e., to at least one) of the grammatical object of the article. The term "or", as used herein, should be understood to mean "and/or", unless the context clearly indicates otherwise.

The term "preferably" is used to describe features or embodiments which are not required in the present invention but may lead to improved technical effects and are thus desirable but not essential.

The term "linked" in the expression "optionally linked" as used herein refers to a linked group which is obtained from two substituents by theoretically abstracting one hydrogen radical from each substituent and forming a single bond between the two radicals thus formed in the two substituents. This may be illustrated as follows:

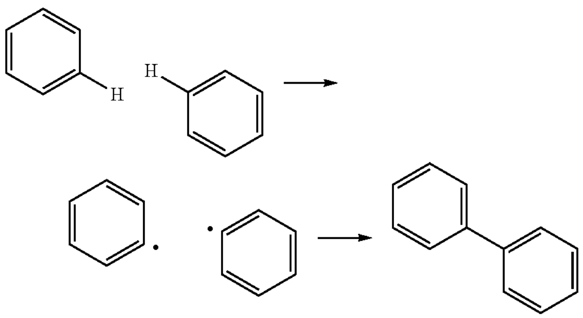

Although this explanation uses two aryl groups as an illustration, the meaning of the term "linked" is obviously not limited to such groups.

The term "hydrocarbon group which contains from 1 to 20 carbon atoms and optionally 1 to 15 heteroatoms selected from O, N and S" refers to any group having 1 to 20 carbon atoms and optionally 1 to 15 (preferably 1 to 10, more preferably 1 to 8) heteroatoms selected from O, N and S which preferably contains at least one ring. The "hydrocarbon group which contains from 1 to 20 carbon atoms and optionally 1 to 15 heteroatoms selected from O, N and S" is not limited in any way, provided that it is a group containing 1 to 20 carbon atoms and optionally 1 to 15 heteroatoms selected from O, N and S. E.g., if the hydrocarbon group is an aliphatic group, it may include one or more of the heteroatoms in the main chain or in one or more side chains. The term is also meant to include bicyclic, tricyclic and polycyclic versions thereof. If more than one ring is present, they can be separate from each other or be annelated. Examples of bicyclic hydrocarbon groups include fused bicyclic hydrocarbon groups such as naphthalene as well as linked hydrocarbon groups such as biphenyl, bridged bicyclic hydrocarbon groups such as 1,4-diazabicyclo[2.2.2]octane and spiro-type hydrogen groups. The ring(s) can be either carbocyclic or heterocyclic and can be saturated, unsaturated or aromatic. The carbon atoms and heteroatoms can either all be present in the one or more rings or some of the carbon atoms and/or heteroatoms can be present outside of the ring, e.g., in a linker group (such as $—(CH_2)_p—$ with p=1 to 6). Examples of these groups include -(optionally substituted heterocyclyl) and -(optionally substituted carbocyclyl).

As used herein, the term "-(optionally substituted $C_{1-6}$ alkyl) which may contain one to three oxygen atoms between carbon atoms" preferably refers to a group in which one or more direct C—C bonds in the $C_{1-6}$ alkyl group are replaced by a C—O—C moiety. Examples thereof are $—CH_2—CH_2—O—CH_3$, $—CH_2—CH_2—O—CH_2—CH_3$, $—CH_2—CH_2—O—CH_2—CH_2—O—CH_3$ and $—CH_2—CH_2—O—CH_2—CH_2—O—CH_2—CH_3$.

As used herein, the term "alkyl" refers to a monovalent saturated acyclic (i.e., non-cyclic) hydrocarbon group which may be linear or branched. Accordingly, an "alkyl" group does not comprise any carbon-to-carbon double bond or any carbon-to-carbon triple bond. A "$C_{1-6}$ alkyl" denotes an alkyl group having 1 to 6 carbon atoms. Preferred exemplary alkyl groups are methyl, ethyl, propyl (e.g., n-propyl or isopropyl), or butyl (e.g., n-butyl, isobutyl, sec-butyl, or tert-butyl). Unless defined otherwise, the term "alkyl" preferably refers to $C_{1-4}$ alkyl, more preferably to methyl or ethyl, and even more preferably to methyl.

As used herein, the term "alkylene" refers to an alkanediyl group, i.e. a divalent saturated acyclic hydrocarbon group which may be linear or branched. A "$C_{1-6}$ alkylene" denotes an alkylene group having 1 to 6 carbon atoms, and the term "$C_{0-3}$ alkylene" indicates that a covalent bond (corresponding to the option "$C_0$ alkylene") or a $C_{1-3}$ alkylene is present. Preferred exemplary alkylene groups are methylene ($-CH_2-$), ethylene (e.g., $-CH_2-CH_2-$ or $-CH(-CH_3)-$), propylene (e.g., $-CH_2-CH_2-CH_2-$, $-CH(-CH_2-CH_3)-$, $-CH_2-CH(-CH_3)-$, or $-CH(-CH_3)-CH_2-$), or butylene (e.g., $-CH_2-CH_2-CH_2-CH_2-$). Unless defined otherwise, the term "alkylene" preferably refers to $C_{1-4}$ alkylene (including, in particular, linear $C_{1-4}$ alkylene), more preferably to methylene or ethylene, and even more preferably to methylene.

As used herein, the term "carbocyclyl" refers to a hydrocarbon ring group, including monocyclic rings as well as bridged ring, spiro ring and/or fused ring systems (which may be composed, e.g., of two or three rings), wherein said ring group may be saturated, partially unsaturated (i.e., unsaturated but not aromatic) or aromatic. Unless defined otherwise, "carbocyclyl" preferably refers to aryl, cycloalkyl or cycloalkenyl. The number of carbon atoms in the carbocyclyl group is not particularly limited and is preferably 3 to 14, more preferably 3 to 7.

As used herein, the term "heterocyclyl" refers to a ring group, including monocyclic rings as well as bridged ring, spiro ring and/or fused ring systems (which may be composed, e.g., of two or three rings), wherein said ring group comprises one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, wherein one or more carbon ring atoms may optionally be oxidized (i.e., to form an oxo group), and further wherein said ring group may be saturated, partially unsaturated (i.e., unsaturated but not aromatic) or aromatic. Unless defined otherwise, "heterocyclyl" preferably refers to heteroaryl, heterocycloalkyl or heterocycloalkenyl. The number of carbon atoms in the carbocyclyl group is not particularly limited and is preferably 5 to 14, preferably 5 to 10.

As used herein, the term "aryl" refers to an aromatic hydrocarbon ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic). "Aryl" may, e.g., refer to phenyl, naphthyl, dialinyl (i.e., 1,2-dihydronaphthyl), tetralinyl (i.e., 1,2,3,4-tetrahydronaphthyl), anthracenyl, or phenanthrenyl. Unless defined otherwise, an "aryl" preferably has 5 to 14 ring atoms, more preferably 5 to 10 ring atoms, and most preferably refers to phenyl.

As used herein, the term "heteroaryl" refers to an aromatic ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic), wherein said aromatic ring group comprises one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). "Heteroaryl" may, e.g., refer to thienyl (i.e., thiophenyl), benzo[b]thienyl, naphtho[2,3-b]thienyl, thianthrenyl, furyl (i.e., furanyl), benzofuranyl, isobenzofuranyl, chromenyl, xanthenyl, phenoxathiinyl, pyrrolyl (e.g., 2H-pyrrolyl), imidazolyl, pyrazolyl, pyridyl (i.e., pyridinyl; e.g., 2-pyridyl, 3-pyridyl, or 4-pyridyl), pyrazinyl, pyrimidinyl, pyridazinyl, indolizinyl, isoindolyl, indolyl (e.g., 3H-indolyl), indazolyl, purinyl, isoquinolyl, quinolyl, phthalazinyl, naphthyridinyl, quinoxalinyl, cinnolinyl, pteridinyl, carbazolyl, beta-carbolinyl, phenanthridinyl, acridinyl, perimidinyl, phenanthrolinyl (e.g., [1,10]phenanthrolinyl, [1,7]phenanthrolinyl, or [4,7]phenanthrolinyl), phenazinyl, thiazolyl, isothiazolyl, phenothiazinyl, oxazolyl, isoxazolyl, furazanyl, phenoxazinyl, pyrazolo[1,5-a]pyrimidinyl (e.g., pyrazolo[1,5-a]pyrimidin-3-yl), 1,2-benzoisoxazol-3-yl, benzothiazolyl, benzoxazolyl, benzisoxazolyl, benzimidazolyl, 1H-tetrazolyl, 2H-tetrazolyl, coumarinyl, or chromonyl. Unless defined otherwise, a "heteroaryl" preferably refers to a 5 to 14 membered (more preferably 5 to 10 membered) monocyclic ring or fused ring system comprising one or more (e.g., one, two, three or four) ring heteroatoms independently selected from O, S and N, wherein one or more S ring atoms (if present) and/or one or more N ring atoms (if present) are optionally oxidized, and wherein one or more carbon ring atoms are optionally oxidized; even more preferably, a "heteroaryl" refers to a 5 or 6 membered monocyclic ring comprising one or more (e.g., one, two or three) ring heteroatoms independently selected from O, S and N, wherein one or more S ring atoms (if present) and/or one or more N ring atoms (if present) are optionally oxidized, and wherein one or more carbon ring atoms are optionally oxidized.

As used herein, the term "cycloalkyl" refers to a saturated hydrocarbon ring group, including monocyclic rings as well as bridged ring, spiro ring and/or fused ring systems (which may be composed, e.g., of two or three rings; such as, e.g., a fused ring system composed of two or three fused rings). "Cycloalkyl" may, e.g., refer to cyclopropyl, cyclobutyl, cyclopentyl, cyclohexyl, cycloheptyl, or adamantyl. Unless defined otherwise, "cycloalkyl" preferably refers to a $C_{3-14}$ cycloalkyl, and more preferably refers to a $C_{3-7}$ cycloalkyl. A particularly preferred "cycloalkyl" is a monocyclic saturated hydrocarbon ring having 3 to 7 ring members.

As used herein, the term "heterocycloalkyl" refers to a saturated ring group, including monocyclic rings as well as bridged ring, spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). "Heterocycloalkyl" may, e.g., refer to oxetanyl, tetrahydrofuranyl, piperidinyl, piperazinyl, aziridinyl, azetidinyl, pyrrolidinyl, imidazolidinyl, morpholinyl (e.g., morpholin-4-yl), pyrazolidinyl, tetrahydrothienyl, octahydroquinolinyl, octahydroisoquinolinyl, oxazolidinyl, isoxazolidinyl, azepanyl, diazepanyl, oxazepanyl or 2-oxa-5-aza-bicyclo[2.2.1]hept-5-yl. Unless defined otherwise, "heterocycloalkyl" preferably refers to a 3 to 14 membered saturated ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, and wherein one or more carbon ring atoms are optionally oxidized; more preferably, "heterocycloalkyl" refers to a 5 to 7 membered saturated monocyclic ring group containing one or more (e.g., one, two, or three) ring heteroatoms independently selected from O, S and N, wherein one or more S ring atoms (if present) and/or one or more N ring atoms (if present) are optionally oxidized, and wherein one or more carbon ring atoms are optionally oxidized.

As used herein, the term "cycloalkenyl" refers to an unsaturated alicyclic (non-aromatic) hydrocarbon ring group, including monocyclic rings as well as bridged ring, spiro ring and/or fused ring systems (which may be composed, e.g., of two or three rings; such as, e.g., a fused ring system composed of two or three fused rings), wherein said hydrocarbon ring group comprises one or more (e.g., one or two) carbon-to-carbon double bonds and does not comprise any carbon-to-carbon triple bond. "Cycloalkenyl" may, e.g., refer to cyclopropenyl, cyclobutenyl, cyclopentenyl, cyclohexenyl, cyclohexadienyl, cycloheptenyl, or cycloheptadienyl. Unless defined otherwise, "cycloalkenyl" preferably refers to a $C_{3-14}$ cycloalkenyl, and more preferably refers to a $C_{3-7}$ cycloalkenyl. A particularly preferred "cycloalkenyl" is a monocyclic unsaturated alicyclic hydrocarbon ring having 3 to 7 ring members and containing one or more (e.g., one or two; preferably one) carbon-to-carbon double bonds.

As used herein, the term "heterocycloalkenyl" refers to an unsaturated alicyclic (non-aromatic) ring group, including monocyclic rings as well as bridged ring, spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from O, S and N, and the remaining ring atoms and carbon atoms, wherein one or more S ring atoms (if present) and/or one or more N ring atoms (if present) may optionally be oxidized, wherein one or more carbon ring atoms may optionally be oxidized (i.e., to form an oxo group), and further wherein said ring group comprises at least one double bond between adjacent ring atoms and does not comprise any triple bond between adjacent ring atoms. "Heterocycloalkenyl" may, e.g., refer to 1,2,3,6-tetrahydropyridinyl. Unless defined otherwise, "heterocycloalkenyl" preferably refers to a 3 to 14 membered unsaturated alicyclic ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, wherein one or more carbon ring atoms are optionally oxidized, and wherein said ring group comprises at least one double bond between adjacent ring atoms and does not comprise any triple bond between adjacent ring atoms; more preferably, "heterocycloalkenyl" refers to a 5 to 7 membered monocyclic unsaturated non-aromatic ring group containing one or more (e.g., one, two, or three) ring heteroatoms independently selected from O, S and N, wherein one or more S ring atoms (if present) and/or one or more N ring atoms (if present) are optionally oxidized, wherein one or more carbon ring atoms are optionally oxidized, and wherein said ring group comprises at least one double bond between adjacent ring atoms and does not comprise any triple bond between adjacent ring atoms.

As used herein, the term "halogen" refers to fluoro (—F), chloro (—Cl), bromo (—Br), or iodo (—I).

As used herein, the term "haloalkyl" refers to an alkyl group substituted with one or more (preferably 1 to 6, more preferably 1 to 3) halogen atoms which are selected independently from fluoro, chloro, bromo and iodo, and are preferably all fluoro atoms. It will be understood that the maximum number of halogen atoms is limited by the number of available attachment sites and, thus, depends on the number of carbon atoms comprised in the alkyl moiety of the haloalkyl group. "Haloalkyl" may, e.g., refer to $—CF_3$, $—CHF_2$, $—CH_2F$, $—CF_2—CH_3$, $—CH_2—CF_3$, $—CH_2—CHF_2$, $—CH_2—CF_2—CH_3$, $—CH_2—CF_2—CF_3$, or $—CH(CF_3)_2$. Very preferred "haloalkyl" as substituents for the inventive compounds are $—CF_3$, $—CHF_2$, and $—CH_2—CF_3$, and again further preferred are $—CF_3$ and $—CHF_2$.

Various groups are referred to as being "optionally substituted" in this specification. Generally, these groups may carry one or more substituents, such as, e.g., one, two, three or four substituents. It will be understood that the maximum number of substituents is limited by the number of attachment sites available on the substituted moiety. Unless defined otherwise, the "optionally substituted" groups referred to in this specification carry preferably not more than two substituents and may, in particular, carry only one substituent. Moreover, unless defined otherwise, it is preferred that the optional substituents are absent, i.e. that the corresponding groups are unsubstituted.

As used herein, the terms "optional", "optionally" and "may" denote that the indicated feature may be present but can also be absent. Whenever the term "optional", "optionally" or "may" is used, the present invention specifically relates to both possibilities, i.e., that the corresponding feature is present or, alternatively, that the corresponding feature is absent. For example, the expression "X is optionally substituted with Y" (or "X may be substituted with Y") means that X is either substituted with Y or is unsubstituted. Likewise, if a component of a composition is indicated to be "optional", the invention specifically relates to both possibilities, i.e., that the corresponding component is present (contained in the composition) or that the corresponding component is absent from the composition.

A skilled person will appreciate that the substituent groups comprised in the compounds of formula (I) may be attached to the remainder of the respective compound via a number of different positions of the corresponding specific substituent group. Unless defined otherwise, the preferred attachment positions for the various specific substituent groups are as illustrated in the examples.

As used herein, the term "about" preferably refers to ±10% of the indicated numerical value, more preferably to ±5% of the indicated numerical value, and in particular to the exact numerical value indicated.

The scope of the invention embraces all pharmaceutically acceptable salt forms of the compounds of formula (I) which may be formed, e.g., by protonation of an atom carrying an electron lone pair which is susceptible to protonation, such as an amino group, with an inorganic or organic acid, or as a salt of an acid group (such as a carboxylic acid group) with a physiologically acceptable cation. Exemplary base addition salts comprise, for example: alkali metal salts such as sodium or potassium salts; alkaline earth metal salts such as calcium or magnesium salts; zinc salts; ammonium salts;

aliphatic amine salts such as trimethylamine, triethylamine, dicyclohexylamine, ethanolamine, diethanolamine, triethanolamine, procaine salts, meglumine salts, ethylenediamine salts, or choline salts; aralkyl amine salts such as N,N-dibenzylethylenediamine salts, benzathine salts, benethamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts, lysine salts, or histidine salts. Exemplary acid addition salts comprise, for example: mineral acid salts such as hydrochloride, hydrobromide, hydroiodide, sulfate salts (such as, e.g., sulfate or hydrogensulfate salts), nitrate salts, phosphate salts (such as, e.g., phosphate, hydrogenphosphate, or dihydrogenphosphate salts), carbonate salts, hydrogencarbonate salts, perchlorate salts, borate salts, orthiocyanate salts; organic acid salts such as acetate, propionate, butyrate, pentanoate, hexanoate, heptanoate, octanoate, cyclopentanepropionate, decanoate, undecanoate, oleate, stearate, lactate, maleate, oxalate, fumarate, tartrate, malate, citrate, succinate, adipate, gluconate, glycolate, nicotinate, benzoate, salicylate, ascorbate, pamoate (embonate), camphorate, glucoheptanoate, or pivalate salts; sulfonate salts such as methanesulfonate (mesylate), ethanesulfonate (esylate), 2-hydroxyethanesulfonate (isethionate), benzenesulfonate (besylate), p-toluenesulfonate (tosylate), 2-naphthalenesulfonate (napsylate), 3-phenylsulfonate, or camphorsulfonate salts; glycerophosphate salts; and acidic amino acid salts such as aspartate or glutamate salts. Preferred pharmaceutically acceptable salts of the compounds of formula (I) include a hydrochloride salt, a hydrobromide salt, a mesylate salt, a sulfate salt, a tartrate salt, a fumarate salt, an acetate salt, a citrate salt, and a phosphate salt. A particularly preferred pharmaceutically acceptable salt of the compound of formula (I) is a hydrochloride salt. Accordingly, it is preferred that the compound of formula (I), including any one of the specific compounds of formula (I) described herein, is in the form of a hydrochloride salt, a hydrobromide salt, a mesylate salt, a sulfate salt, a tartrate salt, a fumarate salt, an acetate salt, a citrate salt, or a phosphate salt, and it is particularly preferred that the compound of formula (I) is in the form of a hydrochloride salt.

A "solvate" refers to an association or complex of one or more solvent molecules and the compound of formula (I). Examples of solvents that form solvates include, but are not limited to, water, isopropanol, ethanol, methanol, dimethyl sulfoxide (DMSO), ethyl acetate, acetic acid, acetonitril, and ethanolamine. The term "hydrate" refers to the complex where the solvent molecule is water. It is to be understood that such solvates of the compounds of the formula (I) also include solvates of pharmaceutically acceptable salts of the compounds of the formula (I).

A "cocrystal" refers to a crystalline structure that contains at least two different compounds that are solid in their pure form under ambient conditions. Cocrystals are made from neutral molecular species, and all species remain neutral after crystallization; further, typically and preferably, they are crystalline homogeneous phase materials where two or more building compounds are present in a defined stoichiometric ratio. See hereto Wang Y and Chen A, 2013; and Springuel G R, et al., 2012; and U.S. Pat. No. 6,570,036.

Furthermore, the compounds of formula (I) may exist in the form of different isomers, in particular stereoisomers (including, e.g., geometric isomers (or cis/trans isomers), enantiomers and diastereomers) or tautomers. All such isomers of the compounds of formula (I) are contemplated as being part of the present invention, either in admixture or in pure or substantially pure form. As for stereoisomers, the invention embraces the isolated optical isomers of the compounds according to the invention as well as any mixtures thereof (including, in particular, racemic mixtures/racemates). The racemates can be resolved by physical methods, such as, e.g., fractional crystallization, separation or crystallization of diastereomeric derivatives, or separation by chiral column chromatography. The individual optical isomers can also be obtained from the racemates via salt formation with an optically active acid followed by crystallization. The present invention further encompasses any tautomers of the compounds provided herein.

The scope of the invention also embraces compounds of formula (I), in which one or more atoms are replaced by a specific isotope of the corresponding atom. For example, the invention encompasses compounds of formula (I), in which one or more hydrogen atoms (or, e.g., all hydrogen atoms) are replaced by deuterium atoms (i.e., $^{2}H$; also referred to as "D"). Accordingly, the invention also embraces compounds of formula (I) which are enriched in deuterium. Naturally occurring hydrogen is an isotopic mixture comprising about 99.98 mol-% hydrogen-1 ($^{1}H$) and about 0.0156 mol-% deuterium ($^{2}H$ or D). The content of deuterium in one or more hydrogen positions in the compounds of formula (I) can be increased using deuteration techniques known in the art. For example, a compound of formula (I) or a reactant or precursor to be used in the synthesis of the compound of formula (I) can be subjected to an H/D exchange reaction using, e.g., heavy water ($D_2O$). Further suitable deuteration techniques are described in: Atzrodt J et al., *Bioorg Med Chem,* 20(18), 5658-5667, 2012; William J S et al., *Journal of Labelled Compounds and Radiopharmaceuticals,* 53(11-12), 635-644, 2010; Modvig A et al., *J Org Chem,* 79, 5861-5868, 2014. The content of deuterium can be determined, e.g., using mass spectrometry or NMR spectroscopy. Unless specifically indicated otherwise, it is preferred that the compound of formula (I) is not enriched in deuterium. Accordingly, the presence of naturally occurring hydrogen atoms or $^{1}H$ hydrogen atoms in the compounds of formula (I) is preferred.

The present invention also embraces compounds of formula (I), in which one or more atoms are replaced by a positron-emitting isotope of the corresponding atom, such as, e.g., $^{18}F$, $^{11}C$, $^{13}N$, $^{15}O$, $^{76}Br$, $^{77}Br$, $^{120}I$ and/or $^{124}I$. Such compounds can be used as tracers or imaging probes in positron emission tomography (PET). The invention thus includes (i) compounds of formula (I), in which one or more fluorine atoms (or, e.g., all fluorine atoms) are replaced by $^{18}F$ atoms, (ii) compounds of formula (I), in which one or more carbon atoms (or, e.g., all carbon atoms) are replaced by $^{11}C$ atoms, (iii) compounds of formula (I), in which one or more nitrogen atoms (or, e.g., all nitrogen atoms) are replaced by $^{13}N$ atoms, (iv) compounds of formula (I), in which one or more oxygen atoms (or, e.g., all oxygen atoms) are replaced by $^{15}O$ atoms, (v) compounds of formula (I), in which one or more bromine atoms (or, e.g., all bromine atoms) are replaced by $^{76}Br$ atoms, (vi) compounds of formula (I), in which one or more bromine atoms (or, e.g., all bromine atoms) are replaced by $^{77}Br$ atoms, (vii) compounds of formula (I), in which one or more iodine atoms (or, e.g., all iodine atoms) are replaced by $^{120}I$ atoms, and (viii) compounds of formula (I), in which one or more iodine atoms (or, e.g., all iodine atoms) are replaced by $^{124}I$ atoms.

In general, it is preferred that none of the atoms in the compounds of formula (I) are replaced by specific isotopes.

In a first aspect, the present invention provides a compound of formula (I), optionally in the form of a pharmaceutically acceptable salt, solvate, cocrystal, tautomer, racemate, enantiomer, or diastereomer or mixture thereof, for use in a method of treating fibrotic disease

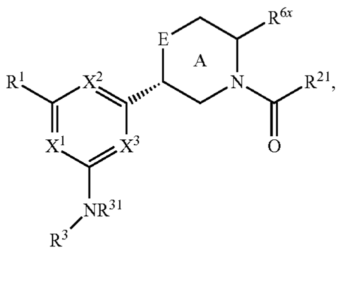

(I)

wherein $R^1$ is selected from halogen and -(optionally substituted hydrocarbon group which contains from 1 to 20 carbon atoms and optionally 1 to 15 heteroatoms selected from O, N and S);

$R^{21}$ is selected from hydrogen, -(optionally substituted $C_{1-6}$ alkyl) which may contain one to three oxygen atoms between carbon atoms, and -(optionally substituted $C_{3-6}$ cycloalkyl);

$R^3$ is selected from -(optionally substituted heterocyclyl), -(optionally substituted carbocyclyl), -(optionally substituted $C_{1-6}$ alkylene)-(optionally substituted heterocyclyl) and -(optionally substituted $C_{1-6}$ alkylene)-(optionally substituted carbocyclyl);

each of $X^1$, $X^2$ and $X^3$ is independently selected from N, CH and $CR^X$, wherein preferably at least one of said $X^1$, $X^2$ and $X^3$ is N, wherein further preferably at least one of said $X^2$ and $X^3$ is N; wherein again further preferably $X^2$ and $X^3$ are both N, and wherein still further preferably $X^2$ and $X^3$ are both N, and $X^1$ is CH;

$R^{31}$ is selected from -hydrogen, —$C_{1-6}$-alkyl, and —($C_{1-6}$-alkyl substituted with one or more F); wherein $R^3$ and any $R^{31}$ can be optionally linked; and E is either absent or is selected from —$CH_2$—, —$CHR^x$—, —$CR^x_2$—, —NH—, —$NR^x$—, —O—, -$L^1$-$L^2$- and -$L^2$-$L^1$-, wherein $L^1$ is selected from —$CH_2$—, —$CHR^x$—, —$CR^x_2$—, —NH—, —$NR^x$— and —O— and $L^2$ is selected from —$CH_2$—, —$CHR^x$— and —$CR^x_2$—;

$R^{6x}$ is -halogen, —OH, =O, $C_{1-6}$ alkyl, $C_{1-6}$ haloalkyl, $C_{1-6}$ alkyl substituted with one or more OH, monocyclic aryl optionally substituted with one or more $R^{xb}$, monocyclic heteroaryl optionally substituted with one or more $R^{xb}$, monocyclic cycloalkyl optionally substituted with one or more $R^{xb}$, monocyclic heterocycloalkyl optionally substituted with one or more $R^{xb}$, monocyclic cycloalkenyl optionally substituted with one or more $R^{xb}$, monocyclic heterocycloalkenyl optionally substituted with one or more $R^{xb}$, wherein said $R^{xb}$ is independently selected from -halogen, —OH, =O, $C_{1-4}$ alkyl, $C_{1-2}$ haloalkyl, $C_{1-2}$ alkyl substituted with one or two OH;

wherein Ring A may further be substituted with one or more groups $R^x$, wherein any two $R^x$ groups at ring A can be optionally linked and/or any $R^x$ group at ring A can be optionally linked with $R^{21}$ and/or wherein Ring A may be further substituted with one group $R^x$ so as to form together with $R^{6x}$ a bicyclic moiety having the following partial structure:

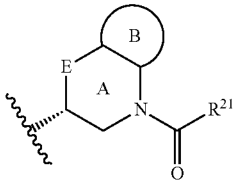

wherein Ring B is an -(optionally substituted heterocycle) or -(optionally substituted carbocycle); each $R^x$ is independently selected from -halogen, —OH, —O-(optionally substituted $C_{1-6}$ alkyl), —NH-(optionally substituted $C_{1-6}$ alkyl), —N(optionally substituted $C_{1-6}$ alkyl)$_2$, =O, -(optionally substituted $C_{1-6}$ alkyl), -(optionally substituted carbocyclyl), -(optionally substituted heterocyclyl), -(optionally substituted $C_{1-6}$ alkylene)-(optionally substituted carbocyclyl), -(optionally substituted $C_{1-6}$ alkylene)-(optionally substituted heterocyclyl), —O-(optionally substituted $C_{1-6}$ alkylene)-(optionally substituted carbocyclyl), and —O-(optionally substituted $C_{1-6}$ alkylene)-(optionally substituted heterocyclyl), and wherein the optional substituent of the optionally substituted hydrocarbon group, optionally substituted $C_{1-6}$ cycloalkyl, optionally substituted heterocyclyl, optionally substituted heterocycle, optionally substituted carbocyclyl, optionally substituted carbocycle and optionally substituted $C_{1-6}$ alkylene is independently selected from —($C_{1-6}$ alkyl which is optionally substituted with one or more halogen), -halogen, —CN, —$NO_2$, oxo, —C(O)R*, —COOR*, —C(O)NR*R*, —NR*R*, —N(R*)—C(O)R*, —N(R*)—C(O)—OR*, —N(R*)—C(O)—NR*R*, —N(R*)—S(O)$_2$R*, —OR*, —O—C(O)R*, —O—C(O)—NR*R*, —SR*, —S(O)R*, —S(O)$_2$R*, —S(O)$_2$—NR*R*, —N(R*)—S(O)$_2$—NR*R*, heterocyclyl which is optionally substituted with halogen or $C_{1-6}$ alkyl, and carbocyclyl which is optionally substituted with halogen or $C_{1-6}$ alkyl; wherein each R* is independently selected from H, $C_{1-6}$ alkyl which is optionally substituted with halogen, heterocyclyl which is optionally substituted with halogen or $C_{1-6}$ alkyl, and carbocyclyl which is optionally substituted with halogen or $C_{1-6}$ alkyl; wherein any two R* connected to the same nitrogen atom can be optionally linked, and wherein the optional substituent of the optionally substituted $C_{1-6}$ alkyl and of the optionally substituted $C_{1-6}$ alkylene is independently selected from -halogen, —CN, —$NO_2$, oxo, —C(O)R, —COOR, —C(O)NRR, —NRR, —N(R)—C(O)R, —N(R)—C(O)—OR, —N(R)—C(O)—NRR, —N(R)—S(O)$_2$R, —OR, —O—C(O)R, —O—C(O)—NRR, —SR, —S(O)R, —S(O)$_2$R, —S(O)$_2$—NRR, and —N(R)—S(O)$_2$—NRR; wherein R is independently selected from H, $C_{1-6}$ alkyl which is optionally substituted with halogen, heterocyclyl which is optionally substituted with halogen or $C_{1-6}$ alkyl, and carbocyclyl which is optionally substituted with halogen or $C_{1-6}$ alkyl; wherein any two R** connected to the same nitrogen atom can be optionally linked.

In a preferred embodiment, at least one of said $X^1$, $X^2$ and $X^3$ is N. In a further preferred embodiment, at least one of said $X^2$ and $X^3$ is N. In a further preferred embodiment, $X^2$ is N. In another preferred embodiment, $X^2$ and $X^3$ are both N. Thus, in a further preferred embodiment, the compound of formula (I) is a compound of formula (Ia)

(Ia)

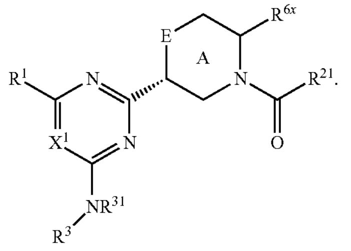

In a further preferred embodiment, $X^1$ is nitrogen or CH, and $X^2$ and $X^3$ are both N. In a further very preferred embodiment, $X^1$ is CH and $X^2$ and $X^3$ are both N. Thus, in a further preferred embodiment, the compound of formula (I) is a compound of formula (Ib)

(Ib)

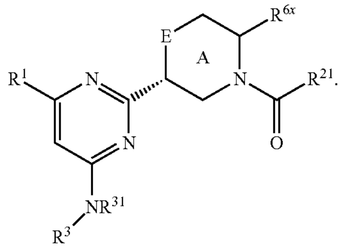

$R^{31}$ is selected from -hydrogen, —$C_{1-6}$-alkyl, and —($C_{1-6}$-alkyl substituted with one or more F); wherein $R^3$ and any $R^{31}$ can be optionally linked. When $R^3$ and an $R^{31}$ are linked, a cyclic group, such as a 3 to 8-membered ring containing 1 to 8 carbon atoms and optionally 1 to 4 heteroatoms selected from N, O and S may be formed. These cyclic groups typically include the carbon or nitrogen to which $R^{31}$ is bound as one ring member. Examples of such a cyclic group are cyclopentane, cyclohexane, pyrrolidine, piperidine and morpholine rings. In a further preferred embodiment, said $R^{31}$ is selected from -hydrogen, —$C_{1-4}$-alkyl, and —$C_{1-2}$-fluoroalkyl. In a further preferred embodiment, said $R^{31}$ is selected from -hydrogen, —$C_{1-2}$-alkyl, and —$C_1$-fluoroalkyl. In a further preferred embodiment, said $R^{31}$ is selected from -hydrogen and methyl. In a further very preferred embodiment, said $R^{31}$ is -hydrogen. Thus, in a further preferred embodiment, the compound of formula (I) is a compound of formula (II)

(II)

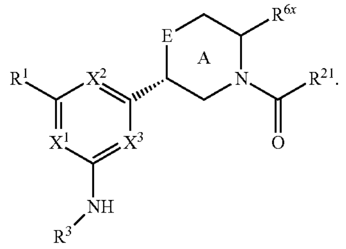

In a further preferred embodiment, the compound of formula (I) is a compound of formula (IIa)

(IIa)

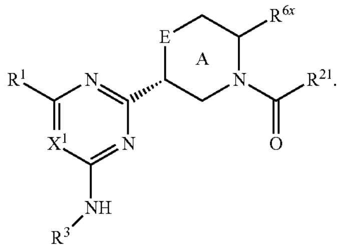

In again a further preferred embodiment, the compound of formula (I) is a compound of formula (IIb)

(IIb)

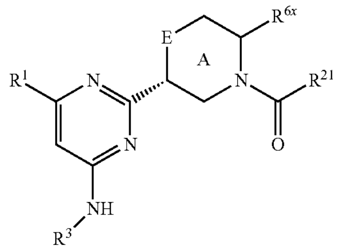

In a further preferred embodiment, E is selected from —$CH_2$—, —NH—, —O—, —$CH_2$—O—, —O—$CH_2$—, —$CH_2$—NH—, —NH—$CH_2$— and —$CH_2$—$CH_2$—. More preferably, E is selected from $CH_2$—, —O—, —$CH_2$—O—, —O—$CH_2$— and —$CH_2$—$CH_2$—. Still more preferably, E is selected from $CH_2$—, —O—, —$CH_2$—O— and —$CH_{2}$-$CH_2$—. Even more preferably, E is $CH_2$. Thus, in a further preferred embodiment, the compound of formula (I) is a compound of formula (III)

(III)

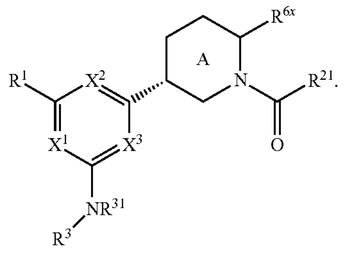

In a further preferred embodiment, the compound of formula (I) is a compound of formula (IIIa)

(IIIa)

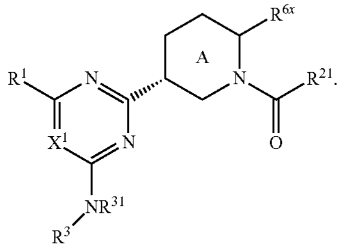

In again a further preferred embodiment, the compound of formula (I) is a compound of formula (IIIb)

(IIIb)

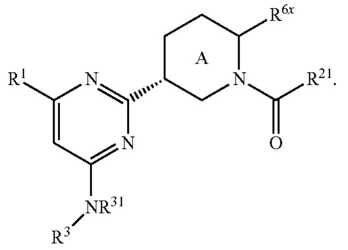

In a further very preferred embodiment, the compound of formula (I) is a compound of formula (IV)

(IV)

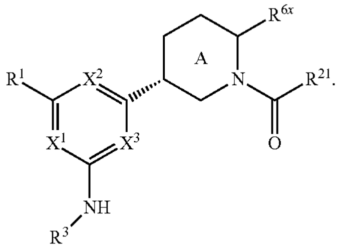

In a further preferred embodiment, the compound of formula (I) is a compound of formula (IVa)

(IVa)

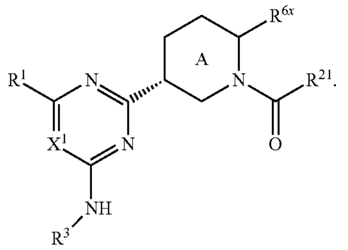

In again a further preferred embodiment, the compound of formula (I) is a compound of formula (IVb)

(IVb)

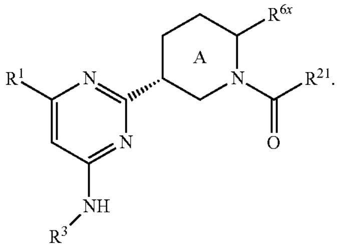

In a further aspect and embodiment, the present invention provides a compound of formula (I), preferably a compound of formula (Ia), and further preferably a compound of formula (Ib), optionally in the form of a pharmaceutically acceptable salt, solvate, cocrystal, tautomer, racemate, enantiomer, or diastereomer or mixture thereof, for use in a method of treating fibrotic disease (I)

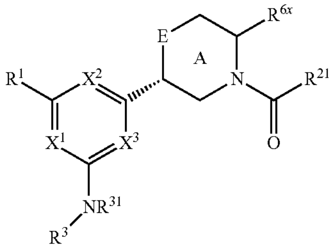

(Ia)

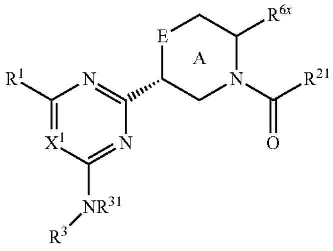

(Ib)

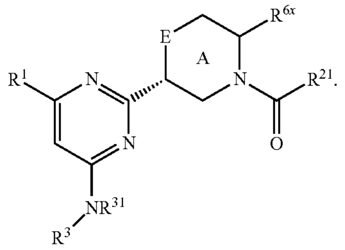

The present inventors have further surprisingly found that the enantiomers of the compounds of the present invention as depicted in formula (V) are significantly more active than the other enantiomers or diastereomers of the said compounds. Thus, in a further aspect and embodiment, the present invention provides a compound of formula (I), wherein said compound of formula (I) is a compound of formula (V), preferably of formula (Va) and further preferably of formula (Vb), optionally in the form of a pharmaceutically acceptable salt, solvate, cocrystal, tautomer, racemate, enantiomer, or diastereomer or mixture thereof, for use in a method of treating fibrotic disease (V)

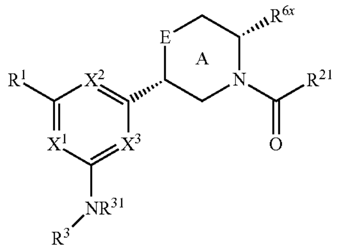

(Va)

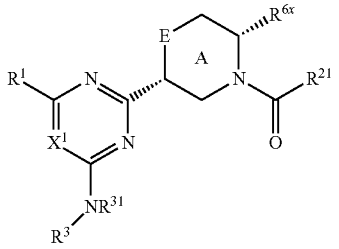

(Vb)

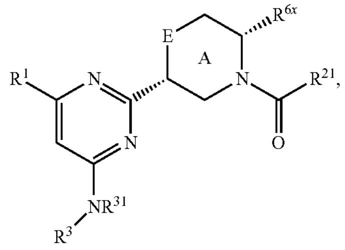

wherein $R^1$ is selected from halogen and -(optionally substituted hydrocarbon group which contains from 1 to 20 carbon atoms and optionally 1 to 15 heteroatoms selected from O, N and S);

$R^{21}$ is selected from hydrogen, -(optionally substituted $C_{1-6}$ alkyl) which may contain one to three oxygen atoms between carbon atoms, and -(optionally substituted $C_{3-6}$ cycloalkyl);

$R^3$ is selected from -(optionally substituted heterocyclyl), -(optionally substituted carbocyclyl), -(optionally substituted $C_{1-6}$ alkylene)-(optionally substituted heterocyclyl) and -(optionally substituted $C_{1-6}$ alkylene)-(optionally substituted carbocyclyl);

each of $X^1$, $X^2$ and $X^3$ is independently selected from N, CH and $CR^X$, wherein preferably at least one of said $X^1$, $X^2$ and $X^3$ is N, wherein further preferably at least one of said $X^2$ and $X^3$ is N; and wherein again further preferably $X^2$ and $X^3$ are both N, and wherein still further preferably $X^2$ and $X^3$ are both N, and $X^1$ is CH;

$R^{31}$ is selected from -hydrogen, —$C_{1-6}$-alkyl, and —($C_{1-6}$-alkyl substituted with one or more F);

wherein $R^3$ and any $R^{31}$ can be optionally linked; and

E is either absent or is selected from —$CH_2$—, —$CHR^x$—, —$CR^x_2$—, —NH—, —$NR^x$— and —O—, -$L^1$-$L^2$- and -$L^2$-$L^1$-, wherein $L^1$ is selected from —$CH_2$—, —$CHR^x$—, —$CR^x_2$—, —NH—, —$NR^x$— and —O— and $L^2$ is selected from —$CH_2$—, —$CHR^x$— and —$CR^x_2$—;

$R^{6x}$ is -halogen, —OH, ═O, $C_{1-6}$ alkyl, $C_{1-6}$ haloalkyl, $C_{1-6}$ alkyl substituted with one or more OH, monocyclic aryl optionally substituted with one or more $R^{xb}$, monocyclic heteroaryl optionally substituted with one or more $R^{xb}$, monocyclic cycloalkyl optionally substituted with one or more $R^{xb}$, monocyclic heterocycloalkyl optionally substituted with one or more $R^{xb}$, monocyclic cycloalkenyl optionally substituted with one or more $R^{xb}$, monocyclic heterocycloalkenyl optionally substituted with one or more $R^{xb}$, wherein said $R^{xb}$ is independently selected from -halogen, —OH, ═O, $C_{1-4}$ alkyl, $C_{1-2}$ haloalkyl, $C_{1-2}$ alkyl substituted with one or two OH;

wherein Ring A may further be substituted with one or more groups $R^x$, wherein any two $R^x$ groups at ring A can be optionally linked and/or any $R^x$ group at ring A can be optionally linked with $R^2$;

and/or wherein Ring A may be further substituted with one group $R^x$ so as to form together with $R^{6x}$ a bicyclic moiety having the following partial structure:

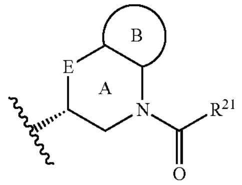

wherein Ring B is an -(optionally substituted heterocycle) or -(optionally substituted carbocycle); each $R^x$ is independently selected from -halogen, —OH, —O-(optionally substituted $C_{1-6}$ alkyl), —NH-(optionally substituted $C_{1-6}$ alkyl), —N(optionally substituted $C_{1-6}$ alkyl)$_2$, ═O, -(optionally substituted $C_{1-6}$ alkyl), -(optionally substituted carbocyclyl), -(optionally substituted heterocyclyl), -(optionally substituted $C_{1-6}$ alkylene)-(optionally substituted carbocyclyl), -(optionally substituted $C_{1-6}$ alkylene)-(optionally substituted heterocyclyl), —O-(optionally substituted $C_{1-6}$ alkylene)-(optionally substituted carbocyclyl), and —O-(optionally substituted $C_{1-6}$ alkylene)-(optionally substituted heterocyclyl), and wherein the optional substituent of the optionally substituted hydrocarbon group, optionally substituted $C_{1-6}$ cycloalkyl, optionally substituted heterocyclyl, optionally substituted heterocycle, optionally substituted carbocyclyl, optionally substituted carbocycle and optionally substituted $C_{1-6}$ alkylene is independently selected from —($C_{1-6}$ alkyl which is optionally substituted with one or more halogen), -halogen, —CN, —$NO_2$, oxo, —C(O)R*, —COOR*, —C(O)NR*R*, —NR*R*, —N(R*)—C(O)R*, —N(R*)—C(O)—OR*, —N(R*)—C(O)—NR*R*, —N(R*)—S(O)$_2$R*, —OR*, —O—C(O)R*, —O—C(O)—NR*R*, —SR*, —S(O)R*, —S(O)$_2$R*, —S(O)$_2$—NR*R*, —N(R*)—S(O)$_2$—NR*R*, heterocyclyl which is optionally substituted with halogen or $C_{1-6}$ alkyl, and carbocyclyl which is optionally substituted with halogen or $C_{1-6}$ alkyl; wherein each R* is independently selected from H, $C_{1-6}$ alkyl which is optionally substituted with halogen, heterocyclyl which is optionally substituted with halogen or $C_{1-6}$ alkyl, and carbocyclyl which is optionally substituted with halogen or $C_{1-6}$ alkyl;

wherein any two R* connected to the same nitrogen atom can be optionally linked, and wherein the optional substituent of the optionally substituted $C_{1-6}$ alkyl and of the optionally substituted $C_{1-6}$ alkylene is independently selected from -halogen, —CN, —$NO_2$, oxo, —C(O)R, —COOR, —C(O)NRR, —NRR, —N(R)—C(O)R, —N(R)—C(O)—OR, —N(R)—C(O)—NRR, —N(R)—S$(O)_2$R, —OR, —O—C(O)R, —O—C(O)—NRR, —SR, —S(O)R, —S$(O)_2$R, —S$(O)_2$—NRR, and —N(R)—S$(O)_2$—NRR; wherein R is independently selected from H, $C_{1-6}$ alkyl which is optionally substituted with halogen, heterocyclyl which is optionally substituted with halogen or $C_{1-6}$ alkyl, and carbocyclyl which is optionally substituted with halogen or $C_{1-6}$ alkyl; wherein any two R** connected to the same nitrogen atom can be optionally linked. In a further preferred embodiment, both $X^2$ and $X^3$ are nitrogen. In a further preferred embodiment, $X^1$ is CH.

In a further preferred embodiment, said $R^{31}$ is selected from -hydrogen, —$C_{1-4}$-alkyl, and —$C_{1-2}$-fluoroalkyl. In a further preferred embodiment, said $R^{31}$ is selected from -hydrogen, —$C_{1-2}$-alkyl, and —$C_1$-fluoroalkyl. In a further preferred embodiment, said $R^{31}$ is selected from -hydrogen and methyl. In a further preferred embodiment, said $R^{31}$ is -hydrogen.

In a preferred embodiment, said $R^{21}$ is selected from hydrogen, $C_{1-6}$ alkyl, $C_{1-6}$ haloalkyl, $C_{1-6}$ alkyl optionally substituted with one or more OH, $C_{1-6}$ alkyl containing one to three oxygen atoms between carbon atoms, and $C_{3-6}$ cycloalkyl optionally substituted with one or more $R^{22}$ wherein $R^{22}$ is selected from halogen, preferably —Cl, —F, and —OH. In a further preferred embodiment, said $R^{21}$ is selected from hydrogen, $C_{1-2}$ alkyl, $C_{1-2}$ haloalkyl, $C_{1-2}$ alkyl optionally substituted with one or two OH, and $C_{3-4}$ cycloalkyl optionally substituted with one or more $R^{22}$ wherein $R^{22}$ is selected from —Cl, —F, and —OH. In a further preferred embodiment, said $R^{21}$ is selected from $C_{1-2}$ alkyl, $C_{1-2}$ haloalkyl and $C_{3-4}$ cycloalkyl. In a further preferred embodiment, said $R^{21}$ is selected from $C_{1-2}$ alkyl and cyclopropyl. In a further preferred embodiment, said $R^{21}$ is methyl. In a further preferred embodiment, said $R^{21}$ is ethyl. In a further preferred embodiment, said $R^{21}$ is cyclopropyl.

It is to be understood that Ring A may be further substituted with one or more groups $R^x$, wherein any two $R^x$ groups, preferably adjacent $R^x$ groups, at ring A are optionally linked and/or any $R^x$ group at ring A is optionally linked with $R^{21}$; the number of groups $R^x$ in Ring A is 0, 1, 2, 3, or 4, preferably 0, 1, 2, or 3, further preferably 0, 1, or 2, or alternatively preferably 0 or 1. In case that Ring A may be substituted with one or more groups $R^x$ and one of said $R^x$ group at ring A is optionally linked with $R^{21}$ then said one of said $R^x$ group at ring A optionally linked with $R^{21}$ is a substituent at the 2-position of Ring A.

Thus, in a preferred embodiment, said Ring A is further substituted with 1, 2, 3 or 4 groups $R^x$, wherein any two $R^x$ groups, preferably adjacent $R^x$ groups, at ring A are optionally linked and/or any $R^x$ group at ring A is optionally linked with $R^{21}$. In case that one of said $R^x$ group at ring A is optionally linked with $R^{21}$ then said one of said $R^x$ group at ring A optionally linked with $R^{21}$ is a substituent at the 2-position of Ring A.

In a preferred embodiment, said Ring A is further substituted with 1, 2 or 3 groups $R^x$, wherein any two $R^x$ groups, preferably adjacent $R^x$ groups, at ring A are optionally linked and/or any $R^x$ group at ring A is optionally linked with $R^{21}$. In case that one of said $R^x$ group at ring A is optionally linked with $R^{21}$ then said one of said $R^x$ group at ring A optionally linked with $R^{21}$ is a substituent at the 2-position of Ring A.

In a preferred embodiment, said Ring A is further substituted with 1 or 2 groups $R^x$, wherein any two $R^x$ groups, preferably adjacent $R^x$ groups, at ring A are optionally linked and/or any $R^x$ group at ring A is optionally linked with $R^{21}$. In case that one of said $R^x$ group at ring A is optionally linked with $R^{21}$ then said one of said $R^x$ group at ring A optionally linked with $R^{21}$ is a substituent at the 2-position of Ring A.

In a preferred embodiment, said Ring A is further substituted with 1 group $R^x$, wherein said $R^x$ group at ring A is optionally linked with $R^{21}$. In case that one of said $R^x$ group at ring A is optionally linked with $R^{21}$ then said one of said $R^x$ group at ring A optionally linked with $R^{21}$ is a substituent at the 2-position of Ring A.

In a preferred embodiment, said Ring A is further substituted with 1 group $R^x$, wherein said $R^x$ group at ring A is not linked with $R^{21}$.

In a preferred embodiment, said Ring A is further substituted with 1 group $R^x$, wherein said $R^x$ group at ring A is not linked with $R^{21}$. In a further preferred embodiment, said group $R^x$ is —F, and wherein preferably said group $R^x$ being —F is at the 3-position of Ring A, said position which connects said Ring A with the $X^1$, $X^2$, $X^3$ ring system.

In a preferred embodiment, said Ring A is not further substituted. Thus, in a preferred embodiment, said Ring A is not further substituted with a group $R^x$.

In a further preferred embodiment, said E is selected from —$CH_2$—, —$CHCH_3$—, —$C(CH_3)_2$—, —NH—, —$N(CH_3)$—, —O—, -$L^1$-$L^2$- and -$L^2$-$L^1$, wherein $L^1$ is selected from —$CH_2$—, —$CHCH_3$—, —$C(CH_3)_2$—, —NH—, —$N(CH_3)$—, and —O— and $L^2$ is selected from —$CH_2$—, —$CHCH_3$—, —$C(CH_3)_2$—. In a further preferred embodiment, said E is —$CH_2$—, —$CHCH_3$—, —NH—, —$N(CH_3)$—, —O—, -$L^1$-$L^2$- and -$L^2$-$L^1$-, wherein $L^1$ is selected from —$CH_2$—, —$CHCH_3$—, —NH—, —$N(CH_3)$—, and —O— and $L^2$ is selected from —$CH_2$— and —$CHCH_3$—. In a further preferred embodiment E is selected from —$CH_2$—, —NH—, —O—, —$CH_2$—O—, —O—$CH_2$—, —$CH_2$—NH—, —NH—$CH_2$— and —$CH_2$—$CH_2$—. Preferably, E is selected from $CH_2$—, —O—, —$CH_2$—O—, —O—$CH_2$— and —$CH_2$—$CH_2$—. More preferably, E is selected from $CH_2$—, —O—, —$CH_2$—O— and —$CH_2$—$CH_2$—. Even more preferably, E is $CH_2$;

In a preferred embodiment, each $R^x$ is independently selected from -halogen, —OH, —O—$C_{1-3}$ alkyl optionally substituted with one or more $R^{xa}$, —NH—$C_{1-3}$ alkyl optionally substituted with one or more $R^{xa}$, —N($C_{1-3}$ alkyl optionally substituted with one or more $R^{xa})_2$, =O, $C_{1-4}$ alkyl optionally substituted with one or more $R^{xa}$, $C_{1-4}$ haloalkyl, —($C_{1-2}$ alkylene optionally substituted with one or more $R^{xa}$)-(optionally substituted carbocyclyl), —($C_{1-2}$ alkylene optionally substituted with one or more $R^{xa}$)-(optionally substituted heterocyclyl), —O—($C_{1-2}$ alkylene optionally substituted with one or more $R^{xa}$)-(optionally substituted carbocyclyl), —O—($C_{1-2}$ alkylene optionally substituted with one or more $R^{xa}$)-(optionally substituted heterocyclyl), -(optionally substituted carbocyclyl) and -(optionally substituted heterocyclyl), wherein said $R^{xa}$ is independently selected from halogen, preferably —C, —F, and —OH.

In a preferred embodiment, each $R^x$ is independently selected from -halogen, —OH, —O—$C_{1-3}$ alkyl optionally substituted with one or more $R^{xa}$, —NH—$C_{1-3}$ alkyl optionally substituted with one or more $R^{xa}$, —N($C_{1-3}$ alkyl optionally substituted with one or more $R^{xa})_2$, =O, $C_{1-4}$ alkyl optionally substituted with one or more $R^{xa}$, $C_{1-4}$ haloalkyl, —($C_{1-2}$ alkylene optionally substituted with one or more $R^{xa}$)-(optionally substituted carbocyclyl), —($C_{1-2}$ alkylene optionally substituted with one or more $R^{xa}$)-

(optionally substituted heterocyclyl), —O—($C_{1-2}$ alkylene optionally substituted with one or more $R^{xa}$)-(optionally substituted carbocyclyl), —O—($C_{1-2}$ alkylene optionally substituted with one or more $R^{xa}$)-(optionally substituted heterocyclyl), -(optionally substituted carbocyclyl) and -(optionally substituted heterocyclyl), wherein said $R^{xa}$ is independently selected from halogen, preferably —Cl, —F, and —OH.

In a preferred embodiment, each $R^x$ is independently selected from -halogen, —OH, —O—$C_{1-3}$ alkyl optionally substituted with one or more $R^{xa}$, —NH—$C_{1-3}$ alkyl optionally substituted with one or more $R^{xa}$, —N($C_{1-3}$ alkyl optionally substituted with one or more $R^{xa}$)$_2$, ═O, $C_{1-4}$ alkyl optionally substituted with one or more $R^{xa}$, $C_{1-4}$ haloalkyl, —($C_{1-2}$ alkylene optionally substituted with one or more $R^{xa}$)-(monocyclic carbocyclyl optionally substituted with one or more $R^{xa}$), —($C_{1-2}$ alkylene optionally substituted with one or more $R^{xa}$)-(monocyclic heterocyclyl optionally substituted with one or more $R^{xa}$), —O—($C_{1-2}$ alkylene optionally substituted with one or more $R^{xa}$)-(monocyclic carbocyclyl optionally substituted with one or more $R^{xa}$), —O—($C_{1-2}$ alkylene optionally substituted with one or more $R^{xa}$)-(monocyclic heterocyclyl optionally substituted with one or more $R^{xa}$), -(optionally substituted carbocyclyl) and -(optionally substituted heterocyclyl), wherein said $R^{xa}$ is independently selected from halogen, preferably —Cl, —F, and —OH.

In a preferred embodiment, each $R^x$ is independently selected from -halogen, —OH, —O—$C_{1-3}$ alkyl optionally substituted with one or more $R^{xa}$, —NH—$C_{1-3}$ alkyl optionally substituted with one or more $R^{xa}$, —N($C_{1-3}$ alkyl optionally substituted with one or more $R^{xa}$)$_2$, ═O, $C_{1-4}$ alkyl optionally substituted with one or more $R^{xa}$, $C_{1-4}$ haloalkyl, —($C_{1-2}$ alkylene optionally substituted with one or more $R^{xa}$)-(monocyclic carbocyclyl optionally substituted with one or more $R^{xa}$), —($C_{1-2}$ alkylene optionally substituted with one or more $R^{xa}$)-(monocyclic heterocyclyl optionally substituted with one or more $R^{xa}$), —O—($C_{1-2}$ alkylene optionally substituted with one or more $R^{xa}$)-(monocyclic carbocyclyl optionally substituted with one or more $R^{xa}$), —O—($C_{1-2}$ alkylene optionally substituted with one or more $R^{xa}$)-(monocyclic heterocyclyl optionally substituted with one or more $R^{xa}$), monocyclic carbocyclyl optionally substituted with one or more $R^{xa}$, monocyclic heterocyclyl optionally substituted with one or more $R^{xa}$, wherein said $R^{xa}$ is independently selected from halogen, preferably —Cl, —F, and —OH.

In a further preferred embodiment, each $R^x$ is independently selected from -halogen, —OH, —O—$C_{1-2}$ alkyl optionally substituted with one or more $R^{xa}$, —NH—$C_{1-2}$ alkyl optionally substituted with one or more $R^{xa}$, —N($C_{1-2}$ alkyl optionally substituted with one or more $R^{xa}$)$_2$, ═O, $C_{1-3}$ alkyl optionally substituted with one or more $R^{xa}$, $C_{1-2}$ haloalkyl, —($C_{1-2}$ alkylene optionally substituted with one or more $R^{xa}$)-(monocyclic carbocyclyl optionally substituted with one or more $R^{xa}$), —($C_{1-2}$ alkylene optionally substituted with one or more $R^{xa}$)-(monocyclic heterocyclyl optionally substituted with one or more $R^{xa}$), —O—($C_{1-2}$ alkylene optionally substituted with one or more $R^{xa}$)-(monocyclic carbocyclyl optionally substituted with one or more $R^{xa}$), —O—($C_{1-2}$ alkylene optionally substituted with one or more $R^{xa}$)-(monocyclic heterocyclyl optionally substituted with one or more $R^{xa}$), monocyclic carbocyclyl optionally substituted with one or more $R^{xa}$, monocyclic heterocyclyl optionally substituted with one or more $R^{xa}$, wherein said $R^{xa}$ is independently selected from halogen, preferably —Cl, —F, and —OH.

In a further preferred embodiment, each $R^x$ is independently selected from -halogen, —OH, —O—$C_{1-2}$ alkyl optionally substituted with one or more $R^{xa}$, —NH—$C_{1-2}$ alkyl optionally substituted with one or more $R^{xa}$, —N($C_{1-2}$ alkyl optionally substituted with one or more $R^{xa}$)$_2$, ═O, $C_{1-3}$ alkyl optionally substituted with one or more $R^{xa}$, $C_{1-2}$ haloalkyl, —W-(monocyclic carbocyclyl optionally substituted with one or more $R^{xa}$), —W-(monocyclic heterocyclyl optionally substituted with one or more $R^{xa}$), and wherein —W— is absent, —($C_{1-2}$ alkylene)- or —O—($C_{1-2}$ alkylene)-, and wherein said $R^{xa}$ is independently selected from —Cl, —F, and —OH.

In a further preferred embodiment, each $R^x$ is independently selected from -halogen, —OH, —O—$C_{1-2}$ alkyl optionally substituted with one or more $R^{xa}$, —NH—$C_{1-2}$ alkyl optionally substituted with one or more $R^{xa}$, —N($C_{1-2}$ alkyl optionally substituted with one or more $R^{xa}$)$_2$, ═O, $C_{1-3}$ alkyl optionally substituted with one or more $R^{xa}$, $C_{1-2}$ haloalkyl, —W-(monocyclic carbocyclyl optionally substituted with one or more $R^{xa}$), —W-(monocyclic heterocyclyl optionally substituted with one or more $R^{xa}$), and wherein —W— is absent, —($C_{1-2}$ alkylene)- or —O—($C_{1-2}$ alkylene)-, and wherein monocyclic carbocyclyl is selected from phenyl and $C_{3-6}$ cycloalkyl, and wherein monocyclic heterocyclyl is selected from thiophenyl, pyridyl, pyrazinyl and pyrimidinyl, and wherein said $R^{xa}$ is independently selected from —Cl, —F, and —OH.

In a further preferred embodiment, each $R^x$ is independently selected from -halogen, —OH, —O—$C_{1-2}$ alkyl, —NH—$C_{1-2}$ alkyl, —N($C_{1-2}$ alkyl)$_2$, ═O, $C_{1-3}$ alkyl, $C_{1-2}$ haloalkyl, —W— (monocyclic carbocyclyl optionally substituted with one $R^{xa}$), —W-(monocyclic heterocyclyl optionally substituted with one $R^{xa}$), and wherein —W— is absent, —($C_{1-2}$ alkylene)- or —O—($C_{1-2}$ alkylene)-, and wherein monocyclic carbocyclyl is selected from phenyl and $C_{3-6}$ cycloalkyl, and wherein monocyclic heterocyclyl is selected from thiophenyl, pyridyl, pyrazinyl and pyrimidinyl, and wherein said $R^{xa}$ is independently selected from —F, and —OH.

It is to be understood that said Ring A may further be substituted with one group $R^x$ so as to form together with $R^{6x}$ a bicyclic moiety having the following partial structure:

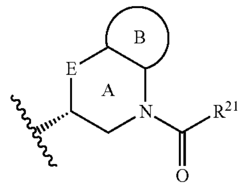

wherein, in a preferred embodiment, said Ring B is an optionally substituted cycloalkyl, optionally substituted cycloalkenyl, optionally substituted heterocycloalkyl, or optionally substituted heterocycloalkenyl, wherein said optional substituent of said cycloalkyl, cycloalkenyl, heterocycloalkyl, heterocycloalkenyl is independently selected from —$C_{1-4}$ alkyl, —$C_{1-2}$ haloalkyl, -halogen, -oxo, —NR*R*, —OR*; wherein each R* is independently selected from H and $C_{1-4}$ alkyl. In a further preferred embodiment, said Ring B is an optionally substituted cycloalkyl or an optionally substituted heterocycloalkyl, wherein said optional substituent of said cycloalkyl or said heterocycloalkyl, is independently selected from —$C_{1-4}$ alkyl, —$C_{1-2}$ haloalkyl, -halogen, -oxo, —NR*R*, —OR*;

wherein each R* is independently selected from H and $C_{1-4}$ alkyl. In a further preferred embodiment, said Ring B is an optionally substituted monocyclic cycloalkyl or an optionally substituted monocyclic heterocycloalkyl, wherein said optional substituent of said monocyclic cycloalkyl or said monocyclic heterocycloalkyl is independently selected from —$C_{1-4}$ alkyl, —$C_{1-2}$ haloalkyl, -halogen, -oxo, —NR*R*, —OR*; wherein each R* is independently selected from H and $C_{1-4}$ alkyl.

In a further preferred embodiment, $R^{6x}$ is selected from -halogen, —OH, ═O, $C_{1-4}$ alkyl, $C_{1-2}$ haloalkyl and $C_{1-3}$ alkyl substituted with one or more OH. In a further preferred embodiment, $R^{6x}$ is selected from -halogen, —OH, ═O, $C_{1-3}$ alkyl, $C_{1-2}$ haloalkyl and $C_{1-3}$ alkyl substituted with one or two OH. In a further preferred embodiment, $R^{6x}$ is selected from $C_{1-3}$ alkyl, $C_{1-2}$ haloalkyl and $C_{1-3}$ alkyl substituted with one or two OH. In a further preferred embodiment, $R^{6x}$ is selected from $C_{1-2}$ alkyl, $C_{1-2}$ haloalkyl and $C_{1-3}$ alkyl substituted with one or two OH. H. In a further preferred embodiment, $R^{6x}$ is selected from $C_{1-3}$alkyl and $C_{1-2}$ haloalkyl. In a further preferred embodiment, $R^{6x}$ is selected from $C_{1-2}$ alkyl and $C_1$ haloalkyl.
In a further preferred embodiment, $R^{6x}$ is $CHF_2$. In a further preferred embodiment, $R^{6x}$ is $CF_3$. In a further preferred embodiment, $R^{6x}$ is ethyl. In a further very preferred embodiment, $R^{6x}$ is methyl.

In a further preferred embodiment, $R^1$— is selected from -(optionally substituted heterocyclyl) and -(optionally substituted carbocyclyl).

In a further preferred embodiment, $R^1$— is selected from -(optionally substituted heteroaryl) and -(optionally substituted aryl), and wherein said, preferably one or two, optional substituent of said heteroaryl or said phenyl is independently selected from —($C_{1-6}$ alkyl which is optionally substituted with one or more halogen), -halogen, —CN, —$NO_2$, oxo, —C(O)R*, —COOR*, —C(O)NR*R*, —NR*R*, —N(R*)—C(O)R*, —N(R*)—C(O)—OR*, —N(R*)—C(O)—NR*R*, —N(R*)—$S(O)_2$R*, —OR*, —O—C(O)R*, —O—C(O)—NR*R*, —SR*, —S(O)R*, —$S(O)_2$R*, —$S(O)_2$—NR*R*, —N(R*)—$S(O)_2$—NR*R*, heterocyclyl which is optionally substituted with halogen or $C_{1-6}$ alkyl, and carbocyclyl which is optionally substituted with halogen or $C_{1-6}$ alkyl; wherein each R* is independently selected from H, $C_{1-6}$ alkyl which is optionally substituted with halogen, heterocyclyl which is optionally substituted with halogen or $C_{1-6}$ alkyl, and carbocyclyl which is optionally substituted with halogen or $C_{1-6}$ alkyl; wherein any two R* connected to the same nitrogen atom can be optionally linked.

In a further preferred embodiment, $R^1$— is selected from -(optionally substituted heteroaryl) and -(optionally substituted phenyl), wherein said heteroaryl is a 5 or 6 membered monocyclic ring or 10 to 12 membered fused ring system comprising one or more ring heteroatoms independently selected from O, S and N, wherein one or two carbon ring atoms are optionally oxidized, and wherein said, preferably one or two, optional substituent of said heteroaryl or said phenyl is independently selected from —$C_{1-6}$ alkyl, $C_{1-6}$ haloalkyl, -halogen, —CN, ═O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, —OR*; and carbocyclyl and heterocyclyl, each independently optionally substituted with, preferably one or two, halogen or $C_{1-4}$ alkyl; wherein each R* is independently selected from H, $C_{1-4}$ alkyl, $C_{1-4}$ haloalkyl.

In a further preferred embodiment, $R^1$ is phenyl, azaindolyl, azaindazolyl, pyrazinyl, pyridyl or pyrimidinyl, wherein the phenyl, azaindolyl, azaindazolyl, pyrazinyl, pyridyl or pyrimidinyl is optionally substituted with one or more, preferably one or two, substituents selected from halogen, —OH, —$C_{1-6}$ alkyl, $C_{1-6}$ haloalkyl, —O—($C_{1-6}$ alkyl), —O—($C_{1-6}$ haloalkyl), —C(O)—$C_{1-6}$ alkyl, —C(O)—$C_{0-6}$ haloalkyl, —NH—C(O)—$C_{1-6}$ alkyl, —NH—C(O)—$C_{1-6}$ haloalkyl and —C(O)—NH—$C_{1-6}$ alkyl, —C(O)—NH—$C_{1-6}$ haloalkyl.

In a further preferred embodiment, $R^1$ is phenyl, azaindolyl, azaindazolyl, pyrazinyl, pyridyl or pyrimidinyl, wherein the phenyl, azaindolyl, azaindazolyl, pyrazinyl, pyridyl or pyrimidinyl is optionally substituted with one or more, preferably one or two, substituents selected from halogen, —OH, —$C_{1-3}$ alkyl, $C_{1-2}$ haloalkyl, —O—($C_{1-3}$ alkyl), —O—($C_{1-2}$ haloalkyl), —C(O)—$C_{1-3}$ alkyl, —C(O)—$C_{1-2}$ haloalkyl, —NH—C(O)—$C_{1\_3}$ alkyl, —NH—C(O)—$C_{1-2}$ haloalkyl and —C(O)—NH—$C_{1-3}$ alkyl, —C(O)—NH—$C_{1-2}$ haloalkyl.

In a further preferred embodiment, $R^1$ is 3-pyridyl or 3-pyridyl substituted at the meta position (5 position) with one substituent selected from halogen, —OH, —$C_{1-3}$ alkyl, $C_{1-2}$ haloalkyl, —O—($C_{1-3}$ alkyl), —O—($C_{1-2}$ haloalkyl), —C(O)—$C_{1-3}$ alkyl, —C(O)—$C_{1-2}$ haloalkyl, —NH—C(O)—$C_{1-3}$ alkyl, —NH—C(O)—$C_{1-2}$ haloalkyl and —C(O)—NH—$C_{1-3}$ alkyl, —C(O)—NH—$C_{1-2}$ haloalkyl. In a further preferred embodiment, $R^1$ is 3-pyridyl.

In a further preferred embodiment, said $R^1$ is selected from phenyl, a 5- or 6-membered monocyclic heteroaryl and a 8-10 membered bicyclic heteroaryl, each independently comprising one or more, preferably 1 to 5, ring heteroatoms independently selected from O, S and N, wherein one or two carbon ring atoms of said monocyclic heteroaryl or said bicyclic heteroaryl are optionally oxidized, and wherein said phenyl, said 5- or 6-membered monocyclic heteroaryl and said 8-10 membered bicyclic heteroaryl is independently optionally substituted with one or more, preferably one or two, substituents selected from halogen, —$C_{1-6}$ alkyl, $C_{1-6}$ haloalkyl, —O—($C_{1-6}$ alkyl), —O—($C_{1-6}$ haloalkyl), —OH, —($C_{1-2}$alkylene)-O—($C_{1-4}$alkylene)-OR*, —O—($C_{1-4}$alkylene)-OR*, —($C_{1-2}$alkylene)-O—($C_{1-4}$alkylene)-N($R^{\circ\circ}$)$_2$, —O—($C_{1-4}$alkylene)-N($R^{\circ\circ}$)$_2$, —CN, ═O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 3-6 membered monocyclic carbocyclyl and 3-6 membered monocyclic heterocyclyl comprising 1 to 4 heteroatoms selected from O, S and N, each monocyclic carbocyclyl and heterocyclyl independently optionally substituted with one or more, preferably one or two, substituents independently selected from halogen, —$C_{1-4}$ alkyl, $C_{1-4}$ haloalkyl, —O—($C_{1-4}$ alkyl), —O—($C_{1-4}$ haloalkyl), —OH, ═O, —C(O)R* and —C(O)NR*R*; wherein each R* is independently selected from H, $C_{1-4}$ alkyl, $C_{1-4}$ haloalkyl, and wherein each $R^{\circ\circ}$ is independently selected from H, $C_{1-4}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from phenyl, a 5- or 6-membered monocyclic heteroaryl and a 8-10 membered bicyclic heteroaryl, each independently comprising one or more, preferably 1 to 5, ring heteroatoms independently selected from O, S and N, wherein one or two carbon ring atoms of said monocyclic heteroaryl or said bicyclic heteroaryl are optionally oxidized, and wherein said phenyl, said 5- or 6-membered monocyclic heteroaryl and said 8-10 membered bicyclic heteroaryl is independently optionally substituted with one or more, preferably one or two, substituents independently selected from halogen, —$C_{1-4}$ alkyl, $C_{1-4}$ haloalkyl, —O—($C_{1-4}$ alkyl), —O—($C_{1-4}$ haloalkyl), —OH, —($C_{1-2}$alkylene)-O—($C_{1-4}$alkylene)-OR*, —O—($C_{1-4}$alkylene)-OR*, —($C_{1-2}$alkylene)-O—($C_{1-4}$alkylene)-N($R^{\circ\circ}$)$_2$, —O—($C_{1-4}$alkylene)-N($R^{\circ\circ}$)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 3-6 membered monocyclic heterocyclyl comprising 1 to 4 heteroatoms selected from O, S and N, each monocyclic heterocyclyl independently optionally substituted with one or more, preferably one or two, substituents selected from halogen, —$C_{1-3}$ alkyl, $C_{1-3}$ haloalkyl, —O—($C_{1-3}$ alkyl), —O—($C_{1-3}$ haloalkyl), —OH, =O, —C(O)R* and —C(O)NR*R*; wherein each R* is independently selected from H, $C_{1-3}$ alkyl, $C_{1-3}$ haloalkyl, and wherein each $R^{\circ\circ}$ is independently selected from H, $C_{1-4}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$alkylene substituted with 1 to 4 F, —$CH_2$—O—$CH_2$— and —$CH_2$—NH—$CH_2$—.

In a further preferred embodiment, said $R^1$ is selected from phenyl, a 5- or 6-membered monocyclic heteroaryl and a 8-10 membered bicyclic heteroaryl, each independently comprising one or more, preferably 1 to 5, ring heteroatoms independently selected from O, S and N, wherein one or two carbon ring atoms of said monocyclic heteroaryl or said bicyclic heteroaryl are optionally oxidized, and wherein said phenyl, said 5- or 6-membered monocyclic heteroaryl and said 8-10 membered bicyclic heteroaryl is independently optionally substituted with one or more, preferably one or two, substituents independently selected from —F, —Cl, —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 3-6 membered monocyclic heterocyclyl comprising 1 to 4 heteroatoms selected from O, S and N, each monocyclic heterocyclyl independently optionally substituted with one or more, preferably one or two, substituents selected from —$C_{1-2}$ alkyl, $C_{1-2}$ haloalkyl, —O—($C_{1-2}$ alkyl), —O—($C_{1-2}$ haloalkyl), —OH, =O, —C(O)R* and —C(O)NR*R*; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from phenyl, a 5- or 6-membered monocyclic heteroaryl comprising one or two heteroatoms independently selected from S and N and a 8-10 membered bicyclic heteroaryl comprising one or more, preferably 1 to 4, ring nitrogen heteroatoms, wherein one or two, preferably one, carbon ring atoms of said monocyclic heteroaryl or said bicyclic heteroaryl are optionally oxidized, and wherein said phenyl, said 5- or 6-membered monocyclic heteroaryl and said 8-10 membered bicyclic heteroaryl is independently optionally substituted with one or more, preferably one or two, substituents independently selected from —F, —Cl, —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 3-6 membered monocyclic heterocyclyl comprising 1 to 4 heteroatoms selected from O, S and N, each monocyclic heterocyclyl independently optionally substituted with one or more, preferably one or two, substituents selected from —$C_{1-2}$ alkyl, $C_{1-2}$ haloalkyl, —O—($C_{1-2}$ alkyl), —O—($C_{1-2}$ haloalkyl), —OH, =O, —C(O)R* and —C(O)NR*R*; wherein each R* is independently selected from H, $C_{1-2}$ alkyl, $C_{1-2}$ haloalkyl, and wherein each $R^{\circ\circ}$ is independently selected from H, $C_{1-2}$alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from a 5- or 6-membered monocyclic heteroaryl comprising one or two heteroatoms independently selected from S and N and a 8-10 membered bicyclic heteroaryl comprising 1 to 5, preferably 1 to 4, ring nitrogen heteroatoms, wherein one or two, preferably one, carbon ring atoms of said monocyclic heteroaryl or said bicyclic heteroaryl are optionally oxidized, and wherein said 5- or 6-membered monocyclic heteroaryl and said 8-10 membered bicyclic heteroaryl is independently optionally substituted with one or two substituents independently selected from —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 4-6 membered monocyclic heterocyclyl comprising 1 or 2 heteroatoms selected from O and N, each monocyclic heterocyclyl independently optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH, =O, —C(O)R* and —C(O)NR*R*; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from a 5- or 6-membered monocyclic heteroaryl comprising one or two heteroatoms independently selected from S and N and a 8-10 membered bicyclic heteroaryl comprising 1 to 5, preferably 1 to 4, ring nitrogen heteroatoms, wherein one or two, preferably one, carbon ring atoms of said monocyclic heteroaryl or said bicyclic heteroaryl are optionally oxidized, and wherein said 5- or 6-membered monocyclic heteroaryl and said 8-10 membered bicyclic heteroaryl is independently optionally substituted with one or two, preferably one, substituents independently selected from —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, and 4-6 membered monocyclic heterocyclyl comprising 1 or 2 heteroatoms selected from 0 and N, each monocyclic heterocyclyl independently optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH and =O; wherein each R* is independently selected from H, $C_{1-2}$ alkyl, $C_{1-2}$ haloalkyl, and wherein each $R^{\circ\circ}$ is independently selected from H, $C_{1-2}$alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$ alkylene substituted with 1 to 4 F, —$CH_2$—O—$CH_2$— and —$CH_2$—NH—$CH_2$—.

In a further preferred embodiment, said $R^1$ is phenyl, thiophenyl, pyrrolyl, pyrazolyl, azaindolyl, azaindazolyl, pyrazinyl, pyridyl or pyrimidinyl, wherein the phenyl, thiophenyl, pyrrolyl, pyrazolyl, azaindolyl, azaindazolyl, pyrazinyl, pyridyl or pyrimidinyl is optionally substituted with one or two, preferably one, substituents independently selected from —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 4-6 membered monocyclic heterocyclyl comprising 1 or 2 heteroatoms selected from O and N, each monocyclic heterocyclyl optionally substituted with one or two, preferably one, substituents independently selected from —$C_{1-2}$ alkyl, $C_{1-2}$ haloalkyl, —O—($C_{1-2}$ alkyl), —O—($C_{1-2}$ haloalkyl), —OH, =O, —C(O)R* and —C(O)NR*R*; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is phenyl, thiophenyl, pyrrolyl, pyrazolyl, azaindolyl, azaindazolyl, pyrazinyl, pyridyl or pyrimidinyl, wherein the phenyl, thiophenyl, pyrrolyl, pyrazolyl, azaindolyl, azaindazolyl, pyrazinyl, pyridyl or pyrimidinyl is optionally substituted with one or two, preferably one, substituents independently selected from —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, and 4-6 membered monocyclic heterocyclyl comprising 1 or 2 heteroatoms selected from 0 and N, each monocyclic heterocyclyl optionally substituted with one or two, preferably one, substituents independently selected from —$C_{1-2}$ alkyl, $C_{1-2}$ haloalkyl, —O—($C_{1-2}$ alkyl), —O—($C_{1-2}$ haloalkyl), —OH and =O; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from a 5-membered monocyclic heteroaryl comprising one or two heteroatoms selected from S and N, wherein said 5-membered monocyclic heteroaryl is optionally substituted with one or two, preferably one, substituents selected from —$C_{1-2}$ alkyl, or $R^1$ is selected from a formula (A) and (B)

(A)

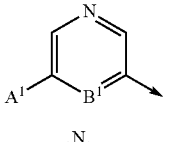

(B)

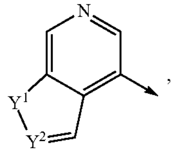

wherein $Y^1$ is NH, N($C_{1-2}$ alkyl) or $CH_2$, and $Y^2$ is N or CH, and wherein $B^1$ is N or CH, and $A^1$ is selected from hydrogen, —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 4-6 membered monocyclic heterocyclyl comprising 1 or 2 heteroatoms selected from O and N, each monocyclic heterocyclyl optionally substituted with one or two, preferably one, substituents independently selected from —$C_{1-2}$ alkyl, $C_{1-2}$ haloalkyl, —O—($C_{1-2}$ alkyl), —O—($C_{1-2}$ haloalkyl), —OH, =O, —C(O)R* and —C(O)NR*R*; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from thiophenyl, pyrrolyl and pyrazolyl, preferably thiophenyl and pyrrolyl, wherein said thiophenyl, pyrrolyl and pyrazolyl is independently optionally substituted with methyl or ethyl, or $R^1$ is selected from a formula (A) and (B)

(A)

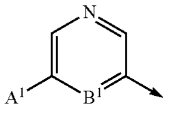

-continued (B)

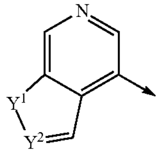, wherein $Y^1$ is NH, N($C_{1-2}$ alkyl) or $CH_2$, and $Y^2$ is N or CH, and wherein $B^1$ is N or CH, and $A^1$ is selected from hydrogen, —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, and a 4-6 membered monocyclic heterocyclyl comprising 1 or 2 heteroatoms selected from O and N, wherein said monocyclic heterocyclyl is optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH and =O; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$alkylene substituted with 1 to 4 F, —$CH_2$—O—$CH_2$— and —$CH_2$—NH—$CH_2$—; and wherein the arrow denotes the bond in the compounds of formula (I).

In a further preferred embodiment, said $R^1$ is selected from a formula (A) and (B)

(A)

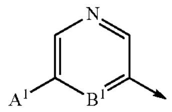

(B)

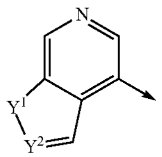, wherein $Y^1$ is NH, N($C_{1-2}$ alkyl) or $CH_2$, and $Y^2$ is N or CH, and wherein $B^1$ is N or CH, and $A^1$ is selected from hydrogen, —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, and a 4-6 membered monocyclic heterocyclyl comprising 1 or 2 heteroatoms selected from O and N, wherein said monocyclic heterocyclyl is optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH and =O; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$alkylene substituted with 1 to 4 F, —$CH_2$—O—$CH_2$— and —$CH_2$—NH—$CH_2$—; and wherein the arrow denotes the bond in the compounds of formula (I).

In a further preferred embodiment, said $R^1$ is of a formula (B)

(B)

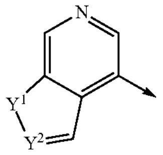, wherein $Y^1$ is NH, N($C_{1-2}$ alkyl) or $CH_2$, and $Y^2$ is N or CH, and wherein the arrow denotes the bond in the compounds of formula (I).

In a further preferred embodiment, said $R^1$ is of a formula (A)

(A)

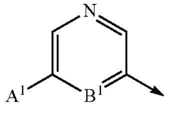, wherein $B^1$ is N or CH, and $A^1$ is selected from hydrogen, —$C_{1-2}$ alkyl, —$CHF_2$, —$CF_3$, —O—($C_{1-2}$ alkyl), —$OCHF_2$, —$OCHF_3$, —OH, =O, and a 4-6 membered monocyclic heterocyclyl comprising 1 or 2 heteroatoms selected from O and N, wherein said monocyclic heterocyclyl is optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH, —O—($C_{1-2}$alkylene)-OR*, —O—($C_{1-2}$alkylene)-N($R^{\circ\circ}$)$_2$ and =O; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$ alkylene substituted with 1 to 4 F, —$CH_2$—O—$CH_2$— and —$CH_2$—NH—$CH_2$—; and wherein the arrow denotes the bond in the compounds of formula (I).

In a further preferred embodiment, said $R^1$ is of a formula (A)

(A)

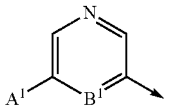, wherein $B^1$ is CH, and $A^1$ is selected from hydrogen, —$C_{1-2}$ alkyl, —$CHF_2$, —$CF_3$, —O—($C_{1-2}$ alkyl), —$OCHF_2$, —$OCHF_3$, —OH, ═O, and a 4-6 membered monocyclic heterocyclyl comprising 1 or 2 heteroatoms selected from O and N, wherein said monocyclic heterocyclyl is optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH, —O—($C_{1-2}$alkylene)-OR*, —O—($C_{1-2}$alkylene)-N($R^{\circ\circ}$)$_2$ and ═O; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—; and wherein the arrow denotes the bond in the compounds of formula (I).

In a further very preferred embodiment, said $R^1$ is of a formula (A)

(A)

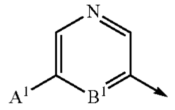

, wherein $B^1$ is CH and $A^1$ is hydrogen, and wherein the arrow denotes the bond in the compounds of formula (I). Thus, in a further very preferred embodiment, said $R^1$ is 3-pyridyl.

In a further preferred embodiment, said $R^1$ is of a formula (A)

(A)

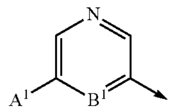

, wherein $B^1$ is N, and $A^1$ is selected from hydrogen and —$C_{1-2}$ alkyl; and wherein the arrow denotes the bond in the compounds of formula (I).

In a further preferred embodiment, said $R^1$ is of a formula (A)

(A)

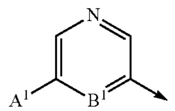

, wherein $B^1$ is N, and $A^1$ is hydrogen, and wherein the arrow denotes the bond in the compounds of formula (I). Thus, in a further very preferred embodiment, said $R^1$ is 2-pyrazinyl.

In a further preferred embodiment, $R^3$ is phenyl or pyridyl, each of which is optionally substituted with one or more, preferably one or two, substituents selected from halogen, —$C_{1-6}$ alkyl, $C_{1-6}$ haloalkyl, —O—$C_{1-6}$ alkyl, and —O—$C_{1-6}$ haloalkyl. In a further preferred embodiment, $R^3$ is phenyl or pyridyl, each of which is optionally substituted with one or more, preferably one or two, substituents selected from halogen, —$C_{1-3}$ alkyl, $C_{1-2}$ haloalkyl, —O—$C_{1-2}$ alkyl, and —O—$C_{1-3}$ haloalkyl. In a further preferred embodiment, $R^3$ is phenyl or pyridyl, each of which is optionally substituted with one or more, preferably one or two, substituents selected from —F, —Cl, —$C_{1-2}$ alkyl, $C_1$ haloalkyl, —$OCH_3$. In a further preferred embodiment, $R^3$ is phenyl or pyridyl, each of which is optionally substituted with one or more, preferably one or two, substituents selected from —F, —Cl, —$CH_3$ and —$OCH_3$. In a further preferred embodiment, $R^3$ is phenyl or pyridyl, each of which is optionally substituted with one substituent selected from —F, —Cl, —$CH_3$ and —$OCH_3$. In a further preferred embodiment, $R^3$ is phenyl or 3-pyridyl or 4-pyridyl, each of which is optionally substituted with one substituent selected from —F, —Cl, —$CH_3$ and —$OCH_3$. In a further preferred embodiment, $R^3$ is phenyl, 3-pyridyl or 4-pyridyl, each of which is optionally substituted at the meta position of said phenyl, 3-pyridyl or 4-pyridyl with one substituent selected from —F, —Cl, —$CH_3$ and —$OCH_3$. In a further preferred embodiment, $R^3$ is phenyl or phenyl substituted at the meta position with one substituent selected from —F, —Cl, —$CH_3$ and —$OCH_3$. In a further preferred embodiment, $R^3$ is 3-pyridyl or 3-pyridyl substituted at the meta position (5 position) with one substituent selected from —F, —Cl, —$CH_3$ and —$OCH_3$. In a further preferred embodiment, $R^3$ is 4-pyridyl or 4-pyridyl substituted at the meta position (5 position) with one substituent selected from —F, —Cl, —$CH_3$ and —$OCH_3$. In a further preferred embodiment, $R^3$ is phenyl. In a further preferred embodiment, $R^3$ is 3-pyridyl. In a further preferred embodiment, $R^3$ is 4-pyridyl.

$R^3$ is selected from -(optionally substituted heterocyclyl), -(optionally substituted carbocyclyl), -(optionally substituted $C_{1-6}$ alkylene)-(optionally substituted heterocyclyl) and -(optionally substituted $C_{1-6}$ alkylene)-(optionally substituted carbocyclyl). Preferably, $R^3$ is -(optionally substituted carbocyclyl). More preferably, $R^3$ is phenyl which is optionally substituted with one or more groups selected from halogen, —($C_{1-6}$ alkyl which is optionally substituted with one or more F) and —O—($C_{1-6}$ alkyl which is optionally substituted with one or more F). Further preferred are compounds in which $R^3$ is pyridinyl which may have the same substituents as the optionally substituted heterocyclyl. In other preferred compounds, $R^3$ is quinazoline or cinnoline, each of which may have the same substituents as the optionally substituted heterocyclyl.

In a further preferred embodiment, said $R^3$ is selected from phenyl, a 6-membered monocyclic heteroaryl and a 8-10 membered bicyclic heteroaryl, each independently comprising one or more, typically 1 to 5, preferably 1 to 4, ring heteroatoms independently selected from O, B, S and N, wherein one or two carbon ring atoms of said monocyclic heteroaryl or said bicyclic heteroaryl are optionally oxidized typically and preferably leading to a C═O functionality, and wherein said phenyl, said 6-membered monocyclic heteroaryl and said 8-10 membered bicyclic heteroaryl is independently optionally substituted with one or more, typically and preferably with 1 to 5, further preferably with 1 to 4, and again further preferably with 1 to 3 substituents selected from halogen, —$C_{1-6}$ alkyl, $C_{1-6}$ haloalkyl, —O—($C_{1-6}$ alkyl), —O—($C_{1-6}$ haloalkyl), —OH, —CN, ═O, —C(O)R*, —COOR*, —C(O)NR*R*, —NR*R*, —N(R**)—C(O)R*, —N(R**)—C(O)—OR*, —N(R**)—C(O)—NR*R*, —O—C(O)R*, —O—C(O)—NR*R*, and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl, cyclopropyl, cyclobutyl, oxetanyl, —$C_{1-2}$alkylene-OH, —$C_{1-2}$alkylene-O($C_{1-2}$alkyl), phenyl, and wherein each R** is independently selected from H, $C_{1-4}$ alkyl, $C_{1-4}$ haloalkyl, and/or wherein each monocyclic heterocyclyl is independently optionally substituted with one bivalent substituent selected from $C_{1-3}$ alkylene such as —$CH_2$—$CH_2$— and —$CH_2$—$CH_2$—$CH_2$—, $C_{1-3}$ alkylene substituted with 1 to 4 F, —$CH_2$—O—$CH_2$— and —$CH_2$—NH—$CH_2$—.

In a further preferred embodiment, said $R^3$ is selected from formula (C), formula (D), formula (E), formula (F) and formula (G)

(C)

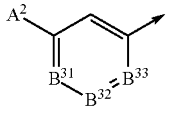

(D)

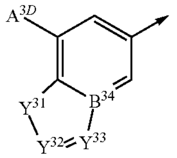

(E)

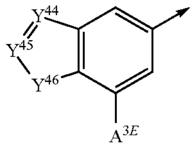

(F)

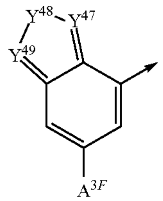

(G)

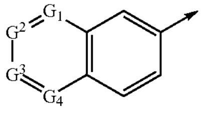

wherein $B^{31}$ is N, CH or C($A^{31}$), wherein $A^{31}$ is selected from —$C_{1-2}$ alkyl, $C_{1-2}$ haloalkyl, —F, —Cl, —O($C_{1-2}$alkyl), —OH, —NHC(O)($C_{1-2}$alkyl), wherein $A^{31}$ is selected from —$C_{1-2}$ alkyl, $C_{1-2}$ haloalkyl, —F, —Cl, —O($C_{1-2}$alkyl), —OH, —NHC(O)($C_{1-2}$alkyl);

$B^{32}$ is N, CH or C($A^{32}$), wherein $A^{32}$ is selected from —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl, phenyl, and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—;

In a further preferred embodiment, $B^{32}$ is N, CH or C($A^{32}$), wherein $A^{32}$ is selected from —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl and phenyl;

In a further preferred embodiment, $B^{32}$ is N, CH or C($A^{32}$), wherein $A^{32}$ is selected from —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$alkylene-OR*, —C(O)R* and —C(O)NR*R*; wherein each R* is independently selected from H, $C_{1-3}$ alkyl, $C_{1-3}$ haloalkyl and phenyl;

$B^{33}$ is N, CH or C($A^{33}$), wherein $A^{33}$ is selected from —$C_{1-2}$ alkyl, $C_{1-2}$ haloalkyl, —F, —Cl, —O($C_{1-2}$alkyl), —OH, —NHC(O)($C_{1-2}$alkyl);

$A^2$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl, phenyl, and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—;

In a further preferred embodiment, $A^2$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC (O)(phenyl), and 3-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$ alkylene-OR*, —C(O)R* and —C(O)NR*R*; wherein each R* is independently selected from H, $C_{1-4}$ alkyl, $C_{1-4}$ haloalkyl and phenyl;

In a further preferred embodiment, $A^2$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$ alkylene-OR*, —C(O)R* and —C(O)NR*R*; wherein each R* is independently selected from H, $C_{1-3}$ alkyl, $C_{1-3}$ haloalkyl and phenyl;

and wherein $Y^{41}$ is N, CH or C($A^{41}$), wherein $A^{41}$ is selected from methyl and ethyl; $Y^{42}$ is N, CH or C($A^{42}$), wherein $A^{42}$ is selected from methyl and ethyl; $Y^{43}$ is N, CH or C($A^{43}$), wherein $A^{43}$ is selected from methyl and ethyl;

$A^{3D}$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl); In a further preferred embodiment, $A^{3E}$ is selected from hydrogen, —$C_{1-2}$ alkyl, $C_{1-2}$ haloalkyl, —F, —Cl, —O($C_{1-2}$alkyl), =O, —OH;

and wherein $Y^{44}$ is N, NH, N($A^{44}$), C(O), CH or C($A^{44}$), wherein $A^{44}$ is independently selected from methyl and ethyl; $Y^{45}$ is N, NH, N($A^{45}$), C(O), CH or C($A^{45}$), wherein $A^{45}$ is independently selected from methyl and ethyl; $Y^{46}$ is N, NH, N($A^{46}$), C(O), CH or C($A^{46}$), wherein $A^{46}$ is independently selected from methyl and ethyl; and wherein at least one of said $Y^{44}$, $Y^{45}$ and $Y^{46}$ is NH, N($CH_3$) or N($C_2H_5$); and wherein $A^{3E}$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl); In a further preferred embodiment, $A^{3E}$ is selected from hydrogen, —$C_{1-2}$ alkyl, $C_{1-2}$ haloalkyl, —F, —Cl, —O($C_{1-2}$alkyl), =O, —OH;

and wherein $Y^{47}$ is N, NH, N($A^{47}$), C(O), CH or C($A^{47}$), wherein $A^{47}$ is independently selected from methyl and ethyl; $Y^{48}$ is N, NH, N($A^{48}$), C(O), CH or C($A^{48}$), wherein $A^{48}$ is independently selected from methyl and ethyl; $Y^{49}$ is N, NH, N($A^{49}$), C(O), CH or C($A^{49}$), wherein $A^{49}$ is independently selected from methyl and ethyl; and wherein at least one of said $Y^{47}$, $Y^{48}$ and $Y^{49}$ is NH, N($CH_3$) or N($C_2H_5$);

$A^{3F}$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl); In a further preferred embodiment, $A^{3E}$ is selected from hydrogen, —$C_{1-2}$ alkyl, $C_{1-2}$ haloalkyl, —F, —Cl, —O($C_{1-2}$alkyl), =O, —OH;

and wherein $G^1$, $G^2$, $G^3$, $G^4$ is independently selected from N, CH, C(O), NH or N($C_{1-2}$ alkyl); and wherein the arrow denotes the bond in the compounds of formula (I).

In a further preferred embodiment, said $R^3$ is selected from the following formulas

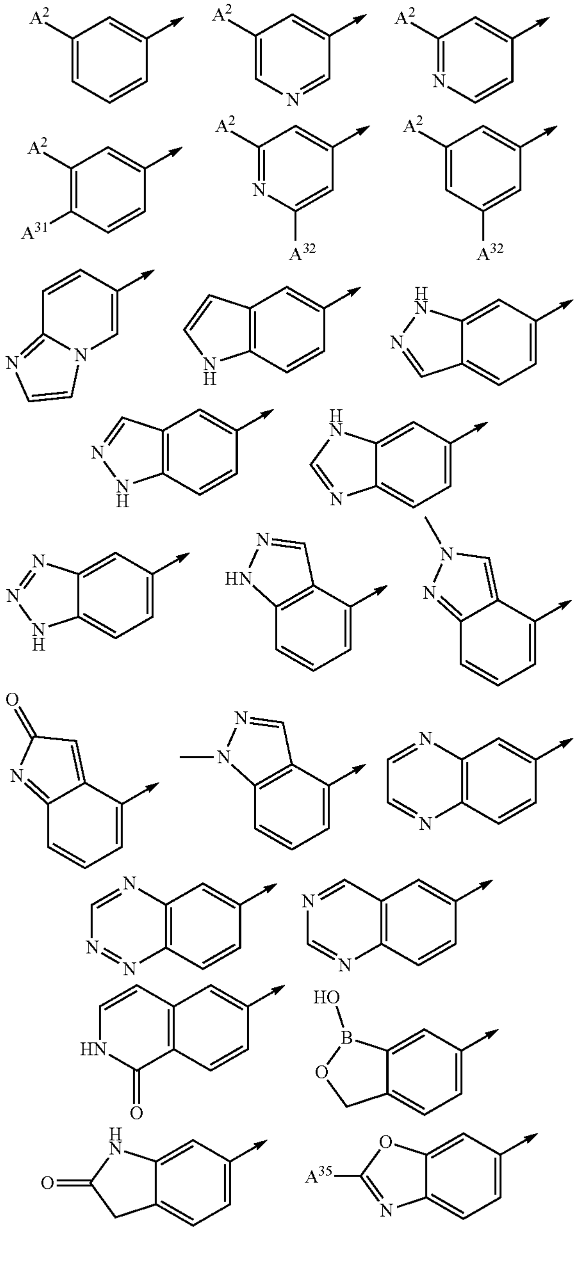

wherein $A^2$ is independently selected for each formula from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, ═O, —$C_{1-3}$alkylene-OR*, —C(O)R* and —C(O)NR*R*; wherein each R* is independently selected from H, $C_{1-4}$ alkyl, $C_{1-4}$ haloalkyl, phenyl, and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—;

In a further preferred embodiment, $A^2$ is independently selected for each formula from hydrogen, —$C_{1-2}$ alkyl, $C_{1-2}$ haloalkyl, —F, —Cl, —O($C_{1-2}$alkyl), ═O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, ═O, —$C_{1-3}$alkylene-OR*, —C(O)R* and —C(O)NR*R*; wherein each R* is independently selected from H, $C_{1-4}$ alkyl, $C_{1-4}$ haloalkyl and phenyl;

In a further preferred embodiment, $A^2$ is independently selected for each formula from hydrogen, —$C_{1-2}$ alkyl, $C_{1-2}$ haloalkyl, —F, —Cl, —O($C_{1-2}$alkyl), ═O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, ═O, —$C_{1-3}$alkylene-OR*, —C(O)R* and —C(O)NR*R*; wherein each R* is independently selected from H, $C_{1-3}$ alkyl, $C_{1-3}$ haloalkyl and phenyl;

$A^{31}$ is independently selected for each formula from —$C_{1-2}$ alkyl, $C_{1-2}$ haloalkyl, —F, —Cl, —O($C_{1-2}$alkyl), —OH, —NHC(O)($C_{1-2}$alkyl);

$A^{32}$ is independently selected for each formula from —$C_{1-2}$ alkyl, $C_{1-2}$ haloalkyl, —F, —Cl, —O($C_{1-2}$alkyl), ═O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, ═O, —$C_{1-3}$alkylene-OR*, —C(O)R* and —C(O)NR*R*; wherein each R* is independently selected from H, $C_{1-4}$ alkyl, $C_{1-4}$ haloalkyl, phenyl, and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—;

In a further preferred embodiment, $A^{32}$ is independently selected for each formula from —$C_{1-2}$ alkyl, $C_{1-2}$ haloalkyl, —F, —Cl, —O($C_{1-2}$alkyl), ═O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, ═O, —$C_{1-3}$alkylene-OR*, —C(O)R* and —C(O)NR*R*; wherein each R* is independently selected from H, $C_{1-4}$ alkyl, $C_{1-4}$ haloalkyl and phenyl;

In a further preferred embodiment, $A^{32}$ is independently selected for each formula from —$C_{1-2}$ alkyl, $C_{1-2}$ haloalkyl, —F, —Cl, —O($C_{1-2}$alkyl), ═O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, ═O, —$C_{1-3}$alkylene-OR*, —C(O)R* and —C(O)NR*R*; wherein each R* is independently selected from H, $C_{1-3}$ alkyl, $C_{1-3}$ haloalkyl and phenyl; and wherein $A^{35}$ is independently selected for each formula from —$C_{1-2}$ alkyl; and wherein the arrow denotes the bond in the compounds of formula (I).

In a further very preferred embodiment, said $R^3$ is selected from the formulas

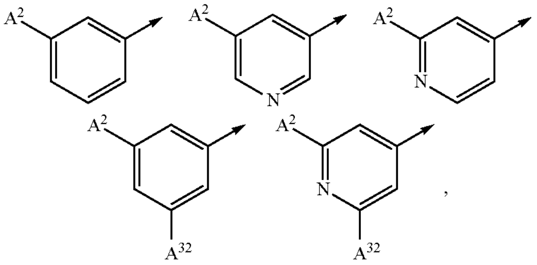

, wherein $A^2$ and $A^{32}$ are independently selected for each formula from hydrogen, —$C_{1-2}$ alkyl, $C_{1-2}$ haloalkyl, —F, —Cl, —O($C_{1-2}$alkyl), ═O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, ═O, —$C_{1-3}$ alkylene-OR*, —C(O)R* and —C(O)NR*R*; wherein each R* is independently selected from H, $C_{1-3}$ alkyl, $C_{1-3}$ haloalkyl and phenyl; and In a further very preferred embodiment, said $R^3$ is selected from the formulas

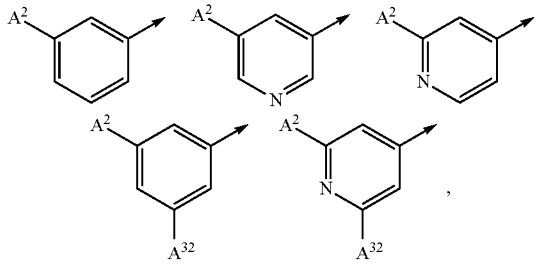
, wherein $A^2$ are independently selected for each formula from hydrogen, —$C_{1-2}$ alkyl, $C_{1-2}$ haloalkyl, —F, —Cl, —O($C_{1-2}$alkyl); and wherein $A^{32}$ is independently selected for each formula from —$C_{1-2}$ alkyl, $C_{1-2}$ haloalkyl, —F, —Cl, —O($C_{1-2}$alkyl), ═O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, ═O, —$C_{1-3}$ alkylene-OR*, —C(O)R* and —C(O)NR*R*; wherein each R* is independently selected from H, $C_{1-3}$ alkyl, $C_{1-3}$ haloalkyl and phenyl.

In a further very preferred embodiment, said $R^3$ is selected from the formulas

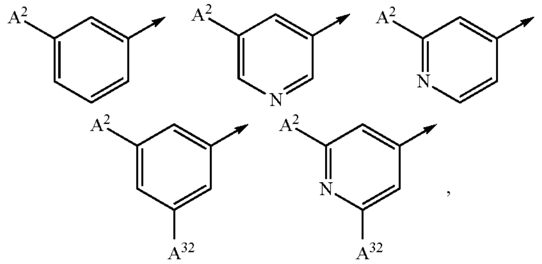
, wherein $A^2$ are independently selected for each formula from hydrogen, —$C_{1-2}$ alkyl, $C_{1-2}$ haloalkyl, —F; and wherein $A^{32}$ is independently selected for each formula from —$C_{1-2}$ alkyl, $C_{1-2}$ haloalkyl, —F, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 3 heteroatoms selected from O and N, each monocyclic heterocyclyl independently optionally substituted with one or two substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, ═O, —$C_{1-3}$alkylene-OR*, —C(O)R* and —C(O)NR*R*; wherein each R* is independently selected from H, $C_{1-3}$ alkyl, $C_{1-3}$ haloalkyl and phenyl.

In a very preferred embodiment, said compound of formula (V) is a compound selected from a compound of formula (VI), (VIa) and (IVb). In a very preferred embodiment, said compound of formula (V) is a compound of formula (VI). In a very preferred embodiment, said compound of formula (V) is a compound of formula (VIa). In a very preferred embodiment, said compound of formula (V) is a compound of formula and (VIb).

Thus, in a further aspect and embodiment, the present invention provides a compound of formula (I), wherein said compound of formula (I) is a compound of formula (VI), preferably of formula (VIa), and further preferably of formula (VIb), optionally in the form of a pharmaceutically acceptable salt, solvate, cocrystal, tautomer, racemate, enantiomer, or diastereomer or mixture thereof, for use in a method of treating fibrotic disease (VI)

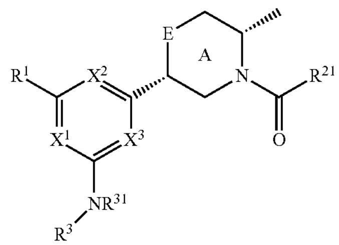

(VIa)

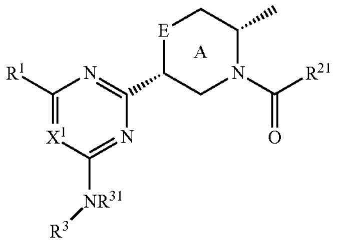

(VIb)

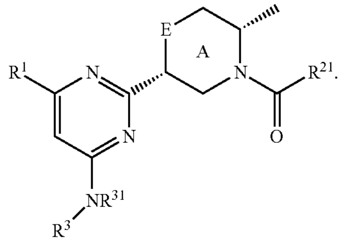

In again a further aspect and embodiment, the present invention provides a compound of formula (I), wherein said compound of formula (I) is a compound of formula (VII), preferably of formula (VIIa) and further preferably of formula (VIIb), optionally in the form of a pharmaceutically acceptable salt, solvate, cocrystal, tautomer, racemate, enantiomer, or diastereomer or mixture thereof, for use in a method of treating fibrotic disease (VII)

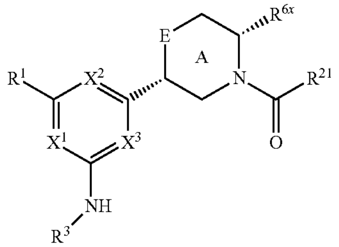

-continued (VIIa)

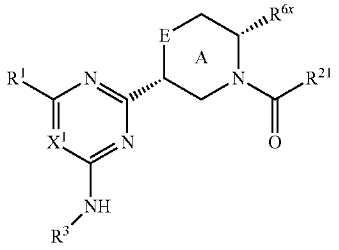

(VIIb)

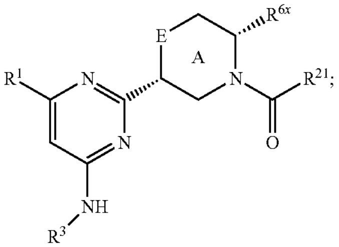

and in a further aspect and embodiment, the present invention provides a compound of formula (I), wherein said compound of formula (I) is a compound of formula (VIII), preferably of formula (VIIIa) and further preferably of formula (VIIIb), optionally in the form of a pharmaceutically acceptable salt, solvate, cocrystal, tautomer, racemate, enantiomer, or diastereomer or mixture thereof, for use in a method of treating fibrotic disease (VIII)

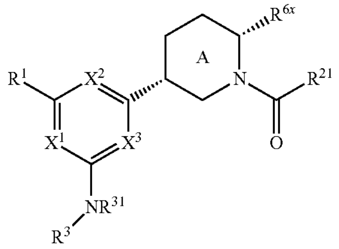

(VIIIa)

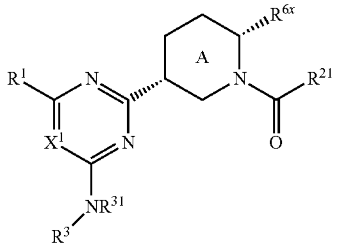

(VIIIb)

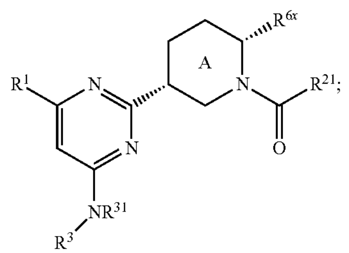

and in again a further aspect and embodiment, the present invention provides a compound of formula (I), wherein said compound of formula (I) is a compound of formula (IX), preferably of formula (IXa) and further preferably of formula (IXb), optionally in the form of a pharmaceutically acceptable salt, solvate, cocrystal, tautomer, racemate, enantiomer, or diastereomer or mixture thereof, for use in a method of treating fibrotic disease (IX)

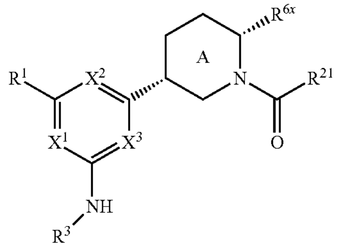

(IXa)

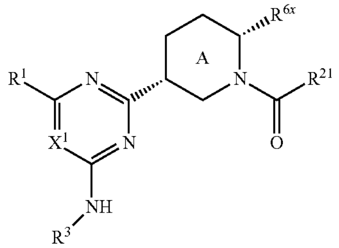

(IXb)

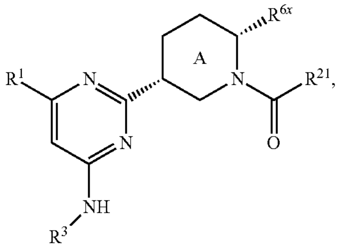

wherein $R^1$ is selected from -(optionally substituted heterocyclyl) and -(optionally substituted carbocyclyl).

In a further preferred embodiment, said $R^1$ is selected from phenyl, a 5- or 6-membered monocyclic heteroaryl and a 8-10 membered bicyclic heteroaryl, each independently comprising one or more, preferably 1 to 5, ring heteroatoms independently selected from O, S and N, wherein one or two carbon ring atoms of said monocyclic heteroaryl or said bicyclic heteroaryl are optionally oxidized, and wherein said phenyl, said 5- or 6-membered monocyclic heteroaryl and said 8-10 membered bicyclic heteroaryl is independently optionally substituted with one or more, preferably one or two, substituents selected from halogen, —$C_{1-6}$ alkyl, $C_{1-6}$ haloalkyl, —O—($C_{1-6}$ alkyl), —O—($C_{1-6}$ haloalkyl), —OH, —($C_{1-2}$alkylene)-O—($C_{1-4}$alkylene)-OR*, —O—($C_{1-4}$alkylene)-OR*, —($C_{1-2}$alkylene)-O—($C_{1-4}$alkylene)-N($R^{\circ\circ}$)$_2$, —O—($C_{1-4}$alkylene)-N($R^{\circ\circ}$)$_2$, —CN, ═O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 3-6 membered monocyclic carbocyclyl and 3-6 membered monocyclic heterocyclyl comprising 1 to 4 heteroatoms selected from O, S and N, each monocyclic carbocyclyl and heterocyclyl independently optionally substituted with one or more, preferably one or two, substituents independently selected from halogen, —$C_{1-4}$ alkyl, $C_{1-4}$ haloalkyl, —O—($C_{1-4}$ alkyl), —O—($C_{1-4}$ haloalkyl), —OH, ═O, —C(O)R* and —C(O)

NR*R*; wherein each R* is independently selected from H, $C_{1-4}$ alkyl, $C_{1-4}$ haloalkyl, and wherein each $R^{\circ\circ}$ is independently selected from H, $C_{1-4}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from phenyl, a 5- or 6-membered monocyclic heteroaryl and a 8-10 membered bicyclic heteroaryl, each independently comprising one or more, preferably 1 to 5, ring heteroatoms independently selected from O, S and N, wherein one or two carbon ring atoms of said monocyclic heteroaryl or said bicyclic heteroaryl are optionally oxidized, and wherein said phenyl, said 5- or 6-membered monocyclic heteroaryl and said 8-10 membered bicyclic heteroaryl is independently optionally substituted with one or more, preferably one or two, substituents independently selected from halogen, —$C_{1-4}$ alkyl, $C_{1-4}$ haloalkyl, —O—($C_{1-4}$ alkyl), —O—($C_{1-4}$ haloalkyl), —OH, —($C_{1-2}$alkylene)-O—($C_{1-4}$alkylene)-OR*, —O—($C_{1-4}$alkylene)-OR*, —($C_{1-2}$alkylene)-O—($C_{1-4}$alkylene)-N($R^{\circ\circ}$)$_2$, —O—($C_{1-4}$alkylene)-N($R^{\circ\circ}$)$_2$, ═O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 3-6 membered monocyclic heterocyclyl comprising 1 to 4 heteroatoms selected from O, S and N, each monocyclic heterocyclyl independently optionally substituted with one or more, preferably one or two, substituents selected from halogen, —$C_{1-3}$ alkyl, $C_{1-3}$ haloalkyl, —O—($C_{1-3}$ alkyl), —O—($C_{1-3}$ haloalkyl), —OH, ═O, —C(O)R* and —C(O)NR*R*; wherein each R* is independently selected from H, $C_{1-3}$ alkyl, $C_{1-3}$ haloalkyl, and wherein each $R^{\circ\circ}$ is independently selected from H, $C_{1-4}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$alkylene substituted with 1 to 4 F, —$CH_2$—O—$CH_2$— and —$CH_2$—NH—$CH_2$—.

In a further preferred embodiment, said $R^1$ is selected from phenyl, a 5- or 6-membered monocyclic heteroaryl and a 8-10 membered bicyclic heteroaryl, each independently comprising one or more, preferably 1 to 5, ring heteroatoms independently selected from O, S and N, wherein one or two carbon ring atoms of said monocyclic heteroaryl or said bicyclic heteroaryl are optionally oxidized, and wherein said phenyl, said 5- or 6-membered monocyclic heteroaryl and said 8-10 membered bicyclic heteroaryl is independently optionally substituted with one or more, preferably one or two, substituents independently selected from —F, —Cl, —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, ═O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 3-6 membered monocyclic heterocyclyl comprising 1 to 4 heteroatoms selected from O, S and N, each monocyclic heterocyclyl independently optionally substituted with one or more, preferably one or two, substituents selected from —$C_{1-2}$ alkyl, $C_{1-2}$ haloalkyl, —O—($C_{1-2}$ alkyl), —O—($C_{1-2}$ haloalkyl), —OH, ═O, —C(O)R* and —C(O)NR*R*; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from phenyl, a 5- or 6-membered monocyclic heteroaryl comprising one or two heteroatoms independently selected from S and N and a 8-10 membered bicyclic heteroaryl comprising one or more, preferably 1 to 4, ring nitrogen heteroatoms, wherein one or two, preferably one, carbon ring atoms of said monocyclic heteroaryl or said bicyclic heteroaryl are optionally oxidized, and wherein said phenyl, said 5- or 6-membered monocyclic heteroaryl and said 8-10 membered bicyclic heteroaryl is independently optionally substituted with one or more, preferably one or two, substituents independently selected from —F, —Cl, —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, ═O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 3-6 membered monocyclic heterocyclyl comprising 1 to 4 heteroatoms selected from O, S and N, each monocyclic heterocyclyl independently optionally substituted with one or more, preferably one or two, substituents selected from —$C_{1-2}$ alkyl, $C_{1-2}$ haloalkyl, —O—($C_{1-2}$ alkyl), —O—($C_{1-2}$ haloalkyl), —OH, ═O, —C(O)R* and —C(O)NR*R*; wherein each R* is independently selected from H, $C_{1-2}$ alkyl, $C_{1-2}$ haloalkyl, and wherein each $R^{\circ\circ}$ is independently selected from H, $C_{1-2}$alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from a 5- or 6-membered monocyclic heteroaryl comprising one or two heteroatoms independently selected from S and N and a 8-10 membered bicyclic heteroaryl comprising 1 to 5, preferably 1 to 4, ring nitrogen heteroatoms, wherein one or two, preferably one, carbon ring atoms of said monocyclic heteroaryl or said bicyclic heteroaryl are optionally oxidized, and wherein said 5- or 6-membered monocyclic heteroaryl and said 8-10 membered bicyclic heteroaryl is independently optionally substituted with one or two substituents independently selected from —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, ═O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 4-6 membered monocyclic heterocyclyl comprising 1 or 2 heteroatoms selected from O and N, each monocyclic heterocyclyl independently optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH, ═O, —C(O)R* and —C(O)NR*R*; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from a 5- or 6-membered monocyclic heteroaryl comprising one or two heteroatoms independently selected from S and N and a 8-10 membered bicyclic heteroaryl comprising 1 to 5, preferably 1 to 4, ring nitrogen heteroatoms, wherein one or two, preferably one, carbon ring atoms of said monocyclic heteroaryl or said bicyclic heteroaryl are optionally oxidized, and wherein said 5- or 6-membered monocyclic heteroaryl and said 8-10 membered bicyclic heteroaryl is independently optionally substituted with one or two, preferably one, substituents independently selected from —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, and 4-6 membered monocyclic heterocyclyl comprising 1 or 2 heteroatoms selected from 0 and N, each monocyclic heterocyclyl independently optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH and =O; wherein each R* is independently selected from H, $C_{1-2}$ alkyl, $C_{1-2}$ haloalkyl, and wherein each $R^{\circ\circ}$ is independently selected from H, $C_{1-2}$alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$ alkylene substituted with 1 to 4 F, —$CH_2$—O—$CH_2$— and —$CH_2$—NH—$CH_2$—.

In a further preferred embodiment, said $R^1$ is phenyl, thiophenyl, pyrrolyl, pyrazolyl, azaindolyl, azaindazolyl, pyrazinyl, pyridyl or pyrimidinyl, wherein the phenyl, thiophenyl, pyrrolyl, pyrazolyl, azaindolyl, azaindazolyl, pyrazinyl, pyridyl or pyrimidinyl is optionally substituted with one or two, preferably one, substituents independently selected from —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 4-6 membered monocyclic heterocyclyl comprising 1 or 2 heteroatoms selected from O and N, each monocyclic heterocyclyl optionally substituted with one or two, preferably one, substituents independently selected from —$C_{1-2}$ alkyl, $C_{1-2}$ haloalkyl, —O—($C_{1-2}$ alkyl), —O—($C_{1-2}$ haloalkyl), —OH, =O, —C(O)R* and —C(O)NR*R*; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is phenyl, thiophenyl, pyrrolyl, pyrazolyl, azaindolyl, azaindazolyl, pyrazinyl, pyridyl or pyrimidinyl, wherein the phenyl, thiophenyl, pyrrolyl, pyrazolyl, azaindolyl, azaindazolyl, pyrazinyl, pyridyl or pyrimidinyl is optionally substituted with one or two, preferably one, substituents independently selected from —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, and 4-6 membered monocyclic heterocyclyl comprising 1 or 2 heteroatoms selected from 0 and N, each monocyclic heterocyclyl optionally substituted with one or two, preferably one, substituents independently selected from —$C_{1-2}$ alkyl, $C_{1-2}$ haloalkyl, —O—($C_{1-2}$ alkyl), —O—($C_{1-2}$ haloalkyl), —OH and =O; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from a 5-membered monocyclic heteroaryl comprising one or two heteroatoms selected from S and N, wherein said 5-membered monocyclic heteroaryl is optionally substituted with one or two, preferably one, substituents selected from —$C_{1-2}$ alkyl, or $R^1$ is selected from a formula (A) and (B)

(A)

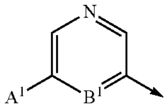

(B)

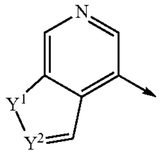

, wherein $Y^1$ is NH, N($C_{1-2}$ alkyl) or $CH_2$, and $Y^2$ is N or CH, and wherein $B^1$ is N or CH, and $A^1$ is selected from hydrogen, —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 4-6 membered monocyclic heterocyclyl comprising 1 or 2 heteroatoms selected from O and N, each monocyclic heterocyclyl optionally substituted with one or two, preferably one, substituents independently selected from —$C_{1-2}$ alkyl, $C_{1-2}$ haloalkyl, —O—($C_{1-2}$ alkyl), —O—($C_{1-2}$ haloalkyl), —OH, =O, —C(O)R* and —C(O)NR*R*; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from thiophenyl, pyrrolyl and pyrazolyl, preferably thiophenyl and pyrrolyl, wherein said thiophenyl, pyrrolyl and pyrazolyl is independently optionally substituted with methyl or ethyl, or $R^1$ is selected from a formula (A) and (B)

(A)

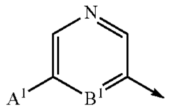

(B)

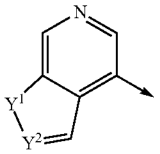

, wherein $Y^1$ is NH, N($C_{1-2}$ alkyl) or $CH_2$, and $Y^2$ is N or CH, and wherein $B^1$ is N or CH, and $A^1$ is selected from hydrogen, —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, and a 4-6 membered monocyclic heterocyclyl comprising 1 or 2 heteroatoms selected from O and N, wherein said monocyclic heterocyclyl is optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH and =O; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$alkylene substituted with 1 to 4 F, —$CH_2$—O—$CH_2$— and —$CH_2$—NH—$CH_2$—; and wherein the arrow denotes the bond in the compounds of formula (I).

In a further preferred embodiment, said $R^1$ is selected from a formula (A) and (B)

(A)

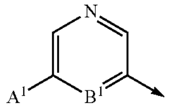

(B)

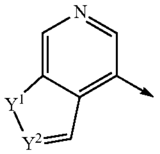

, wherein $Y^1$ is NH, N($C_{1-2}$ alkyl) or $CH_2$, and $Y^2$ is N or CH, and wherein $B^1$ is N or CH, and $A^1$ is selected from hydrogen, —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, and a 4-6 membered monocyclic heterocyclyl comprising 1 or 2 heteroatoms selected from O and N, wherein said monocyclic heterocyclyl is optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH and =O; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$alkylene substituted with 1 to 4 F, —$CH_2$—O—$CH_2$— and —$CH_2$—NH—$CH_2$—; and wherein the arrow denotes the bond in the compounds of formula (I).

In a further preferred embodiment, said $R^1$ is of a formula (B)

(B)

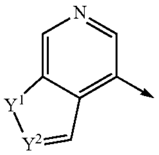

, wherein $Y^1$ is NH, N($C_{1-2}$ alkyl) or $CH_2$, and $Y^2$ is N or CH, and wherein the arrow denotes the bond in the compounds of formula (I).

In a further preferred embodiment, said $R^1$ is of a formula (A)

(A)

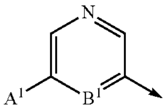

, wherein $B^1$ is N or CH, and $A^1$ is selected from hydrogen, —$C_{1-2}$ alkyl, —$CHF_2$, —$CF_3$, —O—($C_{1-2}$ alkyl), —$OCHF_2$, —$OCHF_3$, —OH, =O, and a 4-6 membered monocyclic heterocyclyl comprising 1 or 2 heteroatoms selected from O and N, wherein said monocyclic heterocyclyl is optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH, —O—($C_{1-2}$alkylene)-OR*, —O—($C_{1-2}$alkylene)-N($R^{\circ\circ}$)$_2$ and =O; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$ alkylene substituted with 1 to 4 F, —$CH_2$—O—$CH_2$— and —$CH_2$—NH—$CH_2$—; and wherein the arrow denotes the bond in the compounds of formula (I).

In a further preferred embodiment, said $R^1$ is of a formula (A)

(A)

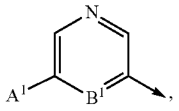

wherein $B^1$ is CH, and $A^1$ is selected from hydrogen, —$C_{1-2}$ alkyl, —$CHF_2$, —$CF_3$, —O—($C_{1-2}$ alkyl), —$OCHF_2$, —$OCHF_3$, —OH, ═O, and a 4-6 membered monocyclic heterocyclyl comprising 1 or 2 heteroatoms selected from O and N, wherein said monocyclic heterocyclyl is optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH, —O—($C_{1-2}$alkylene)-OR*, —O—($C_{1-2}$alkylene)-N($R^{\circ\circ}$)$_2$ and ═O; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—; and wherein the arrow denotes the bond in the compounds of formula (I).

In a further very preferred embodiment, said $R^1$ is of a formula (A)

(A)

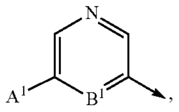

wherein $B^1$ is CH and $A^1$ is hydrogen, and wherein the arrow denotes the bond in the compounds of formula (I). Thus, in a further very preferred embodiment, said $R^1$ is 3-pyridyl.

In a further preferred embodiment, said $R^1$ is of a formula (A)

(A)

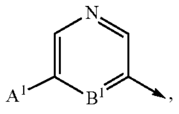

wherein $B^1$ is N, and $A^1$ is selected from hydrogen and —$C_{1-2}$ alkyl; and wherein the arrow denotes the bond in the compounds of formula (I).

In a further preferred embodiment, said $R^1$ is of a formula (A)

(A)

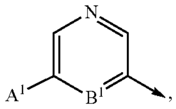

wherein $B^1$ is N, and $A^1$ is hydrogen, and wherein the arrow denotes the bond in the compounds of formula (I). Thus, in a further very preferred embodiment, said $R^1$ is 2-pyrazinyl.

$R^{21}$ is selected from hydrogen, $C_{1-6}$ alkyl, $C_{1-6}$ haloalkyl, $C_{1-6}$ alkyl optionally substituted with one or more OH, $C_{1-6}$ alkyl containing one to three oxygen atoms between carbon atoms, and $C_{3-6}$ cycloalkyl optionally substituted with one or more $R^{22}$, wherein $R^{22}$ is selected from halogen, preferably —Cl, —F, and —OH. In a further preferred embodiment, said $R^{21}$ is selected from hydrogen, $C_{1-2}$ alkyl, $C_{1-2}$ haloalkyl, $C_{1-2}$ alkyl optionally substituted with one or two OH, and $C_{3-4}$ cycloalkyl optionally substituted with one or more $R^{22}$, wherein $R^{22}$ is selected from —Cl, —F, and —OH. In a further preferred embodiment, said $R^{21}$ is selected from $C_{1-2}$ alkyl, $C_{1-2}$ haloalkyl and $C_{3-4}$ cycloalkyl. In a further preferred embodiment, said $R^{21}$ is selected from $C_{1-2}$ alkyl and cyclopropyl. In a further preferred embodiment, said $R^{21}$ is cyclopropyl. In a further very preferred embodiment, said $R^{21}$ is ethyl. In a further very preferred embodiment, said $R^{21}$ is methyl.

$R^3$ is selected from -(optionally substituted heterocyclyl), -(optionally substituted carbocyclyl), -(optionally substituted $C_{1-6}$ alkylene)-(optionally substituted heterocyclyl) and -(optionally substituted $C_{1-6}$ alkylene)-(optionally substituted carbocyclyl). Preferably, $R^3$ is -(optionally substituted carbocyclyl). More preferably, $R^3$ is phenyl which is optionally substituted with one or more groups selected from halogen, —($C_{1-6}$ alkyl which is optionally substituted with one or more F) and —O—($C_{1-6}$ alkyl which is optionally substituted with one or more F). Further preferred are compounds in which $R^3$ is pyridinyl which may have the same substituents as the optionally substituted heterocyclyl. In other preferred compounds, $R^3$ is quinazoline or cinnoline, each of which may have the same substituents as the optionally substituted heterocyclyl.

In a further preferred embodiment, $R^3$ is phenyl or pyridyl, each of which is optionally substituted with one or more, preferably one or two, substituents selected from halogen, —$C_{1-6}$ alkyl, $C_{1-6}$ haloalkyl, —O—$C_{1-6}$ alkyl, and —O—$C_{1-6}$ haloalkyl. In a further preferred embodiment, $R^3$ is phenyl or pyridyl, each of which is optionally substituted with one or more, preferably one or two, substituents selected from halogen, —$C_{1-3}$ alkyl, $C_{1-2}$ haloalkyl, —O—$C_{1-2}$ alkyl, and —O—$C_{1-3}$ haloalkyl. In a further preferred embodiment, $R^3$ is phenyl or pyridyl, each of which is optionally substituted with one or more, preferably one or two, substituents selected from —F, —Cl, —$C_{1-2}$ alkyl, $C_1$ haloalkyl, —$OCH_3$. In a further preferred embodiment, $R^3$ is phenyl or pyridyl, each of which is optionally substituted with one or more, preferably one or two, substituents selected from —F, —Cl, —$CH_3$ and —$OCH_3$. In a further preferred embodiment, $R^3$ is phenyl or pyridyl, each of which is optionally substituted with one substituent selected from —F, —Cl, —$CH_3$ and —$OCH_3$. In a further preferred embodiment, $R^3$ is phenyl or 3-pyridyl or 4-pyridyl, each of which is optionally substituted with one substituent selected from —F, —Cl, —$CH_3$ and —$OCH_3$. In a further preferred embodiment, $R^3$ is phenyl, 3-pyridyl or 4-pyridyl, each of which is optionally substituted at the meta position of said phenyl, 3-pyridyl or 4-pyridyl with one substituent selected from —F, —Cl, —$CH_3$ and —$OCH_3$. In a further preferred embodiment, $R^3$ is phenyl or phenyl substituted at the meta position with one substituent selected from —F, —Cl, —$CH_3$ and —$OCH_3$. In a further preferred embodiment, $R^3$ is 3-pyridyl or 3-pyridyl substituted at the meta position (5 position) with one substituent selected from —F, —Cl, —$CH_3$ and —$OCH_3$. In a further preferred embodiment, $R^3$ is 4-pyridyl or 4-pyridyl substituted at the meta position (5 position) with one substituent selected from —F, —Cl, —$CH_3$ and —$OCH_3$. In a further preferred embodiment, $R^3$ is phenyl. In a further preferred embodiment, $R^3$ is 3-pyridyl. In a further preferred embodiment, $R^3$ is 4-pyridyl.

In a further preferred embodiment, said $R^3$ is selected from phenyl, a 6-membered monocyclic heteroaryl and a 8-10 membered bicyclic heteroaryl, each independently comprising one or more, typically 1 to 5, preferably 1 to 4, ring heteroatoms independently selected from O, B, S and N, wherein one or two carbon ring atoms of said monocyclic heteroaryl or said bicyclic heteroaryl are optionally oxidized typically and preferably leading to a C═O functionality, and wherein said phenyl, said 6-membered monocyclic heteroaryl and said 8-10 membered bicyclic heteroaryl is independently optionally substituted with one or more, typically and preferably with 1 to 5, further preferably with 1 to 4, and again further preferably with 1 to 3 substituents selected from halogen, —$C_{1-6}$ alkyl, $C_{1-6}$ haloalkyl, —O—($C_{1-6}$ alkyl), —O—($C_{1-6}$ haloalkyl), —OH, —CN, ═O, —C(O)R*, —COOR*, —C(O)NR*R*, —NR*R*, —N(R**)—C(O)R*, —N(R**)—C(O)—OR*, —N(R**)—C(O)—NR*R*, —O—C(O)R*, —O—C(O)—NR*R*, and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$alkyl), —O—($C_{1-4}$ haloalkyl), —OH, ═O, —$C_{1-3}$alkylene-OR*, —C(O)R* and —C(O)NR*R*; wherein each R* is independently selected from H, $C_{1-4}$ alkyl, $C_{1-4}$ haloalkyl, cyclopropyl, cyclobutyl, oxetanyl, —$C_{1-2}$alkylene-OH, —$C_{1-2}$alkylene-O($C_{1-2}$alkyl), phenyl, and wherein each R** is independently selected from H, $C_{1-4}$ alkyl, $C_{1-4}$ haloalkyl, and/or wherein each monocyclic heterocyclyl is independently optionally substituted with one bivalent substituent selected from $C_{1-3}$ alkylene such as —$CH_2$—$CH_2$— and —$CH_2$—$CH_2$—$CH_2$—, $C_{1-3}$ alkylene substituted with 1 to 4 F, —$CH_2$—O—$CH_2$— and —$CH_2$—NH—$CH_2$—.

In a further preferred embodiment, said $R^3$ is selected from formula (C), formula (D), formula (E), formula (F) and formula (G)

(C)

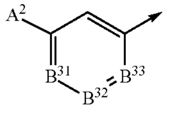

(D)

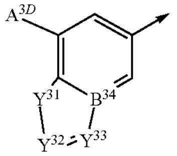

-continued (E)

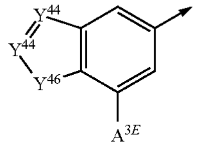

(F)

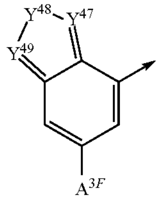

(G)

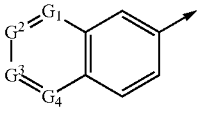

wherein $B^{31}$ is N, CH or C($A^{31}$), wherein $A^{31}$ is selected from —$C_{1-2}$ alkyl, $C_{1-2}$ haloalkyl, —F, —Cl, —O($C_{1-2}$alkyl), —OH, —NHC(O)($C_{1-2}$alkyl), wherein $A^{31}$ is selected from —$C_{1-2}$ alkyl, $C_{1-2}$ haloalkyl, —F, —Cl, —O($C_{1-2}$alkyl), —OH, —NHC(O)($C_{1-2}$alkyl);

$B^{32}$ is N, CH or C($A^{32}$), wherein $A^{32}$ is selected from —$C_{1-2}$ alkyl, $C_{1-2}$ haloalkyl, —F, —Cl, —O($C_{1-2}$alkyl), ═O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, ═O, —$C_{1-3}$alkylene-OR*, —C(O)R* and —C(O)NR*R*; wherein each R* is independently selected from H, $C_{1-4}$ alkyl, $C_{1-4}$ haloalkyl, phenyl, and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—;

In a further preferred embodiment, $B^{32}$ is N, CH or C($A^{32}$), wherein $A^{32}$ is selected from —$C_{1-2}$ alkyl, $C_{1-2}$ haloalkyl, —F, —Cl, —O($C_{1-2}$alkyl), ═O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, ═O, —$C_{1-3}$alkylene-OR*, —C(O)R* and —C(O)NR*R*; wherein each R* is independently selected from H, $C_{1-4}$ alkyl, $C_{1-4}$ haloalkyl and phenyl;

In a further preferred embodiment, $B^{32}$ is N, CH or C($A^{32}$), wherein $A^{32}$ is selected from —$C_{1-2}$ alkyl, $C_{1-2}$ haloalkyl, —F, —Cl, —O($C_{1-2}$alkyl), ═O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$alkylene-OR*, —C(O)R* and —C(O)NR*R*; wherein each R* is independently selected from H, $C_{1-3}$ alkyl, $C_{1-3}$ haloalkyl and phenyl;

$B^{33}$ is N, CH or C($A^{33}$), wherein $A^{33}$ is selected from —$C_{1-2}$ alkyl, $C_{1-2}$ haloalkyl, —F, —Cl, —O($C_{1-2}$alkyl), —OH, —NHC(O)($C_{1-2}$alkyl);

$A^2$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl, phenyl, and/or wherein each monocyclic heterocyclyl is independently optionally substituted with one bivalent substituent selected from $C_{1-3}$alkylene, $C_{1-3}$alkylene substituted with 1 to 4 F, —$CH_2$—O—$CH_2$— and —$CH_2$—NH—$CH_2$—;

In a further preferred embodiment, $A^2$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$ alkylene-OR*, —C(O)R* and —C(O)NR*R*; wherein each R* is independently selected from H, $C_{1-4}$ alkyl, $C_{1-4}$ haloalkyl and phenyl;

In a further preferred embodiment, $A^2$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$ alkylene-OR*, —C(O)R* and —C(O)NR*R*; wherein each R* is independently selected from H, $C_{1-3}$ alkyl, $C_{1-3}$ haloalkyl and phenyl;

and wherein $Y^{41}$ is N, CH or C($A^{41}$), wherein $A^{41}$ is selected from methyl and ethyl; $Y^{42}$ is N, CH or C($A^{42}$), wherein $A^{42}$ is selected from methyl and ethyl; $Y^{43}$ is N, CH or C($A^{43}$), wherein $A^{43}$ is selected from methyl and ethyl;

$A^{3D}$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl); In a further preferred embodiment, $A^{3E}$ is selected from hydrogen, —$C_{1-2}$ alkyl, $C_{1-2}$ haloalkyl, —F, —Cl, —O($C_{1-2}$alkyl), =O, —OH;

and wherein $Y^{44}$ is N, NH, N($A^{44}$), C(O), CH or C($A^{44}$), wherein $A^{44}$ is independently selected from methyl and ethyl; $Y^{45}$ is N, NH, N($A^{45}$), C(O), CH or C($A^{45}$), wherein $A^{45}$ is independently selected from methyl and ethyl; $Y^{46}$ is N, NH, N($A^{46}$), C(O), CH or C($A^{46}$), wherein $A^{46}$ is independently selected from methyl and ethyl; and wherein at least one of said $Y^{44}$, $Y^{45}$ and $Y^{46}$ is NH, N($CH_3$) or N($C_2H_5$); and wherein $A^{3E}$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl); In a further preferred embodiment, $A^{3E}$ is selected from hydrogen, —$C_{1-2}$ alkyl, $C_{1-2}$ haloalkyl, —F, —Cl, —O($C_{1-2}$alkyl), =O, —OH;

and wherein $Y^{47}$ is N, NH, N($A^{47}$), C(O), CH or C($A^{47}$), wherein $A^{47}$ is independently selected from methyl and ethyl; $Y^{48}$ is N, NH, N($A^{48}$), C(O), CH or C($A^{48}$), wherein $A^{48}$ is independently selected from methyl and ethyl; $Y^{49}$ is N, NH, N($A^{49}$), C(O), CH or C($A^{49}$), wherein $A^{49}$ is independently selected from methyl and ethyl; and wherein at least one of said $Y^{47}$, $Y^{48}$ and $Y^{49}$ is NH, N($CH_3$) or N($C_2H_5$);

$A^{3F}$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl); In a further preferred embodiment, $A^{3E}$ is selected from hydrogen, —$C_{1-2}$ alkyl, $C_{1-2}$ haloalkyl, —F, —Cl, —O($C_{1-2}$alkyl), =O, —OH;

and wherein $G^1$, $G^2$, $G^3$, $G^4$ is independently selected from N, CH, C(O), NH or N($C_{1-2}$ alkyl); and wherein the arrow denotes the bond in the compounds of formula (I).

In a further preferred embodiment, said $R^3$ is selected from the following formulas

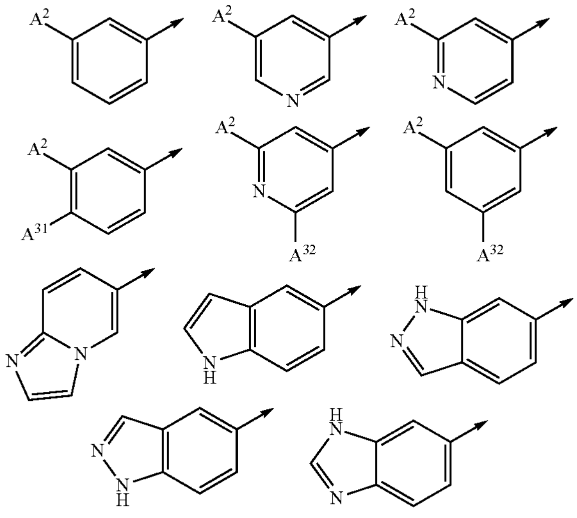

-continued

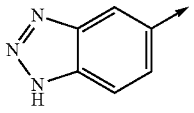 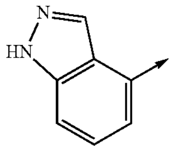 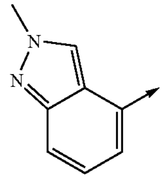

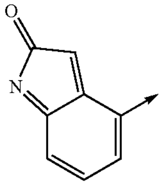 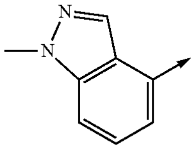 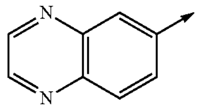

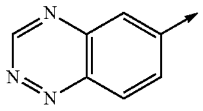 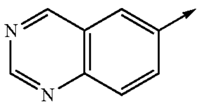

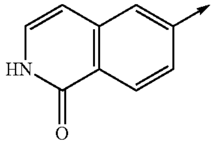 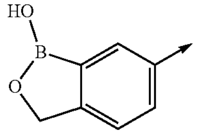

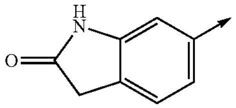 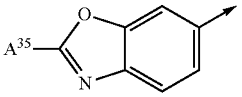

wherein $A^2$ is independently selected for each formula from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl, phenyl, and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—;

In a further preferred embodiment, $A^2$ is independently selected for each formula from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl and phenyl;

In a further preferred embodiment, $A^2$ is independently selected for each formula from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$alkylene-OR*, —C(O)R* and —C(O)NR*R*; wherein each R* is independently selected from H, $C_{1-3}$ alkyl, $C_{1-3}$ haloalkyl and phenyl;

$A^{31}$ is independently selected for each formula from —$C_{1-2}$ alkyl, $C_{1-2}$ haloalkyl, —F, —Cl, —O($C_{1-2}$alkyl), —OH, —NHC(O)($C_{1-2}$alkyl);

$A^{32}$ is independently selected for each formula from —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl, phenyl, and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—;

In a further preferred embodiment, $A^{32}$ is independently selected for each formula from —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl and phenyl;

In a further preferred embodiment, $A^{32}$ is independently selected for each formula from —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$alkylene-OR*, —C(O)R* and —C(O)NR*R*; wherein each R* is independently selected from H, $C_{1-3}$ alkyl, $C_{1-3}$ haloalkyl and phenyl; and wherein $A^{35}$ is independently selected for each formula from —$C_{1-2}$ alkyl; and wherein the arrow denotes the bond in the compounds of formula (I).

In a further very preferred embodiment, said $R^3$ is selected from the formulas $A^2$

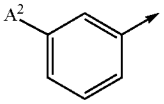

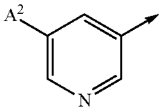

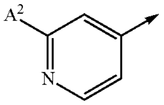

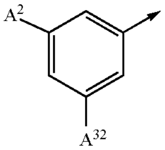

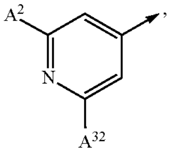
, wherein $A^2$ and $A^{32}$ are independently selected for each formula from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC (O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$alkylene-OR*, —C(O)R* and —C(O)NR*R*; wherein each R* is independently selected from H, $C_{1-3}$ alkyl, $C_{1-3}$ haloalkyl and phenyl; and In a further very preferred embodiment, said $R^3$ is selected from the formulas

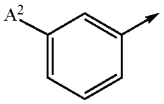

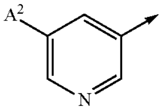

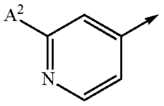

-continued

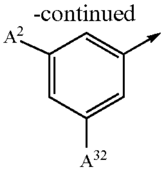

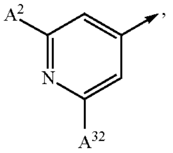
, wherein $A^2$ are independently selected for each formula from hydrogen, —$C_{1-2}$ alkyl, $C_{1-2}$ haloalkyl, —F, —Cl, —O($C_{1-2}$alkyl); and wherein $A^{32}$ is independently selected for each formula from —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$ alkylene-OR*, —C(O)R* and —C(O)NR*R*; wherein each R* is independently selected from H, $C_{1-3}$ alkyl, $C_{1-3}$ haloalkyl and phenyl.

In a further very preferred embodiment, said $R^3$ is selected from the formulas

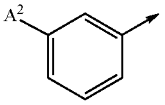

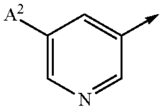

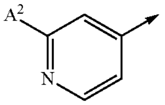

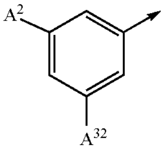

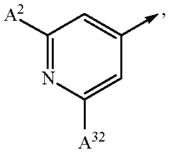
, wherein $A^2$ are independently selected for each formula from hydrogen, —$C_{1-2}$ alkyl, $C_{1-2}$ haloalkyl, —F; and wherein $A^{32}$ is independently selected for each formula from —$C_{1-2}$ alkyl, $C_{1-2}$ haloalkyl, —F, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 3 heteroatoms selected from O and N, each monocyclic heterocyclyl independently optionally substituted with one or two substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$alkylene-OR*, —C(O)R* and —C(O)NR*R*; wherein each R* is independently selected from H, $C_{1-3}$ alkyl, $C_{1-3}$ haloalkyl and phenyl.

Each of $X^1$, $X^2$ and $X^3$ is independently selected from N, CH and $CR^X$, wherein preferably at least one of said $X^1$, $X^2$ and $X^3$ is N, wherein further preferably at least one of said $X^2$ and $X^3$ is N; and wherein again further preferably $X^2$ and $X^3$ are both N, and wherein still further preferably $X^2$ and $X^3$ are both N, and $X^1$ is CH.

E is selected from —$CH_2$—, —$CHR^x$—, —$CR^x_2$—, —NH—, —$NR^x$— and —O—, -$L^1$-$L^2$- and -$L^2$-$L^1$-, wherein $L^1$ is selected from —$CH_2$—, —$CHR^x$—, —$CR^x_2$—, —NH—, —$NR^x$— and —O— and $L^2$ is selected from —$CH_2$-, —$CHR^x$— and —$CR^x_2$—. In a further preferred embodiment, said E is selected from —$CH_2$—, —NH—, —O—, —$CH_2$-O—, —O—$CH_2$—, —$CH_2$—NH—, —NH—$CH_2$— and —$CH_2$—$CH_2$—. Preferably, E is selected from $CH_2$—, —O—, —$CH_2$—O—, —O—$CH_2$— and —$CH_2$—$CH_2$—. More preferably, E is selected from $CH_2$—, —O—, —$CH_2$—O— and —$CH_2$—$CH_2$—. In a very preferred embodiment, E is $CH_2$.

$R^{6x}$ is -halogen, —OH, =O, $C_{1-6}$ alkyl, $C_{1-6}$ haloalkyl, $C_{1-6}$ alkyl substituted with one or more OH, monocyclic aryl optionally substituted with one or more $R^{xb}$, monocyclic heteroaryl optionally substituted with one or more $R^{xb}$, monocyclic cycloalkyl optionally substituted with one or more $R^{xb}$, monocyclic heterocycloalkyl optionally substituted with one or more $R^{xb}$, monocyclic cycloalkenyl optionally substituted with one or more $R^{xb}$, monocyclic heterocycloalkenyl optionally substituted with one or more $R^{xb}$, wherein said $R^{xb}$ is independently selected from -halogen, —OH, =O, $C_{1-4}$ alkyl, $C_{1-2}$ haloalkyl, $C_{1-2}$ alkyl substituted with one or two OH;

In a further preferred embodiment, $R^{6x}$ is selected from -halogen, —OH, =O, $C_{1-4}$ alkyl, $C_{1-2}$ haloalkyl and $C_{1-3}$ alkyl substituted with one or more OH. In a further preferred embodiment, $R^{6x}$ is selected from -halogen, —OH, =O, $C_{1-3}$ alkyl, $C_{1-2}$ haloalkyl and $C_{1-3}$ alkyl substituted with one or two OH. In a further preferred embodiment, $R^{6x}$ is selected from $C_{1-3}$ alkyl, $C_{1-2}$ haloalkyl and $C_{1-3}$ alkyl substituted with one or two OH. In a further preferred embodiment, $R^{6x}$ is selected from $C_{1-2}$ alkyl, $C_{1-2}$ haloalkyl and $C_{1-3}$ alkyl substituted with one or two OH. H. In a further preferred embodiment, $R^{6x}$ is selected from $C_{1-3}$alkyl and $C_{1-2}$ haloalkyl. In a further preferred embodiment, $R^{6x}$ is selected from $C_{1-2}$ alkyl and $C_1$ haloalkyl.

In a further preferred embodiment, $R^{6x}$ is $CHF_2$. In a further preferred embodiment, $R^{6x}$ is $CF_3$. In a further preferred embodiment, $R^{6x}$ is ethyl. In a further very preferred embodiment, $R^{6x}$ is methyl.

It is to be understood that Ring A may further be substituted with one or more groups $R^x$, wherein any two $R^x$ groups, preferably adjacent $R^x$ groups, at ring A are optionally linked and/or any $R^x$ group at ring A is optionally linked with $R^{21}$; the number of groups $R^x$ in Ring A is 0, 1, 2, 3, or 4, preferably 0, 1, 2, or 3, further preferably 0, 1, or 2 or alternatively preferably 0 or 1. In case that Ring A may be substituted with one or more groups $R^x$ and one of said $R^x$ group at ring A is optionally linked with $R^{21}$ then said one of said $R^x$ group at ring A optionally linked with $R^{21}$ is a substituent at the 2-position of Ring A.

Thus, in a preferred embodiment, said Ring A is further substituted with 1, 2, 3 or 4 groups $R^x$, wherein any two $R^x$ groups, preferably adjacent $R^x$ groups, at ring A are optionally linked and/or any $R^x$ group at ring A is optionally linked with $R^{21}$. In case that one of said $R^x$ group at ring A is optionally linked with $R^{21}$ then said one of said $R^x$ group at ring A optionally linked with $R^{21}$ is a substituent at the 2-position of Ring A.

In a preferred embodiment, said Ring A is further substituted with 1, 2 or 3 groups $R^x$, wherein any two $R^x$ groups, preferably adjacent $R^x$ groups, at ring A are optionally linked and/or any $R^x$ group at ring A is optionally linked with $R^{21}$. In case that one of said $R^x$ group at ring A is optionally linked with $R^{21}$ then said one of said $R^x$ group at ring A optionally linked with $R^{21}$ is a substituent at the 2-position of Ring A.

In a preferred embodiment, said Ring A is further substituted with 1 or 2 groups $R^x$, wherein any two $R^x$ groups, preferably adjacent $R^x$ groups, at ring A are optionally linked and/or any $R^x$ group at ring A is optionally linked with $R^{21}$. In case that one of said $R^x$ group at ring A is optionally linked with $R^{21}$ then said one of said $R^x$ group at ring A optionally linked with $R^{21}$ is a substituent at the 2-position of Ring A.

In a preferred embodiment, said Ring A is further substituted with 1 group $R^x$, wherein said $R^x$ group at ring A is optionally linked with $R^{21}$. In case that one of said $R^x$ group at ring A is optionally linked with $R^{21}$ then said one of said $R^x$ group at ring A optionally linked with $R^{21}$ is a substituent at the 2-position of Ring A.

In a preferred embodiment, said Ring A is further substituted with 1 group $R^x$, wherein said $R^x$ group at ring A is not linked with $R^{21}$.

In a preferred embodiment, said Ring A is further substituted with 1 group $R^x$, wherein said $R^x$ group at ring A is not linked with $R^{21}$. In a further preferred embodiment, said group $R^x$ is —F, and wherein preferably said group $R^x$ being —F is at the 3-position of Ring A, said position which connects said Ring A with the $X^1$, $X^2$, $X^3$ ring system.

In a preferred embodiment, said Ring A is not further substituted. Thus, in a preferred embodiment, said Ring A is not further substituted with a group $R^x$.

In a preferred embodiment, said $R^{21}$ is selected from hydrogen, $C_{1-6}$ alkyl, $C_{1-6}$ haloalkyl, $C_{1-6}$ alkyl optionally substituted with one or more OH, $C_{1-6}$ alkyl containing one to three oxygen atoms between carbon atoms, and $C_{3-6}$ cycloalkyl optionally substituted with one or more $R^{22}$ wherein $R^{22}$ is selected from halogen, preferably —Cl, —F, and —OH. In a further preferred embodiment, said $R^{21}$ is selected from hydrogen, $C_{1-2}$ alkyl, $C_{1-2}$ haloalkyl, $C_{1-2}$ alkyl optionally substituted with one or two OH, and $C_{3-4}$ cycloalkyl optionally substituted with one or more $R^{22}$ wherein $R^{22}$ is selected from —Cl, —F, and —OH. In a further preferred embodiment, said $R^{21}$ is selected from $C_{1-2}$ alkyl, $C_{1-2}$ haloalkyl and $C_{3-4}$ cycloalkyl. In a further preferred embodiment, said $R^{21}$ is selected from $C_{1-2}$ alkyl and cyclopropyl. In a further preferred embodiment, said $R^{21}$ is ethyl. In a further preferred embodiment, said $R^{21}$ is cyclopropyl. In a further very preferred embodiment, said $R^{21}$ is methyl.

In a preferred embodiment, each $R^x$ is independently selected from -halogen, —OH, —O—$C_{1-3}$ alkyl optionally substituted with one or more $R^{xa}$, —NH—$C_{1-3}$ alkyl optionally substituted with one or more $R^{xa}$, —N($C_{1-3}$ alkyl optionally substituted with one or more $R^{xa}$)$_2$, =O, $C_{1-4}$ alkyl optionally substituted with one or more $R^{xa}$, $C_{1-4}$ haloalkyl, —($C_{1-2}$ alkylene optionally substituted with one or more $R^{xa}$)-(optionally substituted carbocyclyl), —($C_{1-2}$ alkylene optionally substituted with one or more $R^{xa}$)-(optionally substituted heterocyclyl), —O—($C_{1-2}$ alkylene optionally substituted with one or more $R^{xa}$)-(optionally substituted carbocyclyl), —O—($C_{1-2}$ alkylene optionally substituted with one or more $R^{xa}$)-(optionally substituted heterocyclyl), -(optionally substituted carbocyclyl) and -(optionally substituted heterocyclyl), wherein said $R^{xa}$ is independently selected from halogen, preferably —Cl, —F, and —OH.

In a further preferred embodiment, each $R^x$ is independently selected from -halogen, —OH, —O—$C_{1-2}$ alkyl optionally substituted with one or more $R^{xa}$, —NH—$C_{1-2}$ alkyl optionally substituted with one or more $R^{xa}$, —N($C_{1-2}$ alkyl optionally substituted with one or more $R^{xa}$)$_2$, =O, $C_{1-3}$ alkyl optionally substituted with one or more $R^{xa}$, $C_{1-2}$ haloalkyl, —($C_{1-2}$ alkylene optionally substituted with one or more $R^{xa}$)-(monocyclic carbocyclyl optionally substituted with one or more $R^{xa}$), —($C_{1-2}$ alkylene optionally substituted with one or more $R^{xa}$)-(monocyclic heterocyclyl optionally substituted with one or more $R^{xa}$), —O—($C_{1-2}$ alkylene optionally substituted with one or more $R^{xa}$)-(monocyclic carbocyclyl optionally substituted with one or more $R^{xa}$), —O—($C_{1-2}$ alkylene optionally substituted with one or more $R^{xa}$)-(monocyclic heterocyclyl optionally substituted with one or more $R^{xa}$), monocyclic carbocyclyl optionally substituted with one or more $R^{xa}$, monocyclic heterocyclyl optionally substituted with one or more $R^{xa}$, wherein said $R^{xa}$ is independently selected from halogen, preferably —Cl, —F, and —OH.

In a further preferred embodiment, each $R^x$ is independently selected from -halogen, —OH, —O—$C_{1-2}$ alkyl optionally substituted with one or more $R^{xa}$, —NH—$C_{1-2}$ alkyl optionally substituted with one or more $R^{xa}$, —N($C_{1-2}$ alkyl optionally substituted with one or more $R^{xa}$)$_2$, =O, $C_{1-3}$ alkyl optionally substituted with one or more $R^{xa}$, $C_{1-2}$ haloalkyl, —W-(monocyclic carbocyclyl optionally substituted with one or more $R^{xa}$), —W-(monocyclic heterocyclyl optionally substituted with one or more $R^{xa}$), and wherein —W— is absent, —($C_{1-2}$ alkylene)- or —O—($C_{1-2}$ alkylene)-, and wherein said $R^{xa}$ is independently selected from —Cl, —F, and —OH.

In a further preferred embodiment, each $R^x$ is independently selected from -halogen, —OH, —O—$C_{1-2}$ alkyl optionally substituted with one or more $R^{xa}$, —NH—$C_{1-2}$ alkyl optionally substituted with one or more $R^{xa}$, —N($C_{1-2}$ alkyl optionally substituted with one or more $R^{xa}$)$_2$, =O, $C_{1-3}$ alkyl optionally substituted with one or more $R^{xa}$, $C_{1-2}$ haloalkyl, —W-(monocyclic carbocyclyl optionally substituted with one or more $R^{xa}$), —W-(monocyclic heterocyclyl optionally substituted with one or more $R^{xa}$), and wherein —W— is absent, —($C_{1-2}$ alkylene)- or —O—($C_{1-2}$ alkylene)-, and wherein monocyclic carbocyclyl is selected from phenyl and $C_{3-6}$ cycloalkyl, and wherein monocyclic heterocyclyl is selected from thiophenyl, pyridyl, pyrazinyl and pyrimidinyl, and wherein said $R^{xa}$ is independently selected from —Cl, —F, and —OH.

In a further preferred embodiment, each $R^x$ is independently selected from -halogen, —OH, —O—$C_{1-2}$ alkyl, —NH—$C_{1-2}$ alkyl, —N($C_{1-2}$ alkyl)$_2$, =O, $C_{1-3}$ alkyl, $C_{1-2}$ haloalkyl, —W— (monocyclic carbocyclyl optionally substituted with one $R^{xa}$), —W-(monocyclic heterocyclyl optionally substituted with one $R^{xa}$), and wherein —W— is absent, —($C_{1-2}$ alkylene)- or —O—($C_{1-2}$ alkylene)-, and wherein monocyclic carbocyclyl is selected from phenyl and $C_{3-6}$ cycloalkyl, and wherein monocyclic heterocyclyl is selected from thiophenyl, pyridyl, pyrazinyl and pyrimidinyl, and wherein said $R^{xa}$ is independently selected from —F, and —OH.

In a further very preferred aspect and embodiment, the present invention provides a compound of formula (I), wherein said compound of formula (I) is a compound of formula (IXb), optionally in the form of a pharmaceutically acceptable salt, solvate, cocrystal, tautomer, racemate, enantiomer, or diastereomer or mixture thereof, for use in a method of treating fibrotic disease (IXb)

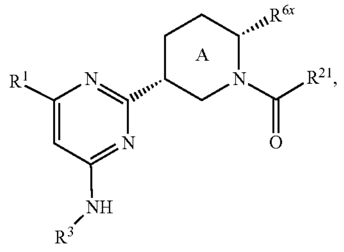

wherein

In a further preferred embodiment, said $R^1$ is selected from phenyl, a 5- or 6-membered monocyclic heteroaryl and a 8-10 membered bicyclic heteroaryl, each independently comprising one or more, preferably 1 to 5, ring heteroatoms independently selected from O, S and N, wherein one or two carbon ring atoms of said monocyclic heteroaryl or said bicyclic heteroaryl are optionally oxidized, and wherein said phenyl, said 5- or 6-membered monocyclic heteroaryl and said 8-10 membered bicyclic heteroaryl is independently optionally substituted with one or more, preferably one or two, substituents selected from halogen, —$C_{1-6}$ alkyl, $C_{1-6}$ haloalkyl, —O—($C_{1-6}$ alkyl), —O—($C_{1-6}$ haloalkyl), —OH, —($C_{1-2}$alkylene)-O—($C_{1-4}$alkylene)-OR*, —O—($C_{1-4}$alkylene)-OR*, —($C_{1-2}$alkylene)-O—($C_{1-4}$alkylene)-N($R^{\circ\circ}$)$_2$, —O—($C_{1-4}$alkylene)-N($R^{\circ\circ}$)$_2$, —CN, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 3-6 membered monocyclic carbocyclyl and 3-6 membered monocyclic heterocyclyl comprising 1 to 4 heteroatoms selected from O, S and N, each monocyclic carbocyclyl and heterocyclyl independently optionally substituted with one or more, preferably one or two, substituents independently selected from halogen, —$C_{1-4}$ alkyl, $C_{1-4}$ haloalkyl, —O—($C_{1-4}$ alkyl), —O—($C_{1-4}$ haloalkyl), —OH, =O, —C(O)R* and —C(O)NR*R*; wherein each R* is independently selected from H, $C_{1-4}$ alkyl, $C_{1-4}$ haloalkyl, and wherein each $R^{\circ\circ}$ is independently selected from H, $C_{1-4}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from phenyl, a 5- or 6-membered monocyclic heteroaryl and a 8-10 membered bicyclic heteroaryl, each independently comprising one or more, preferably 1 to 5, ring heteroatoms independently selected from O, S and N, wherein one or two carbon ring atoms of said monocyclic heteroaryl or said bicyclic heteroaryl are optionally oxidized, and wherein said phenyl, said 5- or 6-membered monocyclic heteroaryl and said 8-10 membered bicyclic heteroaryl is independently optionally substituted with one or more, preferably one or two, substituents independently selected from halogen, —$C_{1-4}$ alkyl, $C_{1-4}$ haloalkyl, —O—($C_{1-4}$ alkyl), —O—($C_{1-4}$ haloalkyl), —OH, —($C_{1-2}$alkylene)-O—($C_{1-4}$alkylene)-OR*, —O—($C_{1-4}$alkylene)-OR*, —($C_{1-2}$alkylene)-O—($C_{1-4}$alkylene)-N($R^{\circ\circ}$)$_2$, —O—($C_{1-4}$alkylene)-N($R^{\circ\circ}$)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 3-6 membered monocyclic heterocyclyl comprising 1 to 4 heteroatoms selected from O, S and N, each monocyclic heterocyclyl independently optionally substituted with one or more, preferably one or two, substituents selected from halogen, —$C_{1-3}$ alkyl, $C_{1-3}$ haloalkyl, —O—($C_{1-3}$ alkyl), —O—($C_{1-3}$ haloalkyl), —OH, =O, —C(O)R* and —C(O)NR*R*; wherein each R* is independently selected from H, $C_{1-3}$ alkyl, $C_{1-3}$ haloalkyl, and wherein each $R^{\circ\circ}$ is independently selected from H, $C_{1-4}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from phenyl, a 5- or 6-membered monocyclic heteroaryl and a 8-10 membered bicyclic heteroaryl, each independently comprising one or more, preferably 1 to 5, ring heteroatoms independently selected from O, S and N, wherein one or two carbon ring atoms of said monocyclic heteroaryl or said bicyclic heteroaryl are optionally oxidized, and wherein said phenyl, said 5- or 6-membered monocyclic heteroaryl and said 8-10 membered bicyclic heteroaryl is independently optionally substituted with one or more, preferably one or two, substituents independently selected from —F, —Cl, —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 3-6 membered monocyclic heterocyclyl comprising 1 to 4 heteroatoms selected from O, S and N, each monocyclic heterocyclyl independently optionally substituted with one or more, preferably one or two, substituents selected from —$C_{1-2}$ alkyl, $C_{1-2}$ haloalkyl, —O—($C_{1-2}$ alkyl), —O—($C_{1-2}$ haloalkyl), —OH, =O, —C(O)R* and —C(O)NR*R*; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from phenyl, a 5- or 6-membered monocyclic heteroaryl comprising one or two heteroatoms independently selected from S and N and a 8-10 membered bicyclic heteroaryl comprising one or more, preferably 1 to 4, ring nitrogen heteroatoms, wherein one or two, preferably one, carbon ring atoms of said monocyclic heteroaryl or said bicyclic heteroaryl are optionally oxidized, and wherein said phenyl, said 5- or 6-membered monocyclic heteroaryl and said 8-10 membered bicyclic heteroaryl is independently optionally substituted with one or more, preferably one or two, substituents independently selected from —F, —Cl, —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 3-6 membered monocyclic heterocyclyl comprising 1 to 4 heteroatoms selected from O, S and N, each monocyclic heterocyclyl independently optionally substituted with one or more, preferably one or two, substituents selected from —$C_{1-2}$ alkyl, $C_{1-2}$ haloalkyl, —O—($C_{1-2}$ alkyl), —O—($C_{1-2}$ haloalkyl), —OH, =O, —C(O)R* and —C(O)NR*R*; wherein each R* is independently selected from H, $C_{1-2}$ alkyl, $C_{1-2}$ haloalkyl, and wherein each $R^{\circ\circ}$ is independently selected from H, $C_{1-2}$alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from a 5- or 6-membered monocyclic heteroaryl comprising one or two heteroatoms independently selected from S and N and a 8-10 membered bicyclic heteroaryl comprising 1 to 5, preferably 1 to 4, ring nitrogen heteroatoms, wherein one or two, preferably one, carbon ring atoms of said monocyclic heteroaryl or said bicyclic heteroaryl are optionally oxidized, and wherein said 5- or 6-membered monocyclic heteroaryl and said 8-10 membered bicyclic heteroaryl is independently optionally substituted with one or two substituents independently selected from —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 4-6 membered monocyclic heterocyclyl comprising 1 or 2 heteroatoms selected from O and N, each monocyclic heterocyclyl independently optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH, =O, —C(O)R* and —C(O)NR*R*; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from a 5- or 6-membered monocyclic heteroaryl comprising one or two heteroatoms independently selected from S and N and a 8-10 membered bicyclic heteroaryl comprising 1 to 5, preferably 1 to 4, ring nitrogen heteroatoms, wherein one or two, preferably one, carbon ring atoms of said monocyclic heteroaryl or said bicyclic heteroaryl are optionally oxidized, and wherein said 5- or 6-membered monocyclic heteroaryl and said 8-10 membered bicyclic heteroaryl is independently optionally substituted with one or two, preferably one, substituents independently selected from —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, and 4-6 membered monocyclic heterocyclyl comprising 1 or 2 heteroatoms selected from 0 and N, each monocyclic heterocyclyl independently optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH and =O; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$ alkylene substituted with 1 to 4 F, —$CH_2$—O—$CH_2$— and —$CH_2$—NH—$CH_2$—.

In a further preferred embodiment, said $R^1$ is phenyl, thiophenyl, pyrrolyl, pyrazolyl, azaindolyl, azaindazolyl, pyrazinyl, pyridyl or pyrimidinyl, wherein the phenyl, thiophenyl, pyrrolyl, pyrazolyl, azaindolyl, azaindazolyl, pyrazinyl, pyridyl or pyrimidinyl is optionally substituted with one or two, preferably one, substituents independently selected from —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 4-6 membered monocyclic heterocyclyl comprising 1 or 2 heteroatoms selected from O and N, each monocyclic heterocyclyl optionally substituted with one or two, preferably one, substituents independently selected from —$C_{1-2}$ alkyl, $C_{1-2}$ haloalkyl, —O—($C_{1-2}$ alkyl), —O—($C_{1-2}$ haloalkyl), —OH, =O, —C(O)R* and —C(O)NR*R*; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is phenyl, thiophenyl, pyrrolyl, pyrazolyl, azaindolyl, azaindazolyl, pyrazinyl, pyridyl or pyrimidinyl, wherein the phenyl, thiophenyl, pyrrolyl, pyrazolyl, azaindolyl, azaindazolyl, pyrazinyl, pyridyl or pyrimidinyl is optionally substituted with one or two, preferably one, substituents independently selected from —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, and 4-6 membered monocyclic heterocyclyl comprising 1 or 2 heteroatoms selected from 0 and N, each monocyclic heterocyclyl optionally substituted with one or two, preferably one, substituents independently selected from —$C_{1-2}$ alkyl, $C_{1-2}$ haloalkyl, —O—($C_{1-2}$ alkyl), —O—($C_{1-2}$ haloalkyl), —OH and =O; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from a 5-membered monocyclic heteroaryl comprising one or two heteroatoms selected from S and N, wherein said 5-membered monocyclic heteroaryl is optionally substituted with one or two, preferably one, substituents selected from —$C_{1-2}$ alkyl, or $R^1$ is selected from a formula (A) and (B)

(A)

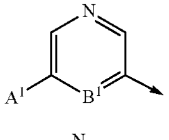

(B)

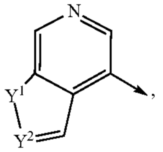

wherein $Y^1$ is NH, N($C_{1-2}$ alkyl) or $CH_2$, and $Y^2$ is N or CH, and wherein $B^1$ is N or CH, and $A^1$ is selected from hydrogen, —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 4-6 membered monocyclic heterocyclyl comprising 1 or 2 heteroatoms selected from O and N, each monocyclic heterocyclyl optionally substituted with one or two, preferably one, substituents independently selected from —$C_{1-2}$ alkyl, $C_{1-2}$ haloalkyl, —O—($C_{1-2}$ alkyl), —O—($C_{1-2}$ haloalkyl), —OH, =O, —C(O)R* and —C(O)NR*R*; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from thiophenyl, pyrrolyl and pyrazolyl, preferably thiophenyl and pyrrolyl, wherein said thiophenyl, pyrrolyl and pyrazolyl is independently optionally substituted with methyl or ethyl, or $R^1$ is selected from a formula (A) and (B)

(A)

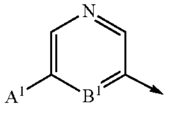

-continued (B)

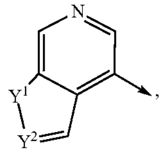

wherein $Y^1$ is NH, N($C_{1-2}$ alkyl) or $CH_2$, and $Y^2$ is N or CH, and wherein $B^1$ is N or CH, and $A^1$ is selected from hydrogen, —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, and a 4-6 membered monocyclic heterocyclyl comprising 1 or 2 heteroatoms selected from O and N, wherein said monocyclic heterocyclyl is optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH and =O; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$alkylene substituted with 1 to 4 F, —$CH_2$—O—$CH_2$— and —$CH_2$—NH—$CH_2$—; and wherein the arrow denotes the bond in the compounds of formula (I).

In a further preferred embodiment, said $R^1$ is selected from a formula (A) and (B)

(A)

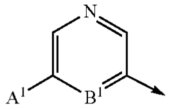

(B)

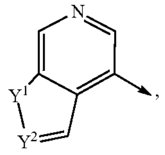

wherein $Y^1$ is NH, N($C_{1-2}$ alkyl) or $CH_2$, and $Y^2$ is N or CH, and wherein $B^1$ is N or CH, and $A^1$ is selected from hydrogen, —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, and a 4-6 membered monocyclic heterocyclyl comprising 1 or 2 heteroatoms selected from O and N, wherein said monocyclic heterocyclyl is optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH and =O; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$alkylene substituted with 1 to 4 F, —$CH_2$—O—$CH_2$— and —$CH_2$—NH—$CH_2$—; and wherein the arrow denotes the bond in the compounds of formula (I).

In a further preferred embodiment, said $R^1$ is of a formula (B)

(B)

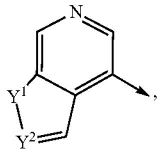

wherein $Y^1$ is NH, N($C_{1-2}$ alkyl) or $CH_2$, and $Y^2$ is N or CH, and wherein the arrow denotes the bond in the compounds of formula (I).

In a further preferred embodiment, said $R^1$ is of a formula (A)

(A)

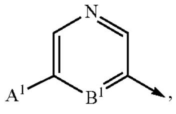

wherein $B^1$ is N or CH, and $A^1$ is selected from hydrogen, —$C_{1-2}$ alkyl, —$CHF_2$, —$CF_3$, —O—($C_{1-2}$ alkyl), —$OCHF_2$, —$OCHF_3$, —OH, =O, and a 4-6 membered monocyclic heterocyclyl comprising 1 or 2 heteroatoms selected from O and N, wherein said monocyclic heterocyclyl is optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH, —O—($C_{1-2}$alkylene)-OR*, —O—($C_{1-2}$alkylene)-N($R^{\circ\circ}$)$_2$ and =O; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$ alkylene substituted with 1 to 4 F, —$CH_2$—O—$CH_2$— and —$CH_2$—NH—$CH_2$—; and wherein the arrow denotes the bond in the compounds of formula (I).

In a further preferred embodiment, said $R^1$ is of a formula (A)

(A)

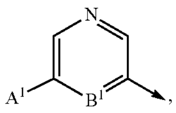

wherein $B^1$ is CH, and $A^1$ is selected from hydrogen, —$C_{1-2}$ alkyl, —$CHF_2$, —$CF_3$, —O—($C_{1-2}$ alkyl), —$OCHF_2$, —$OCHF_3$, —OH, ═O, and a 4-6 membered monocyclic heterocyclyl comprising 1 or 2 heteroatoms selected from O and N, wherein said monocyclic heterocyclyl is optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH, —O—($C_{1-2}$alkylene)-OR*, —O—($C_{1-2}$alkylene)-N($R^{\circ\circ}$)$_2$ and ═O; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—; and wherein the arrow denotes the bond in the compounds of formula (I).

In a further very preferred embodiment, said $R^1$ is of a formula (A)

(A)

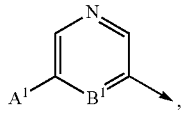

wherein $B^1$ is CH and $A^1$ is hydrogen, and wherein the arrow denotes the bond in the compounds of formula (I). Thus, in a further very preferred embodiment, said $R^1$ is 3-pyridyl.

In a further preferred embodiment, said $R^1$ is of a formula (A)

(A)

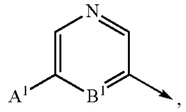

wherein $B^1$ is N, and $A^1$ is selected from hydrogen and —$C_{1-2}$ alkyl; and wherein the arrow denotes the bond in the compounds of formula (I).

In a further preferred embodiment, said $R^1$ is of a formula (A)

(A)

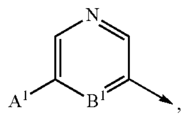

wherein $B^1$ is N, and $A^1$ is hydrogen, and wherein the arrow denotes the bond in the compounds of formula (I). Thus, in a further very preferred embodiment, said $R^1$ is 2-pyrazinyl.

$R^{21}$ is selected from hydrogen, $C_{1-6}$ alkyl, $C_{1-6}$ haloalkyl, $C_{1-6}$ alkyl optionally substituted with one or more OH, $C_{1-6}$ alkyl containing one to three oxygen atoms between carbon atoms, and $C_{3-6}$ cycloalkyl optionally substituted with one or more $R^{22}$, wherein $R^{22}$ is selected from halogen, preferably —Cl, —F, and —OH. In a further preferred embodiment, said $R^{21}$ is selected from hydrogen, $C_{1-2}$ alkyl, $C_{1-2}$ haloalkyl, $C_{1-2}$ alkyl optionally substituted with one or two OH, and $C_{3-4}$ cycloalkyl optionally substituted with one or more $R^{22}$, wherein $R^{22}$ is selected from —Cl, —F, and —OH. In a further preferred embodiment, said $R^{21}$ is selected from $C_{1-2}$ alkyl, $C_{1-2}$ haloalkyl and $C_{3-4}$ cycloalkyl. In a further preferred embodiment, said $R^{21}$ is selected from $C_{1-2}$ alkyl and cyclopropyl. In a further preferred embodiment, said $R^{21}$ is cyclopropyl. In a further very preferred embodiment, said $R^{21}$ is ethyl. In a further very preferred embodiment, said $R^{21}$ is methyl.

In a further preferred embodiment, $R^3$ is phenyl or pyridyl, each of which is optionally substituted with one or more, preferably one or two, substituents selected from halogen, —$C_{1-6}$ alkyl, $C_{1-6}$ haloalkyl, —O—$C_{1-6}$ alkyl, and —O—$C_{1-6}$ haloalkyl. In a further preferred embodiment, $R^3$ is phenyl or pyridyl, each of which is optionally substituted with one or more, preferably one or two, substituents selected from halogen, —$C_{1-3}$ alkyl, $C_{1-2}$ haloalkyl, —O—$C_{1-2}$ alkyl, and —O—$C_{1-3}$ haloalkyl. In a further preferred embodiment, $R^3$ is phenyl or pyridyl, each of which is optionally substituted with one or more, preferably one or two, substituents selected from —F, —Cl, —$C_{1-2}$ alkyl, $C_1$ haloalkyl, —$OCH_3$. In a further preferred embodiment, $R^3$ is phenyl or pyridyl, each of which is optionally substituted with one or more, preferably one or two, substituents selected from —F, —Cl, —$CH_3$ and —$OCH_3$. In a further preferred embodiment, $R^3$ is phenyl or pyridyl, each of which is optionally substituted with one substituent selected from —F, —Cl, —$CH_3$ and —$OCH_3$. In a further preferred embodiment, $R^3$ is phenyl or 3-pyridyl or 4-pyridyl, each of which is optionally substituted with one substituent selected from —F, —Cl, —$CH_3$ and —$OCH_3$. In a further preferred embodiment, $R^3$ is phenyl, 3-pyridyl or 4-pyridyl, each of which is optionally substituted at the meta position of said phenyl, 3-pyridyl or 4-pyridyl with one substituent selected from —F, —Cl, —$CH_3$ and —$OCH_3$. In a further preferred embodiment, $R^3$ is phenyl or phenyl substituted at the meta position with one substituent selected from —F, —Cl, —$CH_3$ and —$OCH_3$. In a further preferred embodiment, $R^3$ is 3-pyridyl or 3-pyridyl substituted at the meta position (5 position) with one substituent selected from —F, —Cl, —$CH_3$ and —$OCH_3$. In a further preferred embodiment, $R^3$ is 4-pyridyl or 4-pyridyl substituted at the meta position (5 position) with one substituent selected from —F, —Cl, —$CH_3$ and —$OCH_3$. In a further preferred embodiment, $R^3$ is phenyl. In a further preferred embodiment, $R^3$ is 3-pyridyl. In a further preferred embodiment, $R^3$ is 4-pyridyl.

In a further preferred embodiment, said $R^3$ is selected from phenyl, a 6-membered monocyclic heteroaryl and a 8-10 membered bicyclic heteroaryl, each independently comprising one or more, typically 1 to 5, preferably 1 to 4, ring heteroatoms independently selected from O, B, S and N, wherein one or two carbon ring atoms of said monocyclic heteroaryl or said bicyclic heteroaryl are optionally oxidized typically and preferably leading to a C═O functionality, and wherein said phenyl, said 6-membered monocyclic heteroaryl and said 8-10 membered bicyclic heteroaryl is independently optionally substituted with one or more, typically and preferably with 1 to 5, further preferably with 1 to 4, and again further preferably with 1 to 3 substituents selected from halogen, —$C_{1-6}$ alkyl, $C_{1-6}$ haloalkyl, —O—($C_{1-6}$ alkyl), —O—($C_{1-6}$ haloalkyl), —OH, —CN, ═O, —C(O)R*, —COOR*, —C(O)NR*R*, —NR*R*, —N(R**)—C(O)R*, —N(R**)—C(O)—OR*, —N(R**)—C(O)—NR*R*, —O—C(O)R*, —O—C(O)—NR*R*, and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$alkyl), —O—($C_{1-4}$ haloalkyl), —OH, ═O, —$C_{1-3}$alkylene-OR*, —C(O)R* and —C(O)NR*R*; wherein each R* is independently selected from H, $C_{1-4}$ alkyl, $C_{1-4}$ haloalkyl, cyclopropyl, cyclobutyl, oxetanyl, —$C_{1-2}$alkylene-OH, —$C_{1-2}$alkylene-O($C_{1-2}$alkyl), phenyl, and wherein each R** is independently selected from H, $C_{1-4}$ alkyl, $C_{1-4}$ haloalkyl, and/or wherein each monocyclic heterocyclyl is independently optionally substituted with one bivalent substituent selected from $C_{1-3}$ alkylene such as —$CH_2$—$CH_2$— and —$CH_2$—$CH_2$—$CH_2$—, $C_{1-3}$ alkylene substituted with 1 to 4 F, —$CH_2$—O—$CH_2$— and —$CH_2$—NH—$CH_2$—.

In a further preferred embodiment, said $R^3$ is selected from formula (C), formula (D), formula (E), formula (F) and formula (G)

(C)

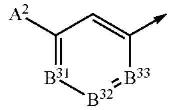

(D)

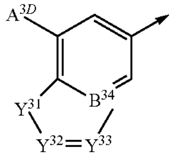

(E)

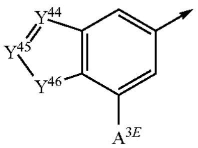

(F)

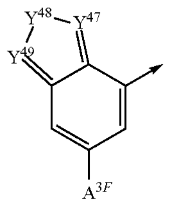

(G)

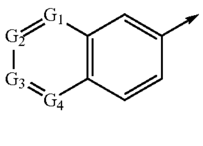

wherein $B^{31}$ is N, CH or C($A^{31}$), wherein $A^{31}$ is selected from —$C_{1-2}$ alkyl, $C_{1-2}$ haloalkyl, —F, —Cl, —O($C_{1-2}$alkyl), —OH, —NHC(O)($C_{1-2}$alkyl), wherein $A^{31}$ is selected from —$C_{1-2}$ alkyl, $C_{1-2}$ haloalkyl, —F, —Cl, —O($C_{1-2}$alkyl), —OH, —NHC(O)($C_{1-2}$alkyl);

$B^{32}$ is N, CH or C($A^{32}$), wherein $A^{32}$ is selected from —$C_{1-2}$ alkyl, $C_{1-2}$ haloalkyl, —F, —Cl, —O($C_{1-2}$alkyl), ═O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, ═O, —$C_{1-3}$alkylene-OR*, —C(O)R* and —C(O)NR*R*; wherein each R* is independently selected from H, $C_{1-4}$ alkyl, $C_{1-4}$ haloalkyl, phenyl, and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—;

In a further preferred embodiment, $B^{32}$ is N, CH or C($A^{32}$), wherein $A^{32}$ is selected from —$C_{1-2}$ alkyl, $C_{1-2}$ haloalkyl, —F, —Cl, —O($C_{1-2}$alkyl), ═O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, ═O, —$C_{1-3}$alkylene-OR*, —C(O)R* and —C(O)NR*R*; wherein each R* is independently selected from H, $C_{1-4}$ alkyl, $C_{1-4}$ haloalkyl and phenyl;

In a further preferred embodiment, $B^{32}$ is N, CH or C($A^{32}$), wherein $A^{32}$ is selected from —$C_{1-2}$ alkyl, $C_{1-2}$ haloalkyl, —F, —Cl, —O($C_{1-2}$alkyl), ═O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, ═O, —$C_{1-3}$alkylene-OR*, —C(O)R* and —C(O)NR*R*; wherein each R* is independently selected from H, $C_{1-3}$ alkyl, $C_{1-3}$ haloalkyl and phenyl;

$B^{33}$ is N, CH or C($A^{33}$), wherein $A^{33}$ is selected from —$C_{1-2}$ alkyl, $C_{1-2}$ haloalkyl, —F, —Cl, —O($C_{1-2}$alkyl), —OH, —NHC(O)($C_{1-2}$alkyl);

$A^2$ is selected from hydrogen, —$C_{1-2}$ alkyl, $C_{1-2}$ haloalkyl, —F, —Cl, —O($C_{1-2}$alkyl), ═O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, ═O, —$C_{1-3}$alkylene-OR*, —C(O)R* and —C(O)NR*R*; wherein each R* is independently selected from H, $C_{1-4}$ alkyl, $C_{1-4}$ haloalkyl, phenyl, and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—;

In a further preferred embodiment, $A^2$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$ alkylene-OR*, —C(O)R* and —C(O)NR*R*; wherein each R* is independently selected from H, $C_{1-4}$ alkyl, $C_{1-4}$ haloalkyl and phenyl;

In a further preferred embodiment, $A^2$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$ alkylene-OR*, —C(O)R* and —C(O)NR*R*; wherein each R* is independently selected from H, $C_{1-3}$ alkyl, $C_{1-3}$ haloalkyl and phenyl;

and wherein $Y^{41}$ is N, CH or C($A^{41}$), wherein $A^{41}$ is selected from methyl and ethyl; $Y^{42}$ is N, CH or C($A^{42}$), wherein $A^{42}$ is selected from methyl and ethyl; $Y^{43}$ is N, CH or C($A^{43}$), wherein $A^{43}$ is selected from methyl and ethyl;

$A^{3D}$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl); In a further preferred embodiment, $A^{3E}$ is selected from hydrogen, —$C_{1-2}$ alkyl, $C_{1-2}$ haloalkyl, —F, —Cl, —O($C_{1-2}$alkyl), =O, —OH;

and wherein $Y^{44}$ is N, NH, N($A^{44}$), C(O), CH or C($A^{44}$), wherein $A^{44}$ is independently selected from methyl and ethyl; $Y^{45}$ is N, NH, N($A^{45}$), C(O), CH or C($A^{45}$), wherein $A^{45}$ is independently selected from methyl and ethyl; $Y^{46}$ is N, NH, N($A^{46}$), C(O), CH or C($A^{46}$), wherein $A^{46}$ is independently selected from methyl and ethyl; and wherein at least one of said $Y^{44}$, $Y^{45}$ and $Y^{46}$ is NH, N($CH_3$) or N($C_2H_5$); and wherein $A^{3E}$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl); In a further preferred embodiment, $A^{3E}$ is selected from hydrogen, —$C_{1-2}$ alkyl, $C_{1-2}$ haloalkyl, —F, —Cl, —O($C_{1-2}$alkyl), =O, —OH;

and wherein $Y^{47}$ is N, NH, N($A^{47}$), C(O), CH or C($A^{47}$), wherein $A^{47}$ is independently selected from methyl and ethyl; $Y^{43}$ is N, NH, N($A^{48}$), C(O), CH or C($A^{48}$), wherein $A^{48}$ is independently selected from methyl and ethyl; $Y^{49}$ is N, NH, N($A^{49}$), C(O), CH or C($A^{49}$), wherein $A^{49}$ is independently selected from methyl and ethyl; and wherein at least one of said $Y^{47}$, $Y^{48}$ and $Y^{49}$ is NH, N($CH_3$) or N($C_2H_5$);

$A^{3F}$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl); In a further preferred embodiment, $A^{3E}$ is selected from hydrogen, —$C_{1-2}$ alkyl, $C_{1-2}$ haloalkyl, —F, —Cl, —O($C_{1-2}$alkyl), =O, —OH;

and wherein $G^1$, $G^2$, $G^3$, $G^4$ is independently selected from N, CH, C(O), NH or N($C_{1-2}$ alkyl); and wherein the arrow denotes the bond in the compounds of formula (I).

In a further preferred embodiment, said $R^3$ is selected from the following formulas

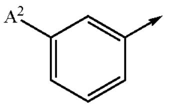
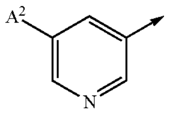
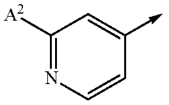
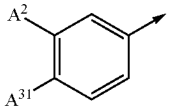
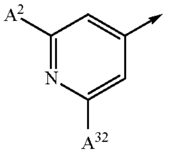
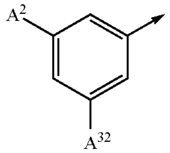
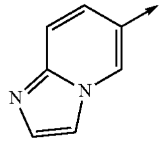
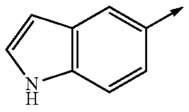
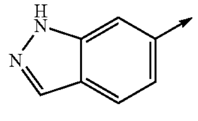
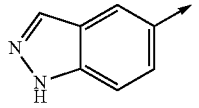
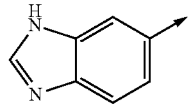
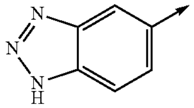
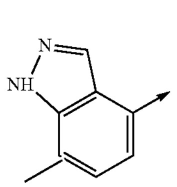
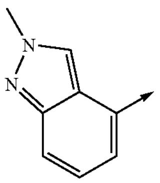
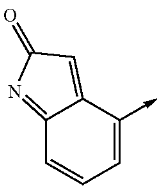
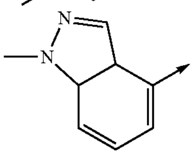
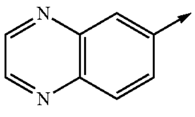
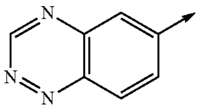
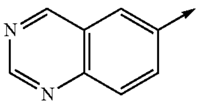

-continued

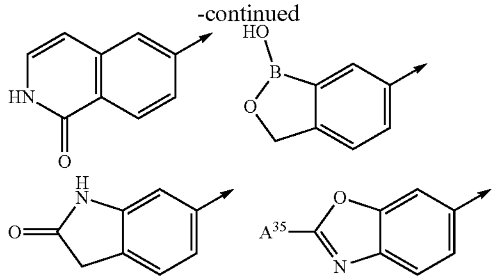

wherein $A^2$ is independently selected for each formula from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl, phenyl, and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—;

In a further preferred embodiment, $A^2$ is independently selected for each formula from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl and phenyl;

In a further preferred embodiment, $A^2$ is independently selected for each formula from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$alkylene-OR*, —C(O)R* and —C(O)NR*R*; wherein each R* is independently selected from H, $C_{1-3}$ alkyl, $C_{1-3}$ haloalkyl and phenyl;

$A^{31}$ is independently selected for each formula from —$C_{1-2}$ alkyl, $C_{1-2}$ haloalkyl, —F, —Cl, —O($C_{1-2}$alkyl), —OH, —NHC(O)($C_{1-2}$alkyl);

$A^{32}$ is independently selected for each formula from —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl, phenyl, and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—;

In a further preferred embodiment, $A^{32}$ is independently selected for each formula from —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl and phenyl;

In a further preferred embodiment, $A^{32}$ is independently selected for each formula from —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$alkylene-OR*, —C(O)R* and —C(O)NR*R*; wherein each R* is independently selected from H, $C_{1-3}$ alkyl, $C_{1-3}$ haloalkyl and phenyl; and wherein $A^{35}$ is independently selected for each formula from —$C_{1-2}$ alkyl; and wherein the arrow denotes the bond in the compounds of formula (I).

In a further very preferred embodiment, said $R^3$ is selected from the formulas

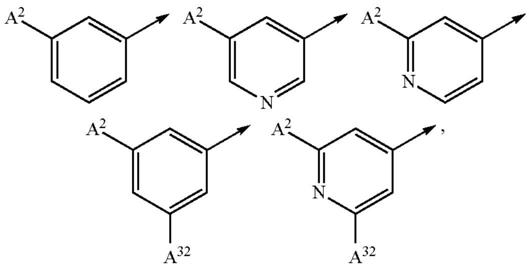

, $A^2$ and $A^{32}$ are independently selected for each formula from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$alkylene-OR*, —C(O)R* and —C(O)NR*R*; wherein each R* is independently selected from H, $C_{1-3}$ alkyl, $C_{1-3}$ haloalkyl and phenyl; and In a further very preferred embodiment, said $R^3$ is selected from the formulas

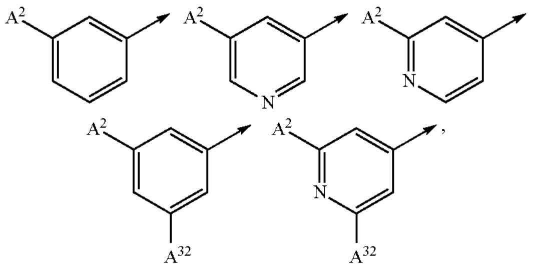

wherein $A^2$ are independently selected for each formula from hydrogen, —$C_{1-2}$ alkyl, $C_{1-2}$ haloalkyl, —F, —Cl, —O($C_{1-2}$alkyl); and wherein $A^{32}$ is independently selected for each formula from —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$ alkylene-OR*, —C(O)R* and —C(O)NR*R*; wherein each R* is independently selected from H, $C_{1-3}$ alkyl, $C_{1-3}$ haloalkyl and phenyl.

In a further very preferred embodiment, said $R^3$ is selected from the formulas

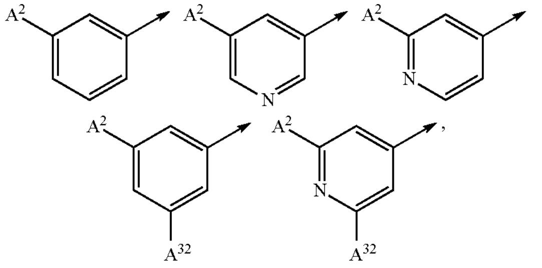

wherein $A^2$ are independently selected for each formula from hydrogen, —$C_{1-2}$ alkyl, $C_{1-2}$ haloalkyl, —F; and wherein $A^{32}$ is independently selected for each formula from —$C_{1-2}$ alkyl, $C_{1-2}$ haloalkyl, —F, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 3 heteroatoms selected from O and N, each monocyclic heterocyclyl independently optionally substituted with one or two substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$alkylene-OR*, —C(O)R* and —C(O)NR*R*; wherein each R* is independently selected from H, $C_{1-3}$ alkyl, $C_{1-3}$ haloalkyl and phenyl.

$R^{6x}$ is selected from -halogen, —OH, =O, $C_{1-4}$ alkyl, $C_{1-2}$ haloalkyl and $C_{1-3}$ alkyl substituted with one or more OH. In a further preferred embodiment, $R^{6x}$ is selected from -halogen, —OH, =O, $C_{1-3}$ alkyl, $C_{1-2}$ haloalkyl and $C_{1-3}$ alkyl substituted with one or two OH. In a further preferred embodiment, $R^{6x}$ is selected from $C_{1-3}$ alkyl, $C_{1-2}$ haloalkyl and $C_{1-3}$ alkyl substituted with one or two OH. In a further preferred embodiment, $R^{6x}$ is selected from $C_{1-2}$ alkyl, $C_{1-2}$ haloalkyl and $C_{1-3}$ alkyl substituted with one or two OH. H. In a further preferred embodiment, $R^{6x}$ is selected from $C_{1-3}$ alkyl and $C_{1-2}$ haloalkyl. In a further preferred embodiment, $R^{6x}$ is selected from $C_{1-2}$ alkyl and C, haloalkyl. In a further preferred embodiment, $R^{6x}$ is $CHF_2$. In a further preferred embodiment, $R^{6x}$ is $CF_3$. In a further preferred embodiment, $R^{6x}$ is ethyl. In a further very preferred embodiment, $R^{6x}$ is methyl.

It is to be understood that Ring A may further be substituted with one or more groups $R^x$, wherein any two $R^x$ groups, preferably adjacent $R^x$ groups, at ring A are optionally linked and/or any $R^x$ group at ring A is optionally linked with $R^{21}$; the number of groups $R^x$ in Ring A is 0, 1, 2, 3, or 4, preferably 0, 1, 2, or 3, further preferably 0, 1, or 2 or alternatively preferably 0 or 1. In case that Ring A may be substituted with one or more groups $R^x$ and one of said $R^x$ group at ring A is optionally linked with $R^{21}$ then said one of said $R^x$ group at ring A optionally linked with $R^{21}$ is a substituent at the 2-position of Ring A.

Thus, in a preferred embodiment, said Ring A is further substituted with 1, 2, 3 or 4 groups $R^x$, wherein any two $R^x$ groups, preferably adjacent $R^x$ groups, at ring A are optionally linked and/or any $R^x$ group at ring A is optionally linked with $R^{21}$. In case that one of said $R^x$ group at ring A is optionally linked with $R^{21}$ then said one of said $R^x$ group at ring A optionally linked with $R^{21}$ is a substituent at the 2-position of Ring A.

In a preferred embodiment, said Ring A is further substituted with 1, 2 or 3 groups $R^x$, wherein any two $R^x$ groups, preferably adjacent $R^x$ groups, at ring A are optionally linked and/or any $R^x$ group at ring A is optionally linked with $R^{21}$. In case that one of said $R^x$ group at ring A is optionally linked with $R^{21}$ then said one of said $R^x$ group at ring A optionally linked with $R^{21}$ is a substituent at the 2-position of Ring A.

In a preferred embodiment, said Ring A is further substituted with 1 or 2 groups $R^x$, wherein any two $R^x$ groups, preferably adjacent $R^x$ groups, at ring A are optionally linked and/or any $R^x$ group at ring A is optionally linked with $R^{21}$. In case that one of said $R^x$ group at ring A is optionally linked with $R^{21}$ then said one of said $R^x$ group at ring A optionally linked with $R^{21}$ is a substituent at the 2-position of Ring A.

In a preferred embodiment, said Ring A is further substituted with 1 group $R^x$, wherein said $R^x$ group at ring A is optionally linked with $R^{21}$. In case that one of said $R^x$ group at ring A is optionally linked with $R^{21}$ then said one of said $R^x$ group at ring A optionally linked with $R^{21}$ is a substituent at the 2-position of Ring A.

In a preferred embodiment, said Ring A is further substituted with 1 group $R^x$, wherein said $R^x$ group at ring A is not linked with $R^{21}$.

In a preferred embodiment, said Ring A is further substituted with 1 group $R^x$, wherein said $R^x$ group at ring A is not linked with $R^{21}$. In a further preferred embodiment, said group $R^x$ is —F, and wherein preferably said group $R^x$ being —F is at the 3-position of Ring A, said position which connects said Ring A with the $X^1$, $X^2$, $X^3$ ring system.

In a preferred embodiment, said Ring A is not further substituted. Thus, in a preferred embodiment, said Ring A is not further substituted with a group $R^x$.

In a preferred embodiment, said $R^{21}$ is selected from hydrogen, $C_{1-6}$ alkyl, $C_{1-6}$ haloalkyl, $C_{1-6}$ alkyl optionally substituted with one or more OH, $C_{1-6}$ alkyl containing one to three oxygen atoms between carbon atoms, and $C_{3-6}$ cycloalkyl optionally substituted with one or more $R^{22}$ wherein $R^{22}$ is selected from halogen, preferably —Cl, —F, and —OH. In a further preferred embodiment, said $R^{21}$ is selected from hydrogen, $C_{1-2}$ alkyl, $C_{1-2}$ haloalkyl, $C_{1-2}$ alkyl optionally substituted with one or two OH, and $C_{3-4}$ cycloalkyl optionally substituted with one or more $R^{22}$ wherein $R^{22}$ is selected from —Cl, —F, and —OH. In a further preferred embodiment, said $R^{21}$ is selected from $C_{1-2}$ alkyl, $C_{1-2}$ haloalkyl and $C_{3-4}$ cycloalkyl. In a further preferred embodiment, said $R^{21}$ is selected from $C_{1-2}$ alkyl and cyclopropyl. In a further preferred embodiment, said $R^{21}$ is ethyl. In a further preferred embodiment, said $R^{21}$ is cyclopropyl. In a further very preferred embodiment, said $R^{21}$ is methyl.

In a preferred embodiment, each $R^x$ is independently selected from -halogen, —OH, —O—$C_{1-3}$ alkyl optionally substituted with one or more $R^{xa}$, —NH—$C_{1-3}$ alkyl optionally substituted with one or more $R^{xa}$, —N($C_{1-3}$ alkyl optionally substituted with one or more $R^{xa}$)$_2$, =O, $C_{1-4}$ alkyl optionally substituted with one or more $R^{xa}$, $C_{1-4}$ haloalkyl, —($C_{1-2}$ alkylene optionally substituted with one or more $R^{xa}$)-(optionally substituted carbocyclyl), —($C_{1-2}$ alkylene optionally substituted with one or more $R^{xa}$)-(optionally substituted heterocyclyl), —O—($C_{1-2}$ alkylene optionally substituted with one or more $R^{xa}$)-(optionally substituted carbocyclyl), —O—($C_{1-2}$ alkylene optionally substituted with one or more $R^{xa}$)-(optionally substituted heterocyclyl), -(optionally substituted carbocyclyl) and -(optionally substituted heterocyclyl), wherein said $R^{xa}$ is independently selected from halogen, preferably —Cl, —F, and —OH.

In a further preferred embodiment, each $R^x$ is independently selected from -halogen, —OH, —O—$C_{1-2}$ alkyl optionally substituted with one or more $R^{xa}$, —NH—$C_{1-2}$ alkyl optionally substituted with one or more $R^{xa}$, —N($C_{1-2}$ alkyl optionally substituted with one or more $R^{xa}$)$_2$, =O, $C_{1-3}$ alkyl optionally substituted with one or more $R^{xa}$, $C_{1-2}$ haloalkyl, —($C_{1-2}$ alkylene optionally substituted with one or more $R^{xa}$)-(monocyclic carbocyclyl optionally substituted with one or more $R^{xa}$), —($C_{1-2}$ alkylene optionally substituted with one or more $R^{xa}$)-(monocyclic heterocyclyl optionally substituted with one or more $R^{xa}$), —O—($C_{1-2}$ alkylene optionally substituted with one or more $R^{xa}$)-(monocyclic carbocyclyl optionally substituted with one or more $R^{xa}$), —O—($C_{1-2}$ alkylene optionally substituted with one or more $R^{xa}$)-(monocyclic heterocyclyl optionally substituted with one or more $R^{xa}$), monocyclic carbocyclyl optionally substituted with one or more $R^{xa}$, monocyclic heterocyclyl optionally substituted with one or more $R^{xa}$, wherein said $R^{xa}$ is independently selected from halogen, preferably —Cl, —F, and —OH.

In a further preferred embodiment, each $R^x$ is independently selected from -halogen, —OH, —O—$C_{1-2}$ alkyl optionally substituted with one or more $R^{xa}$, —NH—$C_{1-2}$ alkyl optionally substituted with one or more $R^{xa}$, —N($C_{1-2}$ alkyl optionally substituted with one or more $R^{xa}$)$_2$, =O, $C_{1-3}$ alkyl optionally substituted with one or more $R^{xa}$, $C_{1-2}$ haloalkyl, —W-(monocyclic carbocyclyl optionally substituted with one or more $R^{xa}$), —W-(monocyclic heterocyclyl optionally substituted with one or more $R^{xa}$), and wherein —W— is absent, —($C_{1-2}$ alkylene)- or —O—($C_{1-2}$ alkylene)-, and wherein said $R^{xa}$ is independently selected from —Cl, —F, and —OH.

In a further preferred embodiment, each $R^x$ is independently selected from -halogen, —OH, —O—$C_{1-2}$ alkyl optionally substituted with one or more $R^{xa}$, —NH—$C_{1-2}$ alkyl optionally substituted with one or more $R^{xa}$, —N($C_{1-2}$ alkyl optionally substituted with one or more $R^{xa}$)$_2$, =O, $C_{1-3}$ alkyl optionally substituted with one or more $R^{xa}$, $C_{1-2}$ haloalkyl, —W-(monocyclic carbocyclyl optionally substituted with one or more $R^{xa}$), —W-(monocyclic heterocyclyl optionally substituted with one or more $R^{xa}$), and wherein —W— is absent, —($C_{1-2}$ alkylene)- or —O—($C_{1-2}$ alkylene)-, and wherein monocyclic carbocyclyl is selected from phenyl and $C_{3-6}$ cycloalkyl, and wherein monocyclic heterocyclyl is selected from thiophenyl, pyridyl, pyrazinyl and pyrimidinyl, and wherein said $R^{xa}$ is independently selected from —Cl, —F, and —OH.

In a further preferred embodiment, each $R^x$ is independently selected from -halogen, —OH, —O—$C_{1-2}$ alkyl, —NH—$C_{1-2}$ alkyl, —N($C_{1-2}$ alkyl)$_2$, =O, $C_{1-3}$ alkyl, $C_{1-2}$ haloalkyl, —W— (monocyclic carbocyclyl optionally substituted with one $R^{xa}$), —W-(monocyclic heterocyclyl optionally substituted with one $R^{xa}$), and wherein —W— is absent, —($C_{1-2}$ alkylene)- or —O—($C_{1-2}$ alkylene)-, and wherein monocyclic carbocyclyl is selected from phenyl and $C_{3-6}$ cycloalkyl, and wherein monocyclic heterocyclyl is selected from thiophenyl, pyridyl, pyrazinyl and pyrimidinyl, and wherein said $R^{xa}$ is independently selected from —F, and —OH.

In a further aspect and embodiment, the present invention provides a compound of formula (I), wherein said compound of formula (I) is a compound of formula (X), preferably of formula (Xa), and further preferably of formula (Xb), optionally in the form of a pharmaceutically acceptable salt, solvate, cocrystal, tautomer, racemate, enantiomer, or diastereomer or mixture thereof, for use in a method of treating fibrotic disease (X)

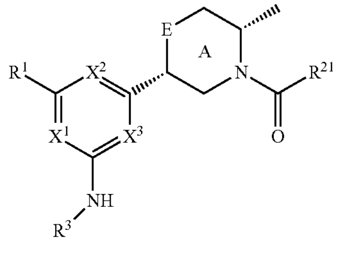

-continued (Xa)

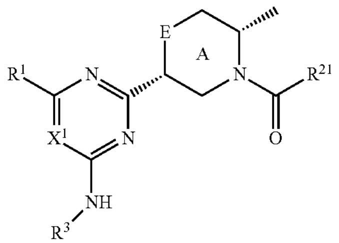

(Xb)

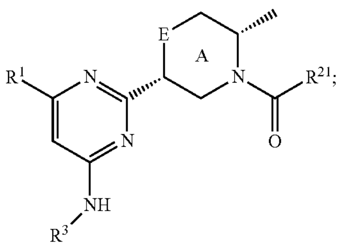

and in a further aspect and embodiment, the present invention provides a compound of formula (I), wherein said compound of formula (I) is a compound of formula (XI), preferably of formula (XIa), and further preferably of formula (XIb), optionally in the form of a pharmaceutically acceptable salt, solvate, cocrystal, tautomer, racemate, enantiomer, or diastereomer or mixture thereof, for use in a method of treating fibrotic disease (XI)

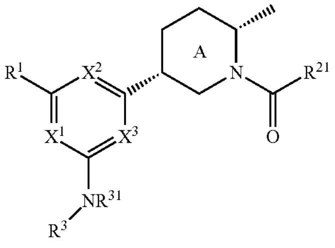

(XIa)

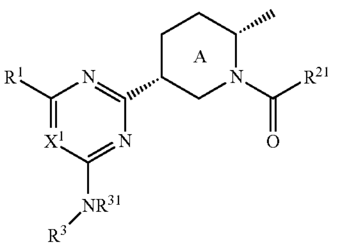

(XIb)

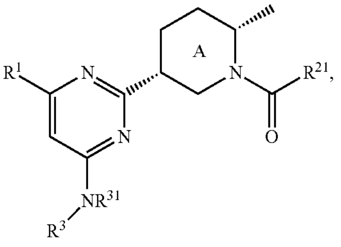

and in again a further aspect and embodiment, the present invention provides a compound of formula (I), for use in a method of treating fibrotic disease wherein said compound of formula (I) is a compound of formula (XII), preferably of formula (XIIa), and further preferably of formula (XIIb), optionally in the form of a pharmaceutically acceptable salt, solvate, cocrystal, tautomer, racemate, enantiomer, or diastereomer or mixture thereof, for use in a method of treating fibrotic disease (XII)

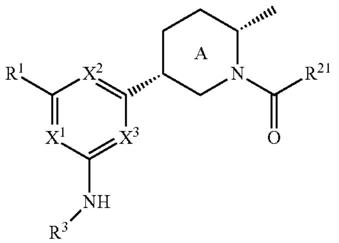

(XIIa)

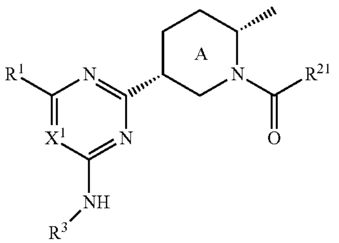

(XIIb)

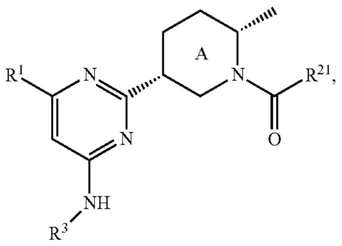

wherein $R^1$ is selected from -(optionally substituted heterocyclyl) and -(optionally substituted carbocyclyl).

In a further preferred embodiment, said $R^1$ is selected from phenyl, a 5- or 6-membered monocyclic heteroaryl and a 8-10 membered bicyclic heteroaryl, each independently comprising one or more, preferably 1 to 5, ring heteroatoms independently selected from O, S and N, wherein one or two carbon ring atoms of said monocyclic heteroaryl or said bicyclic heteroaryl are optionally oxidized, and wherein said phenyl, said 5- or 6-membered monocyclic heteroaryl and said 8-10 membered bicyclic heteroaryl is independently optionally substituted with one or more, preferably one or two, substituents selected from halogen, —$C_{1-6}$ alkyl, $C_{1-6}$ haloalkyl, —O—($C_{1-6}$ alkyl), —O—($C_{1-6}$ haloalkyl), —OH, —($C_{1-2}$alkylene)-O—($C_{1-4}$alkylene)-OR*, —O—($C_{1-4}$alkylene)-OR*, —($C_{1-2}$alkylene)-O—($C_{1-4}$alkylene)-N($R^{\circ\circ}$)$_2$, —O—($C_{1-4}$alkylene)-N($R^{\circ\circ}$)$_2$, —CN, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 3-6 membered monocyclic carbocyclyl and 3-6 membered monocyclic heterocyclyl comprising 1 to 4 heteroatoms selected from O, S and N, each monocyclic carbocyclyl and heterocyclyl independently optionally substituted with one or more, preferably one or two, substituents independently selected from halogen, —$C_{1-4}$ alkyl, $C_{1-4}$ haloalkyl, —O—($C_{1-4}$ alkyl), —O—($C_{1-4}$ haloalkyl), —OH, =O, —C(O)R* and —C(O)NR*R*; wherein each R* is independently selected from H, $C_{1-4}$ alkyl, $C_{1-4}$ haloalkyl, and wherein each R°° is independently selected from H, $C_{1-4}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from phenyl, a 5- or 6-membered monocyclic heteroaryl and a 8-10 membered bicyclic heteroaryl, each independently comprising one or more, preferably 1 to 5, ring heteroatoms independently selected from O, S and N, wherein one or two carbon ring atoms of said monocyclic heteroaryl or said bicyclic heteroaryl are optionally oxidized, and wherein said phenyl, said 5- or 6-membered monocyclic heteroaryl and said 8-10 membered bicyclic heteroaryl is independently optionally substituted with one or more, preferably one or two, substituents independently selected from halogen, —$C_{1-4}$ alkyl, $C_{1-4}$ haloalkyl, —O—($C_{1-4}$ alkyl), —O—($C_{1-4}$ haloalkyl), —OH, —($C_{1-2}$alkylene)-O—($C_{1-4}$alkylene)-OR*, —O—($C_{1-4}$alkylene)-OR*, —($C_{1-2}$alkylene)-O—($C_{1-4}$alkylene)-N(R°°)$_2$, —O—($C_{1-4}$alkylene)-N(R°°)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 3-6 membered monocyclic heterocyclyl comprising 1 to 4 heteroatoms selected from O, S and N, each monocyclic heterocyclyl independently optionally substituted with one or more, preferably one or two, substituents selected from halogen, —$C_{1-3}$ alkyl, $C_{1-3}$ haloalkyl, —O—($C_{1-3}$ alkyl), —O—($C_{1-3}$ haloalkyl), —OH, =O, —C(O)R* and —C(O)NR*R*; wherein each R* is independently selected from H, $C_{1-3}$ alkyl, $C_{1-3}$ haloalkyl, and wherein each R°° is independently selected from H, $C_{1-4}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$alkylene substituted with 1 to 4 F, —$CH_2$—O—$CH_2$— and —$CH_2$—NH—$CH_2$—.

In a further preferred embodiment, said $R^1$ is selected from phenyl, a 5- or 6-membered monocyclic heteroaryl and a 8-10 membered bicyclic heteroaryl, each independently comprising one or more, preferably 1 to 5, ring heteroatoms independently selected from O, S and N, wherein one or two carbon ring atoms of said monocyclic heteroaryl or said bicyclic heteroaryl are optionally oxidized, and wherein said phenyl, said 5- or 6-membered monocyclic heteroaryl and said 8-10 membered bicyclic heteroaryl is independently optionally substituted with one or more, preferably one or two, substituents independently selected from —F, —Cl, —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N(R°°)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 3-6 membered monocyclic heterocyclyl comprising 1 to 4 heteroatoms selected from O, S and N, each monocyclic heterocyclyl independently optionally substituted with one or more, preferably one or two, substituents selected from —$C_{1-2}$ alkyl, $C_{1-2}$ haloalkyl, —O—($C_{1-2}$ alkyl), —O—($C_{1-2}$ haloalkyl), —OH, =O, —C(O)R* and —C(O)NR*R*; wherein each R* is independently selected from H, $C_{1-2}$ alkyl, $C_{1-2}$ haloalkyl, and wherein each R°° is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$alkylene substituted with 1 to 4 F, —$CH_2$—O—$CH_2$— and —$CH_2$—NH—$CH_2$—.

In a further preferred embodiment, said $R^1$ is selected from phenyl, a 5- or 6-membered monocyclic heteroaryl comprising one or two heteroatoms independently selected from S and N and a 8-10 membered bicyclic heteroaryl comprising one or more, preferably 1 to 4, ring nitrogen heteroatoms, wherein one or two, preferably one, carbon ring atoms of said monocyclic heteroaryl or said bicyclic heteroaryl are optionally oxidized, and wherein said phenyl, said 5- or 6-membered monocyclic heteroaryl and said 8-10 membered bicyclic heteroaryl is independently optionally substituted with one or more, preferably one or two, substituents independently selected from —F, —Cl, —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N(R°°)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 3-6 membered monocyclic heterocyclyl comprising 1 to 4 heteroatoms selected from O, S and N, each monocyclic heterocyclyl independently optionally substituted with one or more, preferably one or two, substituents selected from —$C_{1-2}$ alkyl, $C_{1-2}$ haloalkyl, —O—($C_{1-2}$ alkyl), —O—($C_{1-2}$ haloalkyl), —OH, =O, —C(O)R* and —C(O)NR*R*; wherein each R* is independently selected from H, $C_{1-2}$ alkyl, $C_{1-2}$ haloalkyl, and wherein each R°° is independently selected from H, $C_{1-2}$alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from a 5- or 6-membered monocyclic heteroaryl comprising one or two heteroatoms independently selected from S and N and a 8-10 membered bicyclic heteroaryl comprising 1 to 5, preferably 1 to 4, ring nitrogen heteroatoms, wherein one or two, preferably one, carbon ring atoms of said monocyclic heteroaryl or said bicyclic heteroaryl are optionally oxidized, and wherein said 5- or 6-membered monocyclic heteroaryl and said 8-10 membered bicyclic heteroaryl is independently optionally substituted with one or two substituents independently selected from —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N(R°°)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 4-6 membered monocyclic heterocyclyl comprising 1 or 2 heteroatoms selected from O and N, each monocyclic heterocyclyl independently optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH, =O, —C(O)R* and —C(O)NR*R*; wherein each R* is independently selected from H, $C_{1-2}$ alkyl, $C_{1-2}$ haloalkyl, and wherein each R°° is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from a 5- or 6-membered monocyclic heteroaryl comprising one or two heteroatoms independently selected from S and N and a 8-10 membered bicyclic heteroaryl comprising 1 to 5, preferably 1 to 4, ring nitrogen heteroatoms, wherein one or two, preferably one, carbon ring atoms of said monocyclic heteroaryl or said bicyclic heteroaryl are optionally oxidized, and wherein said 5- or 6-membered monocyclic heteroaryl and said 8-10 membered bicyclic heteroaryl is independently optionally substituted with one or two, preferably one, substituents independently selected from —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, and 4-6 membered monocyclic heterocyclyl comprising 1 or 2 heteroatoms selected from O and N, each monocyclic heterocyclyl independently optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH and =O; wherein each R* is independently selected from H, $C_{1-2}$ alkyl, $C_{1-2}$ haloalkyl, and wherein each $R^{\circ\circ}$ is independently selected from H, $C_{1-2}$alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$ alkylene substituted with 1 to 4 F, —$CH_2$—O—$CH_2$— and —$CH_2$—NH—$CH_2$—.

In a further preferred embodiment, said $R^1$ is phenyl, thiophenyl, pyrrolyl, pyrazolyl, azaindolyl, azaindazolyl, pyrazinyl, pyridyl or pyrimidinyl, wherein the phenyl, thiophenyl, pyrrolyl, pyrazolyl, azaindolyl, azaindazolyl, pyrazinyl, pyridyl or pyrimidinyl is optionally substituted with one or two, preferably one, substituents independently selected from —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 4-6 membered monocyclic heterocyclyl comprising 1 or 2 heteroatoms selected from O and N, each monocyclic heterocyclyl optionally substituted with one or two, preferably one, substituents independently selected from —$C_{1-2}$ alkyl, $C_{1-2}$ haloalkyl, —O—($C_{1-2}$ alkyl), —O—($C_{1-2}$ haloalkyl), —OH, =O, —C(O)R* and —C(O)NR*R*; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is phenyl, thiophenyl, pyrrolyl, pyrazolyl, azaindolyl, azaindazolyl, pyrazinyl, pyridyl or pyrimidinyl, wherein the phenyl, thiophenyl, pyrrolyl, pyrazolyl, azaindolyl, azaindazolyl, pyrazinyl, pyridyl or pyrimidinyl is optionally substituted with one or two, preferably one, substituents independently selected from —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, and 4-6 membered monocyclic heterocyclyl comprising 1 or 2 heteroatoms selected from 0 and N, each monocyclic heterocyclyl optionally substituted with one or two, preferably one, substituents independently selected from —$C_{1-2}$ alkyl, $C_{1-2}$ haloalkyl, —O—($C_{1-2}$ alkyl), —O—($C_{1-2}$ haloalkyl), —OH and =O; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from a 5-membered monocyclic heteroaryl comprising one or two heteroatoms selected from S and N, wherein said 5-membered monocyclic heteroaryl is optionally substituted with one or two, preferably one, substituents selected from —$C_{1-2}$ alkyl, or $R^1$ is selected from a formula (A) and (B)

(A)

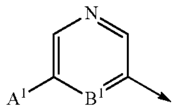

(B)

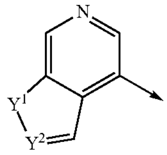

, wherein $Y^1$ is NH, N($C_{1-2}$ alkyl) or $CH_2$, and $Y^2$ is N or CH, and wherein $B^1$ is N or CH, and $A^1$ is selected from hydrogen, —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 4-6 membered monocyclic heterocyclyl comprising 1 or 2 heteroatoms selected from O and N, each monocyclic heterocyclyl optionally substituted with one or two, preferably one, substituents independently selected from —$C_{1-2}$ alkyl, $C_{1-2}$ haloalkyl, —O—($C_{1-2}$ alkyl), —O—($C_{1-2}$ haloalkyl), —OH, =O, —C(O)R* and —C(O)NR*R*; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, $—CH_2—O—CH_2—$ and $—CH_2—NH—CH_2—$.

In a further preferred embodiment, said $R^1$ is selected from thiophenyl, pyrrolyl and pyrazolyl, preferably thiophenyl and pyrrolyl, wherein said thiophenyl, pyrrolyl and pyrazolyl is independently optionally substituted with methyl or ethyl, or $R^1$ is selected from a formula (A) and (B)

(A)

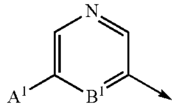

(B)

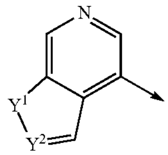, wherein $Y^1$ is NH, N($C_{1-2}$ alkyl) or $CH_2$, and $Y^2$ is N or CH, and wherein $B^1$ is N or CH, and $A^1$ is selected from hydrogen, $—C_{1-2}$ alkyl, $—CHF_2$, $—CF_3$, $—O—(C_{1-2}$ alkyl), $—OCHF_2$, $—OCHF_3$, —OH, $—O—(C_{1-2}$alkylene)-OR*, $—O—(C_{1-2}$alkylene)-$N(R^{\circ\circ})_2$, =O, and a 4-6 membered monocyclic heterocyclyl comprising 1 or 2 heteroatoms selected from O and N, wherein said monocyclic heterocyclyl is optionally substituted with one or two, preferably one, substituents selected from $—C_{1-2}$ alkyl, $C_{1-2}$ haloalkyl, $—O—(C_{1-2}$ alkyl), $—O—(C_{1-2}$ haloalkyl), —OH and =O; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$alkylene substituted with 1 to 4 F, $—CH_2—O—CH_2—$ and $—CH_2—NH—CH_2—$; and wherein the arrow denotes the bond in the compounds of formula (I).

In a further preferred embodiment, said $R^1$ is selected from a formula (A) and (B)

(A)

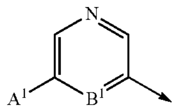

(B)

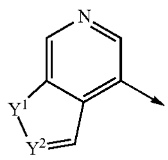, wherein $Y^1$ is NH, N($C_{1-2}$ alkyl) or $CH_2$, and $Y^2$ is N or CH, and wherein $B^1$ is N or CH, and $A^1$ is selected from hydrogen, $—C_{1-2}$ alkyl, $—CHF_2$, $—CF_3$, $—O—(C_{1-2}$ alkyl), $—OCHF_2$, $—OCHF_3$, —OH, $—O—(C_{1-2}$alkylene)-OR*, $—O—(C_{1-2}$alkylene)-$N(R^{\circ\circ})_2$, =O, and a 4-6 membered monocyclic heterocyclyl comprising 1 or 2 heteroatoms selected from O and N, wherein said monocyclic heterocyclyl is optionally substituted with one or two, preferably one, substituents selected from $—C_{1-2}$ alkyl, $C_{1-2}$ haloalkyl, $—O—(C_{1-2}$ alkyl), $—O—(C_{1-2}$ haloalkyl), —OH and =O; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$alkylene substituted with 1 to 4 F, $—CH_2—O—CH_2—$ and $—CH_2—NH—CH_2—$; and wherein the arrow denotes the bond in the compounds of formula (I).

In a further preferred embodiment, said $R^1$ is of a formula (B)

(B)

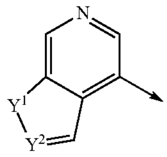, wherein $Y^1$ is NH, N($C_{1-2}$ alkyl) or $CH_2$, and $Y^2$ is N or CH, and wherein the arrow denotes the bond in the compounds of formula (I).

In a further preferred embodiment, said $R^1$ is of a formula (A)

(A)

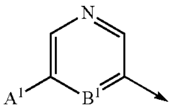, wherein $B^1$ is N or CH, and $A^1$ is selected from hydrogen, $—C_{1-2}$ alkyl, $—CHF_2$, $—CF_3$, $—O—(C_{1-2}$ alkyl), $—OCHF_2$, $—OCHF_3$, —OH, =O, and a 4-6 membered monocyclic heterocyclyl comprising 1 or 2 heteroatoms selected from O and N, wherein said monocyclic heterocyclyl is optionally substituted with one or two, preferably one, substituents selected from $—C_{1-2}$ alkyl, $C_{1-2}$ haloalkyl, $—O—(C_{1-2}$ alkyl), $—O—(C_{1-2}$ haloalkyl), —OH, $—O—(C_{1-2}$alkylene)-OR*, $—O—(C_{1-2}$alkylene)-$N(R^{\circ\circ})_2$ and =O; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$ alkylene substituted with 1 to 4 F, $-CH_2-O-CH_2-$ and $-CH_2-NH-CH_2-$; and wherein the arrow denotes the bond in the compounds of formula (I).

In a further preferred embodiment, said $R^1$ is of a formula (A)

(A)

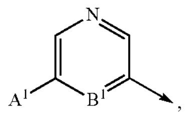

wherein $B^1$ is CH, and $A^1$ is selected from hydrogen, $-C_{1-2}$ alkyl, $-CHF_2$, $-CF_3$, $-O-(C_{1-2}$ alkyl), $-OCHF_2$, $-OCHF_3$, $-OH$, $=O$, and a 4-6 membered monocyclic heterocyclyl comprising 1 or 2 heteroatoms selected from O and N, wherein said monocyclic heterocyclyl is optionally substituted with one or two, preferably one, substituents selected from $-C_{1-2}$ alkyl, $C_{1-2}$ haloalkyl, $-O-(C_{1-2}$ alkyl), $-O-(C_{1-2}$ haloalkyl), $-OH$, $-O-(C_{1-2}$alkylene)-OR*, $-O-(C_{1-2}$alkylene)-$N(R^{\circ\circ})_2$ and $=O$; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, $-CH_2-O-CH_2-$ and $-CH_2-NH-CH_2-$; and wherein the arrow denotes the bond in the compounds of formula (I).

In a further very preferred embodiment, said $R^1$ is of a formula (A)

(A)

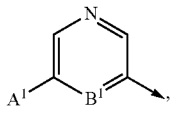

wherein $B^1$ is CH and $A^1$ is hydrogen, and wherein the arrow denotes the bond in the compounds of formula (I). Thus, in a further very preferred embodiment, said $R^1$ is 3-pyridyl.

In a further preferred embodiment, said $R^1$ is of a formula (A)

(A)

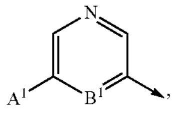

wherein $B^1$ is N, and $A^1$ is selected from hydrogen and $-C_{1-2}$ alkyl; and wherein the arrow denotes the bond in the compounds of formula (I).

In a further preferred embodiment, said $R^1$ is of a formula (A)

(A)

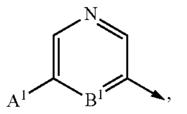

wherein $B^1$ is N, and $A^1$ is hydrogen, and wherein the arrow denotes the bond in the compounds of formula (I). Thus, in a further very preferred embodiment, said $R^1$ is 2-pyrazinyl.

$R^{21}$ is selected from hydrogen, $C_{1-6}$ alkyl, $C_{1-6}$ haloalkyl, $C_{1-6}$ alkyl optionally substituted with one or more OH, $C_{1-6}$ alkyl containing one to three oxygen atoms between carbon atoms, and $C_{3-6}$ cycloalkyl optionally substituted with one or more $R^{22}$, wherein $R^{22}$ is selected from halogen, preferably $-Cl$, $-F$, and $-OH$. In a further preferred embodiment, said $R^{21}$ is selected from hydrogen, $C_{1-2}$ alkyl, $C_{1-2}$ haloalkyl, $C_{1-2}$ alkyl optionally substituted with one or two OH, and $C_{3-4}$ cycloalkyl optionally substituted with one or more $R^{22}$, wherein $R^{22}$ is selected from $-Cl$, $-F$, and $-OH$. In a further preferred embodiment, said $R^{21}$ is selected from $C_{1-2}$ alkyl, $C_{1-2}$ haloalkyl and $C_{3-4}$ cycloalkyl. In a further preferred embodiment, said $R^{21}$ is selected from $C_{1-2}$ alkyl and cyclopropyl. In a further preferred embodiment, said $R^{21}$ is cyclopropyl. In a further very preferred embodiment, said $R^{21}$ is ethyl. In a further very preferred embodiment, said $R^{21}$ is methyl.

$R^3$ is selected from -(optionally substituted heterocyclyl), -(optionally substituted carbocyclyl), -(optionally substituted $C_{1-6}$ alkylene)-(optionally substituted heterocyclyl) and -(optionally substituted $C_{1-6}$ alkylene)-(optionally substituted carbocyclyl). Preferably, $R^3$ is -(optionally substituted carbocyclyl). More preferably, $R^3$ is phenyl which is optionally substituted with one or more groups selected from halogen, $-(C_{1-6}$ alkyl which is optionally substituted with one or more F) and $-O-(C_{1-6}$ alkyl which is optionally substituted with one or more F). Further preferred are compounds in which $R^3$ is pyridinyl which may have the same substituents as the optionally substituted heterocyclyl. In other preferred compounds, $R^3$ is quinazoline or cinnoline, each of which may have the same substituents as the optionally substituted heterocyclyl.

In a further preferred embodiment, $R^3$ is phenyl or pyridyl, each of which is optionally substituted with one or more, preferably one or two, substituents selected from halogen, $-C_{1-6}$ alkyl, $C_{1-6}$ haloalkyl, $-O-C_{1-6}$ alkyl, and $-O-C_{1-6}$ haloalkyl. In a further preferred embodiment, $R^3$ is phenyl or pyridyl, each of which is optionally substituted with one or more, preferably one or two, substituents selected from halogen, $-C_{1-3}$ alkyl, $C_{1-2}$ haloalkyl, $-O-C_{1-2}$ alkyl, and $-O-C_{1-3}$ haloalkyl. In a further preferred embodiment, $R^3$ is phenyl or pyridyl, each of which is optionally substituted with one or more, preferably one or two, substituents selected from $-F$, $-Cl$, $-C_{1-2}$ alkyl, $C_1$ haloalkyl, $-OCH_3$. In a further preferred embodiment, $R^3$ is phenyl or pyridyl, each of which is optionally substituted with one or more, preferably one or two, substituents selected from $-F$, $-Cl$, $-CH_3$ and $-OCH_3$. In a further preferred embodiment, $R^3$ is phenyl or pyridyl, each of which is optionally substituted with one substituent selected from $-F$, $-Cl$, $-CH_3$ and $-OCH_3$. In a further preferred embodiment, $R^3$ is phenyl or 3-pyridyl or 4-pyridyl, each of which is optionally substituted with one substituent selected from $-F$, $-Cl$, $-CH_3$ and $-OCH_3$. In a further preferred embodiment, $R^3$ is phenyl, 3-pyridyl or 4-pyridyl, each of which is optionally substituted at the meta position of said phenyl, 3-pyridyl or 4-pyridyl with one substituent selected from —F, —Cl, —$CH_3$ and —$OCH_3$. In a further preferred embodiment, $R^3$ is phenyl or phenyl substituted at the meta position with one substituent selected from —F, —Cl, —$CH_3$ and —$OCH_3$. In a further preferred embodiment, $R^3$ is 3-pyridyl or 3-pyridyl substituted at the meta position (5 position) with one substituent selected from —F, —Cl, —$CH_3$ and —$OCH_3$. In a further preferred embodiment, $R^3$ is 4-pyridyl or 4-pyridyl substituted at the meta position (5 position) with one substituent selected from —F, —Cl, —$CH_3$ and —$OCH_3$. In a further preferred embodiment, $R^3$ is phenyl. In a further preferred embodiment, $R^3$ is 3-pyridyl. In a further preferred embodiment, $R^3$ is 4-pyridyl.

In a further preferred embodiment, said $R^3$ is selected from phenyl, a 6-membered monocyclic heteroaryl and a 8-10 membered bicyclic heteroaryl, each independently comprising one or more, typically 1 to 5, preferably 1 to 4, ring heteroatoms independently selected from O, B, S and N, wherein one or two carbon ring atoms of said monocyclic heteroaryl or said bicyclic heteroaryl are optionally oxidized typically and preferably leading to a C═O functionality, and wherein said phenyl, said 6-membered monocyclic heteroaryl and said 8-10 membered bicyclic heteroaryl is independently optionally substituted with one or more, typically and preferably with 1 to 5, further preferably with 1 to 4, and again further preferably with 1 to 3 substituents selected from halogen, —$C_{1-6}$ alkyl, $C_{1-6}$ haloalkyl, —O—($C_{1-6}$ alkyl), —O—($C_{1-6}$ haloalkyl), —OH, —CN, ═O, —C(O)R*, —COOR*, —C(O)NR*R*, —NR*R*, —N(R**)—C(O)R*, —N(R**)—C(O)—OR*, —N(R**)—C(O)—NR*R*, —O—C(O)R*, —O—C(O)—NR*R*, and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, ═O, —$C_{1-3}$alkylene-OR*, —C(O)R* and —C(O)NR*R*; wherein each R* is independently selected from H, $C_{1-4}$ alkyl, $C_{1-4}$ haloalkyl, cyclopropyl, cyclobutyl, oxetanyl, —$C_{1-2}$alkylene-OH, —$C_{1-2}$alkylene-O($C_{1-2}$alkyl), phenyl, and wherein each R** is independently selected from H, $C_{1-4}$ alkyl, $C_{1-4}$ haloalkyl, and/or wherein each monocyclic heterocyclyl is independently optionally substituted with one bivalent substituent selected from $C_{1-3}$ alkylene such as —$CH_2$—$CH_2$— and —$CH_2$—$CH_2$—$CH_2$—, $C_{1-3}$ alkylene substituted with 1 to 4 F, —$CH_2$—O—$CH_2$— and —$CH_2$—NH—$CH_2$—.

In a further preferred embodiment, said $R^3$ is selected from formula (C), formula (D), formula (E), formula (F) and formula (G)

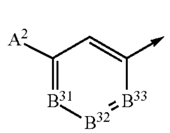
(C)

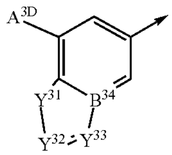
(D)

-continued

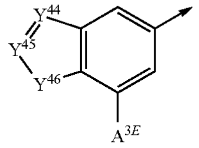
(E)

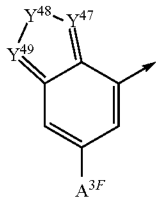
(F)

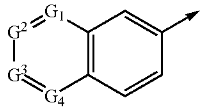
(G)

wherein $B^{31}$ is N, CH or C($A^{31}$), wherein $A^{31}$ is selected from —$C_{1-2}$ alkyl, $C_{1-2}$ haloalkyl, —F, —Cl, —O($C_{1-2}$alkyl), —OH, —NHC(O)($C_{1-2}$alkyl), wherein $A^{31}$ is selected from —$C_{1-2}$ alkyl, $C_{1-2}$ haloalkyl, —F, —Cl, —O($C_{1-2}$alkyl), —OH, —NHC(O)($C_{1-2}$alkyl);

$B^{32}$ is N, CH or C($A^{32}$), wherein $A^{32}$ is selected from —$C_{1-2}$ alkyl, $C_{1-2}$ haloalkyl, —F, —Cl, —O($C_{1-2}$alkyl), ═O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, ═O, —$C_{1-3}$alkylene-OR*, —C(O)R* and —C(O)NR*R*; wherein each R* is independently selected from H, $C_{1-4}$ alkyl, $C_{1-4}$ haloalkyl, phenyl, and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—;

In a further preferred embodiment, $B^{32}$ is N, CH or C($A^{32}$), wherein $A^{32}$ is selected from —$C_{1-2}$ alkyl, $C_{1-2}$ haloalkyl, —F, —Cl, —O($C_{1-2}$alkyl), ═O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, ═O, —$C_{1-3}$alkylene-OR*, —C(O)R* and —C(O)NR*R*; wherein each R* is independently selected from H, $C_{1-4}$ alkyl, $C_{1-4}$ haloalkyl and phenyl;

In a further preferred embodiment, $B^{32}$ is N, CH or C($A^{32}$), wherein $A^{32}$ is selected from —$C_{1-2}$ alkyl, $C_{1-2}$ haloalkyl, —F, —Cl, —O($C_{1-2}$alkyl), ═O, —OH, —NHC(O)($C_{1-2}$alkyl), —C(O)NH($C_{1-2}$alkyl), —C(O)

$N(C_{1-2}alkyl)_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$alkylene-OR*, —C(O)R* and —C(O)NR*R*; wherein each R* is independently selected from H, $C_{1-3}$ alkyl, $C_{1-3}$ haloalkyl and phenyl;

$B^{33}$ is N, CH or C($A^{33}$), wherein $A^{33}$ is selected from —$C_{1-2}$ alkyl, $C_{1-2}$ haloalkyl, —F, —Cl, —O($C_{1-2}$alkyl), —OH, —NHC(O)($C_{1-2}$alkyl);

$A^2$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl, phenyl, and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—;

In a further preferred embodiment, $A^2$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$ alkylene-OR*, —C(O)R* and —C(O)NR*R*; wherein each R* is independently selected from H, $C_{1-4}$ alkyl, $C_{1-4}$ haloalkyl and phenyl;

In a further preferred embodiment, $A^2$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$ alkylene-OR*, —C(O)R* and —C(O)NR*R*; wherein each R* is independently selected from H, $C_{1-3}$ alkyl, $C_{1-3}$ haloalkyl and phenyl;

and wherein $Y^{41}$ is N, CH or C($A^{41}$), wherein $A^{41}$ is selected from methyl and ethyl; $Y^{42}$ is N, CH or C($A^{42}$), wherein $A^{42}$ is selected from methyl and ethyl; $Y^{43}$ is N, CH or C($A^{43}$), wherein $A^{43}$ is selected from methyl and ethyl;

$A^{3D}$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl); In a further preferred embodiment, $A^{3E}$ is selected from hydrogen, —$C_{1-2}$ alkyl, $C_{1-2}$ haloalkyl, —F, —Cl, —O($C_{1-2}$alkyl), =O, —OH;

and wherein $Y^{44}$ is N, NH, N($A^{44}$), C(O), CH or C($A^{44}$), wherein $A^{44}$ is independently selected from methyl and ethyl; $Y^{45}$ is N, NH, N($A^{45}$), C(O), CH or C($A^{45}$), wherein $A^{45}$ is independently selected from methyl and ethyl; $Y^{46}$ is N, NH, N($A^{46}$), C(O), CH or C($A^{46}$), wherein $A^{46}$ is independently selected from methyl and ethyl; and wherein at least one of said $Y^{44}$, $Y^{45}$ and $Y^{46}$ is NH, N($CH_3$) or N($C_2H_5$); and wherein $A^{3E}$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl); In a further preferred embodiment, $A^{3E}$ is selected from hydrogen, —$C_{1-2}$ alkyl, $C_{1-2}$ haloalkyl, —F, —Cl, —O($C_{1-2}$alkyl), =O, —OH;

and wherein $Y^{47}$ is N, NH, N($A^{47}$), C(O), CH or C($A^{47}$), wherein $A^{47}$ is independently selected from methyl and ethyl; $Y^{48}$ is N, NH, N($A^{48}$), C(O), CH or C($A^{48}$), wherein $A^{48}$ is independently selected from methyl and ethyl; $Y^{49}$ is N, NH, N($A^{49}$), C(O), CH or C($A^{49}$), wherein $A^{49}$ is independently selected from methyl and ethyl; and wherein at least one of said $Y^{47}$, $Y^{48}$ and $Y^{49}$ is NH, N($CH_3$) or N($C_2H_5$);

$A^{3F}$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl); In a further preferred embodiment, $A^{3E}$ is selected from hydrogen, —$C_{1-2}$ alkyl, $C_{1-2}$ haloalkyl, —F, —Cl, —O($C_{1-2}$alkyl), =O, —OH;

and wherein $G^1$, $G^2$, $G^3$, $G^4$ is independently selected from N, CH, C(O), NH or N($C_{1-2}$ alkyl); and wherein the arrow denotes the bond in the compounds of formula (I).

In a further preferred embodiment, said $R^3$ is selected from the following formulas

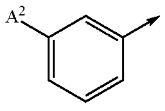
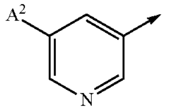
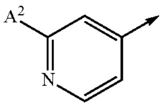
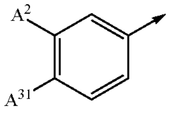
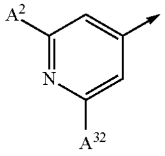
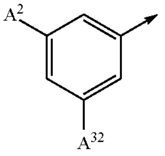
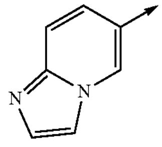
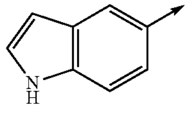
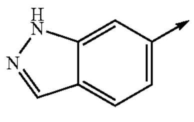
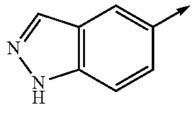
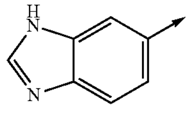

-continued

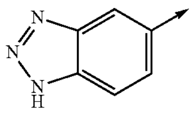
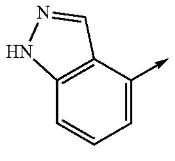
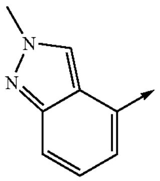
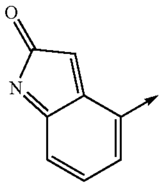
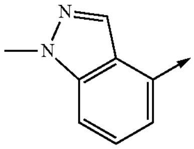
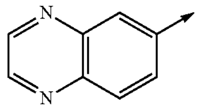
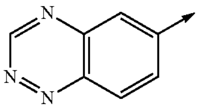
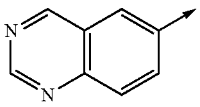
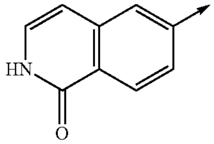
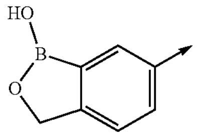
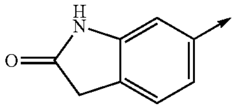
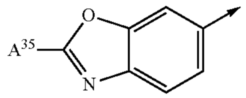

wherein $A^2$ is independently selected for each formula from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl, phenyl, and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—;

In a further preferred embodiment, $A^2$ is independently selected for each formula from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl and phenyl;

In a further preferred embodiment, $A^2$ is independently selected for each formula from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$alkylene-OR*, —C(O)R* and —C(O)NR*R*; wherein each R* is independently selected from H, $C_{1-3}$ alkyl, $C_{1-3}$ haloalkyl and phenyl;

$A^{31}$ is independently selected for each formula from —$C_{1-2}$ alkyl, $C_{1-2}$ haloalkyl, —F, —Cl, —O($C_{1-2}$alkyl), —OH, —NHC(O)($C_{1-2}$alkyl);

$A^{32}$ is independently selected for each formula from —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl, phenyl, and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—;

In a further preferred embodiment, $A^{32}$ is independently selected for each formula from —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl and phenyl;

In a further preferred embodiment, $A^{32}$ is independently selected for each formula from —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$alkylene-OR*, —C(O)R* and —C(O)NR*R*; wherein each R* is independently selected from H, $C_{1-3}$ alkyl, $C_{1-3}$ haloalkyl and phenyl; and wherein $A^{35}$ is independently selected for each formula from —$C_{1-2}$ alkyl; and wherein the arrow denotes the bond in the compounds of formula (I).

In a further very preferred embodiment, said $R^3$ is selected from the formulas

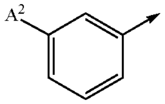

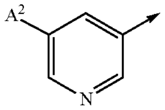

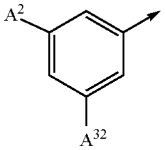

wherein $A^2$ and $A^{32}$ are independently selected for each formula from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$alkylene-OR*, —C(O)R* and —C(O)NR*R*; wherein each R* is independently selected from H, $C_{1-3}$ alkyl, $C_{1-3}$ haloalkyl and phenyl; and In a further very preferred embodiment, said $R^3$ is selected from the formulas

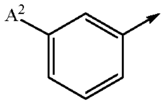

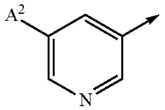

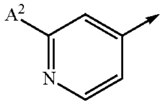

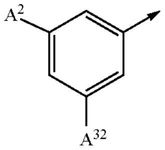

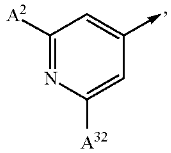, wherein $A^2$ and $A^{32}$ are independently selected for each formula from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$alkylene-OR*, —C(O)R* and —C(O)NR*R*; wherein each R* is independently selected from H, $C_{1-3}$ alkyl, $C_{1-3}$ haloalkyl and phenyl; and In a further very preferred embodiment, said $R^3$ is selected from the formulas

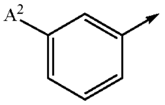

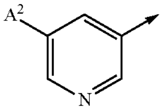

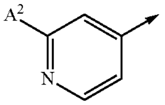

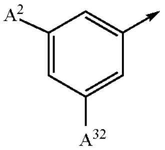

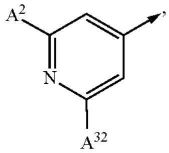, $A^2$ are independently selected for each formula from hydrogen, —$C_{1-2}$ alkyl, $C_{1-2}$ haloalkyl, —F, —Cl, —O($C_{1-2}$alkyl); and wherein $A^{32}$ is independently selected for each formula from —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$ alkylene-OR*, —C(O)R* and —C(O)NR*R*; wherein each R* is independently selected from H, $C_{1-3}$ alkyl, $C_{1-3}$ haloalkyl and phenyl.

In a further very preferred embodiment, said $R^3$ is selected from the formulas

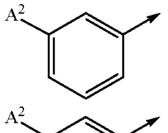

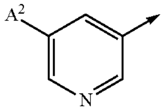

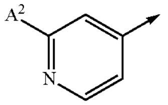

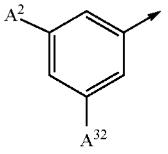

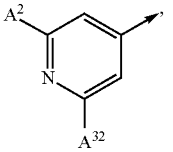

wherein $A^2$ are independently selected for each formula from hydrogen, —$C_{1-2}$ alkyl, $C_{1-2}$ haloalkyl, —F; and wherein $A^{32}$ is independently selected for each formula from —$C_{1-2}$ alkyl, $C_{1-2}$ haloalkyl, —F, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 3 heteroatoms selected from O and N, each monocyclic heterocyclyl independently optionally substituted with one or two substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$alkylene-OR*, —C(O)R* and —C(O)NR*R*; wherein each R* is independently selected from H, $C_{1-3}$ alkyl, $C_{1-3}$ haloalkyl and phenyl.

Each of $X^1$, $X^2$ and $X^3$ is independently selected from N, CH and $CR^X$, wherein preferably at least one of said $X^1$, $X^2$ and $X^3$ is N, wherein further preferably at least one of said $X^2$ and $X^3$ is N; and wherein again further preferably $X^2$ and $X^3$ are both N, and wherein still further preferably $X^2$ and $X^3$ are both N, and $X^1$ is CH.

E is selected from —$CH_2$—, —$CHR^x$—, —$CR^x_2$—, —NH—, —$NR^x$— and —O—, -$L^1$-$L^2$- and -$L^2$-$L^1$-, wherein $L^1$ is selected from —$CH_2$—, —$CHR^x$—, —$CR^x_2$—, —NH—, —$NR^x$— and —O— and $L^2$ is selected from —$CH_2$-, —$CHR^x$— and —$CR^x_2$—. In a further preferred embodiment, said E is selected from —$CH_2$—, —NH—, —O—, —$CH_2$-O—, —O—$CH_2$—, —$CH_2$—NH—, —NH—$CH_2$— and —$CH_2$—$CH_2$—. Preferably, E is selected from $CH_2$—, —O—, —$CH_2$—O—, —O—$CH_2$— and —$CH_2$—$CH_2$—. More preferably, E is selected from $CH_2$—, —O—, —$CH_2$—O— and —$CH_2$—$CH_2$—. In a very preferred embodiment, E is $CH_2$.

It is to be understood that Ring A may further be substituted with one or more groups $R^x$, wherein any two $R^x$ groups, preferably adjacent $R^x$ groups, at ring A are optionally linked and/or any $R^x$ group at ring A is optionally linked with $R^{21}$; the number of groups $R^x$ in Ring A is 0, 1, 2, 3, or 4, preferably 0, 1, 2, or 3, further preferably 0, 1, or 2 or alternatively preferably 0 or 1. In case that Ring A may be substituted with one or more groups $R^x$ and one of said $R^x$ group at ring A is optionally linked with $R^{21}$ then said one of said $R^x$ group at ring A optionally linked with $R^{21}$ is a substituent at the 2-position of Ring A.

Thus, in a preferred embodiment, said Ring A is further substituted with 1, 2, 3 or 4 groups $R^x$, wherein any two $R^x$ groups, preferably adjacent $R^x$ groups, at ring A are optionally linked and/or any $R^x$ group at ring A is optionally linked with $R^{21}$. In case that one of said $R^x$ group at ring A is optionally linked with $R^{21}$ then said one of said $R^x$ group at ring A optionally linked with $R^{21}$ is a substituent at the 2-position of Ring A.

In a preferred embodiment, said Ring A is further substituted with 1, 2 or 3 groups $R^x$, wherein any two $R^x$ groups, preferably adjacent $R^x$ groups, at ring A are optionally linked and/or any $R^x$ group at ring A is optionally linked with $R^{21}$. In case that one of said $R^x$ group at ring A is optionally linked with $R^{21}$ then said one of said $R^x$ group at ring A optionally linked with $R^{21}$ is a substituent at the 2-position of Ring A.

In a preferred embodiment, said Ring A is further substituted with 1 or 2 groups $R^x$, wherein any two $R^x$ groups, preferably adjacent $R^x$ groups, at ring A are optionally linked and/or any $R^x$ group at ring A is optionally linked with $R^{21}$. In case that one of said $R^x$ group at ring A is optionally linked with $R^{21}$ then said one of said $R^x$ group at ring A optionally linked with $R^{21}$ is a substituent at the 2-position of Ring A.

In a preferred embodiment, said Ring A is further substituted with 1 group $R^x$, wherein said $R^x$ group at ring A is optionally linked with $R^{21}$. In case that one of said $R^x$ group at ring A is optionally linked with $R^{21}$ then said one of said $R^x$ group at ring A optionally linked with $R^{21}$ is a substituent at the 2-position of Ring A.

In a preferred embodiment, said Ring A is further substituted with 1 group $R^x$, wherein said $R^x$ group at ring A is not linked with $R^{21}$.

In a preferred embodiment, said Ring A is further substituted with 1 group $R^x$, wherein said $R^x$ group at ring A is not linked with $R^{21}$. In a further preferred embodiment, said group $R^x$ is —F, and wherein preferably said group $R^x$ being —F is at the 3-position of Ring A, said position which connects said Ring A with the $X^1$, $X^2$, $X^3$ ring system.

In a preferred embodiment, said Ring A is not further substituted. Thus, in a preferred embodiment, said Ring A is not further substituted with a group $R^x$.

In a preferred embodiment, said $R^{21}$ is selected from hydrogen, $C_{1-6}$ alkyl, $C_{1-6}$ haloalkyl, $C_{1-6}$ alkyl optionally substituted with one or more OH, $C_{1-6}$ alkyl containing one to three oxygen atoms between carbon atoms, and $C_{3-6}$ cycloalkyl optionally substituted with one or more $R^{22}$ wherein $R^{22}$ is selected from halogen, preferably —Cl, —F, and —OH. In a further preferred embodiment, said $R^{21}$ is selected from hydrogen, $C_{1-2}$ alkyl, $C_{1-2}$ haloalkyl, $C_{1-2}$ alkyl optionally substituted with one or two OH, and $C_{3-4}$ cycloalkyl optionally substituted with one or more $R^{22}$ wherein $R^{22}$ is selected from —Cl, —F, and —OH. In a further preferred embodiment, said $R^{21}$ is selected from $C_{1-2}$ alkyl, $C_{1-2}$ haloalkyl and $C_{3-4}$ cycloalkyl. In a further preferred embodiment, said $R^{21}$ is selected from $C_{1-2}$ alkyl and cyclopropyl. In a further preferred embodiment, said $R^{21}$ is ethyl. In a further preferred embodiment, said $R^{21}$ is cyclopropyl. In a further very preferred embodiment, said $R^{21}$ is methyl.

In a preferred embodiment, each $R^x$ is independently selected from -halogen, —OH, —O—$C_{1-3}$ alkyl optionally substituted with one or more $R^{xa}$, —NH—$C_{1-3}$ alkyl optionally substituted with one or more $R^{xa}$, —N($C_{1-3}$ alkyl optionally substituted with one or more $R^{xa}$)$_2$, =O, $C_{1-4}$ alkyl optionally substituted with one or more $R^{xa}$, $C_{1-4}$ haloalkyl, —($C_{1-2}$ alkylene optionally substituted with one or more $R^{xa}$)-(optionally substituted carbocyclyl), —($C_{1-2}$ alkylene optionally substituted with one or more $R^{xa}$)-(optionally substituted heterocyclyl), —O—($C_{1-2}$ alkylene optionally substituted with one or more $R^{xa}$)-(optionally substituted carbocyclyl), —O—($C_{1-2}$ alkylene optionally substituted with one or more $R^{xa}$)-(optionally substituted heterocyclyl), -(optionally substituted carbocyclyl) and -(optionally substituted heterocyclyl), wherein said $R^{xa}$ is independently selected from halogen, preferably —Cl, —F, and —OH.

In a further preferred embodiment, each $R^x$ is independently selected from -halogen, —OH, —O—$C_{1-2}$ alkyl optionally substituted with one or more $R^{xa}$, —NH—$C_{1-2}$ alkyl optionally substituted with one or more $R^{xa}$, —N($C_{1-2}$ alkyl optionally substituted with one or more $R^{xa}$)$_2$, =O, $C_{1-3}$ alkyl optionally substituted with one or more $R^{xa}$, $C_{1-2}$ haloalkyl, —($C_{1-2}$ alkylene optionally substituted with one or more $R^{xa}$)-(monocyclic carbocyclyl optionally substituted with one or more $R^{xa}$), —($C_{1-2}$ alkylene optionally substituted with one or more $R^{xa}$)-(monocyclic heterocyclyl optionally substituted with one or more $R^{xa}$), —O—($C_{1-2}$ alkylene optionally substituted with one or more $R^{xa}$)-(monocyclic carbocyclyl optionally substituted with one or more $R^{xa}$), —O—($C_{1-2}$ alkylene optionally substituted with one or more $R^{xa}$)-(monocyclic heterocyclyl optionally substituted with one or more $R^{xa}$), monocyclic carbocyclyl optionally substituted with one or more $R^{xa}$, monocyclic heterocyclyl optionally substituted with one or more $R^{xa}$, wherein said $R^{xa}$ is independently selected from halogen, preferably —Cl, —F, and —OH.

In a further preferred embodiment, each $R^x$ is independently selected from -halogen, —OH, —O—$C_{1-2}$ alkyl optionally substituted with one or more $R^{xa}$, —NH—$C_{1-2}$ alkyl optionally substituted with one or more $R^{xa}$, —N($C_{1-2}$ alkyl optionally substituted with one or more $R^{xa}$)$_2$, =O, $C_{1-3}$ alkyl optionally substituted with one or more $R^{xa}$, $C_{1-2}$ haloalkyl, —W-(monocyclic carbocyclyl optionally substituted with one or more $R^{xa}$), —W-(monocyclic heterocyclyl optionally substituted with one or more $R^{xa}$), and wherein —W— is absent, —($C_{1-2}$ alkylene)- or —O—($C_{1-2}$ alkylene)-, and wherein said $R^{xa}$ is independently selected from —Cl, —F, and —OH.

In a further preferred embodiment, each $R^x$ is independently selected from -halogen, —OH, —O—$C_{1-2}$ alkyl optionally substituted with one or more $R^{xa}$, —NH—$C_{1-2}$ alkyl optionally substituted with one or more $R^{xa}$, —N($C_{1-2}$ alkyl optionally substituted with one or more $R^{xa}$)$_2$, =O, $C_{1-3}$ alkyl optionally substituted with one or more $R^{xa}$, $C_{1-2}$ haloalkyl, —W-(monocyclic carbocyclyl optionally substituted with one or more $R^{xa}$), —W-(monocyclic heterocyclyl optionally substituted with one or more $R^{xa}$), and wherein —W— is absent, —($C_{1-2}$ alkylene)- or —O—($C_{1-2}$ alkylene)-, and wherein monocyclic carbocyclyl is selected from phenyl and $C_{3-6}$ cycloalkyl, and wherein monocyclic heterocyclyl is selected from thiophenyl, pyridyl, pyrazinyl and pyrimidinyl, and wherein said $R^{xa}$ is independently selected from —Cl, —F, and —OH.

In a further preferred embodiment, each $R^x$ is independently selected from -halogen, —OH, —O—$C_{1-2}$ alkyl, —NH—$C_{1-2}$ alkyl, —N($C_{1-2}$ alkyl)$_2$, =O, $C_{1-3}$ alkyl, $C_{1-2}$ haloalkyl, —W— (monocyclic carbocyclyl optionally substituted with one $R^{xa}$), —W-(monocyclic heterocyclyl optionally substituted with one $R^{xa}$), and wherein —W— is absent, —($C_{1-2}$ alkylene)- or —O—($C_{1-2}$ alkylene)-, and wherein monocyclic carbocyclyl is selected from phenyl and $C_{3-6}$ cycloalkyl, and wherein monocyclic heterocyclyl is selected from thiophenyl, pyridyl, pyrazinyl and pyrimidinyl, and wherein said $R^{xa}$ is independently selected from —F, and —OH.

In a further very preferred aspect and embodiment, the present invention provides a compound of formula (I), wherein said compound of formula (I) is a compound of formula (XIIb), optionally in the form of a pharmaceutically acceptable salt, solvate, cocrystal, tautomer, racemate, enantiomer, or diastereomer or mixture thereof, for use in a method of treating fibrotic disease (XIIb)

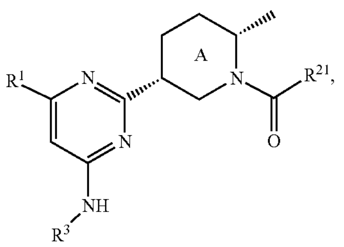

wherein

In a further preferred embodiment, said $R^1$ is selected from phenyl, a 5- or 6-membered monocyclic heteroaryl and a 8-10 membered bicyclic heteroaryl, each independently comprising one or more, preferably 1 to 5, ring heteroatoms independently selected from O, S and N, wherein one or two carbon ring atoms of said monocyclic heteroaryl or said bicyclic heteroaryl are optionally oxidized, and wherein said phenyl, said 5- or 6-membered monocyclic heteroaryl and said 8-10 membered bicyclic heteroaryl is independently optionally substituted with one or more, preferably one or two, substituents selected from halogen, —$C_{1-6}$ alkyl, $C_{1-6}$ haloalkyl, —O—($C_{1-6}$ alkyl), —O—($C_{1-6}$ haloalkyl), —OH, —($C_{1-2}$alkylene)-O—($C_{1-4}$alkylene)-OR*, —O—($C_{1-4}$alkylene)-OR*, —($C_{1-2}$alkylene)-O—($C_{1-4}$alkylene)-N($R^{\circ\circ}$)$_2$, —O—($C_{1-4}$alkylene)-N($R^{\circ\circ}$)$_2$, —CN, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 3-6 membered monocyclic carbocyclyl and 3-6 membered monocyclic heterocyclyl comprising 1 to 4 heteroatoms selected from O, S and N, each monocyclic carbocyclyl and heterocyclyl independently optionally substituted with one or more, preferably one or two, substituents independently selected from halogen, —$C_{1-4}$ alkyl, $C_{1-4}$ haloalkyl, —O—($C_{1-4}$ alkyl), —O—($C_{1-4}$ haloalkyl), —OH, =O, —C(O)R* and —C(O)NR*R*; wherein each R* is independently selected from H, $C_{1-4}$ alkyl, $C_{1-4}$ haloalkyl, and wherein each $R^{\circ\circ}$ is independently selected from H, $C_{1-4}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from phenyl, a 5- or 6-membered monocyclic heteroaryl and a 8-10 membered bicyclic heteroaryl, each independently comprising one or more, preferably 1 to 5, ring heteroatoms independently selected from O, S and N, wherein one or two carbon ring atoms of said monocyclic heteroaryl or said bicyclic heteroaryl are optionally oxidized, and wherein said phenyl, said 5- or 6-membered monocyclic heteroaryl and said 8-10 membered bicyclic heteroaryl is independently optionally substituted with one or more, preferably one or two, substituents independently selected from halogen, —$C_{1-4}$ alkyl, $C_{1-4}$ haloalkyl, —O—($C_{1-4}$ alkyl), —O—($C_{1-4}$ haloalkyl), —OH, —($C_{1-2}$alkylene)-O—($C_{1-4}$alkylene)-OR*, —O—($C_{1-4}$alkylene)-OR*, —($C_{1-2}$alkylene)-O—($C_{1-4}$alkylene)-N($R^{\circ\circ}$)$_2$, —O—($C_{1-4}$alkylene)-N($R^{\circ\circ}$)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 3-6 membered monocyclic heterocyclyl comprising 1 to 4 heteroatoms selected from O, S and N, each monocyclic heterocyclyl independently optionally substituted with one or more, preferably one or two, substituents selected from halogen, —$C_{1-3}$ alkyl, $C_{1-3}$ haloalkyl, —O—($C_{1-3}$ alkyl), —O—($C_{1-3}$ haloalkyl), —OH, =O, —C(O)R* and —C(O)NR*R*; wherein each R* is independently selected from H, $C_{1-3}$ alkyl, $C_{1-3}$ haloalkyl, and wherein each $R^{\circ\circ}$ is independently selected from H, $C_{1-4}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$alkylene substituted with 1 to 4 F, —$CH_2$—O—$CH_2$— and —$CH_2$—NH—$CH_2$—.

In a further preferred embodiment, said $R^1$ is selected from phenyl, a 5- or 6-membered monocyclic heteroaryl and a 8-10 membered bicyclic heteroaryl, each independently comprising one or more, preferably 1 to 5, ring heteroatoms independently selected from O, S and N, wherein one or two carbon ring atoms of said monocyclic heteroaryl or said bicyclic heteroaryl are optionally oxidized, and wherein said phenyl, said 5- or 6-membered monocyclic heteroaryl and said 8-10 membered bicyclic heteroaryl is independently optionally substituted with one or more, preferably one or two, substituents independently selected from —F, —Cl, —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 3-6 membered monocyclic heterocyclyl comprising 1 to 4 heteroatoms selected from O, S and N, each monocyclic heterocyclyl independently optionally substituted with one or more, preferably one or two, substituents selected from —$C_{1-2}$ alkyl, $C_{1-2}$ haloalkyl, —O—($C_{1-2}$ alkyl), —O—($C_{1-2}$ haloalkyl), —OH, =O, —C(O)R* and —C(O)NR*R*; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from phenyl, a 5- or 6-membered monocyclic heteroaryl comprising one or two heteroatoms independently selected from S and N and a 8-10 membered bicyclic heteroaryl comprising one or more, preferably 1 to 4, ring nitrogen heteroatoms, wherein one or two, preferably one, carbon ring atoms of said monocyclic heteroaryl or said bicyclic heteroaryl are optionally oxidized, and wherein said phenyl, said 5- or 6-membered monocyclic heteroaryl and said 8-10 membered bicyclic heteroaryl is independently optionally substituted with one or more, preferably one or two, substituents independently selected from —F, —Cl, —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 3-6 membered monocyclic heterocyclyl comprising 1 to 4 heteroatoms selected from O, S and N, each monocyclic heterocyclyl independently optionally substituted with one or more, preferably one or two, substituents selected from —$C_{1-2}$ alkyl, $C_{1-2}$ haloalkyl, —O—($C_{1-2}$ alkyl), —O—($C_{1-2}$ haloalkyl), —OH, =O, —C(O)R* and —C(O)NR*R*; wherein each R* is independently selected from H, $C_{1-2}$ alkyl, $C_{1-2}$ haloalkyl, and wherein each $R^{\circ\circ}$ is independently selected from H, $C_{1-2}$alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from a 5- or 6-membered monocyclic heteroaryl comprising one or two heteroatoms independently selected from S and N and a 8-10 membered bicyclic heteroaryl comprising 1 to 5, preferably 1 to 4, ring nitrogen heteroatoms, wherein one or two, preferably one, carbon ring atoms of said monocyclic heteroaryl or said bicyclic heteroaryl are optionally oxidized, and wherein said 5- or 6-membered monocyclic heteroaryl and said 8-10 membered bicyclic heteroaryl is independently optionally substituted with one or two substituents independently selected from —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 4-6 membered monocyclic heterocyclyl comprising 1 or 2 heteroatoms selected from O and N, each monocyclic heterocyclyl independently optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH, =O, —C(O)R* and —C(O)NR*R*; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from a 5- or 6-membered monocyclic heteroaryl comprising one or two heteroatoms independently selected from S and N and a 8-10 membered bicyclic heteroaryl comprising 1 to 5, preferably 1 to 4, ring nitrogen heteroatoms, wherein one or two, preferably one, carbon ring atoms of said monocyclic heteroaryl or said bicyclic heteroaryl are optionally oxidized, and wherein said 5- or 6-membered monocyclic heteroaryl and said 8-10 membered bicyclic heteroaryl is independently optionally substituted with one or two, preferably one, substituents independently selected from —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, and 4-6 membered monocyclic heterocyclyl comprising 1 or 2 heteroatoms selected from 0 and N, each monocyclic heterocyclyl independently optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH and =O; wherein each R* is independently selected from H, $C_{1-2}$ alkyl, $C_{1-2}$ haloalkyl, and wherein each $R^{\circ\circ}$ is independently selected from H, $C_{1-2}$alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$ alkylene substituted with 1 to 4 F, —$CH_2$—O—$CH_2$— and —$CH_2$—NH—$CH_2$—.

In a further preferred embodiment, said $R^1$ is phenyl, thiophenyl, pyrrolyl, pyrazolyl, azaindolyl, azaindazolyl, pyrazinyl, pyridyl or pyrimidinyl, wherein the phenyl, thiophenyl, pyrrolyl, pyrazolyl, azaindolyl, azaindazolyl, pyrazinyl, pyridyl or pyrimidinyl is optionally substituted with one or two, preferably one, substituents independently selected from —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 4-6 membered monocyclic heterocyclyl comprising 1 or 2 heteroatoms selected from O and N, each monocyclic heterocyclyl optionally substituted with one or two, preferably one, substituents independently selected from —$C_{1-2}$ alkyl, $C_{1-2}$ haloalkyl, —O—($C_{1-2}$ alkyl), —O—($C_{1-2}$ haloalkyl), —OH, =O, —C(O)R* and —C(O)NR*R*; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is phenyl, thiophenyl, pyrrolyl, pyrazolyl, azaindolyl, azaindazolyl, pyrazinyl, pyridyl or pyrimidinyl, wherein the phenyl, thiophenyl, pyrrolyl, pyrazolyl, azaindolyl, azaindazolyl, pyrazinyl, pyridyl or pyrimidinyl is optionally substituted with one or two, preferably one, substituents independently selected from —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, and 4-6 membered monocyclic heterocyclyl comprising 1 or 2 heteroatoms selected from 0 and N, each monocyclic heterocyclyl optionally substituted with one or two, preferably one, substituents independently selected from —$C_{1-2}$ alkyl, $C_{1-2}$ haloalkyl, —O—($C_{1-2}$ alkyl), —O—($C_{1-2}$ haloalkyl), —OH and =O; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from a 5-membered monocyclic heteroaryl comprising one or two heteroatoms selected from S and N, wherein said 5-membered monocyclic heteroaryl is optionally substituted with one or two, preferably one, substituents selected from —$C_{1-2}$ alkyl, or $R^1$ is selected from a formula (A) and (B)

(A)

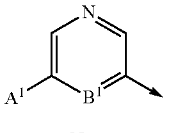

(B)

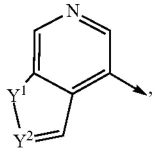

, wherein $Y^1$ is NH, N($C_{1-2}$ alkyl) or $CH_2$, and $Y^2$ is N or CH, and wherein $B^1$ is N or CH, and $A^1$ is selected from hydrogen, —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 4-6 membered monocyclic heterocyclyl comprising 1 or 2 heteroatoms selected from O and N, each monocyclic heterocyclyl optionally substituted with one or two, preferably one, substituents independently selected from —$C_{1-2}$ alkyl, $C_{1-2}$ haloalkyl, —O—($C_{1-2}$ alkyl), —O—($C_{1-2}$ haloalkyl), —OH, =O, —C(O)R* and —C(O)NR*R*; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.

In a further preferred embodiment, said $R^1$ is selected from thiophenyl, pyrrolyl and pyrazolyl, preferably thiophenyl and pyrrolyl, wherein said thiophenyl, pyrrolyl and pyrazolyl is independently optionally substituted with methyl or ethyl, or $R^1$ is selected from a formula (A) and (B)

(A)

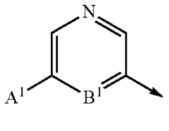

-continued (B)

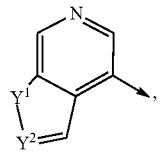

wherein $Y^1$ is NH, N($C_{1-2}$ alkyl) or $CH_2$, and $Y^2$ is N or CH, and wherein $B^1$ is N or CH, and $A^1$ is selected from hydrogen, —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, and a 4-6 membered monocyclic heterocyclyl comprising 1 or 2 heteroatoms selected from O and N, wherein said monocyclic heterocyclyl is optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH and =O; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$alkylene substituted with 1 to 4 F, —$CH_2$—O—$CH_2$— and —$CH_2$—NH—$CH_2$—; and wherein the arrow denotes the bond in the compounds of formula (I).

In a further preferred embodiment, said $R^1$ is selected from a formula (A) and (B)

(A)

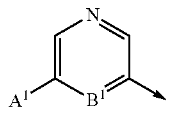

(B)

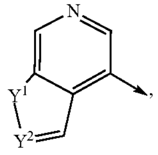

wherein $Y^1$ is NH, N($C_{1-2}$ alkyl) or $CH_2$, and $Y^2$ is N or CH, and wherein $B^1$ is N or CH, and $A^1$ is selected from hydrogen, —$C_{1-2}$ alkyl, —$CHF_2$, —$CF_3$, —O—($C_{1-2}$ alkyl), —$OCHF_2$, —$OCHF_3$, —OH, —O—($C_{1-2}$alkylene)-OR*, —O—($C_{1-2}$alkylene)-N($R^{\circ\circ}$)$_2$, =O, and a 4-6 membered monocyclic heterocyclyl comprising 1 or 2 heteroatoms selected from O and N, wherein said monocyclic heterocyclyl is optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH and =O; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$alkylene substituted with 1 to 4 F, —$CH_2$—O—$CH_2$— and —$CH_2$—NH—$CH_2$—; and wherein the arrow denotes the bond in the compounds of formula (I).

In a further preferred embodiment, said $R^1$ is of a formula (B)

(B)

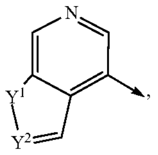

wherein $Y^1$ is NH, N($C_{1-2}$ alkyl) or $CH_2$, and $Y^2$ is N or CH, and wherein the arrow denotes the bond in the compounds of formula (I).

In a further preferred embodiment, said $R^1$ is of a formula (A)

(A)

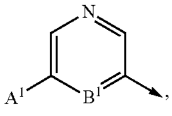

wherein $B^1$ is N or CH, and $A^1$ is selected from hydrogen, —$C_{1-2}$ alkyl, —$CHF_2$, —$CF_3$, —O—($C_{1-2}$ alkyl), —$OCHF_2$, —$OCHF_3$, —OH, =O, and a 4-6 membered monocyclic heterocyclyl comprising 1 or 2 heteroatoms selected from O and N, wherein said monocyclic heterocyclyl is optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH, —O—($C_{1-2}$alkylene)-OR*, —O—($C_{1-2}$alkylene)-N($R^{\circ\circ}$)$_2$ and =O; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$alkylene, $C_{1-3}$ alkylene substituted with 1 to 4 F, —$CH_2$—O—$CH_2$— and —$CH_2$—NH—$CH_2$—; and wherein the arrow denotes the bond in the compounds of formula (I).

In a further preferred embodiment, said $R^1$ is of a formula (A)

(A)

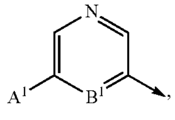

wherein $B^1$ is CH, and $A^1$ is selected from hydrogen, —$C_{1-2}$ alkyl, —$CHF_2$, —$CF_3$, —O—($C_{1-2}$ alkyl), —$OCHF_2$, —$OCHF_3$, —OH, =O, and a 4-6 membered monocyclic heterocyclyl comprising 1 or 2 heteroatoms selected from O and N, wherein said monocyclic heterocyclyl is optionally substituted with one or two, preferably one, substituents selected from —$C_{1-2}$ alkyl, $C_{1-2}$ haloalkyl, —O—($C_{1-2}$ alkyl), —O—($C_{1-2}$ haloalkyl), —OH, —O—($C_{1-2}$alkylene)-OR*, —O—($C_{1-2}$alkylene)-N($R^{\circ\circ}$)$_2$ and =O; wherein each R* is independently selected from H, $C_{1-2}$ alkyl, $C_{1-2}$ haloalkyl, and wherein each $R^{\circ\circ}$ is independently selected from H, $C_{1-2}$ alkyl, or together with the nitrogen atom to which they are attached form a six-membered monocyclic heterocyclyl, preferably selected from morpholine, piperidine and piperazine; and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—; and wherein the arrow denotes the bond in the compounds of formula (I).

In a further very preferred embodiment, said $R^1$ is of a formula (A)

(A)

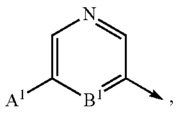

wherein $B^1$ is CH and $A^1$ is hydrogen, and wherein the arrow denotes the bond in the compounds of formula (I). Thus, in a further very preferred embodiment, said $R^1$ is 3-pyridyl.

In a further preferred embodiment, said $R^1$ is of a formula (A)

(A)

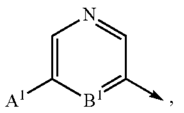

wherein $B^1$ is N, and $A^1$ is selected from hydrogen and —$C_{1-2}$ alkyl; and wherein the arrow denotes the bond in the compounds of formula (I).

In a further preferred embodiment, said $R^1$ is of a formula (A)

(A)

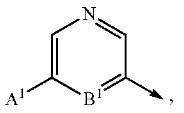

wherein $B^1$ is N, and $A^1$ is hydrogen, and wherein the arrow denotes the bond in the compounds of formula (I). Thus, in a further very preferred embodiment, said $R^1$ is 2-pyrazinyl.

$R^{21}$ is selected from hydrogen, $C_{1-6}$ alkyl, $C_{1-6}$ haloalkyl, $C_{1-6}$ alkyl optionally substituted with one or more OH, $C_{1-6}$ alkyl containing one to three oxygen atoms between carbon atoms, and $C_{3-6}$ cycloalkyl optionally substituted with one or more $R^{22}$, wherein $R^{22}$ is selected from halogen, preferably —Cl, —F, and —OH. In a further preferred embodiment, said $R^{21}$ is selected from hydrogen, $C_{1-2}$ alkyl, $C_{1-2}$ haloalkyl, $C_{1-2}$ alkyl optionally substituted with one or two OH, and $C_{3-4}$ cycloalkyl optionally substituted with one or more $R^{22}$, wherein $R^{22}$ is selected from —Cl, —F, and —OH. In a further preferred embodiment, said $R^{21}$ is selected from $C_{1-2}$ alkyl, $C_{1-2}$ haloalkyl and $C_{3-4}$ cycloalkyl. In a further preferred embodiment, said $R^{21}$ is selected from $C_{1-2}$ alkyl and cyclopropyl. In a further preferred embodiment, said $R^{21}$ is cyclopropyl. In a further very preferred embodiment, said $R^{21}$ is ethyl. In a further very preferred embodiment, said $R^{21}$ is methyl.

In a further preferred embodiment, $R^3$ is phenyl or pyridyl, each of which is optionally substituted with one or more, preferably one or two, substituents selected from halogen, —$C_{1-6}$ alkyl, $C_{1-6}$ haloalkyl, —O—$C_{1-6}$ alkyl, and —O—$C_{1-6}$ haloalkyl. In a further preferred embodiment, $R^3$ is phenyl or pyridyl, each of which is optionally substituted with one or more, preferably one or two, substituents selected from halogen, —$C_{1-3}$ alkyl, $C_{1-2}$ haloalkyl, —O—$C_{1-2}$ alkyl, and —O—$C_{1-3}$ haloalkyl. In a further preferred embodiment, $R^3$ is phenyl or pyridyl, each of which is optionally substituted with one or more, preferably one or two, substituents selected from —F, —Cl, —$C_{1-2}$ alkyl, $C_1$ haloalkyl, —$OCH_3$. In a further preferred embodiment, $R^3$ is phenyl or pyridyl, each of which is optionally substituted with one or more, preferably one or two, substituents selected from —F, —Cl, —$CH_3$ and —$OCH_3$. In a further preferred embodiment, $R^3$ is phenyl or pyridyl, each of which is optionally substituted with one substituent selected from —F, —Cl, —$CH_3$ and —$OCH_3$. In a further preferred embodiment, $R^3$ is phenyl or 3-pyridyl or 4-pyridyl, each of which is optionally substituted with one substituent selected from —F, —Cl, —$CH_3$ and —$OCH_3$. In a further preferred embodiment, $R^3$ is phenyl, 3-pyridyl or 4-pyridyl, each of which is optionally substituted at the meta position of said phenyl, 3-pyridyl or 4-pyridyl with one substituent selected from —F, —Cl, —$CH_3$ and —$OCH_3$. In a further preferred embodiment, $R^3$ is phenyl or phenyl substituted at the meta position with one substituent selected from —F, —Cl, —$CH_3$ and —$OCH_3$. In a further preferred embodiment, $R^3$ is 3-pyridyl or 3-pyridyl substituted at the meta position (5 position) with one substituent selected from —F, —Cl, —$CH_3$ and —$OCH_3$. In a further preferred embodiment, $R^3$ is 4-pyridyl or 4-pyridyl substituted at the meta position (5 position) with one substituent selected from —F, —Cl, —$CH_3$ and —$OCH_3$. In a further preferred embodiment, $R^3$ is phenyl. In a further preferred embodiment, $R^3$ is 3-pyridyl. In a further preferred embodiment, $R^3$ is 4-pyridyl.

In a further preferred embodiment, said $R^3$ is selected from phenyl, a 6-membered monocyclic heteroaryl and a 8-10 membered bicyclic heteroaryl, each independently comprising one or more, typically 1 to 5, preferably 1 to 4, ring heteroatoms independently selected from O, B, S and N, wherein one or two carbon ring atoms of said monocyclic heteroaryl or said bicyclic heteroaryl are optionally oxidized typically and preferably leading to a C=O functionality, and wherein said phenyl, said 6-membered monocyclic heteroaryl and said 8-10 membered bicyclic heteroaryl is independently optionally substituted with one or more, typically and preferably with 1 to 5, further preferably with 1 to 4, and again further preferably with 1 to 3 substituents selected from halogen, —$C_{1-6}$ alkyl, $C_{1-6}$ haloalkyl, —O—($C_{1-6}$ alkyl), —O—($C_{1-6}$ haloalkyl), —OH, —CN, =O, —C(O)R*, —COOR*, —C(O)NR*R*, —NR*R*, —N(R**)—C(O)R*, —N(R**)—C(O)—OR*, —N(R**)—C(O)—NR*R*, —O—C(O)R*, —O—C(O)—NR*R*, and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl, cyclopropyl, cyclobutyl, oxetanyl, —$C_{1-2}$alkylene-OH, —$C_{1-2}$alkylene-O($C_{1-2}$alkyl), phenyl, and wherein each R** is independently selected from H, $C_{1-4}$ alkyl, $C_{1-4}$ haloalkyl, and/or wherein each monocyclic heterocyclyl is independently optionally substituted with one bivalent substituent selected from $C_{1-3}$ alkylene such as —$CH_2$—$CH_2$— and —$CH_2$—$CH_2$—$CH_2$—, $C_{1-3}$ alkylene substituted with 1 to 4 F, —$CH_2$—O—$CH_2$— and —$CH_2$—NH—$CH_2$—.

In a further preferred embodiment, said $R^3$ is selected from formula (C), formula (D), formula (E), formula (F) and formula (G)

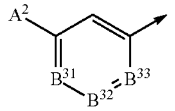
(C)

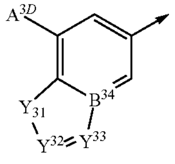
(D)

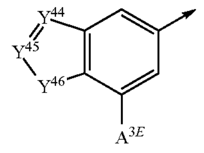
(E)

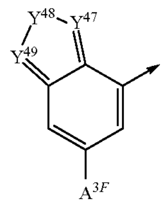
(F)

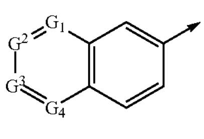
(G)

wherein $B^{31}$ is N, CH or C($A^{31}$), wherein $A^{31}$ is selected from —$C_{1-2}$ alkyl, $C_{1-2}$ haloalkyl, —F, —Cl, —O($C_{1-2}$alkyl), —OH, —NHC(O)($C_{1-2}$alkyl), wherein $A^{31}$ is selected from —$C_{1-2}$ alkyl, $C_{1-2}$ haloalkyl, —F, —Cl, —O($C_{1-2}$alkyl), —OH, —NHC(O)($C_{1-2}$alkyl);

$B^{32}$ is N, CH or C($A^{32}$), wherein $A^{32}$ is selected from —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl, phenyl, and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—;

In a further preferred embodiment, $B^{32}$ is N, CH or C($A^{32}$), wherein $A^{32}$ is selected from —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl and phenyl;

In a further preferred embodiment, $B^{32}$ is N, CH or C($A^{32}$), wherein $A^{32}$ is selected from —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$alkylene-OR*, —C(O)R* and —C(O)NR*R*; wherein each R* is independently selected from H, $C_{1-3}$ alkyl, $C_{1-3}$ haloalkyl and phenyl;

$B^{33}$ is N, CH or C($A^{33}$), wherein $A^{33}$ is selected from —$C_{1-2}$ alkyl, $C_{1-2}$ haloalkyl, —F, —Cl, —O($C_{1-2}$alkyl), —OH, —NHC(O)($C_{1-2}$alkyl);

$A^2$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl, phenyl, and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—;

In a further preferred embodiment, $A^2$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$ alkylene-OR*, —C(O)R* and —C(O)NR*R*; wherein each R* is independently selected from H, $C_{1-4}$ alkyl, $C_{1-4}$ haloalkyl and phenyl;

In a further preferred embodiment, $A^2$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$ alkylene-OR*, —C(O)R* and —C(O)NR*R*; wherein each R* is independently selected from H, $C_{1-3}$ alkyl, $C_{1-3}$ haloalkyl and phenyl;

and wherein $Y^{41}$ is N, CH or C($A^{41}$), wherein $A^{41}$ is selected from methyl and ethyl; $Y^{42}$ is N, CH or C($A^{42}$), wherein $A^{42}$ is selected from methyl and ethyl; $Y^{43}$ is N, CH or C($A^{43}$), wherein $A^{43}$ is selected from methyl and ethyl;

$A^{3D}$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl); In a further preferred embodiment, $A^{3E}$ is selected from hydrogen, —$C_{1-2}$ alkyl, $C_{1-2}$ haloalkyl, —F, —Cl, —O($C_{1-2}$alkyl), =O, —OH;

and wherein $Y^{44}$ is N, NH, N($A^{44}$), C(O), CH or C($A^{44}$), wherein $A^{44}$ is independently selected from methyl and ethyl; $Y^{45}$ is N, NH, N($A^{45}$), C(O), CH or C($A^{45}$), wherein $A^{45}$ is independently selected from methyl and ethyl; $Y^{46}$ is N, NH, N($A^{46}$), C(O), CH or C($A^{46}$), wherein $A^{46}$ is independently selected from methyl and ethyl; and wherein at least one of said $Y^{44}$, $Y^{45}$ and $Y^{46}$ is NH, N($CH_3$) or N($C_2H_5$); and wherein $A^{3E}$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl); In a further preferred embodiment, $A^{3E}$ is selected from hydrogen, —$C_{1-2}$ alkyl, $C_{1-2}$ haloalkyl, —F, —Cl, —O($C_{1-2}$alkyl), =O, —OH;

and wherein $Y^{47}$ is N, NH, N($A^{47}$), C(O), CH or C($A^{47}$), wherein $A^{47}$ is independently selected from methyl and ethyl; $Y^{48}$ is N, NH, N($A^{48}$), C(O), CH or C($A^{48}$), wherein $A^{48}$ is independently selected from methyl and ethyl; $Y^{49}$ is N, NH, N($A^{49}$), C(O), CH or C($A^{49}$), wherein $A^{49}$ is independently selected from methyl and ethyl; and wherein at least one of said $Y^{47}$, $Y^{48}$ and $Y^{49}$ is NH, N($CH_3$) or N($C_2H_5$);

$A^{3F}$ is selected from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl); In a further preferred embodiment, $A^{3E}$ is selected from hydrogen, —$C_{1-2}$ alkyl, $C_{1-2}$ haloalkyl, —F, —Cl, —O($C_{1-2}$alkyl), =O, —OH;

and wherein $G^1$, $G^2$, $G^3$, $G^4$ is independently selected from N, CH, C(O), NH or N($C_{1-2}$ alkyl); and wherein the arrow denotes the bond in the compounds of formula (I).

In a further preferred embodiment, said $R^3$ is selected from the following formulas

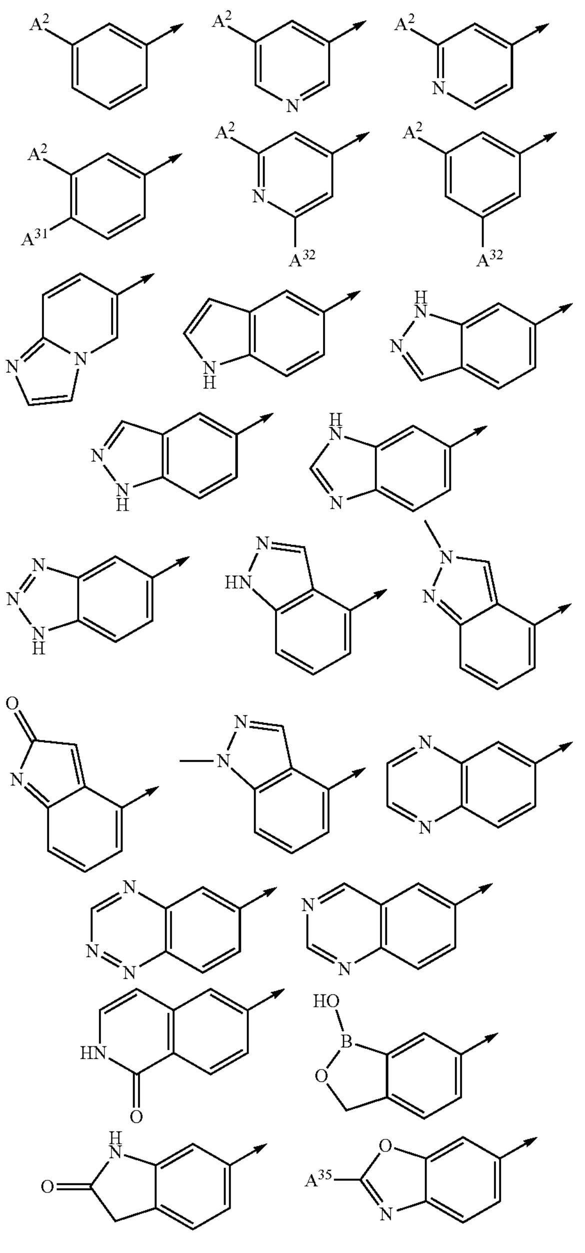

wherein $A^2$ is independently selected for each formula from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl, phenyl, and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—;

In a further preferred embodiment, $A^2$ is independently selected for each formula from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl and phenyl;

In a further preferred embodiment, $A^2$ is independently selected for each formula from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$alkylene-OR*, —C(O)R* and —C(O)NR*R*; wherein each R* is independently selected from H, $C_{1-3}$ alkyl, $C_{1-3}$ haloalkyl and phenyl;

$A^{31}$ is independently selected for each formula from —$C_{1-2}$ alkyl, $C_{1-2}$ haloalkyl, —F, —Cl, —O($C_{1-2}$alkyl), —OH, —NHC(O)($C_{1-2}$alkyl);

$A^{32}$ is independently selected for each formula from —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl, phenyl, and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—;

In a further preferred embodiment, $A^{32}$ is independently selected for each formula from —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 3-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl and phenyl;

In a further preferred embodiment, $A^{32}$ is independently selected for each formula from —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$alkylene-OR*, —C(O)R* and —C(O)NR*R*; wherein each R* is independently selected from H, $C_{1-3}$ alkyl, $C_{1-3}$ haloalkyl and phenyl; and wherein $A^{35}$ is independently selected for each formula from —$C_{1-2}$ alkyl; and wherein the arrow denotes the bond in the compounds of formula (I).

In a further very preferred embodiment, said $R^3$ is selected from the formulas

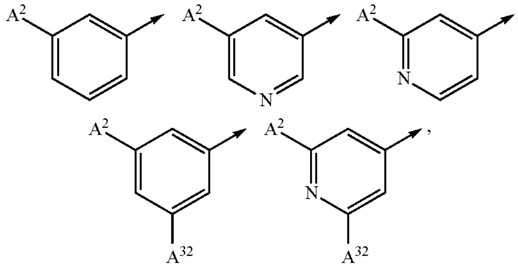

wherein $A^2$ and $A^{32}$ are independently selected for each formula from hydrogen, —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-}$ $_3$alkylene-OR*, —C(O)R* and —C(O)NR*R*; wherein each R* is independently selected from H, $C_{1-3}$ alkyl, $C_{1-3}$ haloalkyl and phenyl; and In a further very preferred embodiment, said $R^3$ is selected from the formulas

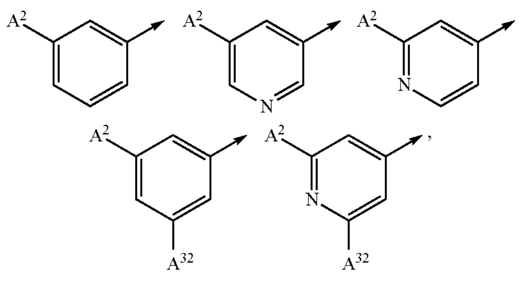

wherein $A^2$ are independently selected for each formula from hydrogen, —$C_{1-2}$ alkyl, $C_{1-2}$ haloalkyl, —F, —Cl, —O($C_{1-2}$alkyl); and wherein $A^{32}$ is independently selected for each formula from —$C_{1-2}$ alkyl, $C_{1-2}$ haloalkyl, —F, —Cl, —O($C_{1-2}$alkyl), =O, —OH, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 4 heteroatoms selected from O, S and N, each monocyclic heterocyclyl independently optionally substituted with one or more, preferably one or two, substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$ alkylene-OR*, —C(O)R* and —C(O)NR*R*; wherein each R* is independently selected from H, $C_{1-3}$ alkyl, $C_{1-3}$ haloalkyl and phenyl.

In a further very preferred embodiment, said $R^3$ is selected from the formulas

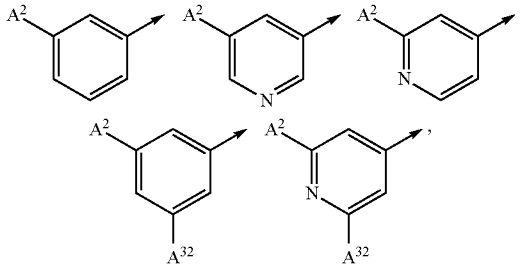

wherein $A^2$ are independently selected for each formula from hydrogen, —$C_{1-2}$ alkyl, $C_{1-2}$ haloalkyl, —F; and wherein $A^{32}$ is independently selected for each formula from —$C_{1-2}$ alkyl, $C_{1-2}$ haloalkyl, —F, —NHC(O)($C_{1-2}$alkyl), —C(O)NH($C_{1-2}$alkyl), —C(O)N($C_{1-2}$alkyl)$_2$, —NHC(O)(phenyl), and 4-6 membered monocyclic heterocyclyl comprising 1 to 3 heteroatoms selected from O and N, each monocyclic heterocyclyl independently optionally substituted with one or two substituents independently selected from halogen, cyclopropyl, —$C_{1-3}$ alkyl, $C_{1-3}$ haloalkyl, —O—($C_{1-3}$ alkyl), —O—($C_{1-3}$ haloalkyl), —OH, =O, —$C_{1-3}$alkylene-OR*, —C(O)R* and —C(O)NR*R*; wherein each R* is independently selected from H, $C_{1-3}$ alkyl, $C_{1-3}$ haloalkyl and phenyl.

It is to be understood that Ring A may further be substituted with one or more groups $R^x$, wherein any two $R^x$ groups, preferably adjacent $R^x$ groups, at ring A are optionally linked and/or any $R^x$ group at ring A is optionally linked with $R^{21}$; the number of groups $R^x$ in Ring A is 0, 1, 2, 3, or 4, preferably 0, 1, 2, or 3, further preferably 0, 1, or 2 or alternatively preferably 0 or 1. In case that Ring A may be substituted with one or more groups $R^x$ and one of said $R^x$ group at ring A is optionally linked with $R^{21}$ then said one of said $R^x$ group at ring A optionally linked with $R^{21}$ is a substituent at the 2-position of Ring A.

Thus, in a preferred embodiment, said Ring A is further substituted with 1, 2, 3 or 4 groups $R^x$, wherein any two $R^x$ groups, preferably adjacent $R^x$ groups, at ring A are optionally linked and/or any $R^x$ group at ring A is optionally linked with $R^{21}$. In case that one of said $R^x$ group at ring A is optionally linked with $R^{21}$ then said one of said $R^x$ group at ring A optionally linked with $R^{21}$ is a substituent at the 2-position of Ring A.

In a preferred embodiment, said Ring A is further substituted with 1, 2 or 3 groups $R^x$, wherein any two $R^x$ groups, preferably adjacent $R^x$ groups, at ring A are optionally linked and/or any $R^x$ group at ring A is optionally linked with $R^{21}$. In case that one of said $R^x$ group at ring A is optionally linked with $R^{21}$ then said one of said $R^x$ group at ring A optionally linked with $R^{21}$ is a substituent at the 2-position of Ring A.

In a preferred embodiment, said Ring A is further substituted with 1 or 2 groups $R^x$, wherein any two $R^x$ groups, preferably adjacent $R^x$ groups, at ring A are optionally linked and/or any $R^x$ group at ring A is optionally linked with $R^{21}$. In case that one of said $R^x$ group at ring A is optionally linked with $R^{21}$ then said one of said $R^x$ group at ring A optionally linked with $R^{21}$ is a substituent at the 2-position of Ring A.

In a preferred embodiment, said Ring A is further substituted with 1 group $R^x$, wherein said $R^x$ group at ring A is optionally linked with $R^{21}$. In case that one of said $R^x$ group at ring A is optionally linked with $R^{21}$ then said one of said $R^x$ group at ring A optionally linked with $R^{21}$ is a substituent at the 2-position of Ring A.

In a preferred embodiment, said Ring A is further substituted with 1 group $R^x$, wherein said $R^x$ group at ring A is not linked with $R^{21}$.

In a preferred embodiment, said Ring A is further substituted with 1 group $R^x$, wherein said $R^x$ group at ring A is not linked with $R^{21}$. In a further preferred embodiment, said group $R^x$ is —F, and wherein preferably said group $R^x$ being —F is at the 3-position of Ring A, said position which connects said Ring A with the $X^1$, $X^2$, $X^3$ ring system.

In a preferred embodiment, said Ring A is not further substituted. Thus, in a preferred embodiment, said Ring A is not further substituted with a group $R^x$.

In a preferred embodiment, said $R^{21}$ is selected from hydrogen, $C_{1-6}$ alkyl, $C_{1-6}$ haloalkyl, $C_{1-6}$ alkyl optionally substituted with one or more OH, $C_{1-6}$ alkyl containing one to three oxygen atoms between carbon atoms, and $C_{3-6}$ cycloalkyl optionally substituted with one or more $R^{22}$ wherein $R^{22}$ is selected from halogen, preferably —Cl, —F, and —OH. In a further preferred embodiment, said $R^{21}$ is selected from hydrogen, $C_{1-2}$ alkyl, $C_{1-2}$ haloalkyl, $C_{1-2}$ alkyl optionally substituted with one or two OH, and $C_{3-4}$ cycloalkyl optionally substituted with one or more $R^{22}$ wherein $R^{22}$ is selected from —Cl, —F, and —OH. In a further preferred embodiment, said $R^{21}$ is selected from $C_{1-2}$ alkyl, $C_{1-2}$ haloalkyl and $C_{3-4}$ cycloalkyl. In a further preferred embodiment, said $R^{21}$ is selected from $C_{1-2}$ alkyl and cyclopropyl. In a further preferred embodiment, said $R^{21}$ is ethyl. In a further preferred embodiment, said $R^{21}$ is cyclopropyl. In a further very preferred embodiment, said $R^{21}$ is methyl.

In a preferred embodiment, each $R^x$ is independently selected from -halogen, —OH, —O—$C_{1-3}$ alkyl optionally substituted with one or more $R^{xa}$, —NH—$C_{1-3}$ alkyl optionally substituted with one or more $R^{xa}$, —N($C_{1-3}$ alkyl optionally substituted with one or more $R^{xa}$)$_2$, =O, $C_{1-4}$ alkyl optionally substituted with one or more $R^{xa}$, $C_{1-4}$ haloalkyl, —($C_{1-2}$ alkylene optionally substituted with one or more $R^{xa}$)-(optionally substituted carbocyclyl), —($C_{1-2}$ alkylene optionally substituted with one or more $R^{xa}$)-(optionally substituted heterocyclyl), —O—($C_{1-2}$ alkylene optionally substituted with one or more $R^{xa}$)-(optionally substituted carbocyclyl), —O—($C_{1-2}$ alkylene optionally substituted with one or more $R^{xa}$)-(optionally substituted heterocyclyl), -(optionally substituted carbocyclyl) and -(optionally substituted heterocyclyl), wherein said $R^{xa}$ is independently selected from halogen, preferably —Cl, —F, and —OH.

In a further preferred embodiment, each $R^x$ is independently selected from -halogen, —OH, —O—$C_{1-2}$ alkyl optionally substituted with one or more $R^{xa}$, —NH—$C_{1-2}$ alkyl optionally substituted with one or more $R^{xa}$, —N($C_{1-2}$ alkyl optionally substituted with one or more $R^{xa}$)$_2$, =O, $C_{1-3}$ alkyl optionally substituted with one or more $R^{xa}$, $C_{1-2}$ haloalkyl, —($C_{1-2}$ alkylene optionally substituted with one or more $R^{xa}$)-(monocyclic carbocyclyl optionally substituted with one or more $R^{xa}$), —($C_{1-2}$ alkylene optionally substituted with one or more $R^{xa}$)-(monocyclic heterocyclyl optionally substituted with one or more $R^{xa}$), —O—($C_{1-2}$ alkylene optionally substituted with one or more $R^{xa}$)-(monocyclic carbocyclyl optionally substituted with one or more $R^{xa}$), —O—($C_{1-2}$ alkylene optionally substituted with one or more $R^{xa}$)-(monocyclic heterocyclyl optionally substituted with one or more $R^{xa}$), monocyclic carbocyclyl optionally substituted with one or more $R^{xa}$, monocyclic heterocyclyl optionally substituted with one or more $R^{xa}$, wherein said $R^{xa}$ is independently selected from halogen, preferably —Cl, —F, and —OH.

In a further preferred embodiment, each $R^x$ is independently selected from -halogen, —OH, —O—$C_{1-2}$ alkyl optionally substituted with one or more $R^{xa}$, —NH—$C_{1-2}$ alkyl optionally substituted with one or more $R^{xa}$, —N($C_{1-2}$ alkyl optionally substituted with one or more $R^{xa}$)$_2$, =O, $C_{1-3}$ alkyl optionally substituted with one or more $R^{xa}$, $C_{1-2}$ haloalkyl, —W-(monocyclic carbocyclyl optionally substituted with one or more $R^{xa}$), —W-(monocyclic heterocyclyl optionally substituted with one or more $R^{xa}$), and wherein —W— is absent, —($C_{1-2}$ alkylene)- or —O—($C_{1-2}$ alkylene)-, and wherein said $R^{xa}$ is independently selected from —Cl, —F, and —OH.

In a further preferred embodiment, each $R^x$ is independently selected from -halogen, —OH, —O—$C_{1-2}$ alkyl optionally substituted with one or more $R^{xa}$, —NH—$C_{1-2}$ alkyl optionally substituted with one or more $R^{xa}$, —N($C_{1-2}$ alkyl optionally substituted with one or more $R^{xa}$)$_2$, =O, $C_{1-3}$ alkyl optionally substituted with one or more $R^{xa}$, $C_{1-2}$ haloalkyl, —W-(monocyclic carbocyclyl optionally substituted with one or more $R^{xa}$), —W-(monocyclic heterocyclyl optionally substituted with one or more $R^{xa}$), and wherein —W— is absent, —($C_{1-2}$ alkylene)- or —O—($C_{1-2}$ alkylene)-, and wherein monocyclic carbocyclyl is selected from phenyl and $C_{3-6}$ cycloalkyl, and wherein monocyclic heterocyclyl is selected from thiophenyl, pyridyl, pyrazinyl and pyrimidinyl, and wherein said $R^{xa}$ is independently selected from —Cl, —F, and —OH.

In a further preferred embodiment, each $R^x$ is independently selected from -halogen, —OH, —O—$C_{1-2}$ alkyl, —NH—$C_{1-2}$ alkyl, —N($C_{1-2}$ alkyl)$_2$, =O, $C_{1-3}$ alkyl, $C_{1-2}$ haloalkyl, —W— (monocyclic carbocyclyl optionally substituted with one $R^{xa}$), —W-(monocyclic heterocyclyl optionally substituted with one $R^{xa}$), and wherein —W— is absent, —($C_{1-2}$ alkylene)- or —O—($C_{1-2}$ alkylene)-, and wherein monocyclic carbocyclyl is selected from phenyl and $C_{3-6}$ cycloalkyl, and wherein monocyclic heterocyclyl is selected from thiophenyl, pyridyl, pyrazinyl and pyrimidinyl, and wherein said $R^{xa}$ is independently selected from —F, and —OH.

Specific examples and very preferred compounds and embodiments of the present invention are any of the compounds 00001 to 00130. Thus, in a very further preferred embodiment, said compound of formula (I) is a compound selected from any one of the compounds 00001 to 00130.

The present inventors have surprisingly found that the compounds of the present invention bind to p300 (also called EP300 or E1A binding protein p300) and CBP (also known as CREB-binding protein or CREBBP) which are two structurally very similar transcriptional co-activating proteins. Without wishing to be limited by theory, it is believed that this binding is a main reason for the activity of the compounds of the present invention as set out herein. It is furthermore believed that the compounds of the present invention bind to the bromodomains of p300 and CBP.

It is therefore preferred that the compounds of the present invention, namely the compounds as defined in claim 1, bind to the bromodomain of p300 and/or the bromodomain of CBP with an EC50 of 10000 nM or less, preferably 2000 nM or less, more preferably 1000 nM or less, even more preferably 500 nM or less, still more preferably 200 nM or less, still more preferably 100 nM or less, still more preferably 50 nM or less, still more preferably 20 nM or less, still more preferably 10 nM or less.

The present invention furthermore relates to a pharmaceutical composition comprising a compound having the formula (I) as defined herein, optionally in the form of a pharmaceutically acceptable salt, solvate, cocrystal, tautomer, racemate, enantiomer, or diastereomer or mixture thereof, and optionally one or more pharmaceutically acceptable excipient(s) and/or carrier(s) for use in a method of treating fibrotic disease.

In addition, the present invention provides the compound having the formula (I) as defined herein, optionally in the form of a pharmaceutically acceptable salt, solvate, cocrystal, tautomer, racemate, enantiomer, or diastereomer or mixture thereof, wherein the compound is for use in the treatment, amelioration or prevention of fibrotic disease. In a preferred embodiment the present invention provides the compound having the formula (I) as defined herein, optionally in the form of a pharmaceutically acceptable salt, solvate, cocrystal, tautomer, racemate, enantiomer, or diastereomer or mixture thereof, wherein the compound is for use in a method of increasing survival time in an individual with fibrotic disease; and/or for use in a method of reducing risk of death in an individual with fibrotic disease and/or delaying progression of fibrotic disease or ameliorating symptoms of fibrotic disease.

The present invention also relates to a method of treating or ameliorating fibrotic disease, the method comprising administering to a patient in need thereof a therapeutically effective amount of a compound having the formula (I), optionally in the form of a pharmaceutically acceptable salt, solvate, cocrystal, tautomer, racemate, enantiomer, or diastereomer or mixture thereof.

In one embodiment the compound having the formula (I) as defined herein, optionally in the form of a pharmaceutically acceptable salt, solvate, cocrystal, tautomer, racemate, enantiomer, or diastereomer or mixture thereof, wherein the fibrotic disease is selected from the group consisting of pulmonary fibrosis, idiopathic pulmonary fibrosis, radiation-induced pneumonitis, radiation fibrosis, acute respiratory distress syndrome, chronic obstructive pulmonary disease, interstitial lung disease, myocardial infarction, cardiac fibrosis and hypertrophy, ischemic stroke, ischemic kidney disease, renal fibrosis, rheumatoid arthritis, liver fibrosis, NASH (non-alcoholic steatohepatitis), chronic hepatitis, cirrhosis, inflammatory bowel disease, Crohn's disease, scleroderma, keloid, post-operative fibrosis, chemotherapy induced fibrosis (e.g., chemotherapy induced pulmonary fibrosis or ovarian cortical fibrosis), nephrogenic systemic fibrosis, retroperitoneal fibrosis, myelofibrosis, mediastinal fibrosis, cystic fibrosis, asbestosis, asthma, pulmonary hypertension, systemic fibrosis, skin fibrosis, hypertension induced renal and cardiac fibrosis.

In another embodiment of the present invention the fibrotic disease is interstitial lung disease (IDL), optionally the interstitial lung disease is idiopathic interstitial pneumonia (IIP). In another embodiment the idiopathic interstitial pneumonia is selected from the group consisting of chronic fibrosing interstitial pneumonia, smoking-related interstitial pneumonia and acute/subacute interstitial pneumonia. In another embodiment the chronic fibrosing interstitial pneumonia is selected from the group comprising idiopathic pulmonary fibrosis (IPF) and non-specific interstitial pneumonia (NSIP). In a preferred embodiment the fibrotic disease is chronic fibrosing interstitial pneumonia. In a most preferred embodiment the chronic fibrosing interstitial pneumonia is idiopathic pulmonary fibrosis (IPF). In another preferred embodiment the fibrotic disease is NASH.

The compounds provided herein may be administered as compounds per se or may be formulated as medicaments. The medicaments/pharmaceutical compositions may optionally comprise one or more pharmaceutically acceptable excipients, such as carriers, diluents, fillers, disintegrants, lubricating agents, binders, colorants, pigments, stabilizers, preservatives, antioxidants, and/or solubility enhancers, or any combination thereof.

In particular, the pharmaceutical compositions may comprise one or more solubility enhancers, such as, e.g., poly (ethylene glycol), including poly(ethylene glycol) having a molecular weight in the range of about 200 to about 5,000 Da, ethylene glycol, propylene glycol, non-ionic surfactants, tyloxapol, polysorbate 80, macrogol-15-hydroxystearate, phospholipids, lecithin, dimyristoyl phosphatidylcholine, dipalmitoyl phosphatidylcholine, distearoyl phosphatidylcholine, cyclodextrins, α-cyclodextrin, p-cyclodextrin, γ-cyclodextrin, hydroxyethyl-p-cyclodextrin, hydroxypropyl-p-cyclodextrin, hydroxyethyl-γ-cyclodextrin, hydroxypropyl-γ-cyclodextrin, dihydroxypropyl-p-cyclodextrin, sulfobutylether-p-cyclodextrin, sulfobutylether-γ-cyclodextrin, glucosyl-α-cyclodextrin, glucosyl-p-cyclodextrin, diglucosyl-p-cyclodextrin, maltosyl-α-cyclodextrin, maltosyl-p-cyclodextrin, maltosyl-γ-cyclodextrin, maltotriosyl-p-cyclodextrin, maltotriosyl-γ-cyclodextrin, dimaltosyl-p-cyclodextrin, methyl-β-cyclodextrin, carboxyalkyl thioethers, hydroxypropyl methylcellulose, hydroxypropylcellulose, polyvinylpyrrolidone, vinyl acetate copolymers, vinyl pyrrolidone, sodium lauryl sulfate, dioctyl sodium sulfosuccinate, or any combination thereof.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

The pharmaceutical compositions can be formulated by techniques known to the person skilled in the art, such as the techniques published in "Remington: The Science and Practice of Pharmacy", Pharmaceutical Press, $22^{nd}$ edition. The pharmaceutical compositions can be formulated as dosage forms for oral, parenteral, such as intramuscular, intravenous, subcutaneous, intradermal, intraarterial, intracardial, rectal, nasal, topical, aerosol or vaginal administration. Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions are a preferred dosage form for parenteral administration. Dosage forms for rectal and vaginal administration include suppositories and ovula. Dosage forms for nasal administration can be administered via inhalation and insufflation, for example by a metered inhaler. Dosage forms for topical administration include creams, gels, ointments, salves, patches and transdermal delivery systems.

The compounds of formula (I) or the above described pharmaceutical compositions comprising a compound of formula (I) may be administered to a subject by any convenient route of administration, whether systemically/peripherally or at the site of desired action, including but not limited to one or more of: oral (e.g., as a tablet, capsule, or as an ingestible solution), topical (e.g., transdermal, intranasal, ocular, buccal, and sublingual), parenteral (e.g., using injection techniques or infusion techniques, and including, for example, by injection, e.g., subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g., through mouth or nose), gastrointestinal, intrauterine, intraocular, subcutaneous, ophthalmic (including intravitreal or intracameral), rectal, and vaginal.

If said compounds or pharmaceutical compositions are administered parenterally, then examples of such administration include one or more of: intravenously, intraarterially, intraperitoneally, intrathecally, intraventricularly, intraurethrally, intrasternally, intracardially, intracranially, intramuscularly or subcutaneously administering the compounds or pharmaceutical compositions, and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Said compounds or pharmaceutical compositions can also be administered orally in the form of tablets, capsules, ovules, elixirs, solutions or suspensions, which may contain flavoring or coloring agents, for immediate-, delayed-, modified-, sustained-, pulsed- or controlled-release applications.

Alternatively, said compounds or pharmaceutical compositions can be administered in the form of a suppository or pessary, or it may be applied topically in the form of a gel, hydrogel, lotion, solution, cream, ointment or dusting powder. The compounds of the present invention may also be dermally or transdermally administered, for example, by the use of a skin patch.

Said compounds or pharmaceutical compositions may also be administered by sustained release systems. Suitable examples of sustained-release compositions include semi-permeable polymer matrices in the form of shaped articles, e.g., films, or microcapsules. Sustained-release matrices include, e.g., polylactides (see, e.g., U.S. Pat. No. 3,773,919), copolymers of L-glutamic acid and gamma-ethyl-L-glutamate (Sidman, U. et al., Biopolymers 22:547-556 (1983)), poly(2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP133988). Sustained-release pharmaceutical compositions also include liposomally entrapped compounds. Liposomes containing a compound of the present invention can be prepared by methods known in the art, such as, e.g., the methods described in any one of: DE3218121; Epstein et al., Proc. Natl. Acad. Sci. (USA) 82:3688-3692 (1985); Hwang et al., Proc. Natl. Acad. Sci. (USA) 77:4030-4034 (1980); EP0052322; EP0036676; EP088046; EP0143949; EP0142641; JP 83-118008; U.S. Pat. Nos. 4,485,045; 4,544,545; and EP0102324.

Said compounds or pharmaceutical compositions may also be administered by the pulmonary route, rectal routes, or the ocular route. For ophthalmic use, they can be formulated as micronized suspensions in isotonic, pH adjusted, sterile saline, or, preferably, as solutions in isotonic, pH adjusted, sterile saline, optionally in combination with a preservative such as a benzalkonium chloride. Alternatively, they may be formulated in an ointment such as petrolatum.

It is also envisaged to prepare dry powder formulations of the compounds of formula (I) for pulmonary administration, particularly inhalation. Such dry powders may be prepared by spray drying under conditions which result in a substantially amorphous glassy or a substantially crystalline bioactive powder. Accordingly, dry powders of the compounds of the present invention can be made according to the emulsification/spray drying process disclosed in WO 99/16419 or WO 01/85136. Spray drying of solution formulations of the compounds of the present invention can be carried out, e.g., as described generally in the "Spray Drying Handbook", 5th ed., K. Masters, John Wiley & Sons, Inc., NY (1991), and in WO 97/41833 or WO 03/053411.

For topical application to the skin, said compounds or pharmaceutical compositions can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, 2-octyldodecanol, benzyl alcohol and water.

The present invention thus relates to the compounds or the pharmaceutical compositions provided herein, wherein the corresponding compound or pharmaceutical composition is to be administered by any one of: an oral route; topical route, including by transdermal, intranasal, ocular, buccal, or sublingual route; parenteral route using injection techniques or infusion techniques, including by subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, intrasternal, intraventricular, intraurethral, or intracranial route; pulmonary route, including by inhalation or insufflation therapy; gastrointestinal route; intrauterine route; intraocular route; subcutaneous route; ophthalmic route, including by intravitreal, or intracameral route; rectal route; or vaginal route. Particularly preferred routes of administration of the compounds or pharmaceutical compositions of the present invention are oral forms of administration.

Typically, a physician will determine the dosage which will be most suitable for an individual subject. The specific dose level and frequency of dosage for any particular individual subject may be varied and will depend upon a variety of factors including the age, body weight, general health, sex, diet, mode and time of administration, rate of excretion, drug combination, the severity of the particular condition, and the individual subject undergoing therapy.

A proposed, yet non-limiting dose of the compounds according to the invention for administration to a human (of approximately 70 kg body weight) may be 0.05 to 2000 mg, preferably 0.1 mg to 1000 mg, of the active ingredient per unit dose. The unit dose may be administered, e.g., 1, 2, 3 or more times per day. The unit dose may also be administered 1 to 7 times per week, e.g., with one, two or more administration(s) per day. It will be appreciated that it may be necessary to make routine variations to the dosage depending on the age and weight of the patient/subject as well as the severity of the condition to be treated. The precise dose and also the route of administration will ultimately be at the discretion of the attendant physician.

In some embodiments, the method for treating fibrotic disease further comprises administering an additional therapeutic agent selected from the group consisting of corticosteroids, antibiotics, immunosuppressive drugs, supplemental oxygen, and mechanical ventilation. In another embodiment the additional therapeutic agent is selected from the group consisting of Nintedanib, Pirfenidone, αvβ1, αvβ3, and αvβ6 integrin antagonists (IDL-2965), αvβ6 integrin antagonist [GSK 3008348, BG-00011 (STX-100)], αvβ1/αvβp6 integrin antagonist (PLN-74809), Rock2 inhibitor (KD025), MAP3K19 inhibitor (MG S 2525), PI3K/mTOR pathway inhibitors [Sirolimus (Rapalogue, mTOR), pan-PI3K inhibitor (GSK 2126458), PI3K/mTOR inhibitor (HEC68489)], tyrosine kinase inhibitors such as Src tyrosine kinase family inhibitors [Src tyrosine kinase family (Dasantinib)] and Imatinib (Gleevec), and GPCR antagonists such as Leuktrien receptor antagonists (Tipelukast, MN-001), Endothelin receptor antagonists [Ambrisentan, Bosentan, Macitentan (ACT-064992)], GPR84 antaginists (GLPG1205, GLPG1690), GPR40 (activating)/GPR84 (inactivating) compound PBI-4050, Lysophosphatidic acid receptor antagonists (BMS986020, BMS986278), Purinergic P2X3 receptor antagonists [Gefapixant (AF-219; MK-7264; R1646; RG-1646; RO 4926219)], and antibodies such as Romilkimab (SAR156597) a bispecific IL-4/IL-13 monoclonal antibody, QAX576, Pamrevlumab (FG-3019) anti-CTGF antibody, VAY-736 (anti-BAFF-Receptor antibody), Simtuzumab (GS-6624; anti-LOXL2 antibody), Retuximab (anti-CD20) and Etanercept TNF-α neutralizing biopharmaceutical and Galectin-3 inhibitor (TD139).

When a compound of the invention is used in combination with an additional therapeutic agent active against the same disease, the dose of each compound may differ from that when the compound is used alone. The combination of a compound of the present invention with an additional therapeutic agent may comprise the administration of the additional therapeutic agent simultaneously/concomitantly or sequentially/separately with the compound of the invention.

The combinations referred to above may conveniently be presented for use in the form of a pharmaceutical formulation. The individual components of such combinations may be administered either sequentially or simultaneously/concomitantly in separate or combined pharmaceutical formulations by any convenient route. When administration is sequential, either the compound of the present invention (i.e., the compound of formula (I) or a pharmaceutically acceptable salt, solvate, cocrystal, tautomer, racemate, enantiomer, or diastereomer or mixture thereof) or the second therapeutic agent may be administered first. When administration is simultaneous, the combination may be administered either in the same pharmaceutical composition or in different pharmaceutical compositions. When combined in the same formulation, it will be appreciated that the two compounds must be stable and compatible with each other and the other components of the formulation. When formulated separately, they may be provided in any convenient formulation.

Yet, the compounds of formula (I) can also be used in monotherapy, particularly in the monotherapeutic treatment or prevention of fibrotic disease (i.e., without administering any other agents until the treatment with the compound(s) of formula (I) is terminated). Accordingly, the invention also relates to a compound of formula (I) or a pharmaceutically acceptable salt, solvate, cocrystal, tautomer, racemate, enantiomer, or diastereomer or mixture thereof, or a pharmaceutical composition comprising any of the aforementioned entities in combination with a pharmaceutically acceptable excipient, for use in the monotherapeutic treatment or prevention of fibrotic disease.

The subject or patient, such as the subject in need of treatment or prevention, may be an animal (e.g., a non-human animal), a vertebrate animal, a mammal, a rodent (e.g., a guinea pig, a hamster, a rat, a mouse), a murine (e.g., a mouse), a canine (e.g., a dog), a feline (e.g., a cat), a porcine (e.g., a pig), an equine (e.g., a horse), a primate, a simian (e.g., a monkey or ape), a monkey (e.g., a marmoset, a baboon), an ape (e.g., a gorilla, chimpanzee, orang-utan, gibbon), or a human. In the context of this invention, it is particularly envisaged that animals are to be treated which are economically, agronomically or scientifically important. Scientifically important organisms include, but are not limited to, mice, rats, and rabbits. Lower organisms such as, e.g., fruit flies like *Drosophila melagonaster* and nematodes like *Caenorhabditis elegans* may also be used in scientific approaches. Non-limiting examples of agronomically important animals are sheep, cattle and pigs, while, for example, cats and dogs may be considered as economically important animals. Preferably, the subject/patient is a mammal; more preferably, the subject/patient is a human or a non-human mammal (such as, e.g., a guinea pig, a hamster, a rat, a mouse, a rabbit, a dog, a cat, a horse, a monkey, an ape, a marmoset, a baboon, a gorilla, a chimpanzee, an orang-utan, a gibbon, a sheep, cattle, or a pig); most preferably, the subject/patient is a human.

The term “treatment” of a disorder or disease as used herein (e.g., “treatment” of fibrotic disease) is well known in the art. “Treatment” of a disorder or disease implies that a disorder or disease is suspected or has been diagnosed in a patient/subject. A patient/subject suspected of suffering from a disorder or disease typically shows specific clinical and/or pathological symptoms which a skilled person can easily attribute to a specific pathological condition (i.e., diagnose a disorder or disease).

The “treatment” of a disorder or disease may, for example, lead to a halt in the progression of the disorder or disease (e.g., no deterioration of symptoms) or a delay in the progression of the disorder or disease (in case the halt in progression is of a transient nature only). The “treatment” of a disorder or disease may also lead to a partial response (e.g., amelioration of symptoms) or complete response (e.g., disappearance of symptoms) of the subject/patient suffering from the disorder or disease. Accordingly, the “treatment” of a disorder or disease may also refer to an amelioration of the disorder or disease, which may, e.g., lead to a halt in the progression of the disorder or disease or a delay in the progression of the disorder or disease. Such a partial or complete response may be followed by a relapse. It is to be understood that a subject/patient may experience a broad range of responses to a treatment (such as the exemplary responses as described herein above). The treatment of a disorder or disease may, interalia, comprise curative treatment (preferably leading to a complete response and eventually to healing of the disorder or disease) and palliative treatment (including symptomatic relief).

The “amelioration” of a disorder or disease may, for example, lead to a halt in the progression of the disorder or disease or a delay in the progression of the disorder or disease.

The term “prevention” of a disorder or disease as used herein (e.g., “prevention” of fibrotic disease) is also well known in the art. For example, a patient/subject suspected of being prone to suffer from a disorder or disease may particularly benefit from a prevention of the disorder or disease. The subject/patient may have a susceptibility or predisposition for a disorder or disease, including but not limited to hereditary predisposition. Such a predisposition can be determined by standard methods or assays, using, e.g., genetic markers or phenotypic indicators. It is to be understood that a disorder or disease to be prevented in accordance with the present invention has not been diagnosed or cannot be diagnosed in the patient/subject (for example, the patient/subject does not show any clinical or pathological symptoms). Thus, the term “prevention” comprises the use of a compound of the present invention before any clinical and/or pathological symptoms are diagnosed or determined or can be diagnosed or determined by the attending physician.

In one embodiment the fibrotic disease is pulmonary fibrosis. As used herein, "pulmonary fibrosis" is defined as excessive accumulation of connective or scar tissue within the lung. The accumulation of connective/scar tissue in pulmonary fibrosis is excessive compared to connective tissue levels in a normal, healthy lung. This fibrosis is often accompanied by necrosis and/or inflammation of lung tissue, p-catenin signaling plays a role in inducing the over-production and excess accumulation of an extracellular matrix such as collagen.

Pulmonary fibrosis can be a secondary effect of connective tissue diseases caused by autoimmune disorders, inhalation of environmental and occupational pollutants, viral infections, or other interstitial lung diseases which cause injuries to the lung. If the cause of the pulmonary fibrosis is known, it is classified as usual interstitial pneumonia (UIP). If the cause is unknown, idiopathic pulmonary fibrosis (IPF) or idiopathic interstitial pneumonia (IIP) is diagnosed.

Treatment of pulmonary fibrosis refers to the administration of a compound or combination described herein to treat a subject suffering from pulmonary fibrosis. One outcome of the treatment of pulmonary fibrosis is to reduce formation of excessive connective tissue. Another outcome of the treatment of pulmonary fibrosis is to reduce inflammation and infiltration of immune cells. Still another outcome of the treatment of pulmonary fibrosis is to reduce lung tissue necrosis. Still another outcome of the treatment of pulmonary fibrosis is to improve lung function.

In one embodiment the fibrotic disease is IPF. In other embodiments, a diagnosis of IPF is a definite or probable IPF made by high resolution computer tomography (HRCT). In a diagnosis by HRCT, the presence of the following characteristics is noted: (1) presence of reticular abnormality and/or traction bronchiectasis with basal and peripheral predominance; (2) presence of honeycombing with basal and peripheral predominance; and (3) absence of atypical features such as micronodules, peribronchovascular nodules, consolidation, isolated (non-honeycomb) cysts, ground glass attenuation (or, if present, is less extensive than reticular opacity), and mediastinal adenopathy (or, if present, is not extensive enough to be visible on chest x-ray). A diagnosis of definite IPF is made if characteristics (1), (2), and (3) are met. A diagnosis of probable IPF is made if characteristics (1) and (3) are met.

In one embodiment the methods are suitable for treatment of individuals diagnosed as having IPF. The methods are also suitable for treatment of individuals having IPF who were previously treated with corticosteroids within the previous 24 months, and who failed to respond to previous treatment with corticosteroids. Subjects that are particularly amenable to treatment with a method are those that have at least 55% of the predicted forced vital capacity (FVC). Also suitable for treatment are subjects that have at least 60% of the predicted FVC, or from 55% to 70% of the predicted FVC. The percent predicted FVC values are based on normal values, which are known in the art. See, e.g., Crapo et al. (1981) Am. Rev. Respir. Dis. 123:659-664. FVC is measured using standard methods of spirometry.

In another embodiment, the method of treating IPF comprising administering to the subject an effective amount of a compound having the formula (I) as defined herein, optionally in the form of a pharmaceutically acceptable salt, solvate, cocrystal, tautomer, racemate, enantiomer, or diastereomer or mixture thereof, and optionally one or more pharmaceutically acceptable excipient(s) and/or carrier(s), wherein the subject has a forced vital capacity (FVC) that is at least about 55% of the normal predicted value.

In another embodiment of the invention, a method is provided for treating IPF in a subject in need thereof, wherein the method comprises administering to the subject an effective amount of a compound having the formula (I) as defined herein, optionally in the form of a pharmaceutically acceptable salt, solvate, cocrystal, tautomer, racemate, enantiomer, or diastereomer or mixture thereof, and optionally one or more pharmaceutically acceptable excipient(s) and/or carrier(s), thereby treating IPF.

In some embodiments, the method for treating IPF with a compound having the formula (I) as defined herein, optionally in the form of a pharmaceutically acceptable salt, solvate, cocrystal, tautomer, racemate, enantiomer, or diastereomer or mixture thereof, and optionally one or more pharmaceutically acceptable excipient(s) and/or carrier(s) reduces the pathologic rate of decline of a pulmonary function parameter by at least 5%. In further embodiments, the pulmonary function parameter is selected from the group consisting of vital capacity (VC), residual volume (RV), forced expiratory volume (FEV), forced vital capacity (FVC), forced vital capacity percent (FVC %) predicted, forced expiratory flow (FEF), peak expiratory flow rate (PEFR), inspiratory reserve volume (IRV), functional residual capacity (FRC), inspiratory capacity (IC), total lung capacity (TLC), expiratory reserve volume (ERV), tidal volume (TV), and maximum voluntary ventilation (MVV). Numerous pulmonary function parameters known in the art can be used to determine an effective amount of Compound (1) of the present invention, i.e., an amount to reduce, stabilize or reverse a pathologic rate of decline in one or more pulmonary functional parameters; or to monitor patient response to Compound (1) therapy. These pulmonary function parameters include the following:

Vital capacity (VC) is the total volume of air that can be moved in and out of the lungs. VC is equal to the combined inspiratory reserve volume, tidal volume, and expiratory reserve volume.

Forced vital capacity (FVC) is the vital capacity from a maximally forced expiratory effort.

FVC % predicted is a subject's measured FVC expressed as the percentage of the predicted FVC for the subject.

Residual volume (RV) is the volume of air remaining in the lungs after a maximal exhalation.

Forced expiratory volume (FEV) is the expiratory volume of air from a maximally forced expiratory effort, usually measured over a set period of time, e.g., 1 second, FEV1; 6 seconds, FEV6; etc.

Forced inspiratory flow (FIF) is the inspiratory volume of air from a maximally forced inspiratory effort, usually measured over a set period of time, e.g., 1 second, FIF1; 6 seconds, FIFE; etc.

Peak expiratory flow rate (PEFR) is the highest forced expiratory flow rate.

Inspiratory reserve volume (IRV) is the maximal volume that can be inhaled after a normal inspiration, measured from the end-inspiratory level.

Tidal volume (TV) is the volume of air inhaled or exhaled during one respiratory cycle, typically measured at rest.

Inspiratory capacity (IC) is the sum of the inspiratory reserve volume and the tidal volume.

Functional residual capacity (FRC) is the sum of the expiratory reserve volume and the residual volume. Typically, FRC represents the volume of air in the lungs at the end of a normal expiration.

Total lung capacity (TLC) is the sum of the vital capacity and residual volume that represents the total volume of air that can be contained in the lung.

Expiratory reserve volume (ERV) is the maximal volume of air that can be exhaled after a normal expiration, measured from the end-expiratory position.

Maximum voluntary ventilation (MVV) is the volume of air expired in a specified time period during repetitive maximal effort.

FEV1/FVC ratio means the ratio between forced expiratory volume in one second and forced vital capacity.

Many of these pulmonary functional parameters are readily obtainable through the use of a spirometer as is well-known in the art. Residual volume can be obtained through indirect methods such as radiographic planimetry, body plethysmography, closed circuit dilution (including the helium dilution technique), and nitrogen washout.

In additional embodiments, the method for treating IPF comprises increasing the subject's FVC by at least 0.05 liters compared to a baseline FVC measurement. In further embodiments, the method for treating IPF comprises increasing the subject's forced vital capacity percent (FVC %) predicted by at least 0.5% compared to a baseline FVC % predicted measurement. In some embodiments, the subject to be treated with the treatment method has a forced vital capacity percent (FVC %) predicted of greater than about 55%, less than 50% parenchymal fibrosis, less than 25% honeycombing within the whole lung or has been diagnosed with IPF for less than 5 years.

In other embodiments, the method for treating IPF comprises producing at least a 5% increase, compared to a baseline measurement, in diffusing capacity of the lung for carbon monoxide (DLCO) corrected for hemoglobin, DLCO percent (DLCO %) predicted, or arterial oxyhaemoglobin saturation (SaO2). In further embodiments, the method for treating IPF produces a decrease of at least 5% in alveolar-arterial oxygen tension gradient (A-a) PO2.

In additional embodiments, the method for treating IPF comprises at least a 5% reduction, compared to a baseline measurement, in the extent of pulmonary infiltration of fibroblasts or myofibroblasts, at least a 5% reduction in the rate of collagen deposition, at least a 5% reduction in the degree type II pneumocyte hyperplasia, at least a 5% reduction in the degree of smooth muscle hyperplasia or at least a 5% reduction in the formation of fibroblastic foci.

In other embodiments, the method for treating IPF comprises stabilizing or producing at least a 2% reduction, compared to a baseline measurement, in one or more pulmonary radiographic parameters selected from the group consisting of ground glass opacities, fibrosis, and honeycomb formation.

In further embodiments, the method for treating IPF comprises extending the subject's progression-free survival or overall survival of at least 1 month compared to historic controls. In other embodiments, the treatment method comprises decreasing the subject's risk of death at 1 year post-diagnosis by at least 10% compared to historical controls.

In still other embodiments, the method for treating IPF comprises preventing a worsening of dyspnea or the development of new dyspnea, reducing the frequency or intensity of coughing, preventing a worsening of hypoxemia; reducing the number or severity of acute exacerbations of IPF, reducing the number of IPF-related hospital admissions, reducing the need for supplemental oxygen, or improving the assessment of health-related quality of life.

In one embodiment the fibrotic disease is NASH. As used herein, "NASH" is defined as non-alcoholic steatohepatitis (NASH), hepatic steatosis accompanied by hepatocyte injury and inflammation; NASH may occur with or without fibrosis, but may progress to fibrosis and cirrhosis. In one embodiment the invention provides methods for sustaining a reduction of nonalcoholic steatohepatitis (NASH) in a subject in need thereof. In some embodiments the methods include reducing liver fibrosis, reducing macrophage infiltration, reducing expression of lipogenic genes, reducing expression of hepatic inflammatory genes, and/or increasing expression of liver fatty acid oxidation genes. The effectiveness of reduction of non-alcoholic steatohepatitis or hepatic steatosis can be ascertained by measuring and monitoring a level of one or more biomarkers or physiological indicators in the subject. In some embodiments, a reduction of a physiological indicator or a biomarker indicates a sustained reduction of non-alcoholic steatohepatitis (NASH) in the subject after commencement of said methods and compositions described herein.

NASH and/or hepatic steatosis can be assessed by any means known to those of skill in the art or otherwise described herein. In some embodiments, reduction of NASH and/or hepatic steatosis can be done by assessing a change of one or more physiological indicators. Non-limiting physiological indicator can include a change of liver morphology, liver stiffness, accumulation of fat in the liver, and size or weight of the liver. Non-alcoholic steatohepatitis (NASH) or hepatic steatosis in a subject can be evidenced, e.g., by an accumulation of fat in the liver of the subject (e.g., by an accumulation of fat in hepatic cells of the subject). Accumulation of fat in the liver can be indicated by several means, for example, by ultrasonography, computed tomography (CT), and magnetic resonance imaging, measurement of liver size or weight, or biopsy. For example, a subject with NASH or hepatic steatosis can exhibit a hepatic fat content of 5% or higher, a hepatic fat content of 10% or higher, a hepatic fat content of 20% or higher, a hepatic fat content of 30% or higher, a hepatic fat content of 40% or higher, a hepatic fat content of 50% or higher, a hepatic fat content of 60% or higher, or a hepatic fat content of 70% or higher. In general, a subject with stage 1 hepatic steatosis typically exhibit 5%-33% fat accumulation in liver. A subject with stage 2 hepatic steatosis can exhibit 33%-66% fat accumulation in liver. A subject with stage 3 hepatic steatosis can exhibit over 66% fat accumulation in liver.

In another embodiment the methods of the present invention to treat NASH are used in combination with an additional agent selected from the group comprising Vitamin E (RRR-α-tocopherol), Pioglitazone (Actos), MGL-3196 (Resmetirom), Elafibranor, selonsertib (SEL; GS-4997), Dapagliflozin, Nesinaact 25/15 (Alogliptin benzoate 25 mg, pioglitazone hydrochloride 15 mg), Losartan, Aramchol, Cenicriviroc, MSDC-0602K and Metformin.

It is to be understood that the present invention specifically relates to each and every combination of features and embodiments described herein, including any combination of general and/or preferred features/embodiments. In particular, the invention specifically relates to each combination of meanings (including general and/or preferred meanings) for the various groups and variables comprised in formula (I).

In this specification, a number of documents including patent applications and scientific literature are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The present invention may be better understood with reference to the following examples. These examples are intended to be representative of specific embodiments of the invention, and are not intended as limiting the scope of the invention.

EXAMPLES

The preparation of the compounds of formula (I) has been described in the PCT application no. PCT/EP2019/085557 entitled "Heterocyclic derivatives, pharmaceutical compositions and their use in the treatment, amelioration or prevention of cancer" filed at the European Patent Office on 17 Dec. 2019 by the present applicant, TOLREMO therapeutics AG, as well as in the European patent application entitled "Heterocyclic derivatives, pharmaceutical compositions and their use in the treatment or amelioration of cancer" filed at the European Patent Office on the filing date of the instant European patent application by the present applicant, TOLREMO therapeutics AG; both applications are incorporated herein by reference in its entirety, in particular with respect to the synthesis of the compounds of formula (I) including the compounds described in this example section, in accordance with and in addition to the following description:

Synthetic Procedures for Key Intermediates

Intermediate 1: 1-(5-(4,6-dichloropyrimidin-2-yl)-2-methylpiperidin-1-yl)ethan-1-one

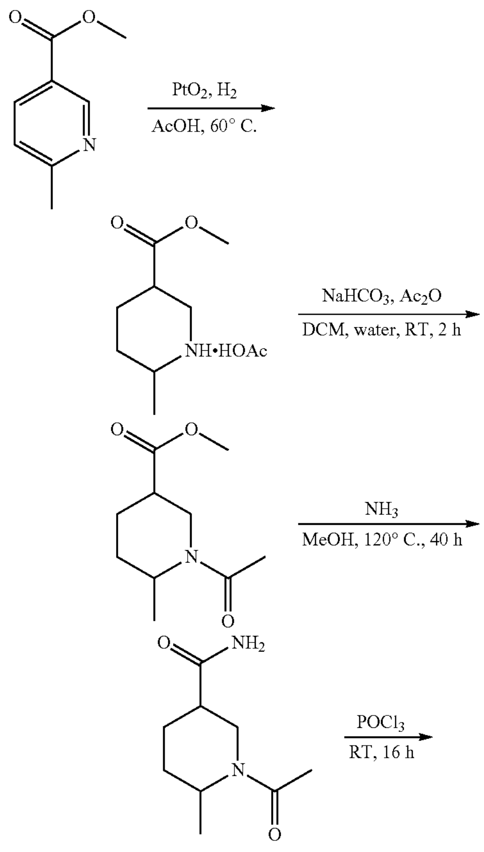

-continued

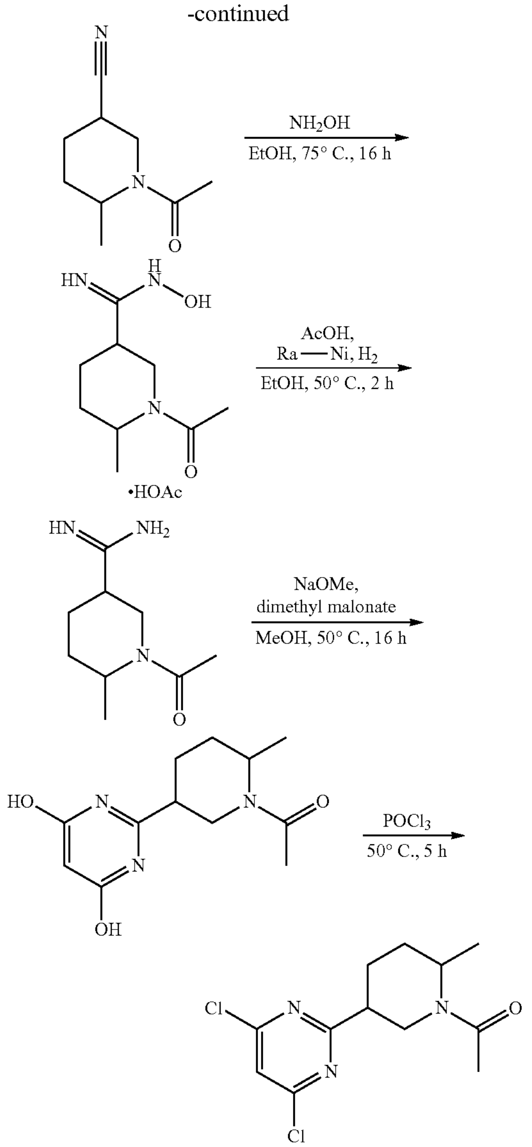

To a solution of methyl 6-methylnicotinate (100 g, 662 mmol) in acetic acid (250 mL) in a 1 L steel autoclave, platinum(IV) oxide (0.5 g, 2.202 mmol) was added after which the reaction mixture was stirred under 10 bar hydrogen atmosphere at 60° C. Rapid hydrogen consumption was observed and the autoclave was refilled several times until hydrogen consumption stopped and the reduction was complete. The mixture was cooled to room temperature and filtrated over Celite. The filtrate was concentrated to afford methyl 6-methylpiperidine-3-carboxylate acetate as a mixture of diastereoisomers (143.8 g, 100%) that was used as such in the next step. GCMS (Method A): $t_R$ 2.40 (80%) and 2.48 min (20%), 100%, MS (EI) 157.1 (M)+, 142.1 (M-Me)+. To a solution of methyl 6-methylpiperidine-3-carboxylate acetate (53 g, 244 mmol) in a mixture of water (500 mL) and dichloromethane (500 mL), sodium bicarbonate (82 g, 976 mmol) was added carefully (effervescence!!) after which acetic anhydride (29.9 g, 293 mmol) was added slowly. The reaction mixture was stirred at room temperature for 2 hours. The organic layer was separated, dried over sodium sulfate, filtered and concentrated in vacuo to afford methyl 1-acetyl-6-methylpiperidine-3-carboxylate (49 g, 100%) as a yellow oil. A solution of methyl 1-acetyl-6-methylpiperidine-3-carboxylate (49 g, 246 mmol) in ammonia in methanol (7N, 500 mL, 3.5 mol) was stirred in a pressure vessel at 120° C. for 40 hours. The mixture was cooled to room temperature and concentrated to afford a light yellow solid. This solid was dissolved in dichloromethane and filtered over a plug of silica. The filtrate was concentrated to afford 1-acetyl-6-methylpiperidine-3-carboxamide as an off white solid that was used as such in the next step. A solution of 1-acetyl-6-methylpiperidine-3-carboxamide (266 mmol) from the previous step in phosphorus oxychloride (500 mL, 5.37 mol) was stirred at room temperature for 16 hours. The reaction mixture was evaporated in vacuo affording a thick oil. This oil was co-evaporated twice with toluene and carefully partitioned between cold saturated sodium carbonate (effervescence!) and ethyl acetate. The organic layer was separated from the basic water layer, dried on sodium sulfate, filtered and concentrated in vacuo to afford the product as a thick oil that solidified upon standing. The crude was dissolved in dichloromethane and filtered over a plug of silica (eluted with 10% methanol in dichloromethane). This afforded 1-acetyl-6-methylpiperidine-3-carbonitrile (28 g, 63%) as an oil that solidified upon standing. GCMS (Method A): $t_R$ 3.78 (63%) and 3.89 min (378%), 100%, MS (EI) 166.1 $(M)^+$. To a solution of 1-acetyl-6-methylpiperidine-3-carbonitrile (23 g, 138 mmol) in ethanol (300 ml), hydroxylamine solution (50% in water, 25.4 mL, 415 mmol) was added after which the reaction mixture was stirred at reflux for 16 hours. The reaction mixture was concentrated and co-evaporated with ethyl acetate three times to dryness to afford 1-acetyl-N-hydroxy-6-methylpiperidine-3-carboximidamide as a sticky solid. LCMS (Method A): $t_R$ 0.13 min, 100%, MS (ESI) 200.2 $(M+H)^+$. Assuming quantitative yield, the product was used as such in the next step. To a solution of 1-acetyl-N-hydroxy-6-methylpiperidine-3-carboximidamide (23 g, 138 mmol) from the previous step in ethanol (500 mL), acetic acid (23.79 mL, 416 mmol) and 50% Raney®-Nickel slurry in water (5 mL) were added after which the reaction mixture was stirred under hydrogen atmosphere for 2 days at 50° C. The mixture was filtered over Celite, washed with some ethanol and concentrated to afford 70 g of a thick oil. This was co-evaporated twice with ethyl acetate and extensively dried in vacuo to afford 1-acetyl-6-methylpiperidine-3-carboximidamide acetate (33 g, 98%) as a greenish yellow oil that was used as such in the next step. LCMS (Method A): $t_R$ 0.14 min, 90%, MS (ESI) 184.1 $(M+H)^+$. To a solution of sodium (18.14 g, 789 mmol) in dry methanol under nitrogen atmosphere (60 mL) 1-acetyl-6-methylpiperidine-3-carboximidamide acetate (32 g, 132 mmol) and dimethyl malonate (26.1 g, 197 mmol) were added, after which the reaction mixture was stirred at 50° C. for 16 hours. The reaction mixture was concentrated, taken up in water (300 mL), acidified to pH 4 using 6N hydrochloric acid and allowed to precipitate. The precipitate was filtered off to afford 1-(5-(4,6-dihydroxypyrimidin-2-yl)-2-methylpiperidin-1-yl) ethan-1-one as a yellow solid (10.4 g, 31%) that was used as such in the next step. A suspension of 1-(5-(4,6-dihydroxypyrimidin-2-yl)-2-methylpiperidin-1-yl)ethan-1-one (10.4 g, 41.4 mmol) in phosphorus oxychloride (200 mL, 2146 mmol) was stirred at 50° C. The solids slowly dissolved after approximately 3 hours. After 5 hours, the reaction mixture was concentrated in vacuo and co-evaporated with toluene twice. The remaining oil was carefully quenched with ice and neutralised with saturated aqueous sodium bicarbonate and extracted with ethyl acetate (2×100 mL). The combined organic layers were dried over sodium sulfate and concentrated in vacuo to afford 1-(5-(4,6-dichloropyrimidin-2-yl)-2-methylpiperidin-1-yl)ethan-1-one (Intermediate 1, 6.8 g, 57%) as a yellow oil that solidified upon standing. LCMS (Method A): $t_R$ 1.88 min, 100%, MS (ESI) 288.1 $(M+H)^+$.

Intermediate 2: 1-((2S,5R)-5-(4,6-dichloropyrimidin-2-yl)-2-methylpiperidin-1-yl)ethan-1-one

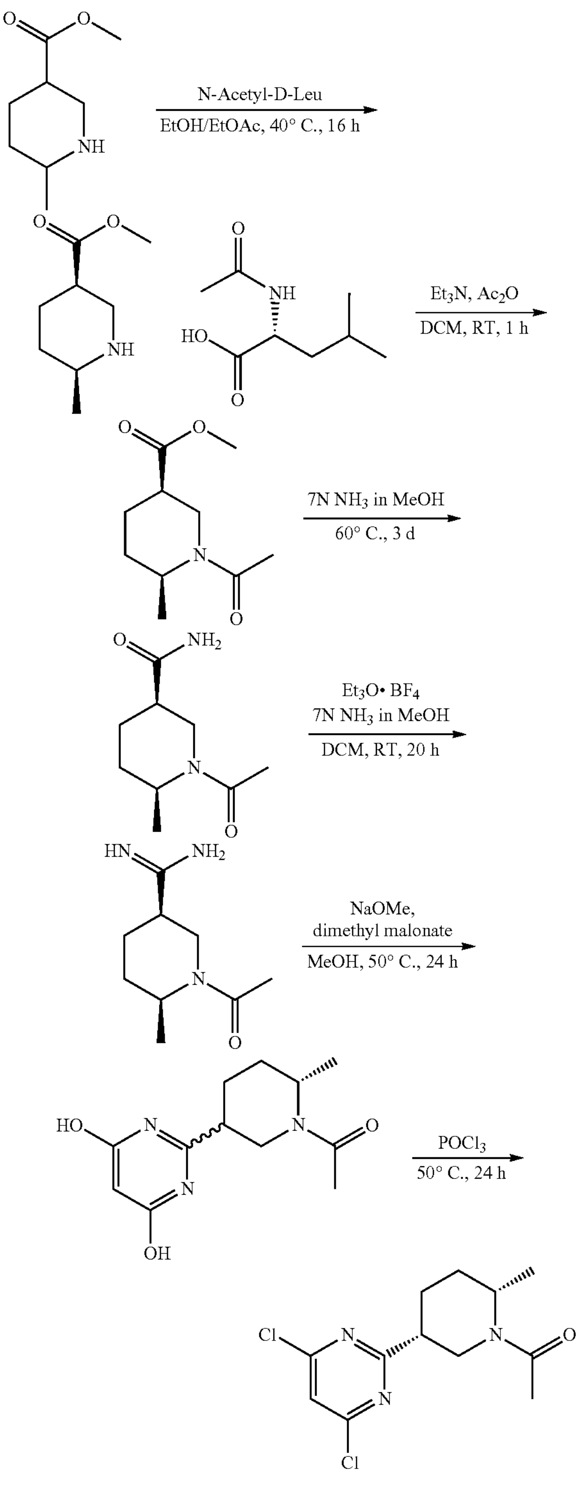

To a solution of N-acetyl-D-leucine (1 kg, 5.77 mol) in ethanol (1.5 L) was added a solution of methyl 6-methylpiperidine-3-carboxylate (934 g, 2.38 mol, prepared under Intermediate 1) in ethyl acetate (3 L) and the mixture was heated to 40° C. The resulting solution was allowed to reach room temperature over 16 hours during which precipitation occurred. The precipitate was filtered off, washed with diethyl ether (500 mL) and air dried to afford crude methyl (3R,6S)-6-methylpiperidine-3-carboxylate acetyl-D-leucinate (287 g, 34%) as a white solid. The crude methyl (3R,6S)-6-methylpiperidine-3-carboxylate acetyl-D-leucinate (287 g, 869 mmol) was crystallised from a hot mixture of ethanol and ethyl acetate 1:2 (1 L). The precipitate was filtered off and the filtercake was triturated in a mixture of diethyl ether and n-pentane 1:1 (500 mL). The precipitate was filtered off and air dried to afford methyl (3R,6S)-6-methylpiperidine-3-carboxylate acetyl-D-leucinate (128 g, 44%) as a white solid. To a solution of methyl (3R,6S)-6-methylpiperidine-3-carboxylate acetyl-D-leucinate (128 g, 387 mmol) in dichloromethane (1 L) was added a saturated sodium carbonate solution (1 L). The biphasic system was stirred vigorous for 10 minutes and the layers were separated. The organic layer was dried with sodium sulfate and filtered to afford a clear solution. Next, triethylamine (65 mL, 465 mmol) and acetic anhydride (44 mL, 465 mmol) were added and the mixture was stirred at room temperature for 1 hour. The mixture was washed with saturated sodium bicarbonate solution, dried over sodium sulfate and concentrated to afford methyl (3R,6S)-1-acetyl-6-methylpiperidine-3-carboxylate (93 g) as a light yellow solid. An autoclave was charged with methyl (3R,6S)-1-acetyl-6-methylpiperidine-3-carboxylate (93 g, 387 mmol) in 7N ammonia in methanol (600 mL, 4200 mmol) and was heated to 60° C. for 3 days. The mixture was concentrated to afford (3R,6S)-1-acetyl-6-methylpiperidine-3-carboxamide (102 g) as a pale yellow oil. Assuming quantitative yield, the product was used as such in the next step. Chiral LC (Method A) $t_R$=12.35 min, >98% ee. To a solution of (3R,6S)-1-acetyl-6-methylpiperidine-3-carboxamide (50 g, 271 mmol) in dichloromethane (500 mL) was added triethyloxonium tetrafluoroborate (77 g, 407 mmol) portion wise and the mixture was stirred at room temperature for 4 hours. Slowly, 7N ammonia in methanol (200 ml, 9.15 mol) was added and the mixture was stirred at room temperature for 16 hours. The mixture was concentrated to afford (3R,6S)-1-acetyl-6-methylpiperidine-3-carboximidamide (50 g) as a pink solid which was used as such in the next step. To a solution of 5.4M sodium methoxide in methanol (99 mL, 535 mmol) in methanol (200 mL) was added, (3R,6S)-1-acetyl-6-methylpiperidine-3-carboximidamide (49 g, 267 mmol) in methanol (400 mL) and dimethyl malonate (61.4 mL, 535 mmol). The mixture was heated to 50° C. and stirred for 24 hours. The mixture was acidified (pH ~3) with concentrated hydrochloric acid and was concentrated to a smaller volume. The residue was filtered through silica (20% methanol in dichloromethane) and concentrated to afford an orange oil. The crude product was purified with silica column chromatography (0% to 20% methanol in dichloromethane) to afford 1-((2S,5R)-5-(4,6-dihydroxypyrimidin-2-yl)-2-methylpiperidin-1-yl)ethan-1-one (12 g, 17%) as a colorless gum. LCMS (Method C): $t_R$ 0.17 min, 100%, MS (ESI) 252.1 $(M+H)^+$. A solution of 1-((2S,5R)-5-(4,6-dihydroxypyrimidin-2-yl)-2-methylpiperidin-1-yl)ethan-1-one (12 g, 47.8 mmol) in phosphorus oxychloride (80 mL, 858 mmol) was stirred at 60° C. for 24 hours. The reaction mixture was concentrated and co-evaporated with toluene twice to afford a yellow oil. The oil was dissolved in ethyl acetate and washed with saturated sodium bicarbonate solution. The aqueous layer was extracted with ethyl acetate twice. The combined organic layers were washed with brine, dried over sodium sulfate and concentrated to afford a yellow oil. The oil was purified with silica column chromatography (0% to 20% tetrahydrofuran in toluene) to afford 1-((2S,5R)-5-(4,6-dichloropyrimidin-2-yl)-2-methylpiperidin-1-yl)ethan-1-one (Intermediate 2, 1.5 g, 11%) as a colorless gum. LCMS (Method B): $t_R$ 3.34 min, 100%, MS (ESI) 288.0 $(M+H)^+$; Chiral UPLC (Method: A) $t_R$ 2.54 min, >95% ee and de.

Intermediate 3: Synthesis of 1-((2S,5R)-5-(4-chloro-6-(pyrazin-2-yl)pyrimidin-2-yl)-2-methylpiperidin-1-yl)ethan-1-one

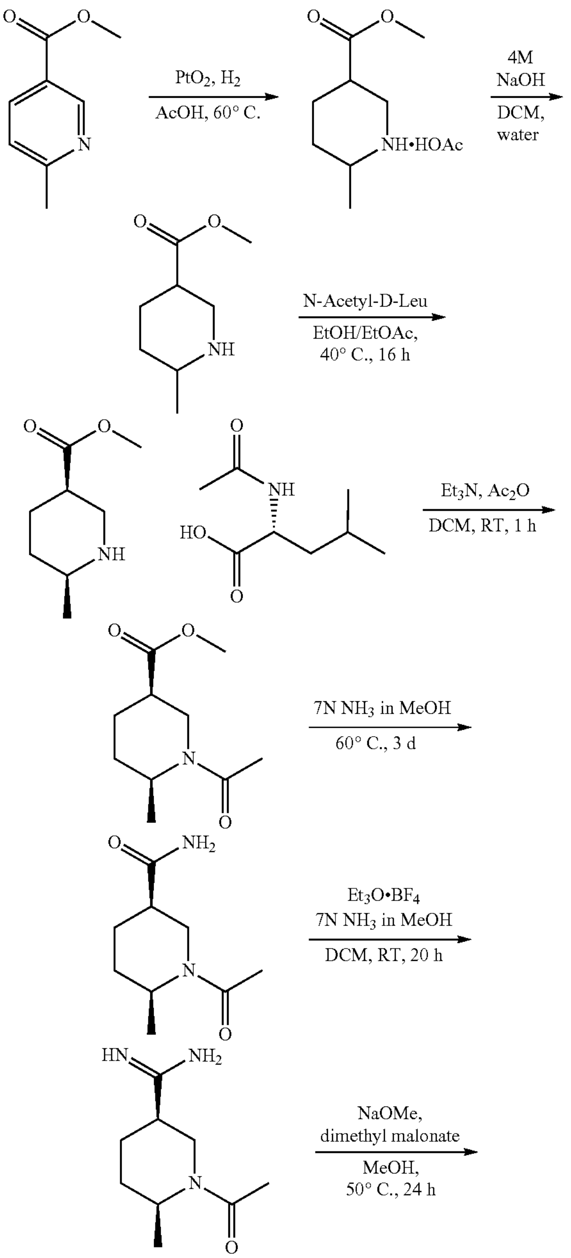

-continued

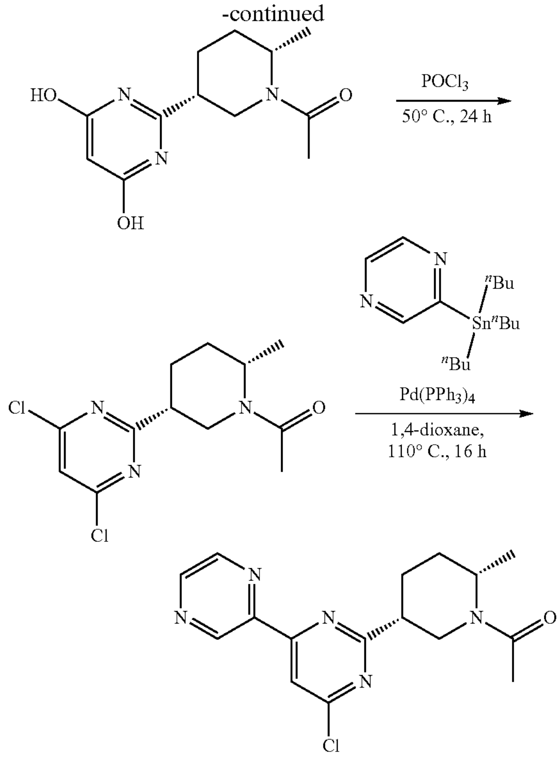

To a solution of methyl 6-methylnicotinate (100 g, 662 mmol) in acetic acid (250 mL) in a 1 L steel autoclave, platinum(IV) oxide (0.5 g, 2.202 mmol) was added after which the reaction mixture was stirred under 10 bar hydrogen atmosphere at 60° C. Rapid hydrogen consumption was observed and the autoclave was refilled several times until hydrogen consumption stopped. The mixture was cooled to room temperature and filtered over Celite. The filtrate was carefully concentrated to afford methyl 6-methylpiperidine-3-carboxylate acetate as a mixture of diastereoisomers (143.8 g, 100%) that was used as such in the next step. GCMS (Method A): $t_R$ 2.40 (80%) and 2.48 min (20%), 100%, MS (EI) 157.1 $(M)^+$. Methyl 6-methylpiperidine-3-carboxylate acetate as a mixture of diastereoisomers (2.1 kg, 9924 mmol) was diluted with dichloromethane (4 L) and 4M sodium hydroxide solution was added slowly until pH ~9. The layers were separated and the aqueous layer was extracted with dichloromethane twice (the aqueous layer was re-basified with 4M sodium hydroxide solution to pH-9 after each extraction). The combined organic layers were dried with sodium sulfate and concentrated (35° C., 450 mbar) to a smaller volume (~2 L) to afford methyl 6-methylpiperidine-3-carboxylate (2.8 kg, 8905 mmol) as a ~50% yellow solution in dichloromethane. $^1H$ NMR (400 MHz, $CDCl_3$, mixture of rotamers) δ 5.10 (s, 3H), 3.63 (s, 1H), 3.49-3.42 (m, 2.2H), 3.41-3.34 (m, 0.8H), 3.18-3.10 (m, 0.8H), 3.09-3.03 (m, 0.2H), 2.64-2.54 (m, 0.8H), 2.53-2.34 (m, 1.2H), 2.30-2.20 (m, 1H), 1.95-1.76 (m, 1H), 1.53-1.36 (m, 1H), 1.35-1.21 (m, 1H), 1.04-0.90 (m, 1H), 0.89-0.84 (m, 0.8H), 0.83-0.76 (m, 2.2H). To a solution of N-acetyl-D-leucine (1 kg, 5.77 mol) in ethanol (1.5 L) was added a solution of methyl 6-methylpiperidine-3-carboxylate (934 g, 2.38 mol) in ethyl acetate (3 L) and the mixture was heated to 40° C. The resulting solution was allowed to reach room temperature over 16 hours during which precipitation occurred. The precipitate was filtered off, washed with diethyl ether (500 mL) and air dried to afford crude methyl (3R,6S)-6-methylpiperidine-3-carboxylate acetyl-D-leucinate (287 g, 34%) as a white solid. The crude methyl (3R,6S)-6-methylpiperidine-3-carboxylate acetyl-D-leucinate (287 g, 869 mmol) was crystallized from a hot mixture of ethanol and ethyl acetate 1:2 (1 L). The precipitate was filtered off and the filter cake was triturated in a 25 mixture of diethyl ether and n-pentane 1:1 (500 mL). The precipitate was filtered off and air dried to afford methyl (3R,6S)-6-methylpiperidine-3-carboxylate acetyl-D-leucinate (128 g, 44%) as a white solid. $^1H$-NMR (400 MHz, DMSO-d6) δ 7.80 (d, J=8.2 Hz, 1H), 5.80-5.00 (s, 2H), 4.20-4.04 (m, 1H), 3.63 (s, 3H), 3.32-3.21 (m, 1H), 2.93-2.80 (m, 2H), 2.73-2.65 (m, 1H), 2.04-1.94 (m, 1H), 1.82 (s, 3H), 1.68-1.49 (m, 3H), 1.49-1.37 (m, 2H), 1.30-1.15 (m, 1H), 1.02 (d, J=6.4 Hz, 3H), 0.85 (m, 6H). To a solution of methyl (3R,6S)-6-methylpiperidine-3-carboxylate acetyl-D-leucinate (128 g, 387 mmol) in dichloromethane (1 L) was added a saturated sodium carbonate solution (1 L). The biphasic system was stirred vigorous for 10 minutes and the layers were separated. The organic layer was dried with sodium sulfate and filtered to afford a clear solution. Next, triethylamine (65 mL, 465 mmol) and acetic anhydride (44 mL, 465 mmol) were added and the mixture was stirred at room temperature for 1 hour. The mixture was washed with saturated aqueous sodium bicarbonate solution, dried over sodium sulfate and concentrated to afford methyl (3R,6S)-1-acetyl-6-methylpiperidine-3-carboxylate (93 g) as a light yellow solid. $^1H$-NMR (400 MHz, $CDCl_3$, mixture of rotamers) δ 5.02-4.87 (m, 0.5H), 4.84-4.68 (m, 0.5H), 4.18-4.05 (m, 0.5H), 3.89-3.77 (m, 0.5H), 3.71 (d, J=11.6 Hz, 3H), 3.31-3.18 (m, 0.5H), 2.79-2.67 (m, 0.5H), 2.51-2.31 (m, 1H), 2.11 (d, J=6.7 Hz, 3H), 2.01-1.90 (m, 1H), 1.88-1.55 (m, 3H), 1.33-1.21 (m, 1.5H), 1.20-1.06 (m, 1.5H). An autoclave was charged with methyl (3R,6S)-1-acetyl-6-methylpiperidine-3-carboxylate (93 g, 387 mmol) in 7N ammonia in methanol (600 mL, 4200 mmol) and was heated to 60° C. for 3 days. The mixture was concentrated to afford (3R,6S)-1-acetyl-6-methylpiperidine-3-carboxamide (102 g) as a pale yellow oil. Assuming quantitative yield, the product was used as such in the next step. $^1H$-NMR (400 MHz, DMSO-d6, mixture of rotamers) δ 7.38 (s, 1H), 6.89 (d, J=24.7 Hz, 1H), 4.76-4.59 (m, 0.5H), 4.39-4.24 (m, 0.5H), 4.16-4.01 (m, 0.5H), 3.72-3.51 (m, 0.5H), 3.14-2.99 (m, 0.5H), 2.68-2.51 (m, 0.5H), 2.30-2.12 (m, 0.5H), 2.11-1.92 (m, 3.5H), 1.78-1.38 (m, 4H), 1.23-1.11 (m, 1.5H), 1.09-0.94 (m, 1.5H); Chiral LC (Method A) $t_R$=12.35 min, >98% ee. To a solution of (3R,6S)-1-acetyl-6-methylpiperidine-3-carboxamide (50 g, 271 mmol) in dichloromethane (500 mL) was added triethyloxonium tetrafluoroborate (77 g, 407 mmol) portion wise and the mixture was stirred at room temperature for 4 hours. Slowly, 7N ammonia in methanol (200 mL, 9.15 mol) was added and the mixture was stirred at room temperature for 16 hours. The mixture was concentrated to afford (3R,6S)-1-acetyl-6-methylpiperidine-3-carboximidamide (50 g) as a pink solid which was used as such in the next step. To a solution of 5.4M sodium methoxide in methanol (99 mL, 535 mmol) in methanol (200 mL) was added, (3R,6S)-1-acetyl-6-methylpiperidine-3-carboximidamide (49 g, 267 mmol) in methanol (400 mL) and dimethyl malonate (61.4 mL, 535 mmol). The mixture was heated to 50° C. and stirred for 24 hours. The mixture was acidified (pH ~3) with concentrated hydrochloric acid and was concentrated to a smaller volume. The residue was filtered through silica (20% methanol in dichloromethane) and concentrated to afford an orange oil. The crude product was purified with silica column chromatography (0% to 20% methanol in dichloromethane) to afford 1-((2S,5R)-5-(4,6-dihydroxypyrimidin-2-yl)-2-methylpiperidin-1-yl)ethan-1-one (12 g, 17%) as a colorless gum. LCMS (Method C): $t_R$ 0.17 min, 100%, MS (ESI) 252.1 $(M+H)^+$. A solution of 1-((2S,5R)-5-(4,6-dihydroxypyrimidin-2-yl)-2-methylpiperidin-1-yl)ethan-1-one (12 g, 47.8 mmol) in phosphorus oxychloride (80 mL, 858 mmol) was stirred at 60° C. for 24 hours. The reaction mixture was concentrated and co-evaporated with toluene twice to afford a yellow oil. The oil was dissolved in ethyl acetate and washed with saturated sodium bicarbonate solution. The aqueous layer was extracted with ethyl acetate twice. The combined organic layers were washed with brine, dried over sodium sulfate and concentrated to afford a yellow oil. The oil was purified with silica column chromatography (0% to 20% tetrahydrofuran in toluene) to afford 1-((2S,5R)-5-(4,6-dichloropyrimidin-2-yl)-2-methylpiperidin-1-yl)ethan-1-one (1.5 g, 11%) as a colorless gum. $^1$H-NMR (400 MHz, DMSO-d6, mixture of rotamers) δ 7.95 (d, J=7.3 Hz, 1H), 4.85-4.72 (m, 1H), 4.69-4.62 (m, 1H), 4.23-4.13 (m, 1H), 4.07-3.98 (m, 1H), 3.97-3.88 (m, 1H), 3.00-2.89 (m, 1H), 2.81-2.67 (m, 1H), 2.09-1.72 (m, 7H), 1.71-1.58 (m, 2H), 1.25-1.14 (m, 3H), 1.12-1.05 (m, 2H); LCMS (Method B): $t_R$ 3.34 min, MS (ESI) 288.0 $(M+H)^+$; Chiral UPLC (Method: A) $t_R$ 2.54 min, >95% ee and de. Under argon, 2-tributylstannylpyrazine (607 mg, 1.65 mmol), 1-((2S,5R)-5-(4,6-dichloropyrimidin-2-yl)-2-methylpiperidin-1-yl)ethan-1-one (500 mg, 1.74 mmol) and bis(triphenylphosphine)palladium(II) chloride (244 mg, 0.34 mmol) in 1,4-dioxane (20 mL) were heated to 100° C. and stirred for 32 hours. The mixture was diluted with dichloromethane containing 1% triethylamine and coated onto silica. This was purified with silica column chromatography (0% to 40% acetonitrile in dichloromethane containing 1% triethylamine) to afford 1-((2S,5R)-5-(4-chloro-6-(pyrazin-2-yl)pyrimidin-2-yl)-2-methylpiperidin-1-yl)ethan-1-one (Intermediate 3, 134 mg, 18%) as an orange gum. $^1$H-NMR (400 MHz, DMSO-d6, mixture of rotamers) δ 9.46-9.41 (m, 1H), 8.80-8.76 (m, 1H), 8.65-8.59 (m, 1H), 8.33-8.29 (m, 1H), 7.66-7.59 (m, 1H), 4.86-4.70 (m, 0.5H), 4.27-4.17 (m, 0.5H), 4.09-3.97 (m, 0.5H), 3.55-3.41 (m, 0.5H), 3.06-2.98 (m, 0.5H), 2.88-2.82 (m, 0.5H), 2.10-1.90 (m, 6H), 1.89-1.76 (m, 0.5H), 1.75-1.61 (m, 1.5H), 1.29-1.20 (m, 1.5H), 1.17-1.10 (m, 1.5H); LCMS (Method C): $t_R$ 1.81 min, MS (ESI) 331.1 $(M+H)^+$.

Synthetic Procedures for Final Products

Example 1: Synthesis of 1-((2S,5R)-2-methyl-5-(4-((5-methylpyridin-3-yl)amino)-6-(pyrazin-2-yl)pyrimidin-2-yl)piperidin-1-yl)ethan-1-one (00001) and 1-((2R,5S)-2-methyl-5-(4-((5-methylpyridin-3-yl)amino)-6-(pyrazin-2-yl)pyrimidin-2-yl)piperidin-1-yl)ethan-1-one (00002)

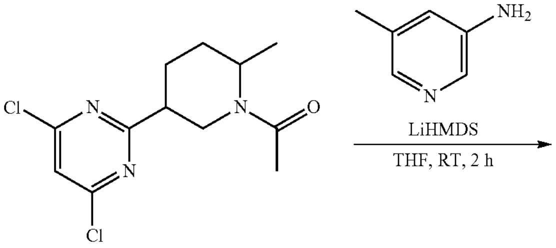

-continued

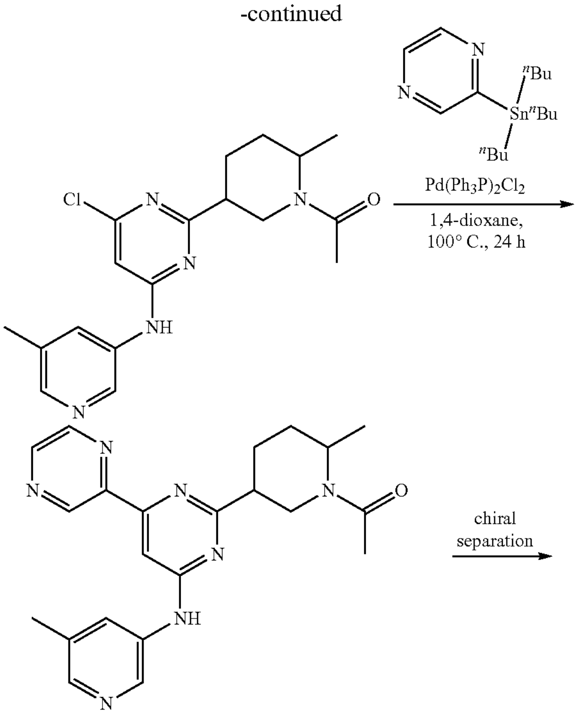

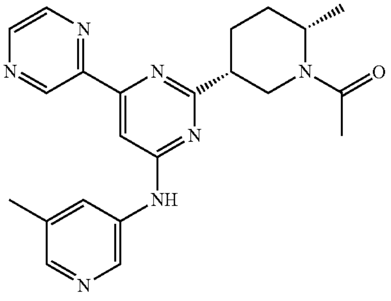

+

00001

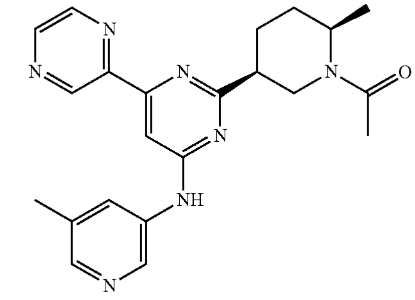

00002

To a solution of 3-amino-5-methylpyridine (0.751 g, 6.94 mmol) in tetrahydrofuran (20 mL) was added 1M lithium bis(trimethylsilyl)amide in tetrahydrofuran (6.94 mL, 6.94 mmol) and the mixture was stirred at room temperature for 10 minutes. Next, 1-(5-(4,6-dichloropyrimidin-2-yl)-2-methylpiperidin-1-yl)ethan-1-one (Intermediate 1, 1 g, 3.47 mmol) in tetrahydrofuran (20 ml) was added and the mixture was stirred at room temperature for 2 hours. The mixture was poured into saturated ammonium chloride solution and was extracted with ethyl acetate twice. The combined organic layers were washed with brine once, dried over sodium sulfate and concentrated to afford a yellow solid. The solid was purified with silica column chromatography (0% to 5% methanol in dichloromethane) to afford 1-(5-(4-chloro-6-((5-methylpyridin-3-yl)amino)pyrimidin-2-yl)-2-methylpiperidin-1-yl)ethan-1-one (788 mg, 60%) as a yellow foam. LCMS (Method B): $t_R$ 1.81 min, 100%, MS (ESI) 360.1 $(M+H)^+$. Under nitrogen, 2-(tributylstannyl)pyrazine (103 mg, 0.28 mmol), 1-(5-(4-chloro-6-((5-methylpyridin-3-yl)amino)pyrimidin-2-yl)-2-methylpiperidin-1-yl)ethan-1-one (50 mg, 0.14 mmol) and bis(triphenylphosphine) palladium(II) dichloride (9.75 mg, 0.01 mmol) were dissolved in N,N-dimethylformamide (3 mL). The mixture was heated to 80° C. for 24 hours and cooled to room temperature. The mixture was eluted through a C18 plug using acetonitrile, the filtrate was purified with reversed phase chromatography (method B) and lyophilized to afford 1-(2-methyl-5-(4-((5-methylpyridin-3-yl)amino)-6-(pyrazin-2-yl)pyrimidin-2-yl)piperidin-1-yl)ethan-1-one (22 mg, 37%) as a white solid. The obtained mixture of cis enantiomers was submitted for chiral preparative SFC (Method A) and lyophilized to afford both stereoisomers. 1-((2S,5R)-2-methyl-5-(4-((5-methylpyridin-3-yl)amino)-6-(pyrazin-2-yl)pyrimidin-2-yl)piperidin-1-yl)ethan-1-one (5 mg, 22%) LCMS (Method D): $t_R$ 3.17 min, 100%, MS (ESI) 404.1 $(M+H)^+$; Chiral UPLC (Method: A): $t_R$ 3.17 min, >95% ee and de. 1-((2R,5S)-2-methyl-5-(4-((5-methylpyridin-3-yl)amino)-6-(pyrazin-2-yl)pyrimidin-2-yl)piperidin-1-yl)ethan-1-one (6 mg, 27%) LCMS (Method D): $t_R$ 3.17 min, 100%, MS (ESI) 404.2 $(M+H)^+$; Chiral UPLC (Method A): $t_R$ 4.60 min, >95% ee and de.

The compounds (00003) to (00012) (as depicted below in Table 1) were prepared using procedures analogous to Example 1, using the appropriate starting materials.

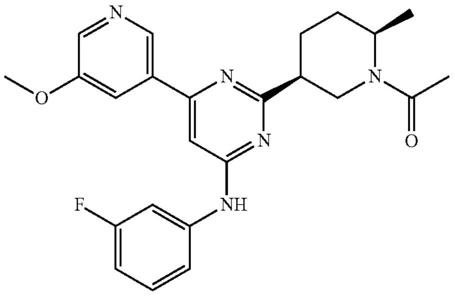 [SMILES: COc1cncc(-c2cc(Nc3cccc(F)c3)nc([C@H]3CC[C@@H](C)N(C(C)=O)C3)n2)c1]

00003

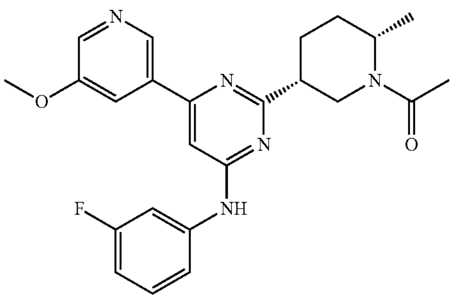 [SMILES: COc1cncc(-c2cc(Nc3cccc(F)c3)nc([C@@H]3CC[C@H](C)N(C(C)=O)C3)n2)c1]

00004

-continued

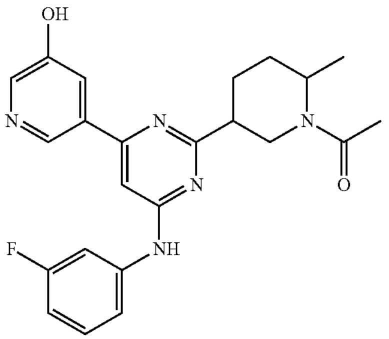 [SMILES: CC(=O)N1CC(c2nc(Nc3cccc(F)c3)cc(-c3cncc(O)c3)n2)CCC1C]

00005

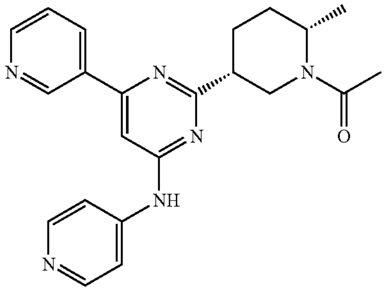 [SMILES: CC(=O)N1C[C@H](c2nc(Nc3ccncc3)cc(-c3cccnc3)n2)CC[C@@H]1C]

00006

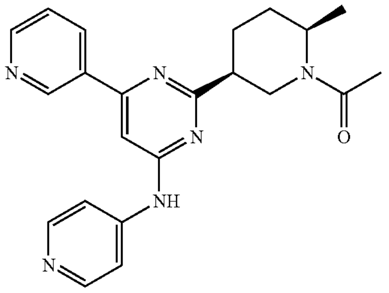 [SMILES: CC(=O)N1C[C@@H](c2nc(Nc3ccncc3)cc(-c3cccnc3)n2)CC[C@H]1C]

00007

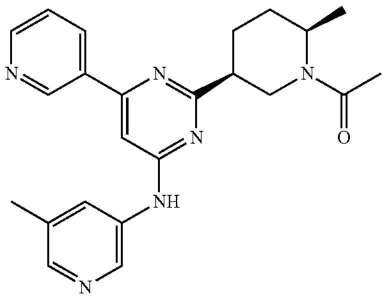 [SMILES: CC(=O)N1C[C@@H](c2nc(Nc3cncc(C)c3)cc(-c3cccnc3)n2)CC[C@H]1C]

00008

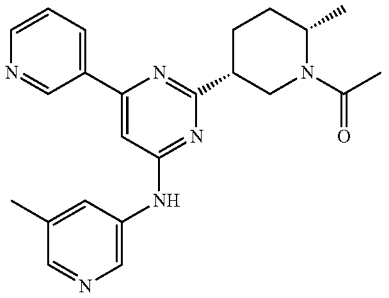 [SMILES: CC(=O)N1C[C@H](c2nc(Nc3cncc(C)c3)cc(-c3cccnc3)n2)CC[C@@H]1C]

00009

-continued

00010

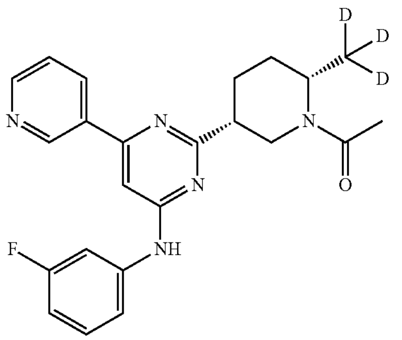 [SMILES: [2H]C([2H])([2H])[C@H]1CC[C@@H](c2nc(Nc3cccc(F)c3)cc(-c3cccnc3)n2)CN1C(C)=O]

00011

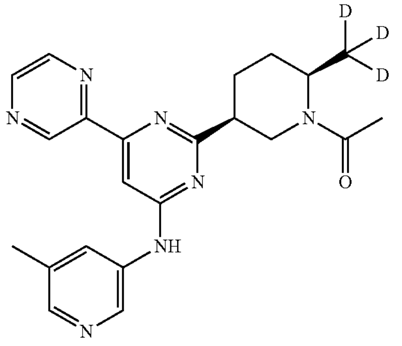 [SMILES: [2H]C([2H])([2H])[C@@H]1CC[C@H](c2nc(Nc3cncc(C)c3)cc(-c3cnccn3)n2)CN1C(C)=O]

00012

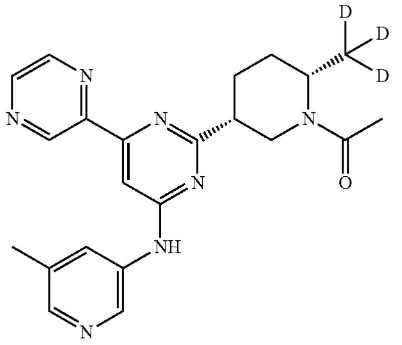 [SMILES: [2H]C([2H])([2H])[C@H]1CC[C@@H](c2nc(Nc3cncc(C)c3)cc(-c3cnccn3)n2)CN1C(C)=O]

Example 2: Synthesis of 1-((2S,5R)-5-(4-(imidazo[1,2-a]pyridin-6-ylamino)-6-(pyridin-3-yl)pyrimidin-2-yl)-2-methylpiperidin-1-yl)ethan-1-one (00013)

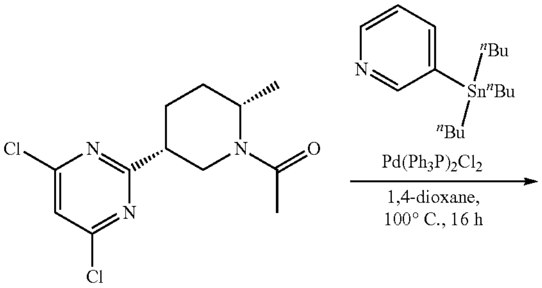

-continued

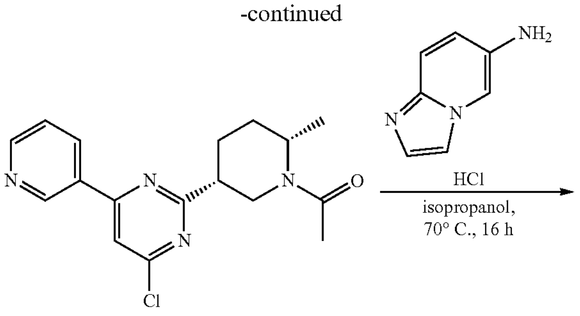

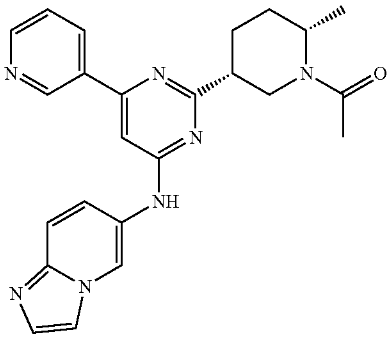

00013

Under argon, 3-(tributylstannyl)pyridine (607 mg, 1.65 mmol), 1-((2S,5R)-5-(4,6-dichloropyrimidin-2-yl)-2-methylpiperidin-1-yl)ethan-1-one (Intermediate 2, 500 mg, 1.74 mmol) and bis(triphenylphosphine)palladium(II) chloride (244 mg, 0.34 mmol) in 1,4-dioxane (20 mL) were heated to 100° C. and stirred for 32 hours. The mixture was diluted with dichloromethane containing 1% triethylamine and coated onto silica. This was purified with silica column chromatography (0% to 40% acetonitrile in dichloromethane containing 1% triethylamine) to afford 1-((2S,5R)-5-(4-chloro-6-(pyridin-3-yl)pyrimidin-2-yl)-2-methylpiperidin-1-yl)ethan-1-one (134 mg, 18%) as an orange gum. LCMS (Method C): $t_R$ 1.81 min, 100%, MS (ESI) 331.1 $(M+H)^+$. To a solution of 1-((2S,5R)-5-(4-chloro-6-(pyridin-3-yl)pyrimidin-2-yl)-2-methylpiperidin-1-yl)ethan-1-one (30 mg, 0.09 mmol) in 2-propanol (2 mL), was added imidazo[1,2-a]pyridin-6-amine (36.2 mg, 0.27 mmol) and hydrochloric acid (0.02 mL, 0.27 mmol). The mixture was stirred at 60° C. for 16 hours, poured into saturated aqueous sodium bicarbonate solution and extracted with ethyl acetate twice. The combined organic layers were dried over sodium sulfate and concentrated to afford a yellow oil. The oil was purified with reversed phase chromatography (method B) and lyophilized to afford 1-((2S,5R)-5-(4-(imidazo[1,2-a]pyridin-6-ylamino)-6-(pyridin-3-yl)pyrimidin-2-yl)-2-methylpiperidin-1-yl)ethan1-one as a blue-ish solid. LCMS (Method B): $t_R$2.19 min, 100%, MS (ESI) 428.1 $(M+H)^+$.

The compounds (00014) to (00060) (as depicted below in Table 1) were prepared following procedures analogous to Example 2, using the appropriate starting materials -continued
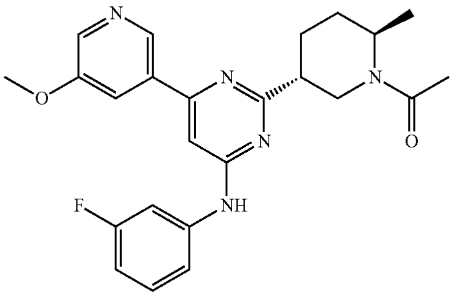 [SMILES: COc1cncc(-c2cc(Nc3cccc(F)c3)nc([C@@H]3CC[C@@H](C)N(C(C)=O)C3)n2)c1]
00014
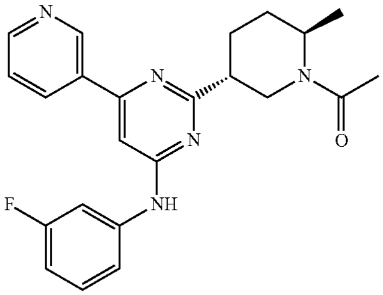 [SMILES: CC(=O)N1C[C@H](c2nc(Nc3cccc(F)c3)cc(-c3cccnc3)n2)CC[C@H]1C]
00015
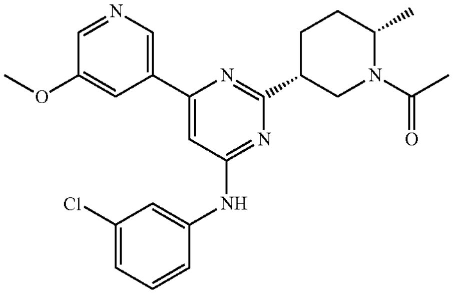 [SMILES: COc1cncc(-c2cc(Nc3cccc(Cl)c3)nc([C@@H]3CC[C@H](C)N(C(C)=O)C3)n2)c1]
00016
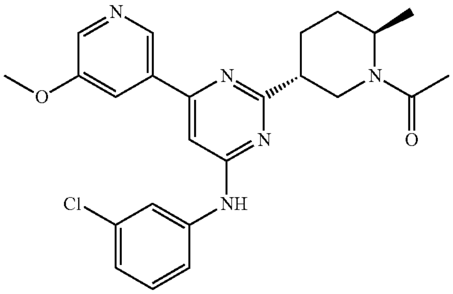 [SMILES: COc1cncc(-c2cc(Nc3cccc(Cl)c3)nc([C@@H]3CC[C@@H](C)N(C(C)=O)C3)n2)c1]
00017
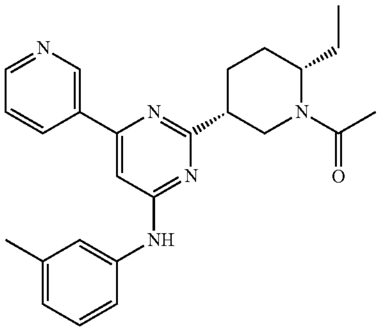 [SMILES: CC[C@H]1CC[C@@H](c2nc(Nc3cccc(C)c3)cc(-c3cccnc3)n2)CN1C(C)=O]
00018
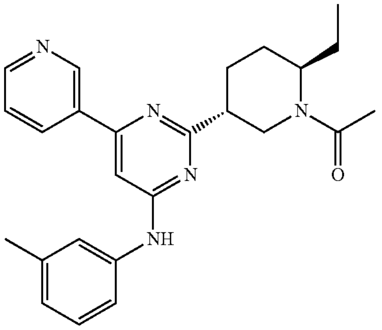 [SMILES: CC[C@@H]1CC[C@@H](c2nc(Nc3cccc(C)c3)cc(-c3cccnc3)n2)CN1C(C)=O]
00019
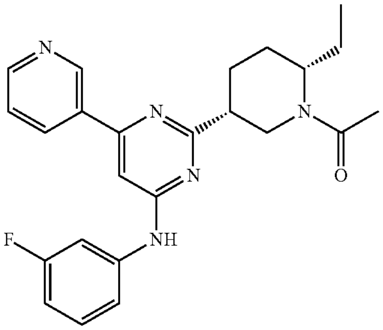 [SMILES: CC[C@H]1CC[C@@H](c2nc(Nc3cccc(F)c3)cc(-c3cccnc3)n2)CN1C(C)=O]
00020
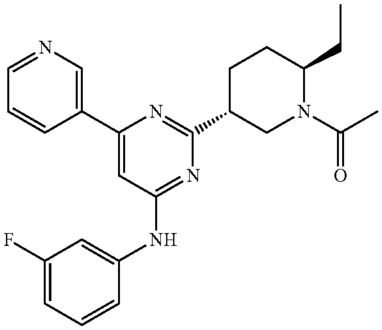 [SMILES: CC[C@@H]1CC[C@@H](c2nc(Nc3cccc(F)c3)cc(-c3cccnc3)n2)CN1C(C)=O]
00021
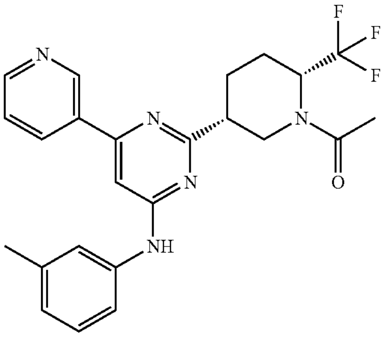 [SMILES: CC(=O)N1C[C@H](c2nc(Nc3cccc(C)c3)cc(-c3cccnc3)n2)CC[C@@H]1C(F)(F)F]
00022

-continued
00023
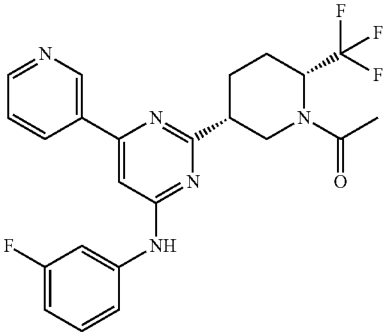 [SMILES: CC(=O)N1C[C@H](c2nc(Nc3cccc(F)c3)cc(-c3cccnc3)n2)CC[C@@H]1C(F)(F)F]
00024
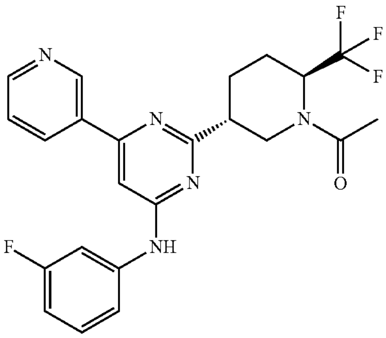 [SMILES: CC(=O)N1C[C@H](c2nc(Nc3cccc(F)c3)cc(-c3cccnc3)n2)CC[C@H]1C(F)(F)F]
00025
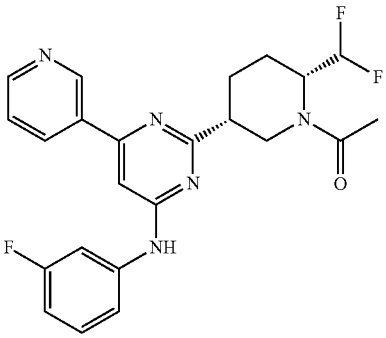 [SMILES: CC(=O)N1C[C@H](c2nc(Nc3cccc(F)c3)cc(-c3cccnc3)n2)CC[C@@H]1C(F)F]
00026
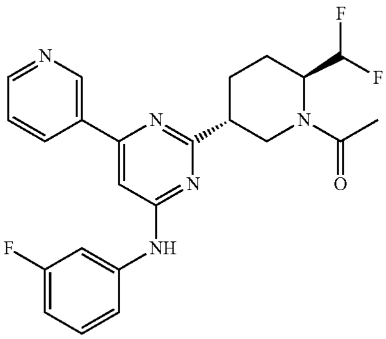 [SMILES: CC(=O)N1C[C@H](c2nc(Nc3cccc(F)c3)cc(-c3cccnc3)n2)CC[C@H]1C(F)F]
-continued
00027
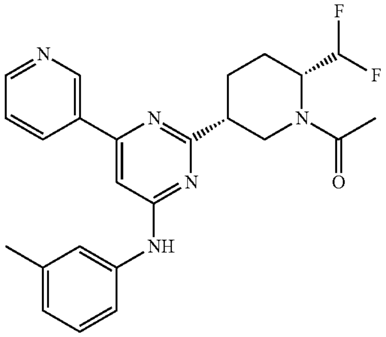 [SMILES: CC(=O)N1C[C@H](c2nc(Nc3cccc(C)c3)cc(-c3cccnc3)n2)CC[C@@H]1C(F)F]
00028
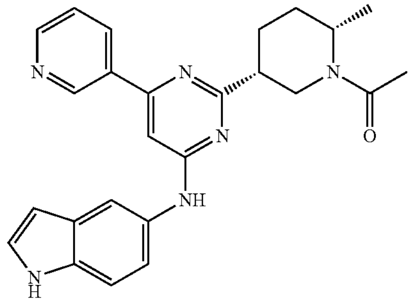 [SMILES: CC(=O)N1C[C@H](c2nc(Nc3ccc4[nH]ccc4c3)cc(-c3cccnc3)n2)CC[C@@H]1C]
00029
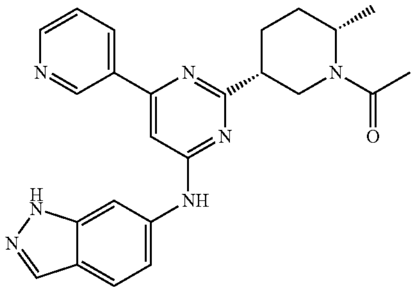 [SMILES: CC(=O)N1C[C@H](c2nc(Nc3ccc4cn[nH]c4c3)cc(-c3cccnc3)n2)CC[C@@H]1C]
00030
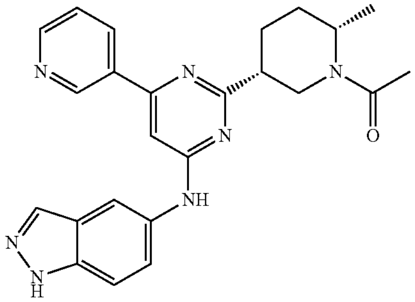 [SMILES: CC(=O)N1C[C@H](c2nc(Nc3ccc4[nH]ncc4c3)cc(-c3cccnc3)n2)CC[C@@H]1C]
00031
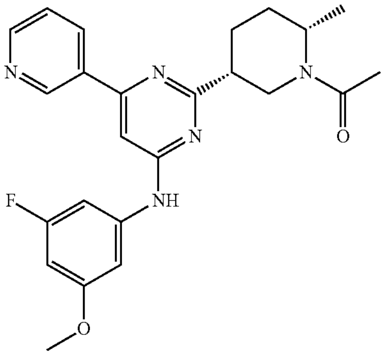 [SMILES: COc1cc(F)cc(Nc2cc(-c3cccnc3)nc([C@@H]3CC[C@H](C)N(C(C)=O)C3)n2)c1]

00032
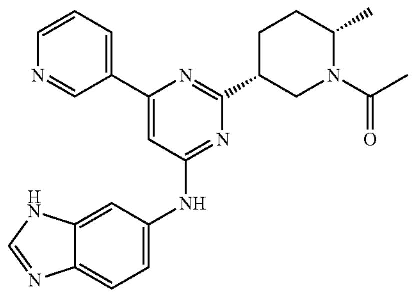 [SMILES: CC(=O)N1C[C@H](c2nc(Nc3ccc4nc[nH]c4c3)cc(-c3cccnc3)n2)CC[C@@H]1C]
00033
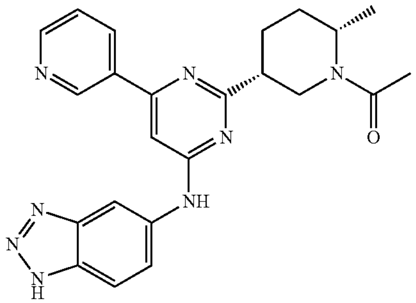 [SMILES: CC(=O)N1C[C@H](c2nc(Nc3ccc4[nH]nnc4c3)cc(-c3cccnc3)n2)CC[C@@H]1C]
00034
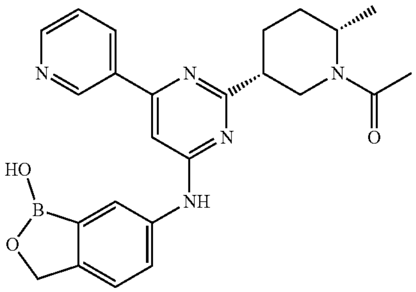 [SMILES: CC(=O)N1C[C@H](c2nc(Nc3ccc4c(c3)B(O)OC4)cc(-c3cccnc3)n2)CC[C@@H]1C]
00035
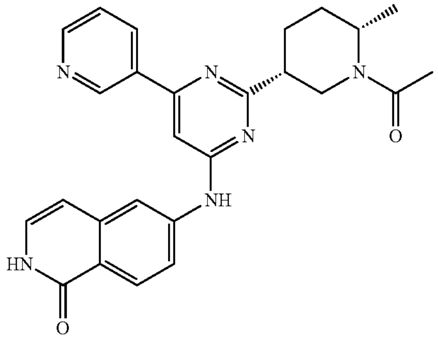 [SMILES: CC(=O)N1C[C@H](c2nc(Nc3ccc4c(=O)[nH]ccc4c3)cc(-c3cccnc3)n2)CC[C@@H]1C]
00036
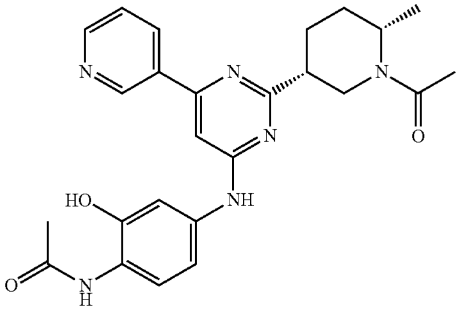 [SMILES: CC(=O)Nc1ccc(Nc2cc(-c3cccnc3)nc([C@@H]3CC[C@H](C)N(C(C)=O)C3)n2)cc1O]
00037
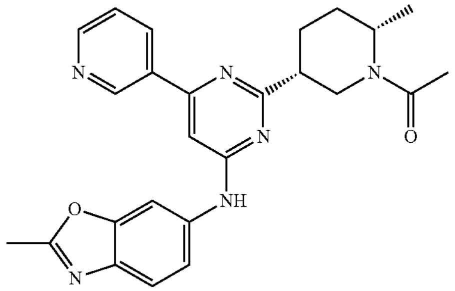 [SMILES: CC(=O)N1C[C@H](c2nc(Nc3ccc4nc(C)oc4c3)cc(-c3cccnc3)n2)CC[C@@H]1C]
00038
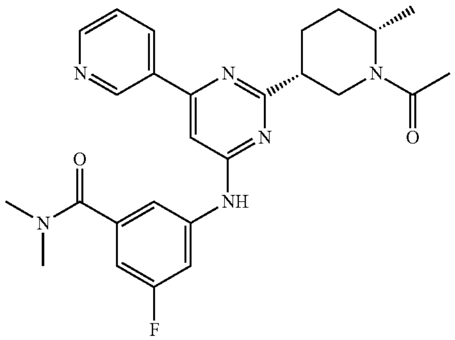 [SMILES: CC(=O)N1C[C@H](c2nc(Nc3cc(F)cc(C(=O)N(C)C)c3)cc(-c3cccnc3)n2)CC[C@@H]1C]
00039
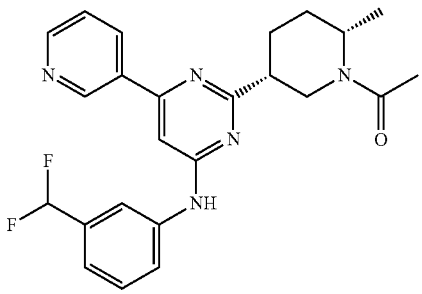 [SMILES: CC(=O)N1C[C@H](c2nc(Nc3cccc(C(F)F)c3)cc(-c3cccnc3)n2)CC[C@@H]1C]
00040
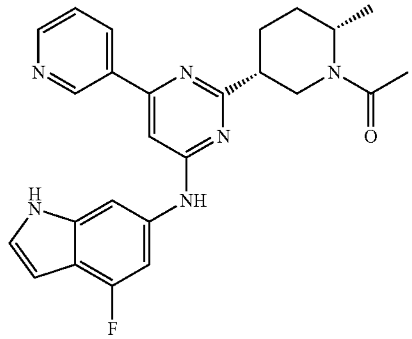 [SMILES: CC(=O)N1C[C@H](c2nc(Nc3cc(F)c4cc[nH]c4c3)cc(-c3cccnc3)n2)CC[C@@H]1C]
00041
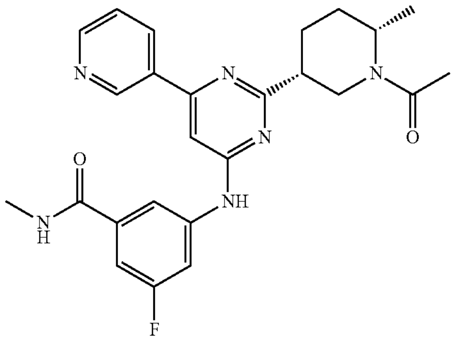

-continued
00042
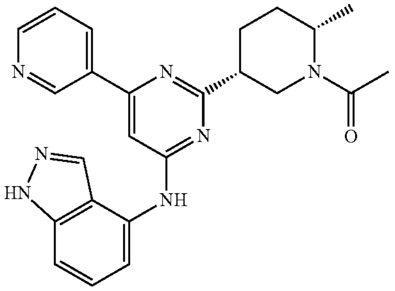 [SMILES: CC(=O)N1C[C@H](c2nc(Nc3cccc4[nH]ncc34)cc(-c3cccnc3)n2)CC[C@@H]1C]
00043
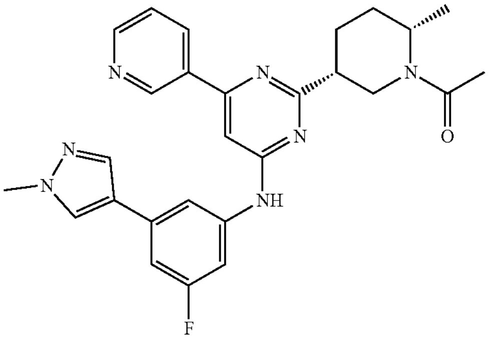 [SMILES: CC(=O)N1C[C@H](c2nc(Nc3cc(F)cc(-c4cnn(C)c4)c3)cc(-c3cccnc3)n2)CC[C@@H]1C]
00044
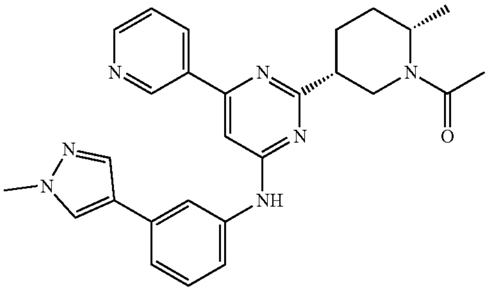 [SMILES: CC(=O)N1C[C@H](c2nc(Nc3cccc(-c4cnn(C)c4)c3)cc(-c3cccnc3)n2)CC[C@@H]1C]
00045
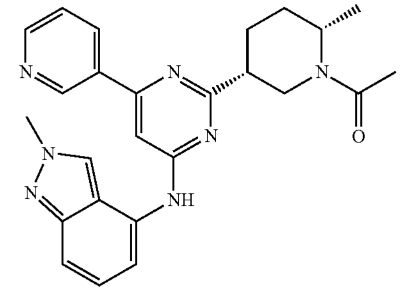 [SMILES: CC(=O)N1C[C@H](c2nc(Nc3cccc4nn(C)cc34)cc(-c3cccnc3)n2)CC[C@@H]1C]
00046
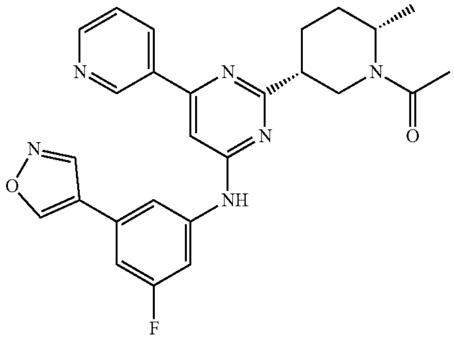 [SMILES: CC(=O)N1C[C@H](c2nc(Nc3cc(F)cc(-c4cnoc4)c3)cc(-c3cccnc3)n2)CC[C@@H]1C]
-continued
00047
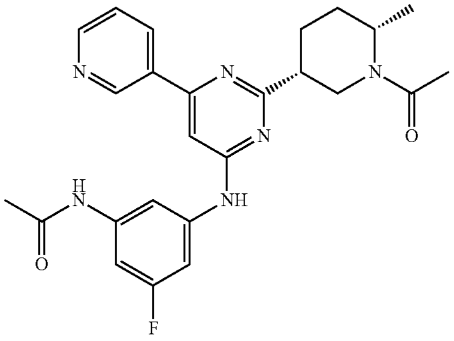 [SMILES: CC(=O)Nc1cc(F)cc(Nc2cc(-c3cccnc3)nc([C@@H]3CC[C@H](C)N(C(C)=O)C3)n2)c1]
00048
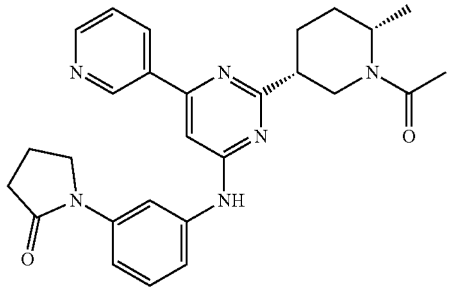 [SMILES: CC(=O)N1C[C@H](c2nc(Nc3cccc(N4CCCC4=O)c3)cc(-c3cccnc3)n2)CC[C@@H]1C]
00049
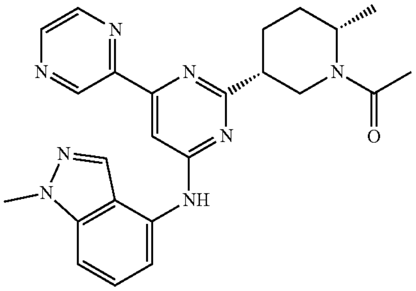 [SMILES: CC(=O)N1C[C@H](c2nc(Nc3cccc4c3cnn4C)cc(-c3cnccn3)n2)CC[C@@H]1C]
00050
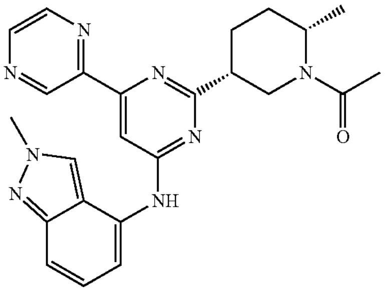
00051
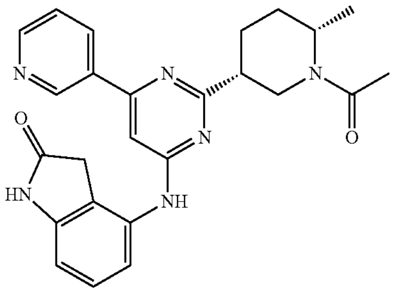 [SMILES: CC(=O)N1C[C@H](c2nc(Nc3cccc4c3CC(=O)N4)cc(-c3cccnc3)n2)CC[C@@H]1C]

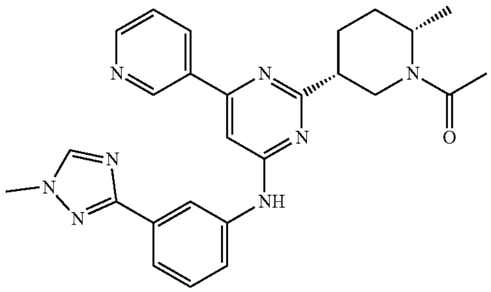 [SMILES: CC(=O)N1C[C@H](c2nc(Nc3cccc(-c4ncn(C)n4)c3)cc(-c3cccnc3)n2)CC[C@@H]1C]
00052
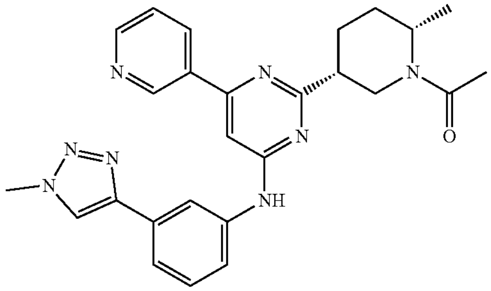
00053
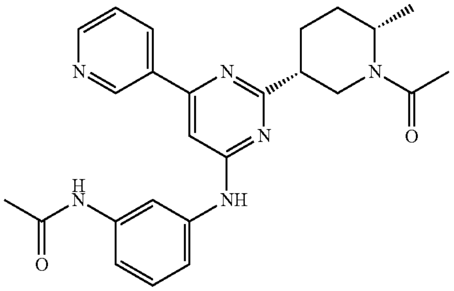 [SMILES: CC(=O)Nc1cccc(Nc2cc(-c3cccnc3)nc([C@@H]3CC[C@H](C)N(C(C)=O)C3)n2)c1]
00054
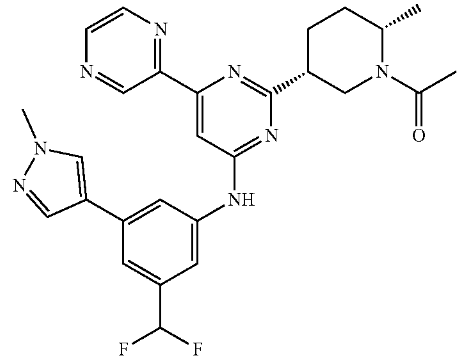 [SMILES: CC(=O)N1C[C@H](c2nc(Nc3cc(-c4cnn(C)c4)cc(C(F)F)c3)cc(-c3cnccn3)n2)CC[C@@H]1C]
00055
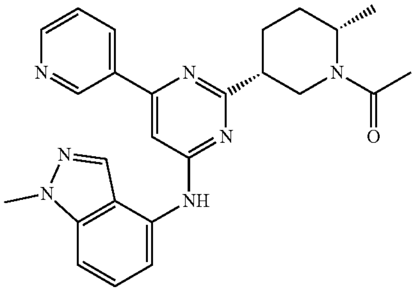 [SMILES: CC(=O)N1C[C@H](c2nc(Nc3cccc4c3cnn4C)cc(-c3cccnc3)n2)CC[C@@H]1C]
00056
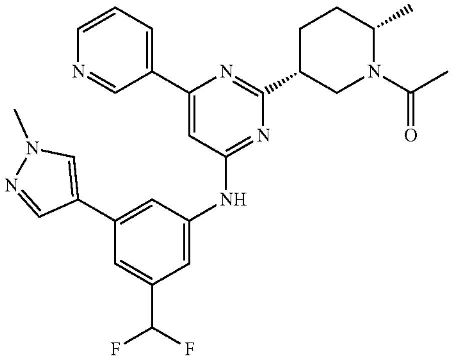 [SMILES: CC(=O)N1C[C@H](c2nc(Nc3cc(-c4cnn(C)c4)cc(C(F)F)c3)cc(-c3cccnc3)n2)CC[C@@H]1C]
00057
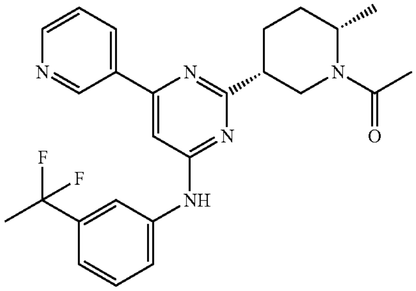 [SMILES: CC(=O)N1C[C@H](c2nc(Nc3cccc(C(C)(F)F)c3)cc(-c3cccnc3)n2)CC[C@@H]1C]
00058
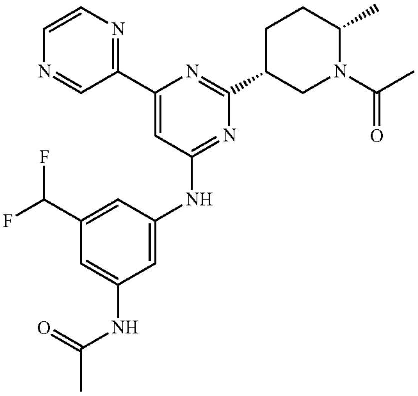 [SMILES: CC(=O)Nc1cc(Nc2cc(-c3cnccn3)nc([C@@H]3CC[C@H](C)N(C(C)=O)C3)n2)cc(C(F)F)c1]
00059
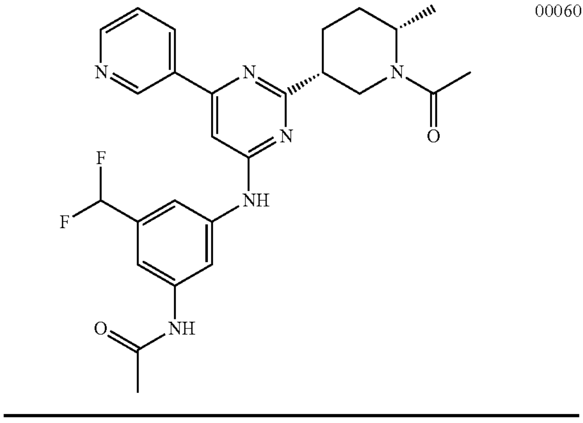
00060

Example 3: Synthesis of 1-((2S,5R)-5-(4-((4-hydroxyphenyl)amino)-6-(pyridin-3-yl)pyrimidin-2-yl)-2-methylpiperidin-1-yl)ethan-1-one (00061)

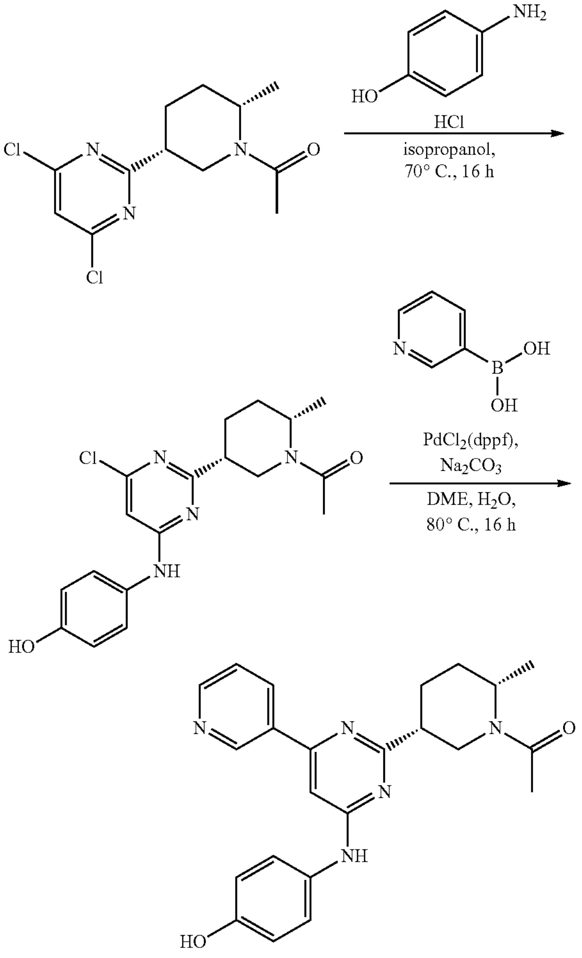

00061

To a solution of 1-((2S,5R)-5-(4,6-dichloropyrimidin-2-yl)-2-methylpiperidin-1-yl)ethan-1-one (Intermediate 2, 50 mg, 0.17 mmol) in 2-propanol (2 mL) was added 4-aminophenol (19.9 mg, 0.18 mmol) and concentrated hydrochloric acid (0.03 mL, 0.35 mmol). The mixture was stirred at 70° C. for 16 hours and concentrated. The residue was redissolved in water, neutralized with saturated aqueous sodium bicarbonate solution and extracted with ethyl acetate three times. The combined organic layers were dried over sodium sulfate and concentrated to afford a solid. The solid was purified with reversed phase chromatography (method A) and lyophilized to afford 1-((2S,5R)-5-(4-chloro-6-((4-hydroxyphenyl)amino)pyrimidin-2-yl)-2-methylpiperidin-1-yl)ethan-1-one (20 mg, 32%) as a white solid. LCMS (Method A): $t_R$ 1.81 min, 100%, MS (ESI) 361.1 (M+H)$^+$. Under nitrogen, 1-((2S,5R)-5-(4-chloro-6-((4-hydroxyphenyl)amino)pyrimidin-2-yl)-2-methylpiperidin-1-yl)ethan-1-one (18.7 mg, 0.05 mmol), pyridine-3-boronic acid (24 mg, 0.20 mmol), sodium carbonate (22 mg, 0.20 mmol) and PdCl$_2$(dppf) (8.4 mg, 11 μmol) were dissolved in a mixture of 1,2-dimethoxyethane (3 mL) and water (1 mL). The mixture was stirred at 80° C. for 16 hours. The mixture was filtered through a short C18-column plug, was purified with reversed phase chromatography (method A) and lyophilized to afford a white solid with 82% de. The product was further purified by chiral preparative SFC (Method A) and lyophilized to afford 1-((2S,5R)-5-(4-((4-hydroxyphenyl)amino)-6-(pyridin-3-yl)pyrimidin-2-yl)-2-methylpiperidin-1-yl)ethan-1-one (5.6 mg, 27%) as a white solid. LCMS (Method B): $t_R$ 2.48 min, 100%, MS (ESI) 404.1 (M+H)$^+$; Chiral SFC (Method C): $t_R$ 5.39 min, >95% ee and de.

The compounds (00062) to (00070) (as depicted below in Table 1) were prepared following procedures analogous to Example 3, using the appropriate starting materials.

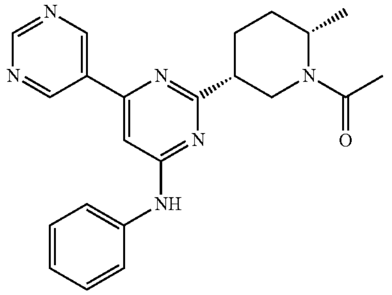 [SMILES: CC(=O)N1C[C@H](c2nc(Nc3ccccc3)cc(-c3cncnc3)n2)CC[C@@H]1C]

00062

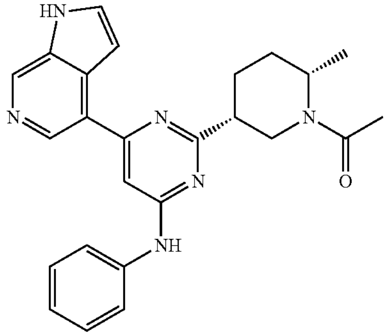 [SMILES: CC(=O)N1C[C@H](c2nc(Nc3ccccc3)cc(-c3cncc4[nH]ccc34)n2)CC[C@@H]1C]

00063

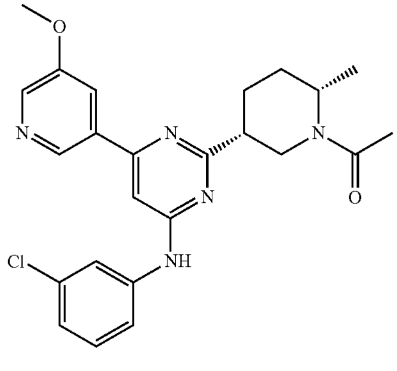 [SMILES: COc1cncc(-c2cc(Nc3cccc(Cl)c3)nc([C@@H]3CC[C@H](C)N(C(C)=O)C3)n2)c1]

00064

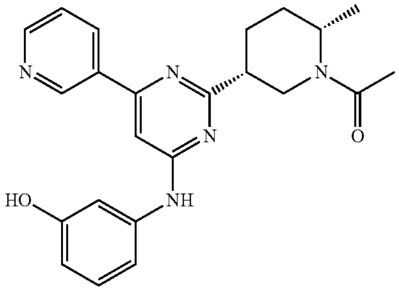 [SMILES: CC(=O)N1C[C@H](c2nc(Nc3cccc(O)c3)cc(-c3cccnc3)n2)CC[C@@H]1C]

00065

-continued

00066

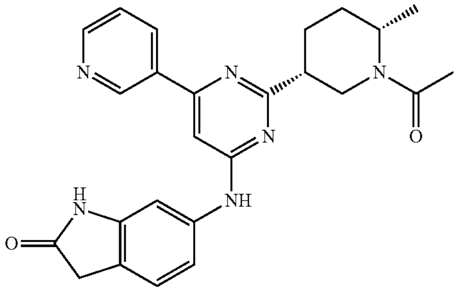 [SMILES: CC(=O)N1C[C@H](c2nc(Nc3ccc4c(c3)NC(=O)C4)cc(-c3cccnc3)n2)CC[C@@H]1C]

00067

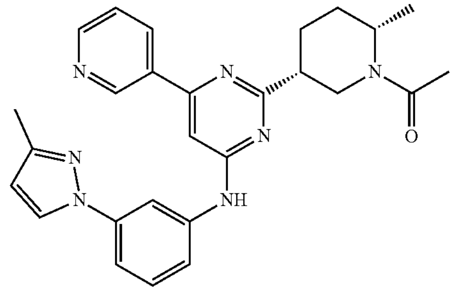 [SMILES: CC(=O)N1C[C@H](c2nc(Nc3cccc(-n4ccc(C)n4)c3)cc(-c3cccnc3)n2)CC[C@@H]1C]

00068

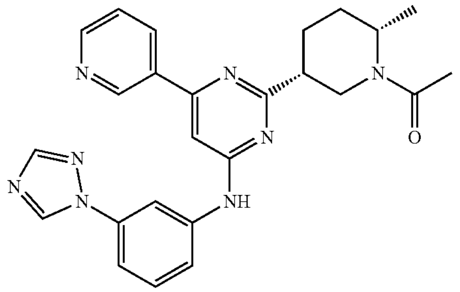 [SMILES: CC(=O)N1C[C@H](c2nc(Nc3cccc(-n4cncn4)c3)cc(-c3cccnc3)n2)CC[C@@H]1C]

00069

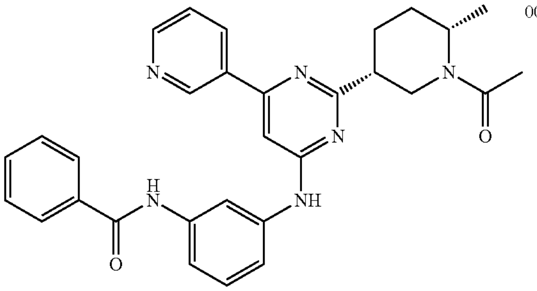

00070

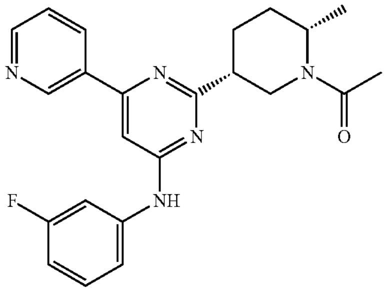 [SMILES: CC(=O)N1C[C@H](c2nc(Nc3cccc(F)c3)cc(-c3cccnc3)n2)CC[C@@H]1C]

Example 4: Synthesis of 1-((2S,5R)-2-methyl-5-(4-((2-methylpyridin-4-yl)amino)-6-(pyridin-3-yl)pyrimidin-2-yl)piperidin-1-yl)ethan-1-one (00071)

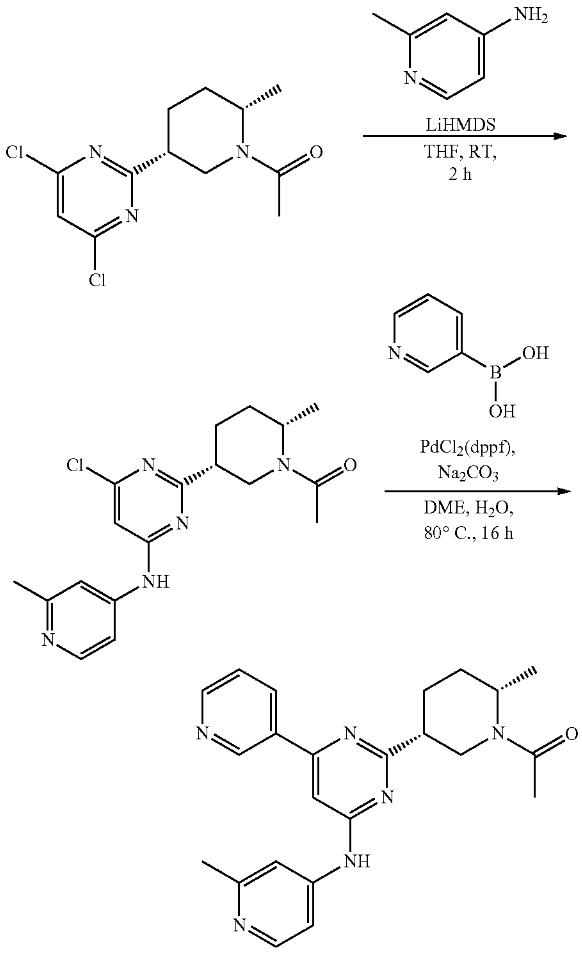

00071

To a solution of 2-methylpyridin-4-amine (3.19 g, 29.5 mmol) in dry tetrahydrofuran (100 mL) was added 1M lithium bis(trimethylsilyl)amide in tetrahydrofuran (29.5 mL, 29.5 mmol) and the mixture was stirred for 10 minutes. Next, 1-((2S,5R)-5-(4,6-dichloropyrimidin-2-yl)-2-methylpiperidin-1-yl)ethan-1-one (Intermediate 2, 850 mg, 2.95 mmol) in dry tetrahydrofuran (100 mL) was added over 10 minutes and the mixture was stirred at room temperature for 2 hours. The mixture was poured into saturated ammonium chloride solution and was extracted with ethyl acetate twice. The combined organic layers were washed with brine once, dried over sodium sulfate and concentrated to afford a brown oil. The oil was purified with silica column chromatography (80% to 100% ethyl acetate in n-heptane followed by 0% to 10% methanol in dichloromethane) to afford 1-((2S,5R)-5-(4-chloro-6-((2-methylpyridin-4-yl)amino)pyrimidin-2-yl)-2-methylpiperidin-1-yl)ethan-1-one (275 mg 25%) as a yellow oil. LCMS (Method A): $t_R$ 1.49 min, 100%, MS (ESI) 360.1 $(M+H)^+$. Under nitrogen, 1-((2S,5R)-5-(4-chloro-6-((2-methylpyridin-4-yl)amino)pyrimidin-2-yl)-2-methylpiperidin-1-yl)ethan-1-one (275 mg, 0.76 mmol), sodium carbonate (162 mg, 1.53 mmol), pyridine-3-boronic acid (188 mg, 1.53 mmol) and $PdCl_2(dppf)-CH_2Cl_2$ adduct (62.4 mg, 0.08 mmol) were dissolved in a mixture of 1,2-dimethoxyethane (6 mL) and water (2 mL). The mixture was heated to 80° C. for 1 hour, filtered through a C18-plug and concentrated to afford a dark residue. The residue was purified with reversed phase chromatography (method B) and lyophilized to afford a light yellow solid. The product was further purified by chiral preparative SFC (Method B) and lyophilized to afford 1-((2S,5R)-2-methyl-5-(4-((2-methylpyridin-4-yl)amino)-6-(pyridin-3-yl)pyrimidin-2-yl)piperidin-1-yl)ethan-1-one (135 mg, 41%) as beige solid. LCMS (Method D): $t_R$ 3.06 min, 100%, MS (ESI) 403.2 $(M+H)^+$; Chiral SFC (Method B): $t_R$ 3.60 min, >95% ee and de.

The compounds (00072) to (00094) (as depicted below in Table 1) were prepared following procedures analogous to Example 4, using the appropriate starting materials.

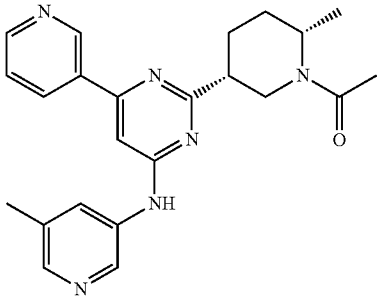 [SMILES: CC(=O)N1C[C@H](c2nc(Nc3cncc(C)c3)cc(-c3cccnc3)n2)CC[C@@H]1C]
00072

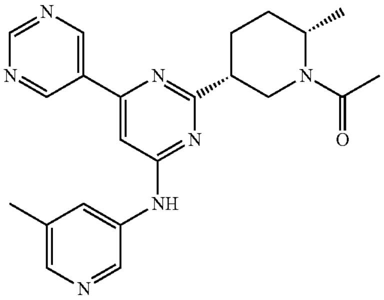 [SMILES: CC(=O)N1C[C@H](c2nc(Nc3cncc(C)c3)cc(-c3cncnc3)n2)CC[C@@H]1C]
00073

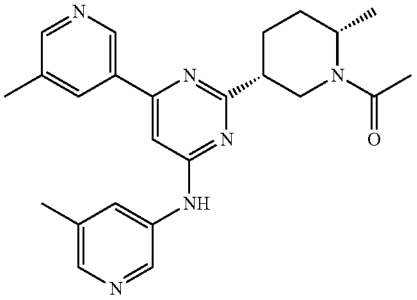 [SMILES: CC(=O)N1C[C@H](c2nc(Nc3cncc(C)c3)cc(-c3cncc(C)c3)n2)CC[C@@H]1C]
00074

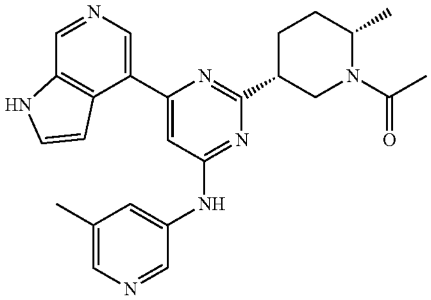 [SMILES: CC(=O)N1C[C@H](c2nc(Nc3cncc(C)c3)cc(-c3cncc4[nH]ccc34)n2)CC[C@@H]1C]
00075

-continued

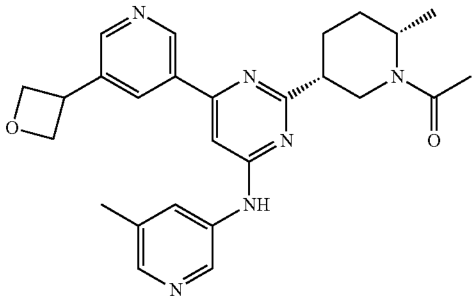 [SMILES: CC(=O)N1C[C@H](c2nc(Nc3cncc(C)c3)cc(-c3cncc(C4COC4)c3)n2)CC[C@@H]1C]
00076

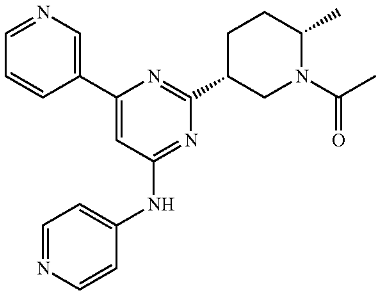 [SMILES: CC(=O)N1C[C@H](c2nc(Nc3ccncc3)cc(-c3cccnc3)n2)CC[C@@H]1C]
00077

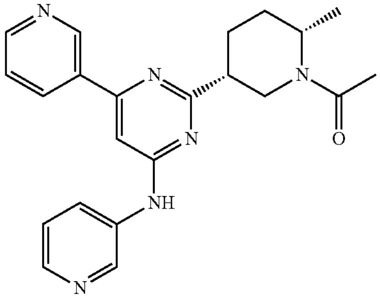 [SMILES: CC(=O)N1C[C@H](c2nc(Nc3cccnc3)cc(-c3cccnc3)n2)CC[C@@H]1C]
00078

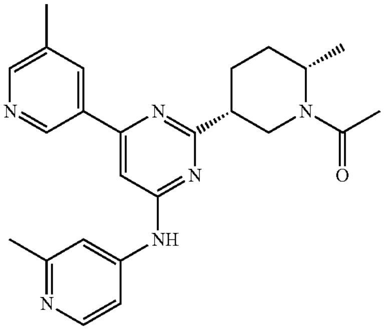 [SMILES: CC(=O)N1C[C@H](c2nc(Nc3ccnc(C)c3)cc(-c3cncc(C)c3)n2)CC[C@@H]1C]
00079

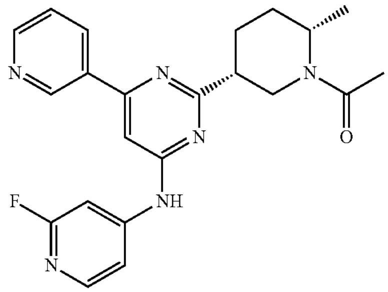 [SMILES: CC(=O)N1C[C@H](c2nc(Nc3ccnc(F)c3)cc(-c3cccnc3)n2)CC[C@@H]1C]
00080

00081
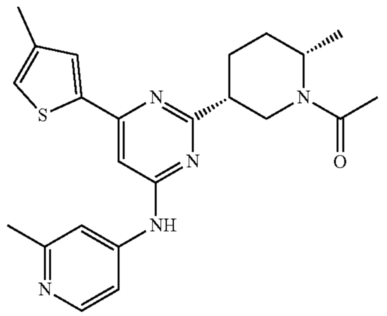 [SMILES: CC(=O)N1C[C@H](c2nc(Nc3ccnc(C)c3)cc(-c3cc(C)cs3)n2)CC[C@@H]1C]
00082
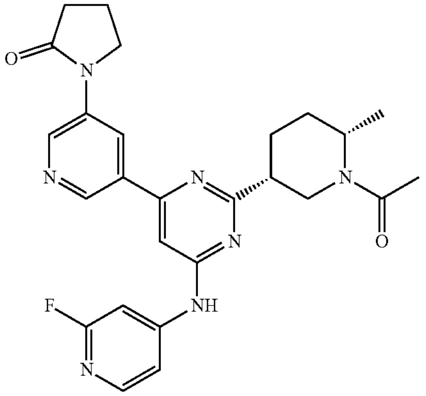 [SMILES: CC(=O)N1C[C@H](c2nc(Nc3ccnc(F)c3)cc(-c3cncc(N4CCCC4=O)c3)n2)CC[C@@H]1C]
00083
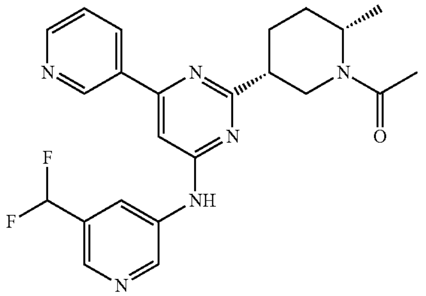
00084
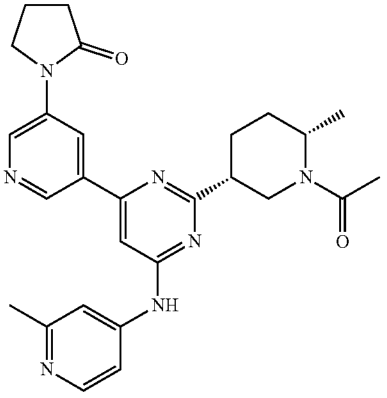 [SMILES: CC(=O)N1C[C@H](c2nc(Nc3ccnc(C)c3)cc(-c3cncc(N4CCCC4=O)c3)n2)CC[C@@H]1C]
00085
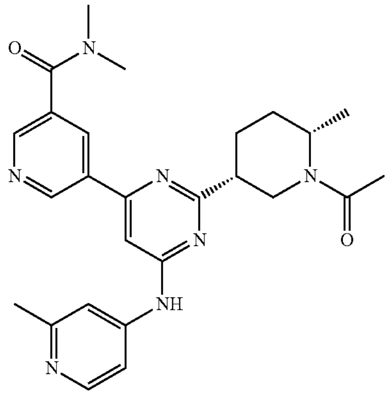 [SMILES: CC(=O)N1C[C@H](c2nc(Nc3ccnc(C)c3)cc(-c3cncc(C(=O)N(C)C)c3)n2)CC[C@@H]1C]
00086
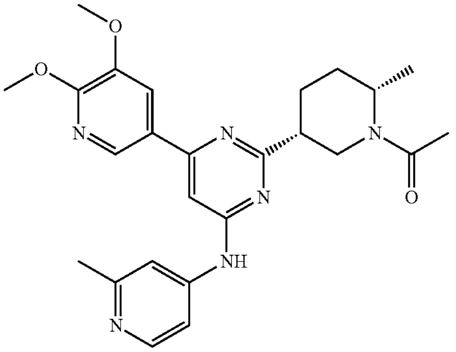 [SMILES: COc1cc(-c2cc(Nc3ccnc(C)c3)nc([C@@H]3CC[C@H](C)N(C(C)=O)C3)n2)cnc1OC]
00087
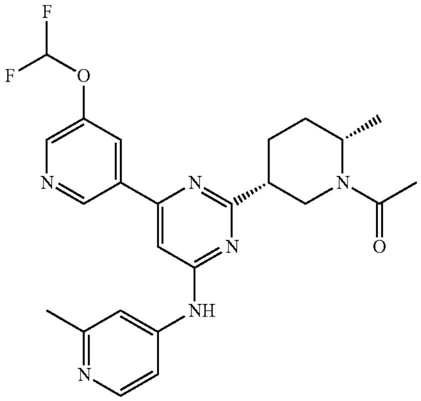 [SMILES: CC(=O)N1C[C@H](c2nc(Nc3ccnc(C)c3)cc(-c3cncc(OC(F)F)c3)n2)CC[C@@H]1C]
00088
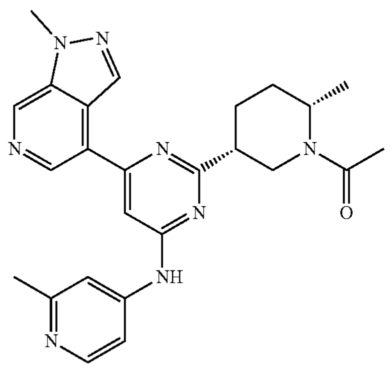 [SMILES: CC(=O)N1C[C@H](c2nc(Nc3ccnc(C)c3)cc(-c3cncc4c3cnn4C)n2)CC[C@@H]1C]

-continued
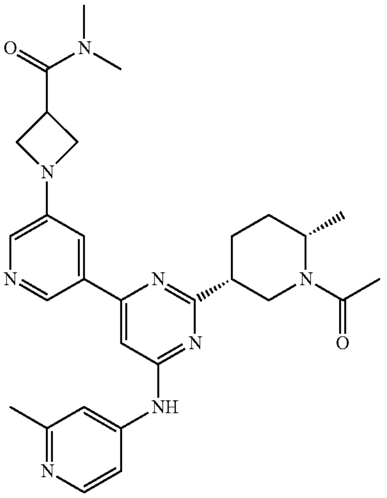 [SMILES: CC(=O)N1C[C@H](c2nc(Nc3ccnc(C)c3)cc(-c3cncc(N4CC(C(=O)N(C)C)C4)c3)n2)CC[C@@H]1C]
00089
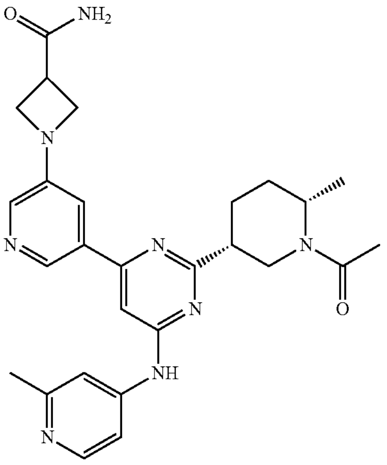 [SMILES: CC(=O)N1C[C@H](c2nc(Nc3ccnc(C)c3)cc(-c3cncc(N4CC(C(N)=O)C4)c3)n2)CC[C@@H]1C]
00090
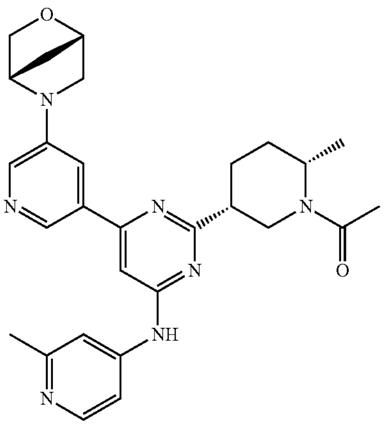 [SMILES: CC(=O)N1C[C@H](c2nc(Nc3ccnc(C)c3)cc(-c3cncc(N4C[C@@H]5C[C@H]4CO5)c3)n2)CC[C@@H]1C]
00091
-continued
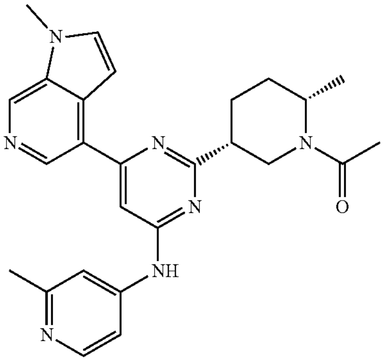 [SMILES: CC(=O)N1C[C@H](c2nc(Nc3ccnc(C)c3)cc(-c3cncc4c3ccn4C)n2)CC[C@@H]1C]
00092
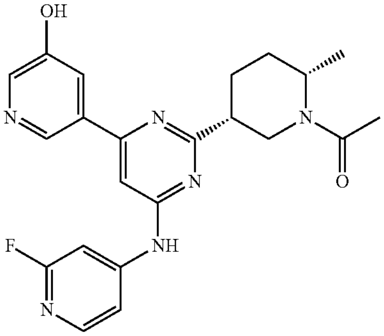 [SMILES: CC(=O)N1C[C@H](c2nc(Nc3ccnc(F)c3)cc(-c3cncc(O)c3)n2)CC[C@@H]1C]
00093
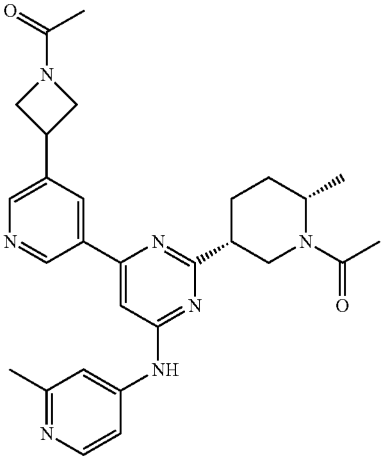 [SMILES: CC(=O)N1CC(c2cncc(-c3cc(Nc4ccnc(C)c4)nc([C@@H]4CC[C@H](C)N(C(C)=O)C4)n3)c2)C1]
00094
Example 5: Synthesis of 1-((2S,5R)-2-methyl-5-(4-(pyridin-3-yl)-6-(quinoxalin-6-ylamino)pyrimidin-2-yl)piperidin-1-yl)ethan-1-one (00095)
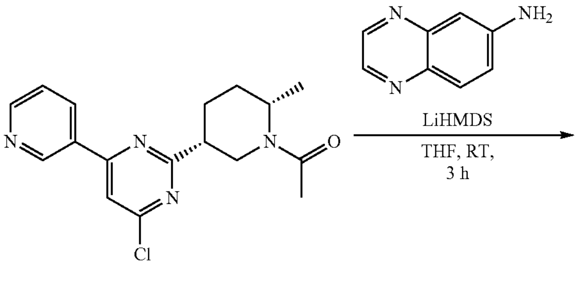

-continued

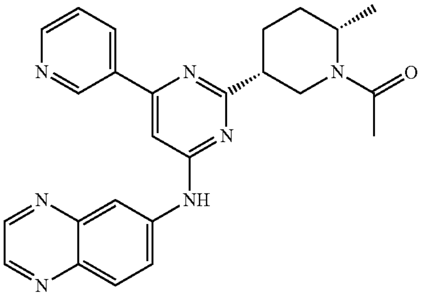

00095

To a solution of quinoxalin-6-amine (26.3 mg, 0.18 mmol) in tetrahydrofuran (2 mL) was added 1M lithium bis(trimethylsilyl)amide in tetrahydrofuran (0.18 ml, 0.18 mmol). Next, 1-((2S,5R)-5-(4-chloro-6-(pyridin-3-yl)pyrimidin-2-yl)-2-methylpiperidin-1-yl)ethan-1-one (30 mg, 0.09 mmol, prepared under Example 2) was added and the mixture was stirred at room temperature for 3 hours. The mixture was diluted with water (2 mL) and concentrated to afford a dark brown residue. The residue was purified with reversed phase chromatography (method B) followed by reversed phase chromatography (method A) and lyophilized to afford 1-((2S,5R)-2-methyl-5-(4-(pyridin-3-yl)-6-(quinoxalin-6-ylamino)pyrimidin-2-yl)piperidin-1-yl)ethan-1-one (5 mg, 12%) as a yellow solid. LCMS (Method B): $t_R$ 2.79 min, 100%, MS (ESI) 440.1 $(M+H)^+$.

The compounds (00096) to (00100) (as depicted below in Table 1) were prepared following procedures analogous to Example 5, using the appropriate starting materials.

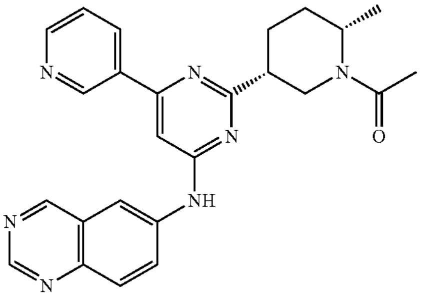 [SMILES: CC(=O)N1C[C@H](c2nc(Nc3ccc4ncncc4c3)cc(-c3cccnc3)n2)CC[C@@H]1C]

00096

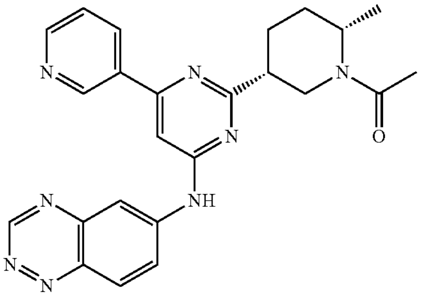 [SMILES: CC(=O)N1C[C@H](c2nc(Nc3ccc4nncnc4c3)cc(-c3cccnc3)n2)CC[C@@H]1C]

00097

-continued

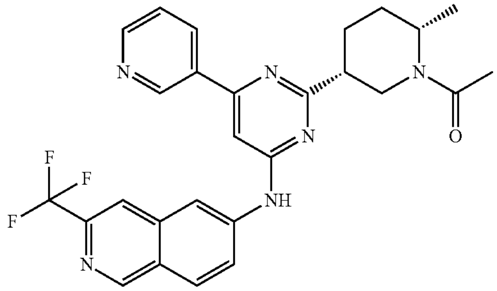 [SMILES: CC(=O)N1C[C@H](c2nc(Nc3ccc4cnc(C(F)(F)F)cc4c3)cc(-c3cccnc3)n2)CC[C@@H]1C]

00098

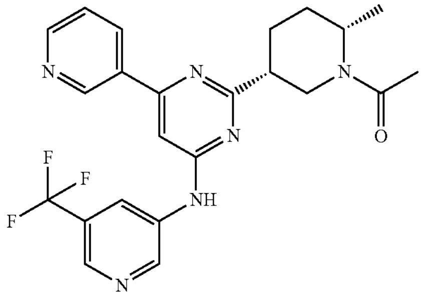 [SMILES: CC(=O)N1C[C@H](c2nc(Nc3cncc(C(F)(F)F)c3)cc(-c3cccnc3)n2)CC[C@@H]1C]

00099

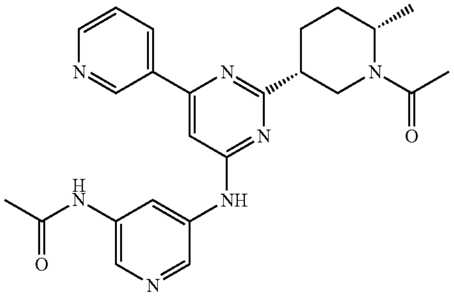 [SMILES: CC(=O)Nc1cncc(Nc2cc(-c3cccnc3)nc([C@@H]3CC[C@H](C)N(C(C)=O)C3)n2)c1]

00100

Example 6: Synthesis of 1-((2S,5R)-2-methyl-5-(4-((2-methylpyridin-4-yl)amino)-6-(pyrazin-2-yl)pyrimidin-2-yl)piperidin-1-yl)ethan-1-one (00101)

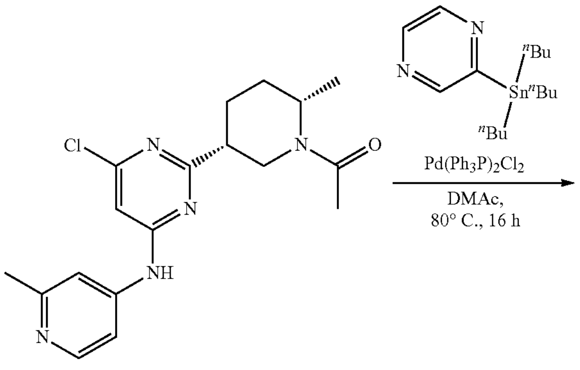

-continued

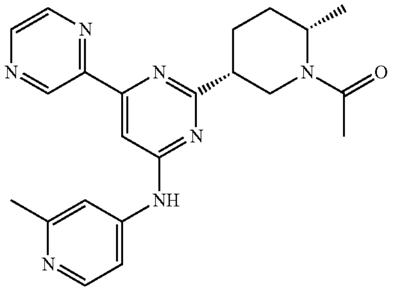

00101

Under nitrogen, 1-((2S,5R)-5-(4-chloro-6-((2-methylpyridin-4-yl)amino)pyrimidin-2-yl)-2-methylpiperidin-1-yl)ethan-1-one (75 mg, 0.21 mmol, prepared under Example 4), 2-tributylstannylpyrazine (154 mg, 0.42 mmol) and bis(triphenylphosphine)palladium(II) chloride (14.63 mg, 0.02 mmol) in N,N-dimethylacetamide (3 mL) were heated to 80° C. for 16 hours. The mixture was cooled to room temperature and eluted through a C18-plug with acetonitrile. The filtrate was purified with reversed phase chromatography (method B) and preparative SFC (method B) to afford 1-((2S,5R)-2-methyl-5-(4-((2-methylpyridin-4-yl)amino)-6-(pyrazin-2-yl)pyrimidin-2-yl)piperidin-1-yl)ethan-1-one (24 mg, 28%) as a white solid. LCMS (Method D): $t_R$3.08 min, 100%, MS (ESI) 404.2 $(M+H)^+$; Chiral SFC (Method B): $t_R$ 3.77 min, >95% ee and de.

The compounds (00102) to (00105) (as depicted below in Table 1) were prepared following procedures analogous to Example 6, using the appropriate starting materials.

00102

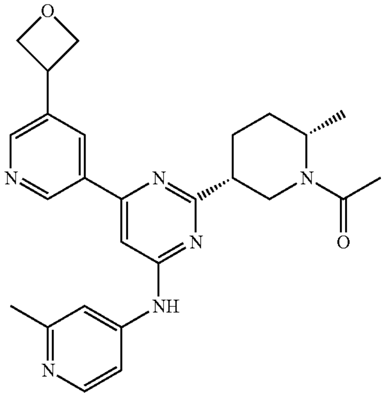 [SMILES: CC(=O)N1C[C@H](c2nc(Nc3ccnc(C)c3)cc(-c3cncc(C4COC4)c3)n2)CC[C@@H]1C]

00103

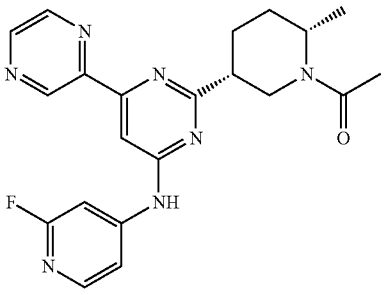 [SMILES: CC(=O)N1C[C@H](c2nc(Nc3ccnc(F)c3)cc(-c3cnccn3)n2)CC[C@@H]1C]

-continued

00104

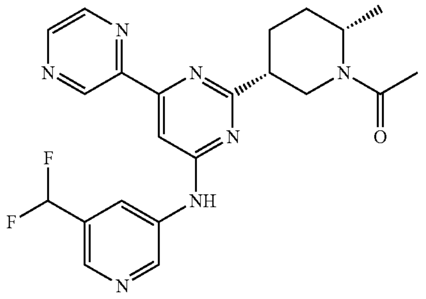 [SMILES: CC(=O)N1C[C@H](c2nc(Nc3cncc(C(F)F)c3)cc(-c3cnccn3)n2)CC[C@@H]1C]

00105

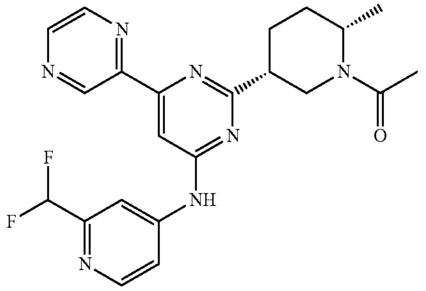 [SMILES: CC(=O)N1C[C@H](c2nc(Nc3ccnc(C(F)F)c3)cc(-c3cnccn3)n2)CC[C@@H]1C]

Example 7: Synthesis of 1-((2S,5R)-2-methyl-5-(4-(6-methylpyrazin-2-yl)-6-((2-methylpyridin-4-yl)amino)pyrimidin-2-yl)piperidin-1-yl)ethan-1-one (00106)

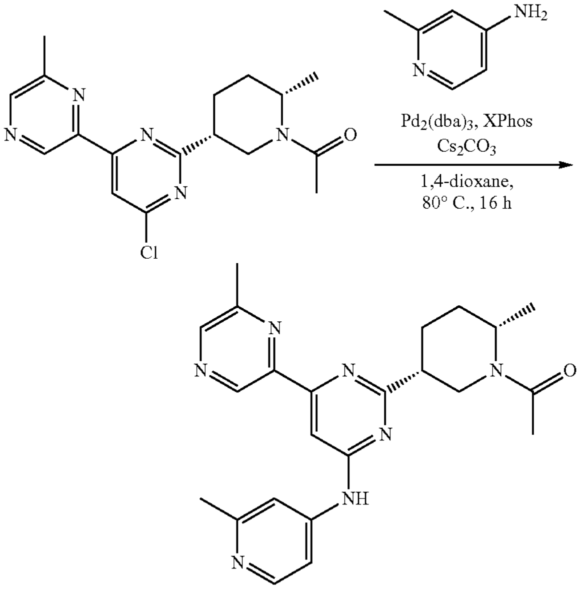

00106

Under argon, 2-methylpyridin-4-amine (188 mg, 1.74 mmol), 1-((2S,5R)-5-(4-chloro-6-(6-methylpyrazin-2-yl)pyrimidin-2-yl)-2-methylpiperidin1-yl)ethan-1-one (200 mg, 0.58 mmol, prepared analogous to Example 2), $Pd_2(dba)_3$ (26.5 mg, 0.03 mmol), XPhos (27.6 mg, 0.06 mmol) and cesium carbonate (659 mg, 2.02 mmol) in 1,4-dioxane (15 mL) was heated to 80° C. for 16 hours. The mixture was poured into water and extracted with ethyl acetate twice. The combined organic layers were washed with brine, dried over sodium sulfate and concentrated to afford a gum. The gum was purified with reversed phase chromatography (method A) followed by reversed phase chromatography (method B) and lyophilized to afford 1-((2S,5R)-2-methyl-5-(4-(6-methylpyrazin-2-yl)-6-((2-methylpyridin-4-yl)amino)pyrimidin-2-yl)piperidin-1-yl)ethan-1-one (20 mg, 16%) as a white solid. LCMS (Method D): $t_R$ 3.19 min, 100%, MS (ESI) 418.2 $(M+H)^+$.

The compounds (00107) to (00121) (as depicted below in Table 1) were prepared following procedures analogous to Example 7 using the appropriate starting materials.

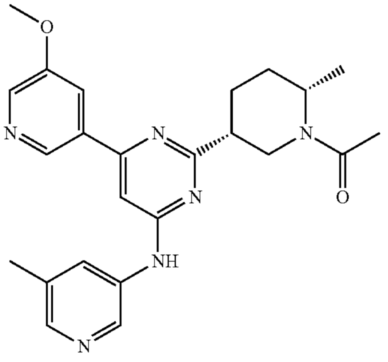 [SMILES: COc1cncc(-c2cc(Nc3cncc(C)c3)nc([C@@H]3CC[C@H](C)N(C(C)=O)C3)n2)c1]

00107

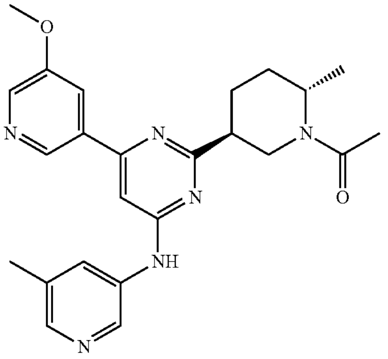 [SMILES: COc1cncc(-c2cc(Nc3cncc(C)c3)nc([C@H]3CC[C@H](C)N(C(C)=O)C3)n2)c1]

00108

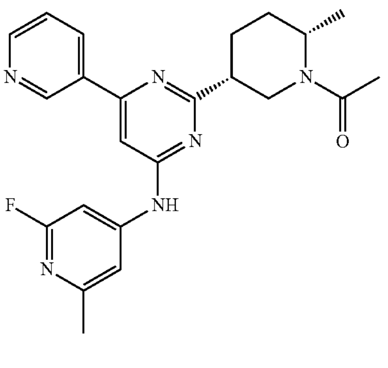 [SMILES: CC(=O)N1C[C@H](c2nc(Nc3cc(C)nc(F)c3)cc(-c3cccnc3)n2)CC[C@@H]1C]

00109

-continued

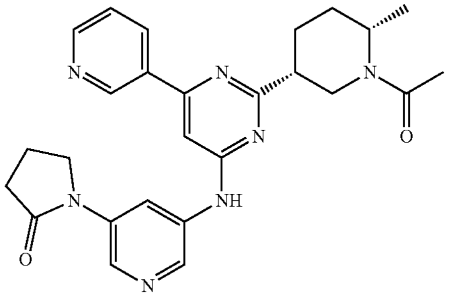 [SMILES: CC(=O)N1C[C@H](c2nc(Nc3cncc(N4CCCC4=O)c3)cc(-c3cccnc3)n2)CC[C@@H]1C]

00110

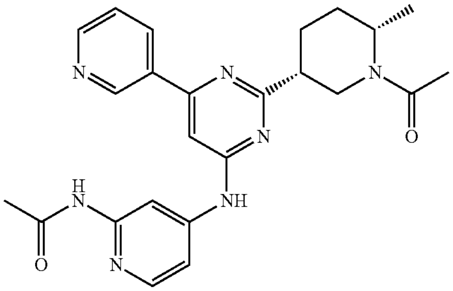 [SMILES: CC(=O)Nc1cc(Nc2cc(-c3cccnc3)nc([C@@H]3CC[C@H](C)N(C(C)=O)C3)n2)ccn1]

00111

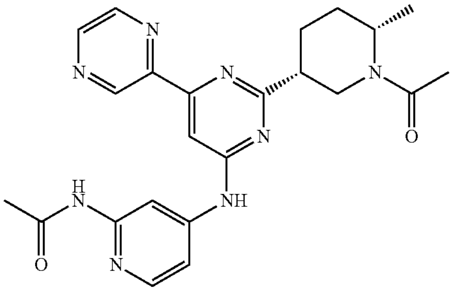 [SMILES: CC(=O)Nc1cc(Nc2cc(-c3cnccn3)nc([C@@H]3CC[C@H](C)N(C(C)=O)C3)n2)ccn1]

00112

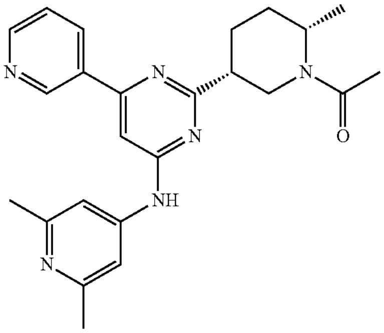 [SMILES: CC(=O)N1C[C@H](c2nc(Nc3cc(C)nc(C)c3)cc(-c3cccnc3)n2)CC[C@@H]1C]

00113

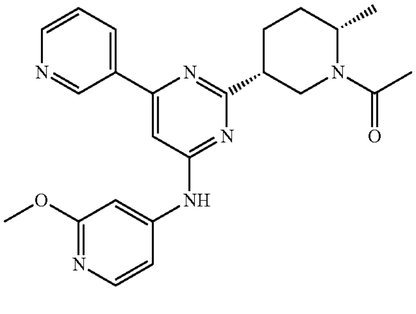 [SMILES: COc1cc(Nc2cc(-c3cccnc3)nc([C@@H]3CC[C@H](C)N(C(C)=O)C3)n2)ccn1]

00114

-continued
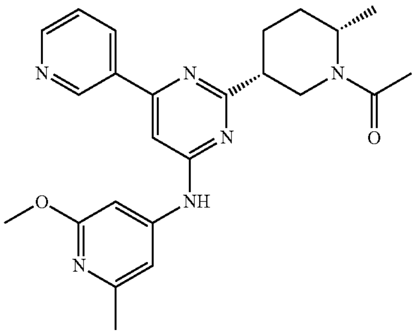 [SMILES: COc1cc(Nc2cc(-c3cccnc3)nc([C@@H]3CC[C@H](C)N(C(C)=O)C3)n2)cc(C)n1]
00115
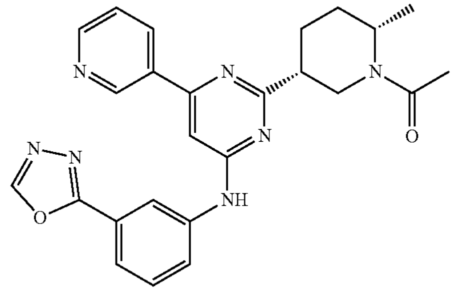 [SMILES: CC(=O)N1C[C@H](c2nc(Nc3cccc(-c4nnco4)c3)cc(-c3cccnc3)n2)CC[C@@H]1C]
00116
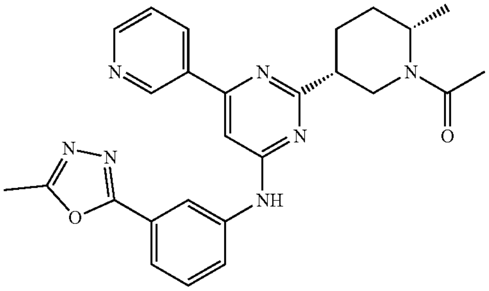 [SMILES: CC(=O)N1C[C@H](c2nc(Nc3cccc(-c4nnc(C)o4)c3)cc(-c3cccnc3)n2)CC[C@@H]1C]
00117
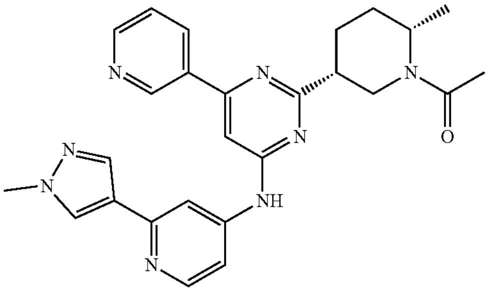 [SMILES: CC(=O)N1C[C@H](c2nc(Nc3ccnc(-c4cnn(C)c4)c3)cc(-c3cccnc3)n2)CC[C@@H]1C]
00118
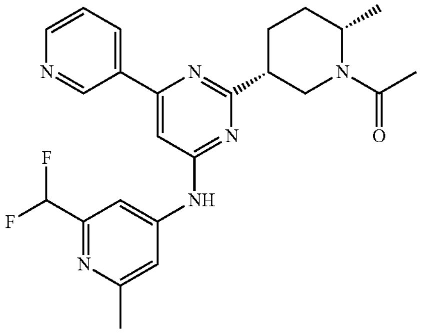 [SMILES: CC(=O)N1C[C@H](c2nc(Nc3cc(C)nc(C(F)F)c3)cc(-c3cccnc3)n2)CC[C@@H]1C]
00119
-continued
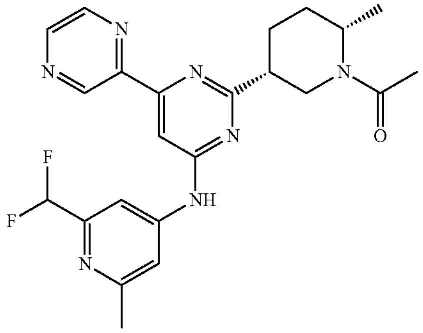 [SMILES: CC(=O)N1C[C@H](c2nc(Nc3cc(C)nc(C(F)F)c3)cc(-c3cnccn3)n2)CC[C@@H]1C]
00120
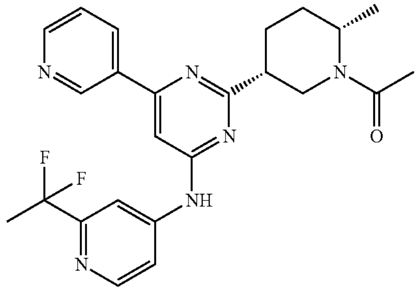 [SMILES: CC(=O)N1C[C@H](c2nc(Nc3ccnc(C(C)(F)F)c3)cc(-c3cccnc3)n2)CC[C@@H]1C]
00121
Example 8: Synthesis of 1-((2S,5R)-5-(4-((2-(1-cyclopropyl-1H-pyrazol-4-yl)pyridin-4-yl)amino)-6-(pyridin-3-yl)pyrimidin-2-yl)-2-methylpiperidin-1-yl)ethan-1-one (00122)
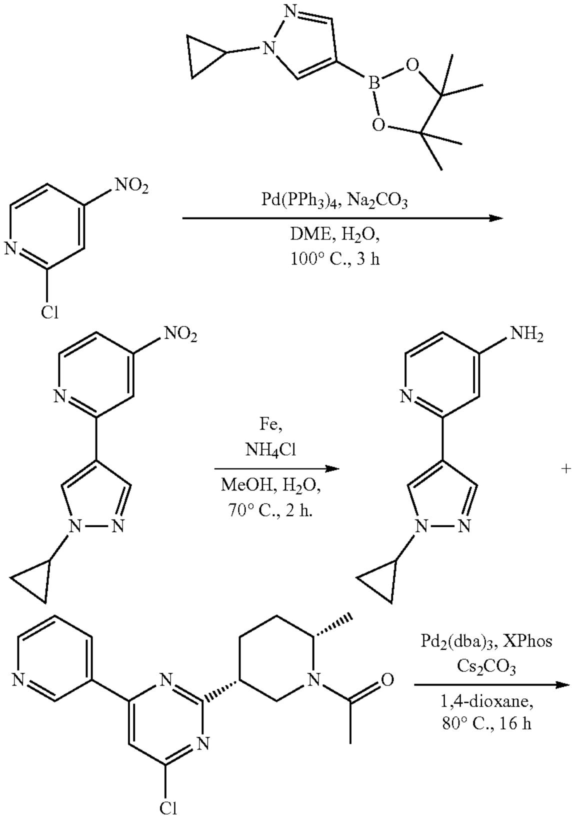

-continued

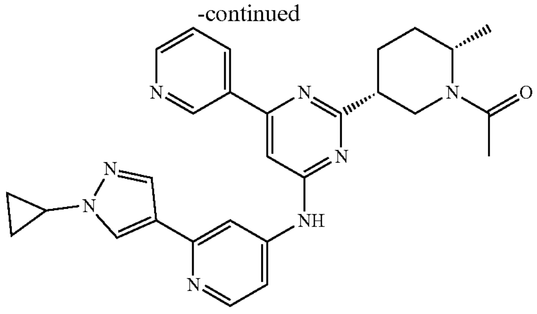

00122

Under argon, 2-chloro-4-nitropyridine (150 mg, 0.95 mmol), 1-cyclopropyl-4-(4,4,5,5-tetramethyl-1,3,2-dioxaborolan-2-yl)-1H-pyrazole (244 mg, 1.04 mmol), tetrakis (triphenyl phosphine)palladium(0) (54.7 mg, 0.05 mmol) and sodium carbonate (201 mg, 1.89 mmol) in 1,2-dimethoxyethane (6.5 mL) and water (1.63 mL) was heated to 100° C. for 3 hours. The mixture was diluted with ethyl acetate and water. The layers were separated and the aqueous layer was extracted with ethyl acetate twice. The combined organic layers were washed with water followed by brine, dried over sodium sulfate and concentrated to afford a brown solid. The solid was purified by column chromatography (5% to 40% ethyl acetate in n-heptane) to afford 2-(1-cyclopropyl-1H-pyrazol-4-yl)-4-nitropyridine (190 mg, 0.83 mmol, 87%) as a yellow solid. LCMS (Method C): $t_R$ 1.79 min, 100%, MS (ESI) 231.1 $(M+H)^+$. To a suspension of 2-(1-cyclopropyl-1H-pyrazol-4-yl)-4-nitropyridine (190 mg, 0.83 mmol) in methanol (4 mL), was added iron (230 mg, 4.13 mmol) and ammonium chloride (221 mg, 4.13 mmol) followed by water (12 mL). The mixture was heated to 70° C. for 2 hours. The mixture was cooled to room temperature and partitioned between ethyl acetate and a mixture of water and brine (1:1). The layers were separated and the aqueous layer was extracted with ethyl acetate three times. The combined organic layers were dried over sodium sulfate and concentrated to afford 2-(1-cyclopropyl-1H-pyrazol-4-yl)pyridin-4-amine (148 mg, 0.74 mmol, 90%) as a light yellow oil. LCMS (Method C): $t_R$ 1.44 min, 98%, MS (ESI) 201.1 $(M+H)^+$. A solution of 1-((2S,5R)-5-(4-chloro-6-(pyridin-3-yl)pyrimidin-2-yl)-2-methylpiperidin-1-yl) ethan-1-one (75 mg, 0.23 mmol, prepared under Example 2), 2-(1-cyclopropyl-1H-pyrazol-4-yl)pyridin-4-amine (55 mg, 0.27 mmol), $Pd_2(dba)_3$ (10 mg, 0.01 mmol), XPhos (11 mg, 0.02 mmol) and cesium carbonate (148 mg, 0.45 mmol) in 1,4-dioxane (3 mL) was heated to 90° C. and stirred for 16 hours. The mixture was filtered through Celite and rinsed with ethyl acetate and methanol (1:1). The filtrate was concentrated, purified with reversed phase chromatography (method B) followed by prep-SFC (method B) to afford 1-((2S,5R)-5-(4-((2-(1-cyclopropyl-1H-pyrazol-4-yl)pyridin-4-yl)amino)-6-(pyridin-3-yl)pyrimidin-2-yl)-2-methylpiperidin-1-yl)ethan-1-one (13 mg, 0.03 mmol, 12%) as a white solid. LCMS (Method D): $t_R$ 3.17 min, 100%, MS (ESI) 495.2 $(M+H)^+$ The compounds (00123) to (00125) (as depicted below in Table 1) were prepared following procedures analogous to Example 8 using the appropriate starting materials.

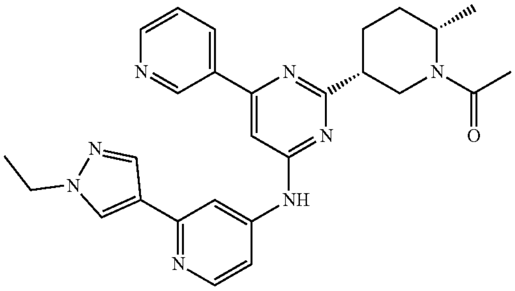 [SMILES: CCn1cc(-c2cc(Nc3cc(-c4cccnc4)nc([C@@H]4CC[C@H](C)N(C(C)=O)C4)n3)ccn2)cn1]

00123

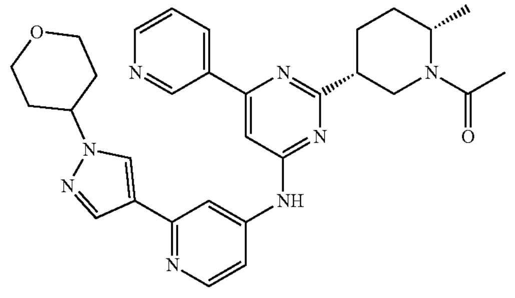 [SMILES: CC(=O)N1C[C@H](c2nc(Nc3ccnc(-c4cnn(C5CCOCC5)c4)c3)cc(-c3cccnc3)n2)CC[C@@H]1C]

00124

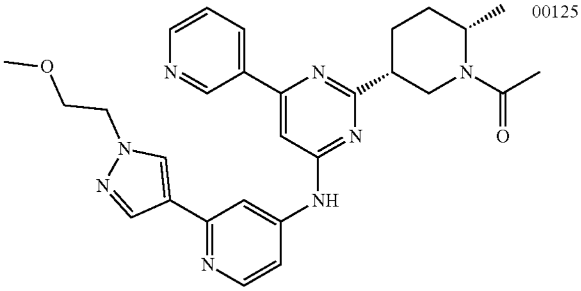

00125

Example 9: Synthesis of (+/−)-cis-1-(2-methyl-5-(4-((5-methylpyridin-3-yl)amino)-6-(1H-pyrazolo[3,4-c]pyridin-4-yl)pyrimidin-2-yl)piperidin-1-yl)ethan-1-one (00126)

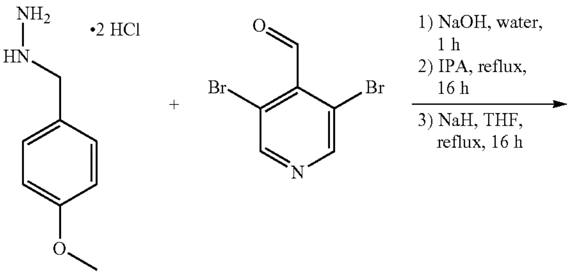

-continued

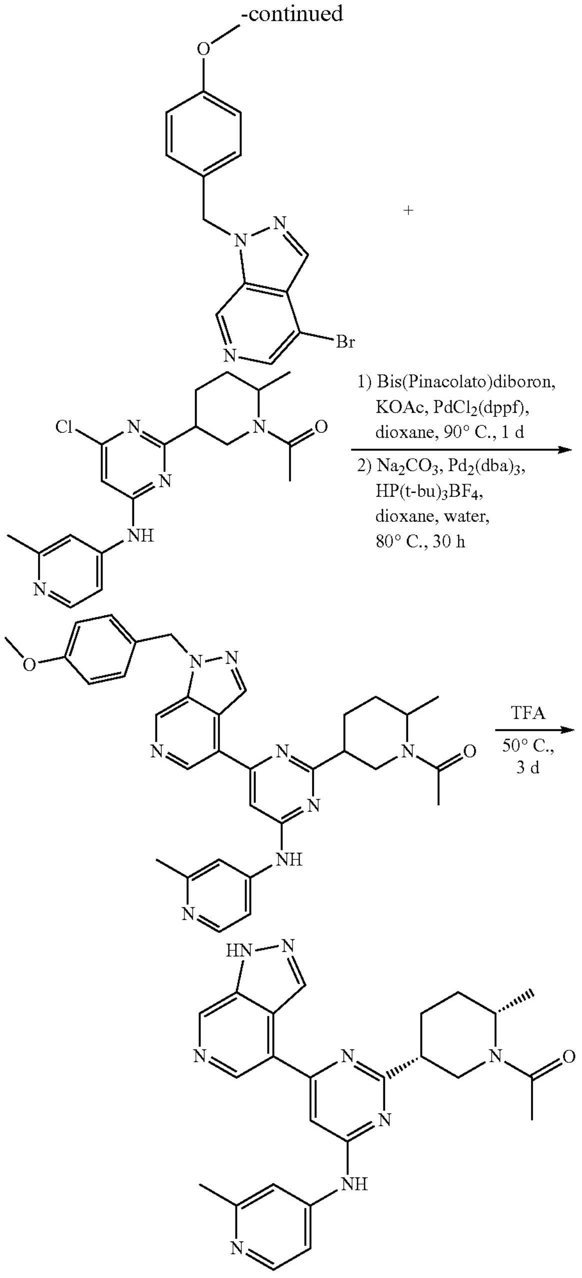

00126

A solution of 50% sodium hydroxide in water (1.0 mL, 38 mmol) was added to a suspension of (4-methoxybenzyl) hydrazine dihydrochloride (4.3 g, 19 mmol) in methanol (50 mL) and the mixture was stirred at room temperature for 1 hour. The salts were filtrated off over a glass filter and washed with methanol. The filtrate was concentrated to afford a sticky white solid. The solid was suspended in 2-propanol (50 mL) and 3,5-dibromoisonicotinaldehyde (5.0 g, 19 mmol) was added. The mixture was stirred at reflux for 16 hours resulting in an orange suspension. The suspension was allowed to cool to room temperature and water (25 mL) was added. The mixture was stirred at room temperature for 1 hour and the resulting precipitate was filtrated off and washed with 2-propanol/water (4/1, v/v, 50 mL). The solid was transferred to a flask and co-evaporated twice with ethyl acetate. The residue was suspended in tetrahydrofuran (100 mL) at room temperature and sodium hydride (0.38 g, 9.5 mmol) was added. The mixture was stirred for 10 minutes at room temperature and was then stirred at reflux for 16 hours. The mixture was cooled to room temperature, poured into water (300 mL) and extracted with ethyl acetate twice. The combined organic layers were washed with brine, dried over sodium sulfate and concentrated to afford 4-bromo-1-(4-methoxybenzyl)-1H-pyrazolo[3,4-c]pyridine (515 mg, 18%) that was used as such in the next step. LCMS (Method A): $t_R$ 2.00 min, 92%, MS (ESI) 318.0/320.0 $(M+H)^+$. A nitrogen flushed mixture of 4-bromo-1-(4-methoxybenzyl)-1H-pyrazolo[3,4-c]pyridine (177 mg, 0.56 mmol), bis(pinacolato)diboron (155 mg, 0.61 mmol), potassium acetate (82 mg, 0.83 mmol) and 1,1'-bis(diphenylphosphino)ferrocene-palladium(II) dichloride (23 mg, 0.028 mmol) in 1,4-dioxane (3 mL) was stirred at 80° C. for 2 hours. Additional bis(pinacolato)diboron (155 mg, 0.61 mmol), potassium acetate (82 mg, 0.83 mmol) and 1,1'-bis(diphenylphosphino) ferrocene-palladium(II) dichloride (23 mg, 0.028 mmol) were added and the reaction was stirred at 90° C. for 16 hours. The mixture was cooled to room temperature and 1-(5-(4-chloro-6-((5-methylpyridin-3-yl)amino)pyrimidin-2-yl)-2-methylpiperidin-1-yl)ethan-1-one (100 mg, 0.28 mmol, prepared analogous to Example 4), sodium carbonate (59 mg, 0.56 mmol), tri-tert-butylphosphonium tetrafluoroborate (8.1 mg, 30 μmol), tris(dibenzylideneacetone)dipalladium(0) (13 mg, 10 μmol), 1,4-dioxane (3 mL) and water (1 mL) were added. The mixture was stirred at 80° C. for 30 hours. The reaction mixture was allowed to cool to room temperature and stirred overnight. Solids were removed by filtration and the reaction mixture was filtered over a small $C_{18}$-plug using acetonitrile as eluent. The product was purified by reversed phase chromatography (Method A) followed by a second purification using reversed phase chromatography (Method B) to afford 1-(5-(4-(1-(4-methoxybenzyl)-1H-pyrazolo[3,4-c]pyridin-4-yl)-6-((5-methylpyridin-3-yl)amino)pyrimidin-2-yl)-2-methylpiperidin-1-yl)ethan-1-one (13 mg, 8%) as a light brown solid. LCMS (Method C): $t_R$ 2.01 min, 98%, MS (ESI) 563.2 $(M+H)^+$. A solution of 1-(5-(4-(1-(4-methoxybenzyl)-1H-pyrazolo[3,4-c]pyridin-4-yl)-6-((5-methylpyridin-3-yl) amino)pyrimidin-2-yl)-2-methylpiperidin-1-yl)ethan-1-one (13 mg, 23 μmol) in trifluoroacetic acid (1 mL) was stirred at room temperature for 3 hours, heated to 50° C. and stirred for 3 days. The reaction mixture was concentrated and purified using reversed phase chromatography (Method B) to afford (+/−)-cis-1-(2-methyl-5-(4-((5-methylpyridin-3-yl) amino)-6-(1H-pyrazolo[3,4-c]pyridin-4-yl)pyrimidin-2-yl) piperidin-1-yl)ethan-1-one (9 mg, 88%) as a white solid. LCMS (Method D): $t_R$ 3.02 min, 10097%, MS (ESI) 443.2 $(M+H)^+$.

Example 10: Synthesis of 1-((2S,5R)-2-methyl-5-(4-(4-methyl-1H-imidazol-1-yl)-6-(phenylamino) pyrimidin-2-yl)piperidin-1-yl)ethan-1-one (00127)

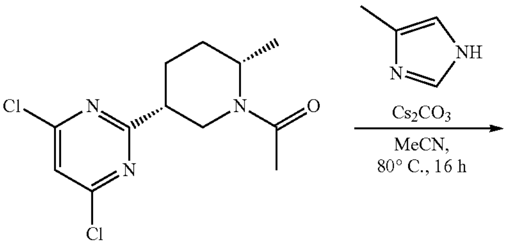

-continued

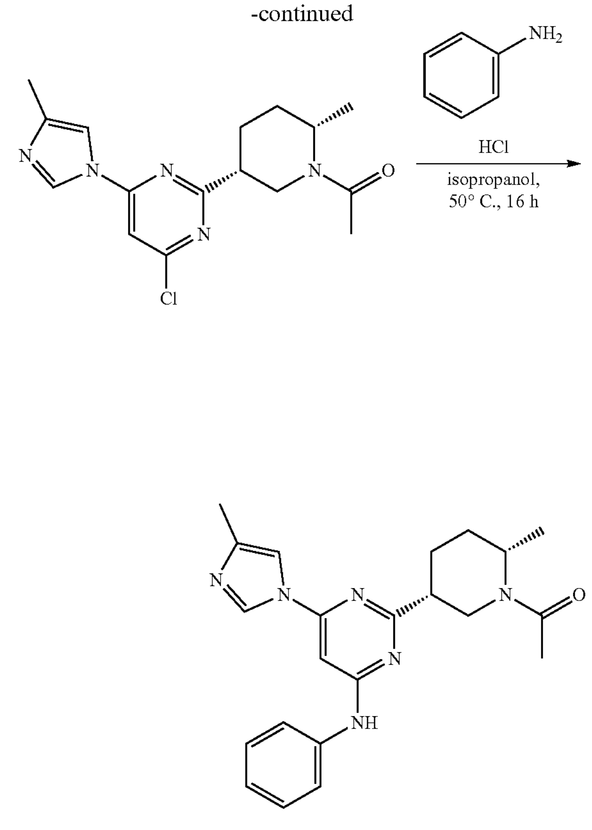

00127

To a mixture of 4-methylimidazole (8 mg, 0.10 mmol) and cesium carbonate (34 mg, 0.10 mmol) in acetonitrile (2 mL) was added 1-((2S,5R)-5-(4,6-dichloropyrimidin-2-yl)-2-methylpiperidin-1-yl)ethan-1-one (Intermediate 2, 30 mg, 0.1 mmol) in acetonitrile (1 mL). The mixture was stirred at 80° C. for 16 hours. The mixture was diluted with water (0.5 mL) and DMSO (1 mL), purified using by reverse phase chromatography (Method A) and lyophilized to afford 1-((2S,5R)-5-(4-chloro-6-(4-methyl-1H-imidazol-1-yl)pyrimidin-2-yl)-2-methylpiperidin-1-yl)ethan-1-one (16 mg, 0.05 mmol, 43%) as a white solid. LCMS (Method A): $t_R$ 1.55 min, 98%, MS (ESI) 334.1 $(M+H)^+$. A solution of 1-((2S,5R)-5-(4-chloro-6-(4-methyl-1H-imidazol-1-yl)pyrimidin-2-yl)-2-methylpiperidin-1-yl)ethan-1-one (15 mg, 0.05 mmol), aniline (0.01 mL, 0.14 mmol) and hydrochloric acid (0.01 mL, 0.14 mmol) in 2-propanol (2 mL) was stirred at 50° C. for 16 hours. The mixture was diluted with DMSO, purified by reverse phase chromatography (Method A and B) and lyophilized to afford 1-((2S,5R)-2-methyl-5-(4-(4-methyl-1H-imidazol-1-yl)-6-(phenylamino)pyrimidin-2-yl)piperidin-1-yl)ethan-1-one (9 mg, 0.02 mmol, 46%) as a white solid. LCMS (Method B): $t_R$ 2.72 min, 100%, MS (ESI) 391.1 $(M+H)^+$.

Example 11: Synthesis of 1-((2S,5R)-5-(4-(1H-imidazol-1-yl)-6-(phenylamino)pyrimidin-2-yl)-2-methylpiperidin-1-yl)ethan-1-one (00128)

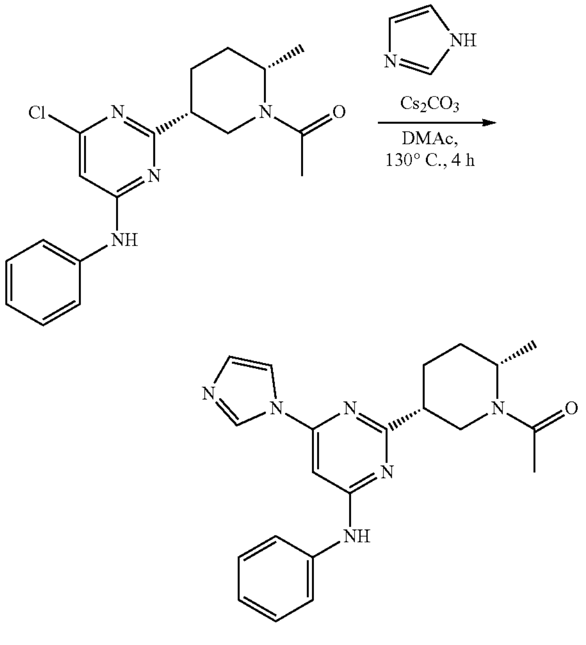

00128

A solution of 1-((2S,5R)-5-(4-chloro-6-(phenylamino)pyrimidin-2-yl)-2-methylpiperidin-1-yl)ethan-1-one (37 mg, 0.10 mmol, prepared analogous to Example 3), imidazole (149 mg, 0.20 mmol) and cesium carbonate (65 mg, 0.20 mmol) in N,N-dimethylacetamide (1 mL) was stirred at 130° C. for 4 hours. The mixture was cooled to room temperature and diluted with methanol (1 mL). The solution was purified by reverse phase chromatography (Method B) followed by preparative SFC (Method A) and lyophilized to afford 1-((2S,5R)-5-(4-(1H-imidazol-1-yl)-6-(phenylamino)pyrimidin-2-yl)-2-methylpiperidin-1-yl)ethan-1-one (8 mg, 0.01 mmol, 21%). LCMS (Method D): $t_R$ 3.39 min, 100%, MS (ESI) 377.2 $(M+H)^+$.

Reference Example 12: Synthesis of (2S,5R)-5-(4-((3-fluorophenyl)amino)-6-(pyridin-3-yl)pyrimidin-2-yl)-2-methylpiperidine-1-carboxamide (00129)

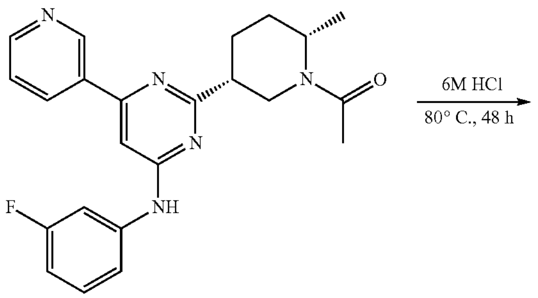

-continued

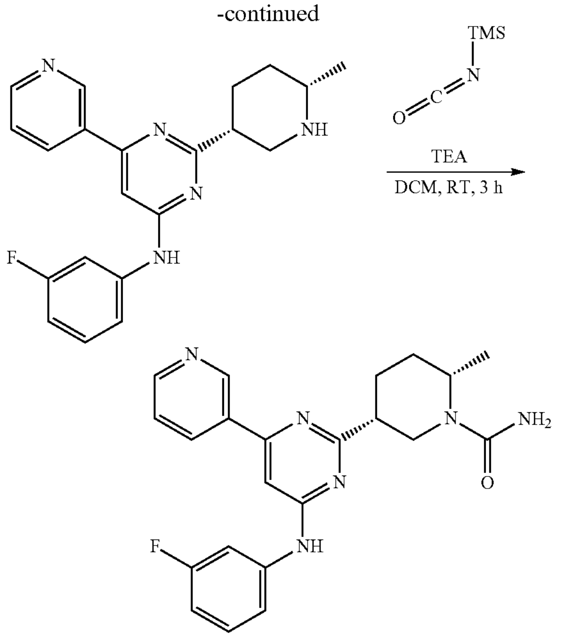

00129

A solution of 1-((2S,5R)-5-(4-((3-fluorophenyl)amino)-6-(pyridin-3-yl)pyrimidin-2-yl)-2-methylpiperidin-1-yl) ethan-1-one (26 mg, 0.06 mmol, prepared analogous to Example 3) and 6M hydrochloric acid (6 mL, 36.0 mmol) was stirred at 80° C. for 48 hours. The mixture was concentrated and purified with SCX (ion exchange) chromatography (washed with methanol and eluted with 3.5M ammonia in methanol) to afford N-(3-fluorophenyl)-2-((3R,6S)-6-methylpiperidin-3-yl)-6-(pyridin3-yl)pyrimidin-4-amine (26 mg, 93%) as a beige solid. LCMS (Method C): $t_R$1.87 min, 83%, MS (ESI) 364.2 $(M+H)^+$. To a solution of N-(3-fluorophenyl)-2-((3R,6S)-6-methylpiperidin-3-yl)-6-(pyridin-3-yl)pyrimidin-4-amine (26 mg, 0.06 mmol) in dichloromethane (3 mL) was added triethylamine (0.03 mL, 0.18 mmol) and trimethylsilyl isocyanate (8.04 μl, 0.06 mmol). The mixture was stirred at room temperature for 3 hours and concentrated. The residue was purified with reverse phase chromatography (method B) and lyophilized to afford (2S,5R)-5-(4-((3-fluorophenyl)amino)-6-(pyridin-3-yl)pyrimidin-2-yl)-2-methylpiperidine-1-carboxamide (7 mg, 27%) as a white solid. LCMS (Method D): $t_R$ 3.38 min, 99%, MS (ESI) 407.2 (M+H)

Example 13: Synthesis of 1-((2S,5R)-5-(4-((3-fluoro-5-(1,3,4-oxadiazol-2-yl)phenyl)amino)-6-(pyridin-3-yl)pyrimidin-2-yl)-2-methylpiperidin-1-yl)ethan-1-one (00130)

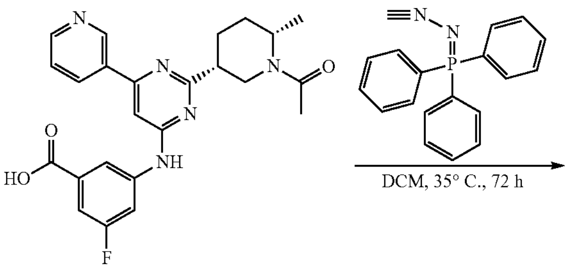

-continued

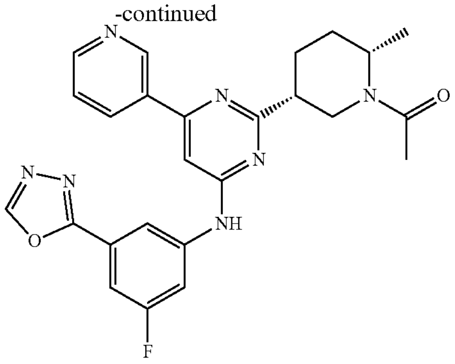

00130

To a suspension of 3-((2-((3R,6S)-1-acetyl-6-methylpiperidin-3-yl)-6-(pyridin-3-yl)pyrimidin-4-yl)amino)-5-fluorobenzoic acid (46 mg, 0.10 mmol, prepared analogous to Example 2) in dichloromethane (5 mL) was added a solution of (isocyanoimino)triphenylphosphorane (62 mg, 0.20 mmol) in dichloromethane (1 mL). The mixture was stirred at 35° C. for 72 hours and concentrated. The residue was purified with reverse phase chromatography (Method B) and lyophilized to afford 1-((2S,5R)-5-(4-((3-fluoro-5-(1,3,4-oxadiazol-2-yl)phenyl)amino)-6-(pyridin-3-yl)pyrimidin-2-yl)-2-methylpiperidin-1-yl)ethan-1-one (129 mg, 24%) as a white solid. LCMS (Method B): $t_R$ 3.03 min, 96%, MS (ESI) 474.2 $(M+H)^+$.

Example 14: Synthesis of 1-((2S,5R)-2-methyl-5-(4-((3-(1-methyl-1H-1,2,3-triazol-4-yl)phenyl) amino)-6-(pyrazin-2-yl)pyrimidin-2-yl)piperidin-1-yl)ethan-1-one (00131)

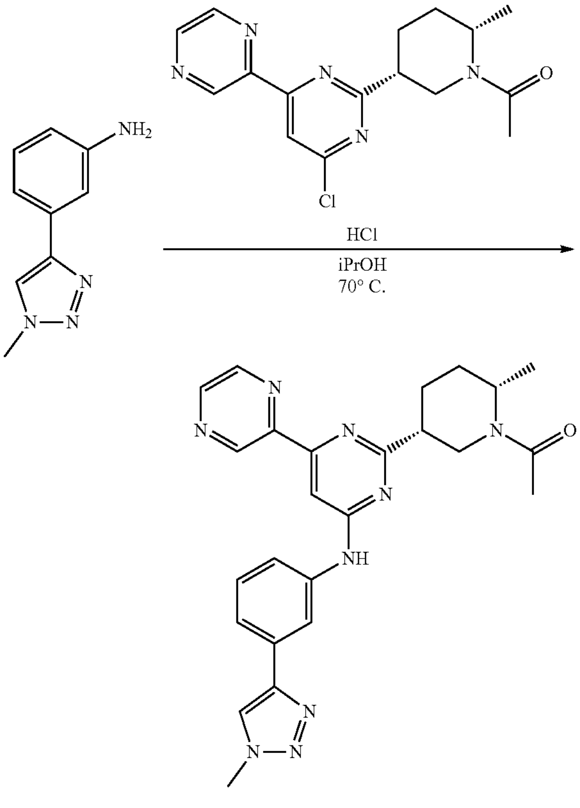

(00131)

To a solution of 1-((2S,5R)-5-(4-chloro-6-(pyrazin-2-yl)pyrimidin-2-yl)-2-methylpiperidin-1-yl)ethan-1-one (Intermediate 3, 120 mg, 0.36 mmol) in 2-propanol (2 mL), was added 3-(1-methyl-1H-1,2,3-triazol-4-yl)aniline (188 mg, 1.08 mmol) and hydrochloric acid (0.08 mL, 1.08 mmol). The mixture was stirred at 70° C. for 16 hours, poured into saturated aqueous sodium bicarbonate solution and extracted with ethyl acetate twice. The combined organic layers were dried over sodium sulfate and concentrated to afford a yellow oil. The oil was purified with reversed phase chromatography (method B) and lyophilized to afford 1-((2S,5R)-2-methyl-5-(4-((3-(1-methyl-1H-1,2,3-triazol-4-yl)phenyl)amino)-6-(pyrazin-2-yl)pyrimidin-2-yl)piperidin-1-yl)ethan-1-one (102 mg, 60%) as a white solid. $^1$H-NMR (400 MHz, DMSO-d6, mixture of rotamers) δ 10.01 (d, J=5.6 Hz, 1H), 9.56 (dd, J=11.0, 1.1 Hz, 1H), 8.80 (d, J=1.5 Hz, 2H), 8.54-8.42 (m, 2H), 7.72-7.54 (m, 2H), 7.53-7.39 (m, 2H), 4.86-4.76 (m, 1H), 4.27-4.16 (m, 0.5H), 4.15-4.03 (m, 3.5H), 3.58-3.42 (m, 0.5H), 3.00-2.86 (m, 1H), 2.86-2.68 (m, 0.5H), 2.17-1.96 (m, 5H), 1.93-1.77 (m, 0.5H), 1.76-1.64 (m, 1.5H), 1.27 (d, J=6.8 Hz, 1.5H), 1.13 (d, J=7.0 Hz, 1.5H); LCMS (Method D): $t_R$ 3.31 min, MS (ESI) 470.2 $(M+H)^+$.

Example 15: Crystal Structure of the Bromodomain of Human CREBBP in Complex with Compound 00004

Crystallization

Experimental Setup

The construct used for crystallization comprised residues 1081 to 1197. Crystals of CREBBP in complex with compound 00004 were obtained using hanging-drop vapour-diffusion set-ups. CREBBP at a concentration of 20.3 mg/ml (10 mM Hepes, 500 mM NaCl, 5% Glycerol, 0.5 mM TCEP, pH 7.4) was pre-incubated with 4.3 mM (3.0-fold molar excess) of 00004 (150 mM in DMSO) for 1 h. 1 μl of the protein solution was then mixed with 1 μl of reservoir solution (0.1 M $MgCl_2$, 0.1 M MES/NaOH pH 6.3, 18% (w/v) PEG 6000 and 10% (v/v) ethylene glycol) and equilibrated at 4° C. over 0.4 ml of reservoir solution. Well diffracting crystals appeared and grew to full size over 4 days.

Data Collection

Crystals were cryo-protected by addition of 10% glycerol (final concentration) to the crystallization drop before mounting. A complete 1.6 Å data set of a CREBBP/00004crystal was collected at Diamond Light Source (Didcot, UK, beamline i03) and the data were integrated, analyzed and scaled by XDS, Pointless and Aimless within the autoPROC pipeline (Table 1).

TABLE 1

| Data collection statistics | |
|---|---|
| Space group | $P2_1$ |
| Unit cell parameters [Å] | a = 70.4, b = 58.6, c = 73.2 |
| | α = 90.0, β = 115.4, γ = 90.0 |
| Resolution [Å] | 66.14-1.60 (1.63-1.60) |
| # Unique reflections | 68872 (2664) |
| I/σ(I) | 14.9 (2.2) |
| Completeness [%] | 97.2 (75.5) |
| Multiplicity | 3.3 (2.1) |
| $R_{meas}$ | 0.050 (0.460) |

Structure Determination and Refinement

Molecular replacement was done using a previously determined structure of CREBBP as a starting model. Several rounds of alternating manual re-building and refinement with REFMAC5 resulted in the final model (Table 2). Atomic displacement factors were modelled with a single isotropic B-factor per atom.

TABLE 2

| Refinement statistics | |
|---|---|
| Resolution | 35.00-1.60 (1.64-1.60) |
| $R_{work}$ | 0.151 (0.305) |
| $R_{free}$ | 0.190 (0.351) |
| Completeness [%] | 97.2 (77.6) |

Results

We have produced crystals of CREBBP/00004 that diffracted to 1.6 Å resolution and determined the 3-dimensional structure of the protein-ligand complex. Clear electron density in the Fo-F, omit map of the initial model at the compound binding site in each chain of CREBBP revealed the binding of the entire compound (FIG. 3) and allowed its unambiguous placement. Additionally, the structure also confirms the absolute stereochemistry of compound 00004 (2S, 5R on the piperidine moiety).

BromoKdMAX-Assay

A BromoKdMAX was performed at DiscoverX. This assay may be used for determining whether the compounds of the present invention bind to the bromodomain of p300 and/or the bromodomain of CBP with a particular $K_d$ (e.g. 100 nM or less).

The assay principle is the following:

BROMOscan™ is a novel industry leading platform for identifying small molecule bromodomain inhibitors. Based on proven KINOMEscan™ technology, BROMOscan™ employs a proprietary ligand binding site-directed competition assay to quantitatively measure interactions between test compounds and bromodomains. This robust and reliable assay panel is suitable for high throughput screening and delivers quantitative ligand binding data to facilitate the identification and optimization of potent and selective small molecule bromodomain inhibitors. BROMOscan™ assays include trace bromodomain concentrations (<0.1 nM) and thereby report true thermodynamic inhibitor Kd values over a broad range of affinities (<0.1 nM to >10 uM).

The assay was conducted as follows:

For the Bromodomain assays, T7 phage strains displaying bromodomains were grown in parallel in 24-well blocks in an *E. coli* host derived from the BL21 strain. *E. coli* were grown to log-phase and infected with T7 phage from a frozen stock (multiplicity of infection=0.4) and incubated with shaking at 32° C. until lysis (90-150 minutes). The lysates were centrifuged (5,000×g) and filtered (0.2 μm) to remove cell debris. Streptavidin-coated magnetic beads were treated with biotinylated small molecule or acetylated peptide ligands for 30 minutes at room temperature to generate affinity resins for bromodomain assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining bromodomains, liganded affinity beads, and test compounds in 1× binding buffer (17% SeaBlock, 0.33×PBS, 0.04% Tween 20, 0.02% BSA, 0.004% Sodium azide, 7.4 mM DTT). Test compounds were prepared as 1000× stocks in 100% DMSO. Kds were determined using an 11-point 3-fold compound dilution series with one DMSO control point. All compounds for Kd measurements are distributed by acoustic transfer (noncontact dispensing) in 100% DMSO. The compounds were then diluted directly into the assays such that the final concentration of DMSO was 0.09%. All reactions performed in polypropylene 384-well plates. Each was a final volume of 0.02 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 2 μM non-biotinylated affinity ligand) and incubated at room temperature with shaking for 30 minutes. The bromodomain concentration in the eluates was measured by qPCR.

The results were as follows:

| Compound Name | DiscoveRx Gene Symbol | Entrez Gene Symbol | Modifier | Kd (nM) |
|---|---|---|---|---|
| 00004 | ATAD2A | ATAD2 | > | 10000 |
| 00004 | ATAD2B | ATAD2B | > | 10000 |
| 00004 | BAZ2A | BAZ2A | > | 10000 |
| 00004 | BAZ2B | BAZ2B | > | 10000 |
| 00004 | BRD1 | BRD1 | > | 10000 |
| 00004 | BRD2(1) | BRD2 | > | 10000 |
| 00004 | BRD2(1, 2) | BRD2 | = | 7600 |
| 00004 | BRD2(2) | BRD2 | > | 10000 |
| 00004 | BRD3(1) | BRD3 | > | 10000 |
| 00004 | BRD3(1, 2) | BRD3 | > | 10000 |
| 00004 | BRD3(2) | BRD3 | > | 10000 |
| 00004 | BRD4(1) | BRD4 | > | 10000 |
| 00004 | BRD4(1, 2) | BRD4 | > | 10000 |
| 00004 | BRD4(2) | BRD4 | > | 10000 |
| 00004 | BRD4(full-length, short-iso.) | BRD4 | = | 7100 |
| 00004 | BRD7 | BRD7 | > | 10000 |
| 00004 | BRD8(1) | BRD8 | > | 10000 |
| 00004 | BRD8(2) | BRD8 | > | 10000 |
| 00004 | BRD9 | BRD9 | > | 10000 |
| 00004 | BRDT(1) | BRDT | > | 10000 |
| 00004 | BRDT(1, 2) | BRDT | > | 10000 |
| 00004 | BRDT(2) | BRDT | > | 10000 |
| 00004 | BRPF1 | BRPF1 | > | 10000 |
| 00004 | BRPF3 | BRPF3 | > | 10000 |
| 00004 | CECR2 | CECR2 | > | 10000 |
| 00004 | CREBBP | CREBBP | = | 29 |
| 00004 | EP300 | EP300 | = | 12 |
| 00004 | FALZ | BPTF | > | 10000 |
| 00004 | GCN5L2 | KAT2A | > | 10000 |
| 00004 | PBRM1(2) | PBRM1 | > | 10000 |
| 00004 | PBRM1(5) | PBRM1 | > | 10000 |
| 00004 | PCAF | KAT2B | > | 10000 |
| 00004 | SMARCA2 | SMARCA2 | > | 10000 |
| 00004 | SMARCA4 | SMARCA4 | > | 10000 |
| 00004 | TAF1(2) | TAF1 | > | 10000 |
| 00004 | TAF1L(2) | TAF1L | > | 10000 |
| 00004 | TRIM24(Bromo.) | TRIM24 | > | 10000 |
| 00004 | TRIM24(PHD, Bromo.) | TRIM24 | > | 10000 |
| 00004 | TRIM33(PHD, Bromo.) | TRIM33 | > | 10000 |
| 00004 | WDR9(2) | BRWD1 | > | 10000 |

Example 16: Inhibition of Fibrotic Gene Expression of in Lung Cancer Cell Lines by Compound 00004

Materials and Methods:

Gene Expression Analysis/RNA Sequencing:

250000 HCC827 (ATCC; CRL 2868) cells/well or 200000 NCI-H1975 (ATCC; CRL 5908) cells/well were seeded in 6-well dishes (Greiner Bio-One, 7657160) the day before drug treatment in RPMI medium containing 10% FCS and 2 mM L-Glutamine. Cells were then treated for 24 h either with DMSO, with 1 μM Compound 00004. Subsequently cells were washed 3 times with 2 ml PBS and lysed in 300 μl lysis buffer (RA1+1% TCEP [Sigma 646547]). RNA is extracted according to Macherey-Nagel NucleoSpin 8 RNA Kit protocol for vacuum (740698.5) for RNA extraction and RNA is eluted in H2O. RNA Library preparation and sequqnening was done externally. In short, RNA sequencing libraries were generated using TruSeq RNA Sample Prep Kit v2 following manufacturer's recommendations and index codes were added to attribute sequences to each sample. Samples were sequenced using an Illumnia platform, with paired-end reads. Illumina SBS technology utilizes a proprietary reversible terminator-based method that detects single bases as they are incorporated into DNA template strands. The original data obtained from the high throughput sequencing platforms were transformed to sequenced reads by base calling. Raw data are recorded in a FASTQ file which contains sequenced reads and corresponding sequencing quality information and were further processed to obtain transcripts per million values (TPM) for variable genes.

Figure 2:
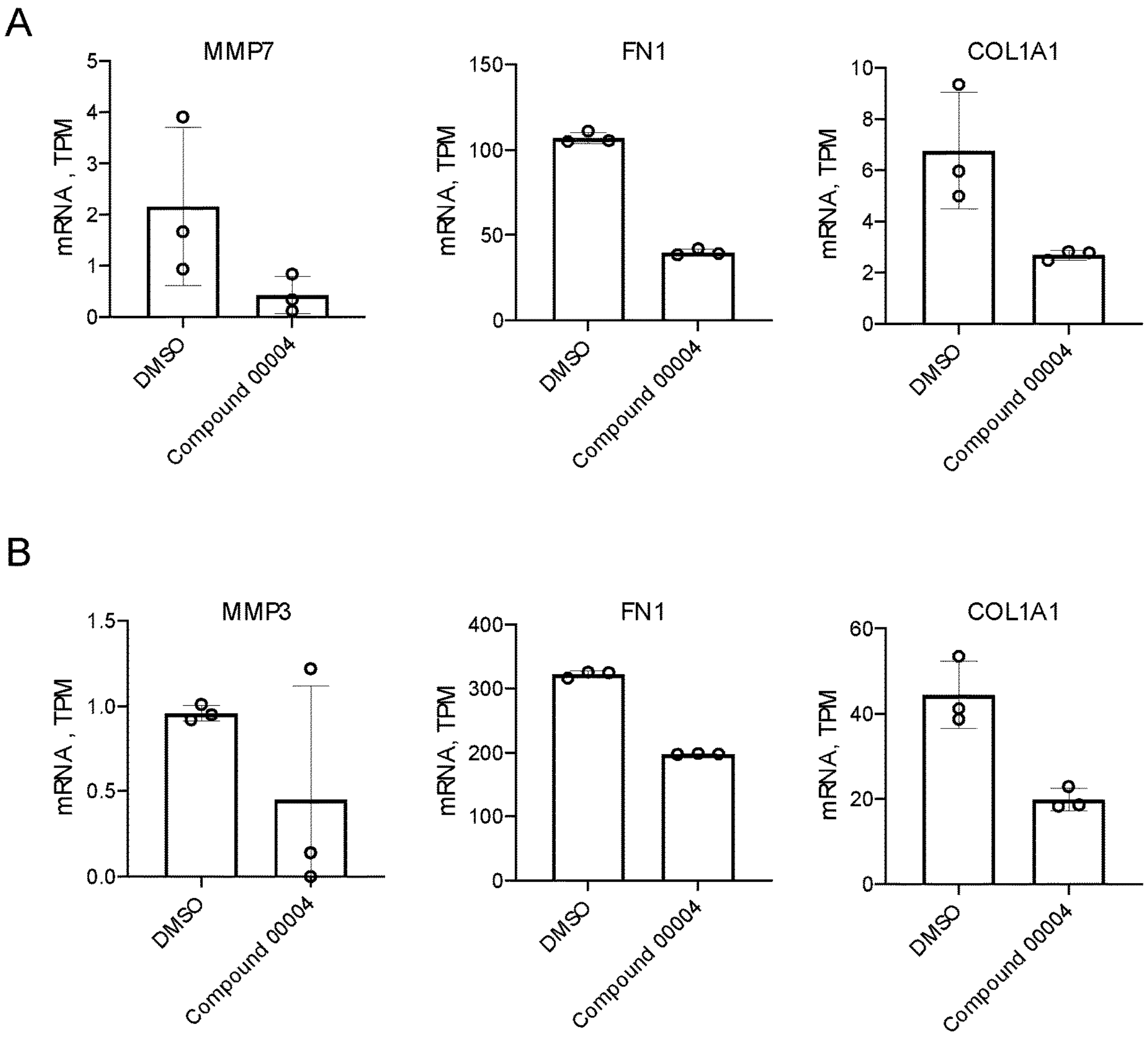
FIG. 2. Inhibition of fibrotic gene expression in lung cancer cell lines by compound 00004. mRNA abundance in HCC827 (A) or NCI-H1975 (B) lung cancer cells was determined using RNA-sequencing in cells treated for 24 h with DMSO or Compound 00004. mRNA abundance of selected genes induced in fibrosis is given as transcripts per million (TPM). Mean±SD from 3 experiments.

Results: FIG. 2 shows how compound 00004 reduces expression of genes, which are up-regulated during fibrotic disease (fibrotic gene signature), exemplified here with Matrix-Metalloproteinases (MMP), Fibronectin (FN1) or Collagen (COL1A1) in both lung cancer cell lines HCC827 and NCI-H1975. Regulation of pro-fibrotic genes is in line with the functional reduction of FN1 at protein level in primary IPF donor fibroblasts upon pro-fibrotic TGF-3 challenge (Example 16).

Example 17: Inhibition of TGF-β1 Induced α-Smooth Muscle Actin (αSMA) Production by IPF Diseased Donor's Lung Fibroblast (FMT Assay) and Inhibition of TGF-β1 Induced Fibronectin 1 (FN1) Production by IPF Diseased Donor's Bronchial Epithelial Cells (EMT Assay)

Materials and Methods:

Fibroblast-to-Myofibroblast Transition (FMT) Assay:

Lung fibroblasts from 3 IPF donors (Pat1-3) were seeded for automated high-content/high-throughput microscopy. At day 2 cell culture medium was refreshed in the wells and fibroblast grown until day 5, at which point drug treatment was initiated.

Drug addition was done 1 h before stimuli addition (1.25 ng/ml TGF-β1). For trigger controls wells with fibroblasts were treated with medium (unstimulated control) or 1.25 ng/ml TGF-β1 (stimulated control). For assay controls fibroblasts were treated with 1.25 ng/ml TGF-β1+0.1% DMSO (unstimulated control) or 1.25 ng/ml TGF-β1+1 μM SB525334 (positive control for inhibition). Reference compound and clinically approved drug nintedanib was added as concentration response curve (CRC) with 8-points in a semi-Log dilution starting from 10 μM. Compound 00004 was added as 8-point CRC, semi-Log dilutions starting from 20 μM.

One hour after Nintedanib or Compound 00004 addition fibroblasts were stimulated with 1.25 ng/ml TGF-β1 and culture for 72 h. Wells were fixed with 4% paraformaldehyde and stained for α-smooth muscle actin (αSMA) expression using immunofluorescence and with DAPI to assess nuclei number per well. Image acquisition and high content analysis (HCA) of αSMA and DAPI was done on a high content microscope.

Epithelial-to-Mesenchymal Transition (EMT) Assay:

Bronchial epithelial cells (BEC) from 3 IPF donors (PatA-C) were seeded for automated high-content/high-throughput microscopy. At day 2 cell culture medium was refreshed in the wells and cells grown until day 5, at which drug treatment was initiated.

Drug addition was done 1 h before stimuli addition (5.0 ng/ml TGF-β1). For trigger controls wells with BEC were treated with medium (unstimulated control) or 5.0 ng/ml TGF-β1 (stimulated control). For assay controls fibroblasts were treated with 5.0 ng/ml TGF-β1+0.1% DMSO (unstimulated control) or 5.0 ng/ml TGF-β1+1 μM SB525334 (positive control for inhibition). The reference compound and clinically approved drug nintedanib was added as concentration response curve (CRC) with 8-points in a semi-Log dilution staring from 10 μM. Compound 00004 was added as 8-point CRC, semi-Log dilutions starting from 20 μM. One hour after Nintedanib or Compound 00004 addition BEC were stimulated with 5.0 ng/ml TGF-β1 and culture for 72 h. Wells were fixed with 4% paraformaldehyde and stained for Fibronectin (FN1) expression using immunofluorescence and with DAPI to assess nuclei number per well. Image acquisition and high content analysis (HCA) of FN1 and DAPI was done on a high content microscope.

Data Analysis FMT/EMT Assays:

Analysis of αSMA/FN1: Images were segmented and quantificatied for αSMA/FN1 immunoreactivity by an HCA algorithm, with density x area (DxA) output. Data were normalized from raw αSMA/FN1 (DxA) to percentage inhibition (PIN) values, on a plate-to-plate basis $$PIN = 100 - \left(\frac{\mu_p - X_i}{\mu - \mu}\right) \times 100$$

μp is the average αSMA/FN1 value of the positive control (TGF-β1+1 μM SB525334)

μn is the average of αSMA/FN1 value of the vehicle control (TGF-β1+0.1% DMSO)

Xi is the compound αSMA/FN1 value $IC_{50}$ values (if calculable) for compound 00004 and Nintedanib were calculated form the CRC.

Analysis of % Remaining cells: DAPI fluorescence applied for HCA-based quantification of the number of imaged cells, on a plate-to-plate basis.

$$\% \text{ remaining cells} = \left(\frac{X}{\mu}\right) \times 100$$

$\mu_n$ is the average numbers of nuclei of the vehicle control (TGF-β1+0.1% DMSO)

$X_i$ is the compound number of nuclei

Results: Compound 00004 induced a full concentration-dependent inhibition of TGF-β1-mediated αSMA expression in all 3 IPF donors' lung fibroblast (see Table 3 below), as a measure of reduced lung fibroblast-to-myofibroblast transition. Compound 00004 induced loss of nuclei was only observed at the highest test concentration (20 μM).

TABLE 3

| | $IC_{50}$ αSMA, Log [M] | | | Max. Percentage Inhibition (PIN), [%] | | | Potential toxicity Log [M] | | |
|---|---|---|---|---|---|---|---|---|---|
| Compound | Pat1 | Pat2 | Pat3 | Pat1 | Pat2 | Pat3 | Pat1 | Pat2 | Pat3 |
| 00004 | −5.9 | −5.6 | −5.7 | 90.3 | 127.1 | 105.1 | >−5.2 | >−5.2 | >−5.2 |
| Nintedanib | −6.2 | −6.4 | −6.7 | 109.3 | 101 | 98.4 | >−5.5 | >−7.0 | >−6.0 |

Pat1, Pat2, Pat3: different lung fibroblast donors, potential toxicity: concentration with >25% cell loss Compound 00004 induced a full concentration-dependent inhibition of TGF-β1-mediated FN1 expression in BEC from 2 IPF donors and a partial (i.e. ΔPIN <75) concentration-dependent inhibition of TGF-β1-mediated FN1 expression in one IPF donor (see Table 4 below). FN1 deposition is induces during epithelial-to-mesenchymal transition of BECs. No modulation of the number of nuclei was observed by Compound 00004 treatment, indicative of absence of potential cytotoxic side-effects.

TABLE 4

| | $IC_{50}$ FN1, Log [M] | | | Δ Percentage Inhibition (PIN), [%] | | | Potential toxicity Log [M] | | |
|---|---|---|---|---|---|---|---|---|---|
| Compound | PatA | PatB | PatC | PatA | PatB | PatC | PatA | PatB | PatC |
| 00004 | −5.3 | −6.0 | −5.7 | 62.5 | 84.9 | 116.3 | — | — | — |
| Nintedanib | −5.0* | n.c. | −7.2 | 45.9 | 81.7 | 72.1 | — | — | — |

Pat1, Pat2, Pat3: different lung fibroblast donors, potential toxicity: concentration with >25% cell loss,
*incomplete sigmoidal curve,
n.c.: not calculatable

Example 18: CBP Bromodomain Binding Assay

Materials and Methods:

CBP Bromodomain Binding Assay (TR-FRET):

Compounds solutions of 10 mM in DMSO were prediluted in DSMO to 25× stock solutions in DMSO. These were then diluted down to 4× in Assay buffer. A dilution series in Assay buffer was performed keeping the DMSO concentration stable. 5 μl compound in assay buffer was transferred into the assay plate (provided by assay kit) and the TR-FRET assay Cayman chemicals; 600850) was performed using the manufacture's instructions. After 1 hour incubation at room temperature in the darks, assay plates were read in a Tecan M1000 μlate reader using the TR-FRET mode (top read; excitation 340 nM bandwidth 20 nM; emission 620 nM bandwidth 7 nM; gain optimal determined for the first well, number of flashes: 5; flash frequency 100 Hz; integration time: 500 μs, lag time: 100 μs, room temperature). The TR-FRET ratio was calculated by dividing 670 nm emission by 620 nm emission. Calculataion of EC50 was done on normalized values (DMSO=1) and positive control (0). Values were log transformed and non-linear regression with variable slope (4 parameters) was used to fit values to a dose-response curve to evaluate EC50 values (see table 5 below).

TABLE 5

| Compound # | $EC_{50}$ |
|---|---|
| 00001 | A* |
| 00003 | C |
| 00004 | A* |
| 00009 | A* |
| 00013 | A |
| 00030 | A |
| 00038 | A |
| 00039 | A |
| 00040 | A* |
| 00041 | A* |
| 00042 | A |
| 00043 | A* |
| 00044 | A* |
| 00045 | A* |
| 00046 | A* |
| 00062 | A |
| 00063 | A* |
| 00071 | A* |
| 00075 | A* |

TABLE 5-continued

| Compound # | $EC_{50}$ |
|---|---|
| 00077 | A |
| 00079 | A* |
| 00080 | A* |
| 00101 | A* |
| 00103 | A* |
| 00127 | B |
| 00129 (Ref.) | B |

Legend $EC_{50}$: A* < 0.2 μM < A < 1 μM < B < 10 μM < C

The present invention in particular relates to the following items:

1. A compound of formula (I), optionally in the form of a pharmaceutically acceptable salt, solvate, cocrystal, tautomer, racemate, enantiomer, or diastereomer or mixture thereof, for use in a method of treating fibrotic disease (I)

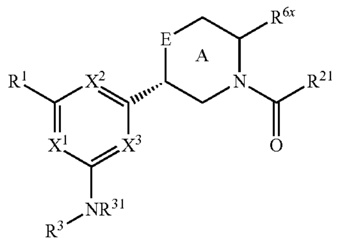

wherein $R^1$ is selected from halogen and -(optionally substituted hydrocarbon group which contains from 1 to 20 carbon atoms and optionally 1 to 15 heteroatoms selected from O, N and S);

$R^{21}$ is selected from hydrogen, -(optionally substituted $C_{1-6}$ alkyl) which may contain one to three oxygen atoms between carbon atoms, and -(optionally substituted $C_{3-6}$ cycloalkyl);

$R^3$ is selected from -(optionally substituted heterocyclyl), -(optionally substituted carbocyclyl), -(optionally substituted $C_{1-6}$ alkylene)-(optionally substituted heterocyclyl) and -(optionally substituted $C_{1-6}$ alkylene)-(optionally substituted carbocyclyl);

each of $X^1$, $X^2$ and $X^3$ is independently selected from N, CH and $CR^X$, wherein at least one of said $X^1$, $X^2$ and $X^3$ is N;

$R^{31}$ is selected from -hydrogen, —$C_{1-6}$-alkyl, and —($C_{1-6}$-alkyl substituted with one or more F); wherein $R^3$ and any $R^{31}$ can be optionally linked; and E is either absent or is selected from —$CH_2$—, —$CHR^x$—, —$CR^x_2$—, —NH—, —$NR^x$—, —O—, -$L^1$-$L^2$- and -$L^2$-$L^1$-, wherein $L^1$ is selected from —$CH_2$—, —$CHR^x$—, —$CR^x_2$—, —NH—, —$NR^x$— and —O— and $L^2$ is selected from —$CH_2$—, —$CHR^x$— and —$CR^x_2$—;

$R^{6x}$ is -halogen, —OH, =O, $C_{1-6}$ alkyl, $C_{1-6}$ haloalkyl, $C_{1-6}$ alkyl substituted with one or more OH, monocyclic aryl optionally substituted with one or more $R^{xb}$, monocyclic heteroaryl optionally substituted with one or more $R^{xb}$, monocyclic cycloalkyl optionally substituted with one or more $R^{xb}$, monocyclic heterocycloalkyl optionally substituted with one or more $R^{xb}$, monocyclic cycloalkenyl optionally substituted with one or more $R^{xb}$, monocyclic heterocycloalkenyl optionally substituted with one or more $R^{xb}$, wherein said R* is independently selected from -halogen, —OH, =O, $C_{1-4}$ alkyl, $C_{1-2}$ haloalkyl, $C_{1-2}$ alkyl substituted with one or two OH;

wherein Ring A may further be substituted with one or more groups $R^x$, wherein any two $R^x$ groups at ring A can be optionally linked and/or any $R^x$ group at ring A can be optionally linked with $R^{21}$; and/or wherein Ring A may be further substituted with one group $R^x$ so as to form together with $R^{6x}$ a bicyclic moiety having the following partial structure:

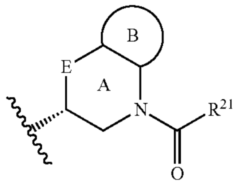

wherein Ring B is an -(optionally substituted heterocycle) or -(optionally substituted carbocycle);

each $R^x$ is independently selected from -halogen, —OH, —O-(optionally substituted $C_{1-6}$ alkyl), —NH-(optionally substituted $C_{1-6}$ alkyl), —N(optionally substituted $C_{1-6}$ alkyl)$_2$, =O, -(optionally substituted $C_{1-6}$ alkyl), -(optionally substituted carbocyclyl), -(optionally substituted heterocyclyl), -(optionally substituted $C_{1-6}$ alkylene)-(optionally substituted carbocyclyl), -(optionally substituted $C_{1-6}$ alkylene)-(optionally substituted heterocyclyl), —O-(optionally substituted $C_{1-6}$ alkylene)-(optionally substituted carbocyclyl), and —O-(optionally substituted $C_{1-6}$ alkylene)-(optionally substituted heterocyclyl), and wherein the optional substituent of the optionally substituted hydrocarbon group, optionally substituted $C_{3-6}$ cycloalkyl, optionally substituted heterocyclyl, optionally substituted heterocycle, optionally substituted carbocyclyl, optionally substituted carbocycle and optionally substituted $C_{1-6}$ alkylene is independently selected from —($C_{1-6}$ alkyl which is optionally substituted with one or more halogen), -halogen, —CN, —$NO_2$, oxo, —C(O)R*, —COOR*, —C(O)NR*R*, —NR*R*, —N(R*)—C(O)R*, —N(R*)—C(O)—OR*, —N(R*)—C(O)—NR*R*, —N(R*)—S(O)$_2$R*, —OR*, —O—C(O)R*, —O—C(O)—NR*R*, —SR*, —S(O)R*, —S(O)$_2$R*, —S(O)$_2$—NR*R*, —N(R*)—S(O)$_2$—NR*R*, heterocyclyl which is optionally substituted with halogen or $C_{1-6}$ alkyl, and carbocyclyl which is optionally substituted with halogen or $C_{1-6}$ alkyl; wherein each R* is independently selected from H, $C_{1-6}$ alkyl which is optionally substituted with halogen, heterocyclyl which is optionally substituted with halogen or $C_{1-6}$ alkyl, and carbocyclyl which is optionally substituted with halogen or $C_{1-6}$ alkyl; wherein any two R* connected to the same nitrogen atom can be optionally linked, and wherein the optional substituent of the optionally substituted $C_{1-6}$ alkyl and of the optionally substituted $C_{1-6}$ alkylene is independently selected from -halogen, —CN, —$NO_2$, oxo, —C(O)R, —COOR, —C(O)NRR, —NRR, —N(R)—C(O)R, —N(R)—C(O)—OR, —N(R)—C (O)—NRR, —N(R)—S(O)$_2$R, —OR, —O—C(O)R, —O—C(O)—NRR, —SR, —S(O)R, —S(O)$_2$R, —S(O)$_2$—NRR, and —N(R)—S(O)$_2$—NRR; wherein R is independently selected from H, $C_{1-6}$ alkyl which is optionally substituted with halogen, heterocyclyl which is optionally substituted with halogen or $C_{1-6}$ alkyl, and carbocyclyl which is optionally substituted with halogen or $C_{1-6}$ alkyl; wherein any two R** connected to the same nitrogen atom can be optionally linked.

2. The compound for use according to item 1, wherein the compound of formula (I) is a compound of formula (V)

(V)

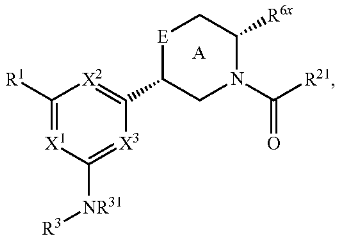

3. The compound for use according to item 1 or item 2, wherein the compound of formula (I) is a compound of formula (VI)

(VI)

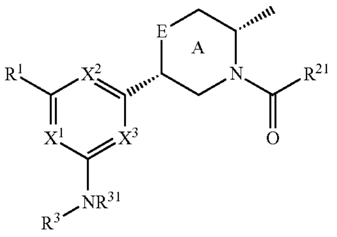

4. The compound for use according to any one of the preceding items, wherein $X^2$ and $X^3$ are N, and wherein preferably $X^1$ is CH.
5. The compound for use according to any one of the preceding items, wherein $R^{21}$ is —$CH_3$ or —$CH_2CH_3$, and wherein preferably $R^{21}$ is —$CH_3$.
6. The compound for use according to any one of the preceding items, wherein $R^{31}$ is selected from -hydrogen and —$C_{1-2}$-alkyl, and wherein preferably $R^{31}$ is -hydrogen.
7. The compound for use according to any one of the preceding items, wherein E is selected from $CH_2$—, —O—, —$CH_2$—O— and —$CH_2$—$CH_2$—, and wherein preferably E is —$CH_2$.
8. The compound for use according to any one of the preceding items, wherein the number of groups $R^x$ in Ring A is 0, 1, or 2, and wherein preferably each $R^x$ is independently selected from -halogen, —OH, —O—$C_{1-2}$ alkyl optionally substituted with one or more $R^{xa}$, —NH—$C_{1-2}$ alkyl optionally substituted with one or more $R^{xa}$, —N($C_{1-2}$ alkyl optionally substituted with one or more $R^{xa}$)$_2$, =O, $C_{1-3}$ alkyl optionally substituted with one or more $R^{xa}$, $C_{1-2}$ haloalkyl, —W-(monocyclic carbocyclyl optionally substituted with one or more $R^{xa}$), —W-(monocyclic heterocyclyl optionally substituted with one or more $R^{xa}$), and wherein —W— is absent, —($C_{1-2}$ alkylene)- or —O—($C_{1-2}$ alkylene)-, and wherein monocyclic carbocyclyl is selected from phenyl and $C_{3-6}$ cycloalkyl, and wherein monocyclic heterocyclyl is selected from thiophenyl, pyridyl, pyrazinyl and pyrimidinyl, and wherein said $R^{xa}$ is independently selected from —C, —F, and —OH.
9. The compound for use according to any one of the preceding items, wherein $R^1$ is selected from -(optionally substituted heterocyclyl) and -(optionally substituted carbocyclyl), and wherein preferably $R^1$ is selected from phenyl, a 5- or 6-membered monocyclic heteroaryl and a 8-10 membered bicyclic heteroaryl, each independently comprising one or more ring heteroatoms independently selected from O, S and N, wherein one or two carbon ring atoms of said monocyclic or said bicyclic heteroaryl are optionally oxidized, and wherein said phenyl, said 5- or 6-membered monocyclic heteroaryl and said 8-10 membered bicyclic heteroaryl is independently optionally substituted with one or more, substituents selected from halogen, —$C_{1-6}$ alkyl, $C_{1-6}$ haloalkyl, —O—($C_{1-6}$ alkyl), —O—($C_{1-6}$ haloalkyl), —OH, —CN, =O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, and 3-6 membered monocyclic carbocyclyl and 3-6 membered monocyclic heterocyclyl comprising 1 to 4 heteroatoms selected from O, S and N, each monocyclic carbocyclyl and heterocyclyl independently optionally substituted with one or more substituents independently selected from halogen, —$C_{1-4}$ alkyl, $C_{1-4}$ haloalkyl, —O—($C_{1-4}$ alkyl), —O—($C_{1-4}$ haloalkyl), —OH, =O, —C(O)R* and —C(O)NR*R*; wherein each R* is independently selected from H, $C_{1-4}$ alkyl, $C_{1-4}$ haloalkyl and/or wherein each monocyclic heterocyclyl is independently optionally substituted with one bivalent substituent selected from $C_{1-3}$ alkylene, $C_{1-3}$ alkylene substituted with 1 to 4 F, —$CH_2$—O—$CH_2$— and —$CH_2$—NH—$CH_2$—.
10. The compound for use according to any one of the preceding items, wherein $R^3$ is selected from phenyl, a 6-membered monocyclic heteroaryl and a 8-10 membered bicyclic heteroaryl, each independently comprising one or more ring heteroatoms independently selected from O, B, S and N, wherein one or two carbon ring atoms of said monocyclic or said bicyclic heteroaryl are optionally oxidized, and wherein said phenyl, said 6-membered monocyclic heteroaryl and said 8-10 membered bicyclic heteroaryl is independently optionally substituted with one or more substituents selected from halogen, —$C_{1-6}$ alkyl, $C_{1-6}$ haloalkyl, —O—($C_{1-6}$ alkyl), —O—($C_{1-6}$ haloalkyl), —OH, —CN, =O, —C(O)R*, —COOR*, —C(O)NR*R*, —NR*R*, —N(R**)—C(O)R*, —N(R**)—C(O)—OR*, —N(R**)—C(O)—NR*R*, —O—C(O)R*, —O—C(O)—NR*R*, and 3-6 membered monocyclic carbocyclyl and 3-6 membered monocyclic heterocyclyl comprising 1 to 4 heteroatoms selected from O, B, S and N, each monocyclic carbocyclyl and heterocyclyl independently optionally substituted with one or more substituents independently selected from halogen, cyclopropyl, —$C_{1-4}$ alkyl, $C_{1-4}$ haloalkyl, —O—($C_{1-4}$ alkyl), —O—($C_{1-4}$ haloalkyl), —OH, =O, —$C_{1-3}$alkylene-OR*, —C(O)R* and —C(O)NR*R*; wherein each R* is independently selected from H, $C_{1-4}$ alkyl, $C_{1-4}$ haloalkyl, cyclopropyl, cyclobutyl, oxetanyl, —$C_{1-2}$alkylene-OH, —$C_{1-2}$alkylene-O($C_{1-2}$alkyl), phenyl, and wherein each R** is independently selected from H, $C_{1-4}$ alkyl, $C_{1-4}$ haloalkyl, and/or wherein each monocyclic heterocyclyl is independently optionally substituted with one bivalent substituent selected from $C_{1-3}$ alkylene such as —$CH_2$—$CH_2$— and —$CH_2$—$CH_2$—$CH_2$—, $C_{1-3}$alkylene substituted with 1 to 4 F, —$CH_2$—O—$CH_2$— and —$CH_2$—NH—$CH_2$—.

11. The compound for use according to any one of the preceding items, wherein the fibrotic disease is selected from the group consisting of pulmonary fibrosis, idiopathic pulmonary fibrosis, radiation-induced pneumonitis, radiation fibrosis, acute respiratory distress syndrome, chronic obstructive pulmonary disease, interstitial lung disease, myocardial infarction, cardiac fibrosis and hypertrophy, ischemic stroke, ischemic kidney disease, renal fibrosis, rheumatoid arthritis, liver fibrosis, NASH (non-alcoholic steatohepatitis), chronic hepatitis, cirrhosis, inflammatory bowel disease, Crohn's disease, scleroderma, keloid, post-operative fibrosis, chemotherapy induced fibrosis (e.g., chemotherapy induced pulmonary fibrosis or ovarian cortical fibrosis), nephrogenic systemic fibrosis, retroperitoneal fibrosis, myelofibrosis, mediastinal fibrosis, cystic fibrosis, asbestosis, asthma, pulmonary hypertension, systemic fibrosis, skin fibrosis, hypertension induced renal and cardiac fibrosis.

12. The compound for use according to item 11, wherein the fibrotic disease is interstitial lung disease (IDL), optionally the interstitial lung disease is idiopathic interstitial pneumonia (IIP).

13. The compound for use according to item 12, wherein the idiopathic interstitial pneumonia is selected from the group consisting of chronic fibrosing interstitial pneumonia, smoking-related interstitial pneumonia and acute/subacute interstitial pneumonia.

14. The compound for use according to item 13, wherein the chronic fibrosing interstitial pneumonia is idiopathic pulmonary fibrosis (IPF).

15. The compound for use according to item 11, wherein the fibrotic disease is non-hepatic steatohepatitis (NASH).

The invention claimed is:

1. A method of treating fibrotic disease, the method comprising administering to a patient in need thereof a therapeutically effective amount of a compound of formula (I) or a pharmaceutically acceptable salt, solvate, cocrystal, tautomer, racemate, enantiomer, or diastereomer or mixture thereof (I)

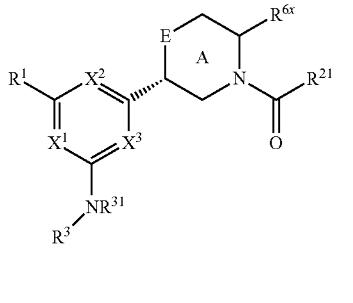

wherein $R^1$ is selected from halogen, unsubstituted or substituted hydrocarbon group which contains from 1 to 20 carbon atoms and unsubstituted or substituted hydrocarbon group which contains from 1 to 20 carbon atoms and 1 to 15 heteroatoms selected from O, N and S;

$R^{21}$ is selected from hydrogen, unsubstituted or substituted $C_{1-6}$ alkyl, unsubstituted or substituted $C_{1-6}$ alkyl which contains one to three oxygen atoms between carbon atoms, and unsubstituted or substituted $C_{3-6}$ cycloalkyl;

$R^3$ is selected from unsubstituted or substituted heterocyclyl, unsubstituted or substituted carbocyclyl, unsubstituted or substituted $C_{1-6}$ alkylene-heterocyclyl, and unsubstituted or substituted $C_{1-6}$ alkylene-carbocyclyl;

each of $X^1$, $X^2$ and $X^3$ is independently selected from N, CH and $CR^x$, wherein at least one of said $X^1$, $X^2$ and $X^3$ is N;

$R^{31}$ is selected from hydrogen, $C_{1-6}$-alkyl, and $C_{1-6}$-alkyl substituted with one or more F; wherein $R^3$ and any $R^{31}$ are separate substituents or linked with each other; and E is either absent or is selected from —$CH_2$—, —$CHR^x$—, —$CR^x_2$—, —NH—, —$NR^x$—, —O—, -$L^1$-$L^2$- and -$L^2$-$L^1$-, wherein $L^1$ is selected from —$CH_2$—, —$CHR^x$—, —$CR^x_2$—, —NH—, —$NR^x$— and —O— and $L^2$ is selected from —$CH_2$-, —$CHR^x$— and —$CR^x_2$—;

$R^{6x}$ is halogen, OH, =O, $C_{1-6}$ alkyl, $C_{1-6}$ haloalkyl, $C_{1-6}$ alkyl substituted with one or more OH, monocyclic aryl unsubstituted or substituted with one or more $R^{xb}$, monocyclic heteroaryl unsubstituted or substituted with one or more $R^{xb}$, monocyclic cycloalkyl unsubstituted or substituted with one or more $R^{xb}$, monocyclic heterocycloalkyl unsubstituted or substituted with one or more $R^{xb}$, monocyclic cycloalkenyl unsubstituted or substituted with one or more $R^{xb}$, monocyclic heterocycloalkenyl unsubstituted or substituted with one or more $R^{xb}$, wherein said $R^{xb}$ is independently selected from halogen, OH, =O, $C_{1-4}$ alkyl, $C_{1-2}$ haloalkyl, $C_{1-2}$ alkyl substituted with one or two OH;

wherein Ring A is further unsubstituted or substituted with one or more groups $R^x$, wherein any two $R^x$ groups at ring A are separate substituents or linked with each other, or any $R^x$ group at ring A is a separate substituent or linked with $R^{21}$; or wherein Ring A is further unsubstituted or substituted with one group $R^x$ so as to form together with $R^{6x}$ a bicyclic moiety having the following partial structure:

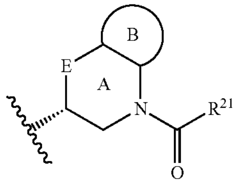

wherein Ring B is an unsubstituted or substituted heterocycle or unsubstituted or substituted carbocycle;

each $R^x$ is independently selected from halogen, OH, unsubstituted or substituted O—$C_{1-6}$ alkyl, unsubstituted or substituted NH—$C_{1-6}$ alkyl, unsubstituted or substituted N($C_{1-6}$ alkyl)$_2$, =O, unsubstituted or substituted $C_{1-6}$ alkyl, unsubstituted or substituted carbocyclyl, unsubstituted or substituted heterocyclyl, unsubstituted or substituted $C_{1-6}$ alkylene-carbocyclyl, unsubstituted or substituted $C_{1-6}$ alkylene-heterocyclyl, unsubstituted or substituted O—$C_{1-6}$ alkylene-carbocyclyl, and unsubstituted or substituted O—$C_{1-6}$ alkylene-heterocyclyl, and wherein the substituent of the substituted hydrocarbon group, substituted $C_{3-6}$ cycloalkyl, substituted heterocyclyl, substituted heterocycle, substituted carbocyclyl, substituted carbocycle and substituted $C_{1-6}$ alkylene is independently selected from $C_{1-6}$ alkyl, $C_{1-6}$ alkyl substituted with one or more halogen, halogen, CN, $NO_2$, oxo, —C(O)R*, —COOR*, —C(O)NR*R*, —NR*R*, —N(R*)—C(O)R*, —N(R*)—C(O)—OR*, —N(R*)—C(O)—NR*R*, —N(R*)—$S(O)_2$R*, —OR*, —O—C(O)R*, —O—C(O)—NR*R*, —SR*, —S(O)R*, —$S(O)_2$R*, —$S(O)_2$—NR*R*, —N(R*)—$S(O)_2$—NR*R*, heterocyclyl, heterocyclyl substituted with halogen or $C_{1-6}$ alkyl, carbocyclyl, and carbocyclyl substituted with halogen or $C_{1-6}$ alkyl; wherein each R* is independently selected from H, $C_{1-6}$ alkyl, $C_{1-6}$ alkyl substituted with halogen, heterocyclyl, heterocyclyl substituted with halogen or $C_{1-6}$ alkyl, carbocyclyl, and carbocyclyl substituted with halogen or $C_{1-6}$ alkyl; wherein any two R* connected to the same nitrogen atom are either separate substituents or linked with each other, and wherein the substituent of the substituted $C_{1-6}$ alkyl is independently selected from -halogen, —CN, —$NO_2$, oxo, —C(O)R, —COOR, —C(O)NRR, —NRR, —N(R)—C(O)R, —N(R)—C(O)—OR, —N(R)—C(O)—NRR, —N(R)—$S(O)_2$R, —OR, —O—C(O)R, —O—C(O)—NRR, —SR, —S(O)R, —$S(O)_2$R, —$S(O)_2$—NRR, and —N(R)—$S(O)_2$—NRR**;

wherein R is independently selected from H, $C_{1-6}$ alkyl, $C_{1-6}$ alkyl substituted with halogen, heterocyclyl, heterocyclyl substituted with halogen or $C_{1-6}$ alkyl, carbocyclyl, and carbocyclyl substituted with halogen or $C_{1-6}$ alkyl; wherein any two R connected to the same nitrogen atom are either separate substituents or linked with each other.

2. The method according to claim 1, wherein the compound of formula (I) is a compound of formula (V)

(V)

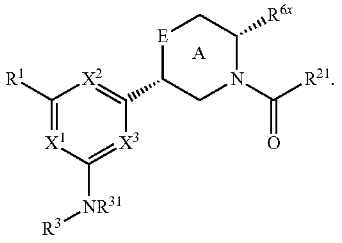

3. The method according to claim 1, wherein the compound of formula (I) is a compound of formula (VI)

(VI)

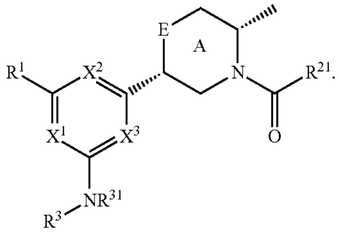

4. The method according to claim 1, wherein $X^2$ and $X^3$ are N.

5. The method according to claim 1, wherein $R^{21}$ is $CH_3$ or $CH_2CH_3$.

6. The method according to claim 1, wherein $R^{31}$ is selected from hydrogen and $C_{1-2}$-alkyl.

7. The method according to claim 1, wherein E is selected from —$CH_2$—, —O—, —$CH_2$—O— and —$CH_2$—$CH_2$—.

8. The method according to claim 1, wherein the number of groups $R^x$ in Ring A is 0, 1, or 2.

9. The method according to claim 1, wherein $R^1$ is selected from unsubstituted or substituted heterocyclyl and unsubstituted or substituted carbocyclyl.

10. The method according to claim 1, wherein $R^3$ is selected from phenyl, a 6-membered monocyclic heteroaryl and a 8-10 membered bicyclic heteroaryl, each independently comprising one or more ring heteroatoms independently selected from O, B, S and N, and wherein said phenyl, said 6-membered monocyclic heteroaryl and said 8-10 membered bicyclic heteroaryl is independently unsubstituted or substituted with one or more substituents selected from halogen, $C_{1-6}$ alkyl, $C_{1-6}$ haloalkyl, —O—$C_{1-6}$ alkyl, —O—$C_{1-6}$ haloalkyl, —OH, —CN, =O, —C(O)R*, —COOR*, —C(O)NR*R*, —NR*R*, —N(R**)—C(O)R*, —N(R**)—C(O)—OR*, —N(R**)—C(O)—NR*R*, —O—C(O)R*, —O—C(O)—NR*R*, 3-6 membered monocyclic carbocyclyl and 3-6 membered monocyclic heterocyclyl comprising 1 to 4 heteroatoms selected from O, B, S and N, each monocyclic carbocyclyl and heterocyclyl independently unsubstituted or substituted with one or more substituents independently selected from halogen, cyclopropyl, —$C_{1-4}$ alkyl, $C_{1-4}$ haloalkyl, —O—$C_{1-4}$ alkyl, —O—$C_{1-4}$ haloalkyl, —OH, —O, —$C_{1-3}$alkylene-OR*, —C(O)R* and —C(O)NR*R*; wherein each R* is independently selected from H, $C_{1-4}$ alkyl, $C_{1-4}$ haloalkyl, cyclopropyl, cyclobutyl, oxetanyl, —$C_{1-2}$alkylene-OH, —$C_{1-2}$alkylene-O—$C_{1-2}$alkyl, phenyl, and wherein each R** is independently selected from H, $C_{1-4}$ alkyl, $C_{1-4}$ haloalkyl, or wherein each monocyclic heterocyclyl is independently unsubstituted or substituted with one bivalent substituent selected from $C_{1-3}$ alkylene, $C_{1-3}$ alkylene substituted with 1 to 4 F, —$CH_2$—O—$CH_2$—, and —$CH_2$—NH—$CH_2$—.

11. The method according to claim 1, wherein
$X^2$ and $X^3$ are N, and $X^1$ is CH;
E is —$CH_2$—;
$R^{21}$ is $CH_3$;
$R^{6x}$ is $CH_3$; and
Ring A does not form a bicyclic moiety.

12. The method according to claim 1, wherein the fibrotic disease is selected from the group consisting of pulmonary fibrosis, idiopathic pulmonary fibrosis, radiation-induced pneumonitis, radiation fibrosis, acute respiratory distress syndrome, chronic obstructive pulmonary disease, interstitial lung disease, myocardial infarction, cardiac fibrosis and hypertrophy, ischemic stroke, ischemic kidney disease, renal fibrosis, rheumatoid arthritis, liver fibrosis, NASH (non-alcoholic steatohepatitis), chronic hepatitis, cirrhosis, inflammatory bowel disease, Crohn's disease, scleroderma, keloid, post-operative fibrosis, chemotherapy induced fibrosis (e.g., chemotherapy induced pulmonary fibrosis or ovarian cortical fibrosis), nephrogenic systemic fibrosis, retroperitoneal fibrosis, myelofibrosis, mediastinal fibrosis, cystic fibrosis, asbestosis, asthma, pulmonary hypertension, systemic fibrosis, skin fibrosis, hypertension induced renal and cardiac fibrosis.

13. The method according to claim 12, wherein the fibrotic disease is interstitial lung disease (IDL), wherein the interstitial lung disease is idiopathic interstitial pneumonia (IIP).

14. The method according to claim 13, wherein the idiopathic interstitial pneumonia is selected from the group consisting of chronic fibrosing interstitial pneumonia, smoking-related interstitial pneumonia and acute/subacute interstitial pneumonia.

15. The method according to claim 14, wherein the chronic fibrosing interstitial pneumonia is idiopathic pulmonary fibrosis (IPF).

16. The method according to claim 12, wherein the fibrotic disease is non-hepatic steatohepatitis (NASH).

17. The method according to claim 12, wherein the fibrotic disease is interstitial lung disease (IDL).

18. The method according to claim 1, wherein $X^1$ is CH.

19. The method according to claim 1, wherein the number of groups $R^x$ in Ring A is 0, 1, or 2, and wherein each $R^x$ is independently selected from halogen, OH, O—$C_{1-2}$ alkyl, O—$C_{1-2}$ alkyl substituted with one or more $R^{xa}$, NH—$C_{1-2}$ alkyl, NH—$C_{1-2}$ alkyl substituted with one or more $R^{xa}$, N($C_{1-2}$ alkyl)$_2$, N($C_{1-2}$ alkyl)$_2$ substituted with one or more $R^{xa}$, ═O, $C_{1-3}$ alkyl, $C_{1-3}$ alkyl substituted with one or more $R^{xa}$, $C_{1-2}$ haloalkyl, —W-monocyclic carbocyclyl, —W-monocyclic carbocyclyl substituted with one or more $R^{xa}$, —W-monocyclic heterocyclyl, —W-monocyclic heterocyclyl substituted with one or more $R^{xa}$, and wherein —W— is absent, —$C_{1-2}$ alkylene- or —O—$C_{1-2}$ alkylene-, and wherein monocyclic carbocyclyl is selected from phenyl and $C_{3-6}$ cycloalkyl, and wherein monocyclic heterocyclyl is selected from thiophenyl, pyridyl, pyrazinyl and pyrimidinyl, and wherein said $R^{xa}$ is independently selected from Cl, F, and OH.

20. The method according to claim 1, wherein $R^1$ is selected from phenyl, a 5- or 6-membered monocyclic heteroaryl, and a 8-10 membered bicyclic heteroaryl, each independently comprising one or more ring heteroatoms independently selected from O, S and N, and wherein said phenyl, said 5- or 6-membered monocyclic heteroaryl and said 8-10 membered bicyclic heteroaryl is independently unsubstituted or substituted with one or more substituents selected from halogen, $C_{1-6}$ alkyl, $C_{1-6}$ haloalkyl, —O—$C_{1-6}$ alkyl, —O—$C_{1-6}$ haloalkyl, OH, CN, ═O, —C(O)R*, —COOR*, —C(O)NR*R*, —NR*R*, —N(R*)—C(O)R*, —N(R*)—C(O)—OR*, —N(R*)—C(O)—NR*R*, —O—C(O)R*, —O—C(O)—NR*R*, 3-6 membered monocyclic carbocyclyl and 3-6 membered monocyclic heterocyclyl comprising 1 to 4 heteroatoms selected from O, S and N, each monocyclic carbocyclyl and heterocyclyl independently unsubstituted or substituted with one or more substituents independently selected from halogen, $C_{1-4}$ alkyl, $C_{1-4}$ haloalkyl, —O—$C_{1-4}$ alkyl, —O—$C_{1-4}$ haloalkyl, —OH, ═O, —C(O)R* and —C(O)NR*R*; wherein each R* is independently selected from H, $C_{1-4}$ alkyl, $C_{1-4}$ haloalkyl or wherein each monocyclic heterocyclyl is independently unsubstituted or substituted with one bivalent substituent selected from $C_{1-3}$ alkylene, $C_{1-3}$ alkylene substituted with 1 to 4 F, —$CH_2$—O—$CH_2$—, and —$CH_2$—NH—$CH_2$—.

* * * * *